(12) United States Patent
Ring et al.

(10) Patent No.: US 10,800,830 B2
(45) Date of Patent: *Oct. 13, 2020

(54) HIGH AFFINITY PD-1 AGENTS AND METHODS OF USE

(71) Applicant: The Board of Trustees of the Leland Stanford Junior University, Stanford, CA (US)

(72) Inventors: Aaron Michael Ring, New Haven, CT (US); Andrew Kruse, Roslindale, MA (US); Aashish Manglik, Menlo Park, CA (US); Irving L. Weissman, Stanford, CA (US); Roy Louis Maute, San Francisco, CA (US); Melissa N. McCracken, Mountain View, CA (US); Sydney Gordon, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 225 days.

This patent is subject to a terminal disclaimer.

(21) Appl. No.: 15/502,439

(22) PCT Filed: Aug. 7, 2015

(86) PCT No.: PCT/US2015/044356

§ 371 (c)(1),
(2) Date: Feb. 7, 2017

(87) PCT Pub. No.: WO2016/022994
PCT Pub. Date: Feb. 11, 2016

(65) Prior Publication Data
US 2017/0233451 A1 Aug. 17, 2017

Related U.S. Application Data

(60) Provisional application No. 62/150,789, filed on Apr. 21, 2015, provisional application No. 62/035,316, filed on Aug. 8, 2014.

(51) Int. Cl.
| | | |
|---|---|---|
| *C07K 14/47* | (2006.01) | |
| *A61K 38/17* | (2006.01) | |
| *C07K 14/705* | (2006.01) | |
| *A61K 35/17* | (2015.01) | |
| *A61K 45/06* | (2006.01) | |
| *A61K 48/00* | (2006.01) | |
| *A61K 51/08* | (2006.01) | |
| *A61K 51/10* | (2006.01) | |
| *C07K 14/725* | (2006.01) | |
| *A61K 38/00* | (2006.01) | |

(52) U.S. Cl.
CPC ........ *C07K 14/70503* (2013.01); *A61K 35/17* (2013.01); *A61K 38/1761* (2013.01); *A61K 45/06* (2013.01); *A61K 48/00* (2013.01); *A61K 51/08* (2013.01); *A61K 51/088* (2013.01); *A61K 51/10* (2013.01); *C07K 14/4747* (2013.01); *C07K 14/7051* (2013.01); *C07K 14/70532* (2013.01); *A61K 38/00* (2013.01); *C07K 2319/30* (2013.01)

(58) Field of Classification Search
CPC . C07K 14/7051; C07K 14/4746; A61K 35/17
See application file for complete search history.

(56) References Cited

U.S. PATENT DOCUMENTS

| | | |
|---|---|---|
| 2011/0159023 A1 | 6/2011 | Langermann |
| 2012/0121634 A1 | 5/2012 | Chen et al. |
| 2013/0149305 A1 | 6/2013 | Ostrand-Rosenberg |
| 2014/0134142 A1 | 5/2014 | Smith et al. |

FOREIGN PATENT DOCUMENTS

| | | |
|---|---|---|
| JP | 2012-500855 | 1/2012 |
| WO | WO2012145493 | 10/2012 |
| WO | 2013/112986 A1 | 8/2013 |
| WO | WO2014/022758 A1 | 2/2014 |

OTHER PUBLICATIONS

Dolan et al., "PD-1 Pathway Inhibitors: Changing the Landscape of Cancer Immunotherapy", Cancer Control, Jul. 2014, p. 231-237, vol. 21 No. 3.
Maute et al., "Engineering high-affinity PD-1 variants for optimized immunotherapy and immuno-PET imaging", Proceedings National Academy of Sciences PNAS, Nov. 2015, pp. E6506-E6514, vol. 112 No. 47, Washington, DC.
Topalian et al., "Safety, Activity, and Immune Correlates of Anti-PD-1 Antibody in Cancer", The New England Journal of Medicine, Jun. 2012, pp. 2443-2454, vol. 366 No. 26, Boston, Ma.
Yin-Wei Lin et al., "The PD-1/PD-L1 complex resembles the antigen-binding Fv domains of antibodies and T cell receptors" Proceedings National Academy of Sciences PNAS, Feb. 2008, pp. 3011-3016, vol. 105 No. 8, Washington, DC.
Ho et al., "Adoptive immunotherapy: engineering T cells responses as biologic weapons for tumor mass destruction", Cancer Cell, May 31, 2003, pp. 431-437, vol. 3, Cell Press, Cambridge, MA.

(Continued)

*Primary Examiner* — Robert C Hayes
(74) *Attorney, Agent, or Firm* — Bozicevic, Field & Francis LLP; Kyle A. Gurley

(57) ABSTRACT

High affinity PD-1 mimic polypeptides are provided, which (i) comprise at least one amino acid change relative to a wild-type PD-1 protein; and (ii) have an increased affinity for PD-L1 relative to the wild-type protein. Compositions and methods are provided for modulating the activity of immune cells in a mammal by administering a therapeutic dose of a pharmaceutical composition comprising a high affinity PD-1 mimic polypeptide, which blocks the physiological binding interaction between PD-1 and its ligand PD-L1 and/or PD-L2.

17 Claims, 36 Drawing Sheets
Specification includes a Sequence Listing.

(56) References Cited

OTHER PUBLICATIONS

Lazar-Molnar et al., "Crystal structure of the complex between programmed death-1 (PD-1) and its ligand PD-L2", Proceedings of the National Academy of Sciences, Jul. 29, 2008, pp. 10483-10488, vol. 105, PNAS, Washington, DC.
Huanjing Shi et al., "Preparation of Anti-Human PD-1 Antiserum with High-affinity and Its Application in PD-1 Immunoblotting Analysis" (*Chinese*), *Journal of Jinan University (Natural Science)*, Jun. 2008, 29(3): 315-319.
Binder DC et al., "High-Affinity Peptide-Based Anticancer Vaccination to Overcome Resistance to Immunostimulatory Antibodies," *Oncoimmunology*, Dec. 2013, 2(12): e26704.

Fig. 2B
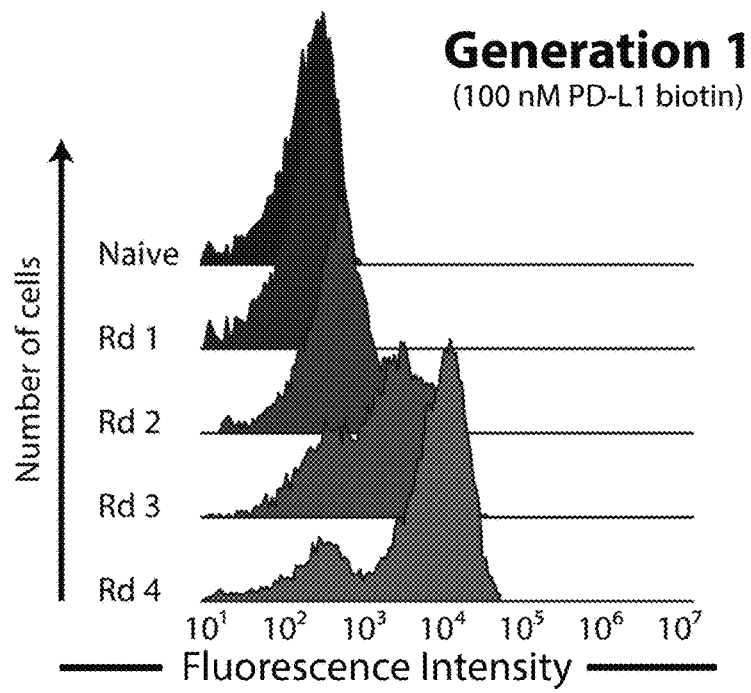
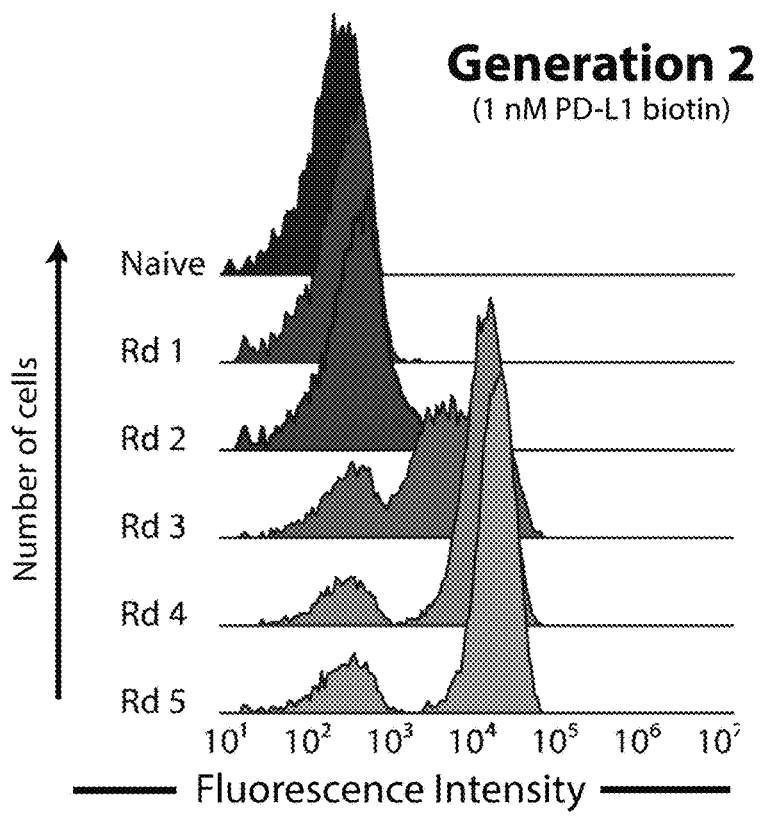

Fig. 3

| SEQ ID NO | A.A. Position | 39 | 40 | 41 | 43 | 44 | 45 | 48 | 49 | 50 | 51 | 52 | 53 | 56 | 60 | 63 | 65 | 66 | 72 | 82 | 83 | 90 | 96 | 97 | 100 | 102 | 103 | 104 | 105 | 106 | 107 | 111 | PD-L1 affinity |
|---|---|---|---|---|---|---|---|---|---|---|---|---|---|---|---|---|---|---|---|---|---|---|---|---|---|---|---|---|---|---|---|---|---|
| 2 | hPD-1 | V | L | N | Y | R | M | S | N | Q | T | D | K | A | D | Q | Q | G | Q | V | H | M | R | Y | L | A | S | L | L | A | P | K | A | E | 3.88 µM |
| 10 | G14-12 | H | – | – | F | – | Q | Q | – | K | V | F | – | T | – | N | P | – | – | – | – | – | – | Y | – | T | – | S | – | G | P | – |  |
| 11 | G14-2 | H | – | V | F | – | Q | L | G | – | – | F | – | – | – | R | – | – | – | – | – | – | – | Y | – | Y | – | S | – | E | – | – |  |
| 12 | G14-5 | H | V | V | H | – | Q | Q | N | G | Y | R | – | – | – | – | P | – | – | Q | – | – | – | V | – | – | – | – | – | A | V | – | 7.78 nM |
| 13 | G14-1 | R | – | V | H | – | E | E | G | Y | E | T | S | T | – | L | P | – | – | – | – | – | – | V | – | A | – | H | – | – | – | – | 10.7 nM |
| 14 | G14-4 | R | – | V | H | – | E | N | Y | A | Y | T | L | L | – | L | P | – | – | – | – | – | – | V | – | F | F | D | – | V | – | – |  |
| 15 | G14-10 | H | – | V | H | L | L | V | Y | V | L | L | – | – | – | P | V | – | – | – | – | – | – | – | – | – | – | Y | D | – | – | – |  |
| 9 | G24-12 | H | V | V | H | Y | E | E | G | – | – | – | T | – | – | – | P | – | – | – | – | – | – | V | – | – | – | – | – | – | – | – | 218 pM |
| 5 | G24-1 | H | V | – | H | Y | E | G | S | – | – | – | T | – | – | – | P | – | – | – | L | – | – | V | – | – | – | – | – | – | – | – | 267 pM |
| 8 | G24-5 | H | V | V | H | Y | E | S | C | – | – | – | T | – | – | – | P | – | – | – | L | – | – | V | – | – | – | – | – | – | – | – | 196 pM |
| 16 | G24-10 | H | V | V | H | Y | E | G | G | – | – | – | T | – | – | – | P | – | – | – | L | F | – | V | – | – | – | – | – | – | – | – |  |
| 17 | G24-1A | H | V | – | H | Y | E | – | G | – | – | – | T | – | – | – | P | – | – | – | F | F | – | – | – | – | – | – | – | – | – | – |  |
| 18 | G24-4 | H | – | V | H | – | E | E | G | – | – | – | T | – | – | – | – | – | – | – | F | F | – | V | – | – | – | – | – | – | – | – |  |
| 19 | G24-22 | H | – | V | H | – | E | G | G | – | – | – | T | – | – | – | P | – | – | – | F | F | – | V | – | – | – | – | – | – | – | – |  |
| 20 | G24-5 | R | V | – | H | – | E | G | G | – | – | – | T | – | – | – | P | – | – | – | L | F | – | V | – | – | – | F | – | – | – | – |  |
| 21 | G24-7 | H | V | V | H | – | E | – | G | – | – | – | T | – | – | – | – | – | – | – | L | – | K | V | – | – | – | – | – | – | – | – |  |
| 22 | G24-18 | H | V | V | H | – | E | G | G | – | – | – | T | – | – | – | P | – | – | – | – | – | – | V | – | – | – | – | – | – | – | – | 222 pM |
| 6 | G24-2 | H | V | V | H | – | E | G | G | – | – | – | T | – | – | – | – | – | – | – | – | – | – | V | – | – | – | – | – | – | – | – | 101 pM |
| 23 | G24-23 | H | – | V | H | – | E | G | G | – | – | – | T | – | – | – | – | – | – | – | – | – | – | V | – | – | – | – | – | – | – | – |  |
| 7 | G24-3 | H | V | V | H | – | L | E | G | – | – | – | T | – | – | – | – | – | – | – | – | – | – | V | – | – | – | – | – | – | – | – |  |
| 3 | Consensus 1 (HAC-I) | H | V | V | H | – | E | – | G | – | – | – | T | – | – | – | – | – | – | – | – | – | – | V | – | – | – | – | – | – | – | – | 107 pM |
| 4 | Consensus 2 (HAC-V) | H | V | V | H | – | E | – | G | – | – | – | T | – | – | – | – | – | – | – | – | – | – | V | – | – | – | – | – | – | – | – | 110 pM |

Blockade of PD-1 tetramer on human PD-L1 yeast

Blockade of PD-1 tetramer on human PD-L2 yeast

Fig. 7C

| Residue # | 39 | 40 | 41 | 43 | 44 | 45 | 48 | 49 | 50 | 51 | 52 | 53 | 56 | 60 | 63 | 65 | 66 | 72 | 82 | 83 | 90 | 96 | 97 | 100 | 102 | 103 | 104 | 105 | 106 | 107 | 111 | PD-L1 affinity |
|---|---|---|---|---|---|---|---|---|---|---|---|---|---|---|---|---|---|---|---|---|---|---|---|---|---|---|---|---|---|---|---|---|
| hPD-1 | V | L | N | Y | R | M | S | N | Q | T | D | K | A | D | Q | G | Q | V | H | M | R | Y | L | A | S | L | A | P | K | A | E | |
| G14-12 | H | | | | | Q | D | K | V | F | | | | | T | N | P | | | | | | Y | T | I | S | G | P | | | | 3.88 µM |
| G14-2 | H | - | F | | | Q | L | G | L | L | | | | | - | R | | | | | | | | | | | | | | | | |
| G14-5 | H | - | | F | | Q | Q | N | V | R | | | | | E | - | P | | | | | | | Y | | A | - | | | | | |
| G14-1 | R | V | H | | | E | E | Y | E | | T | S | | | T | L | P | | | | | | | | A | F | H | E | - | V | - | 7.78 nM |
| G14-4 | R | V | H | | | E | N | H | A | | T | L | | | L | F | P | | | | | | | A | T | F | D | R | | | | 10.7 nM |
| G14-10 | H | V | | | | L | V | Y | Y | | L | V | L | | P | V | | | | | | | | Y | Y | D | - | T | - | | | |
| G24-12 | H | V | V | Y | | E | | G | | | | T | | | | | P | | | | | - | V | - | | | | | | | | 218 pM |
| G24-1 | H | V | V | H | | E | | G | | | | T | | | | | P | | L | | | | V | V | | | | | | | | 267 pM |
| G24-5 | H | V | V | H | | E | | S | | | | T | | | | | P | - | Q | L | | | V | V | | | | | | | | 196 pM |
| G24-10 | H | V | V | H | Y | D | | G | | | | T | | | | | P | | F | F | | F | - | V | | | | | | | | |
| G24-14 | H | V | V | H | Y | E | | G | | | | T | | | | | P | - | F | F | | F | V | V | F | | | | | | | |
| G24-4 | H | V | - | H | | E | | C | | | | T | | | | | | - | L | F | | F | V | V | | | | | | | | |
| G24-22 | H | V | - | H | | E | | G | | | | T | | | | | | - | L | L | | F | V | V | | | | | | | | |
| G24-6 | R | V | - | H | | E | | G | | | | T | | | | | | - | L | L | | F | V | V | | | | | | | | |
| G24-7 | H | - | - | H | | E | | G | | | | T | | | | | P | - | F | F | K | | - | V | | | | | | | | 222 pM |
| G24-18 | H | V | - | H | | E | | G | | | | T | | | | | | - | L | L | | | V | V | | | | | | | | |
| G24-2 | H | - | - | H | | E | | G | | | | T | | | | | P | | L | | | | V | V | | | | | | | | 101 pM |
| G24-23 | H | V | - | H | L | E | | G | | | | T | | | | | | - | L | | | | V | V | | | | | | | | |
| G24-3 | H | - | V | H | | E | | G | | | | T | | | | | P | | | | | | V | V | | | | | | | | |
| Consensus 1 (HAC-I) | H | - | - | H | | E | | G | | | | T | | | | | | | | | | | V | V | | | | | - | | - | 107 pM |
| Consensus 2 (HAC-V) | H | V | V | H | | E | | G | | | | T | | | | | | | | | | | V | V | | | | | - | | - | 110 pM |

Contact consensus sites

Core consensus sites

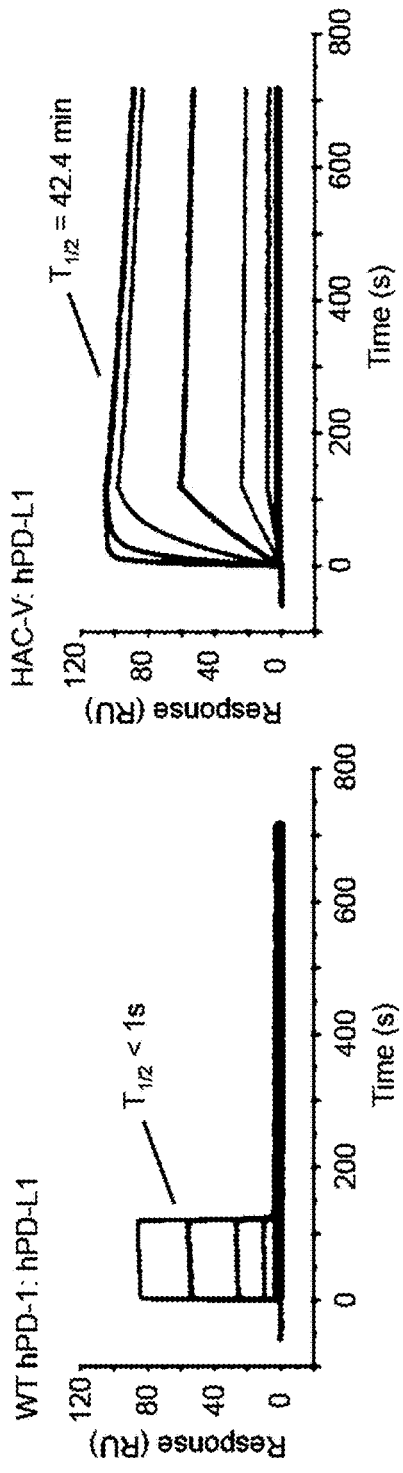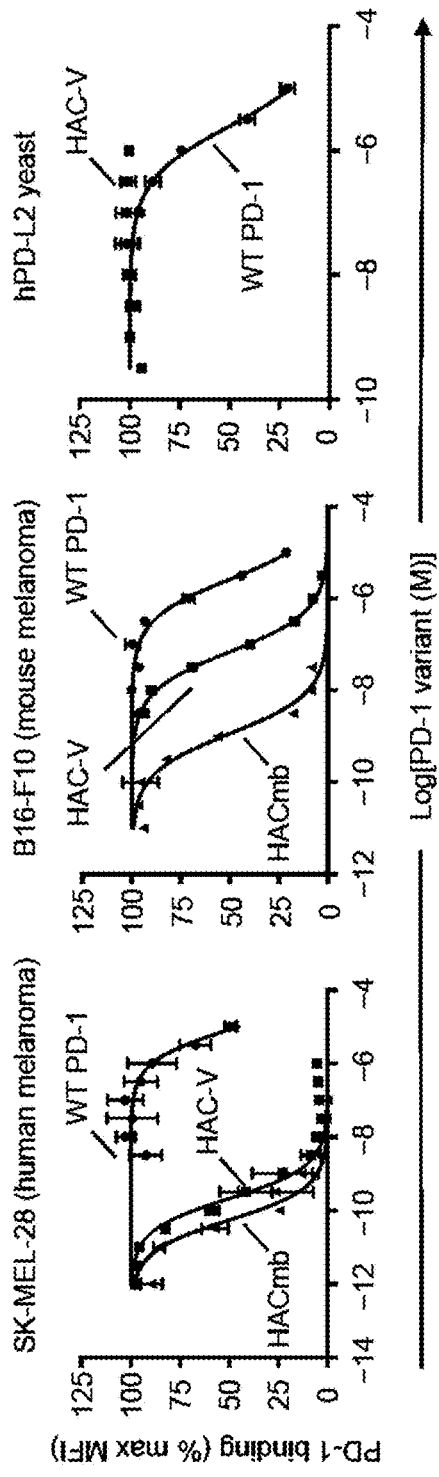
Fig. 8A
Fig. 8B

Fig. 9A
CT26, PD-L1 negative tumor
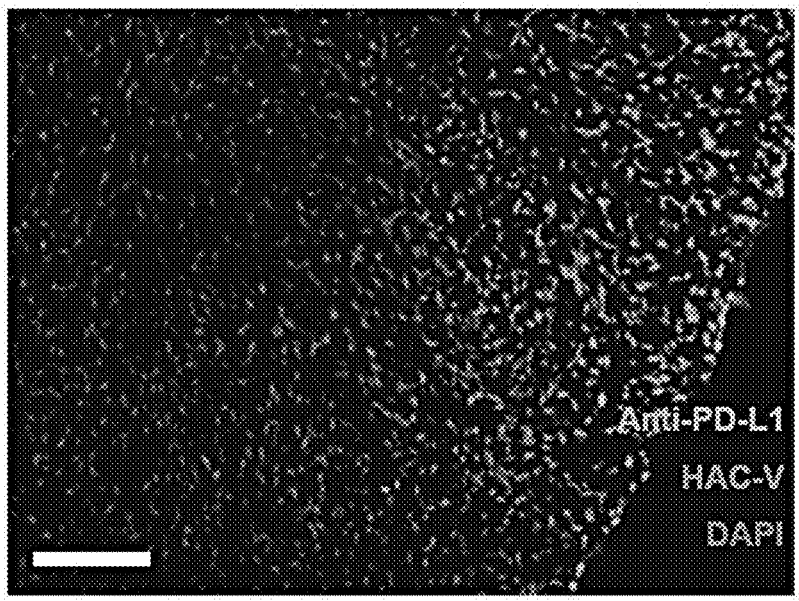
CT26, hPD-L1 positive tumor
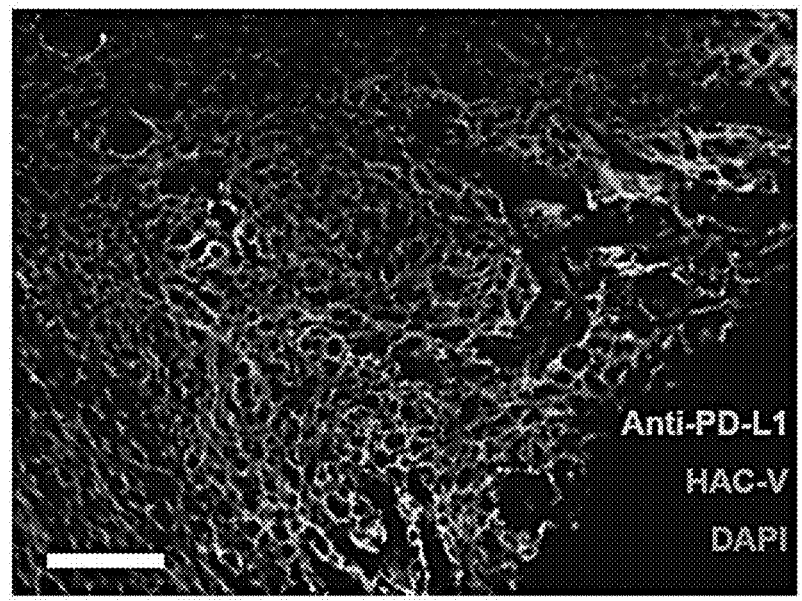

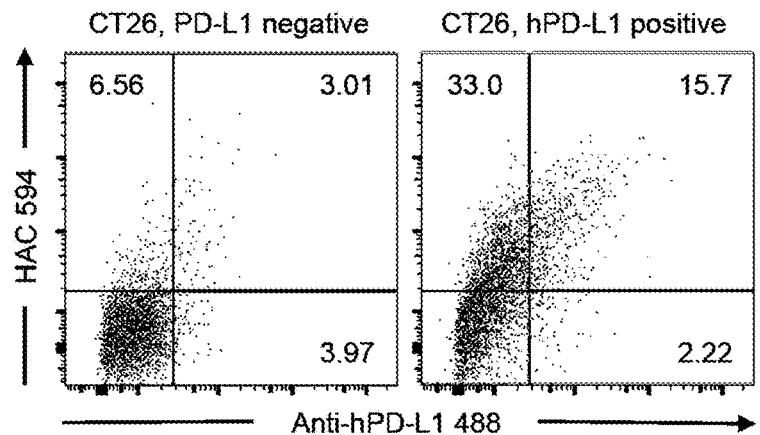
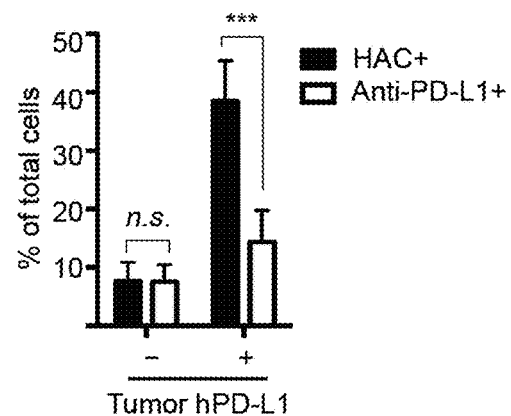
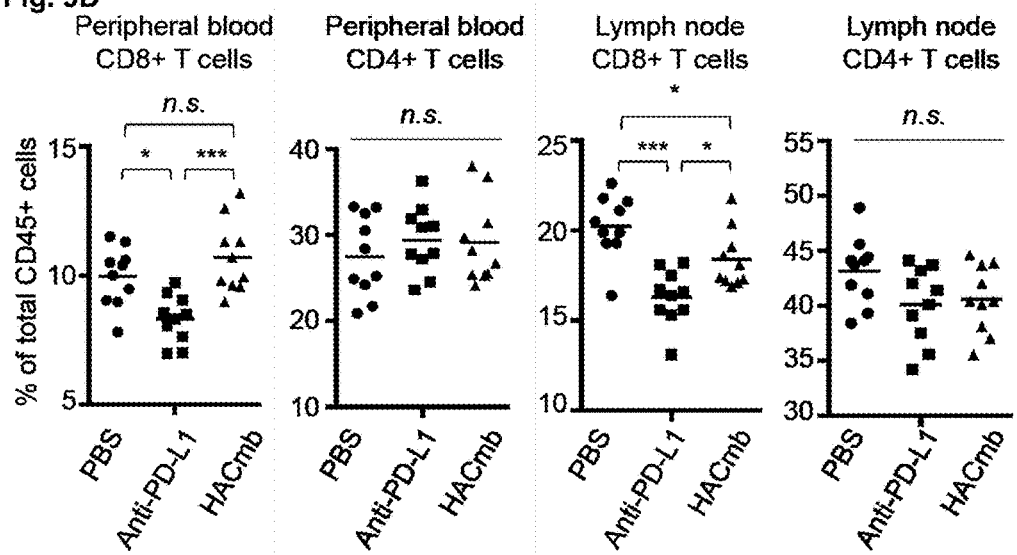

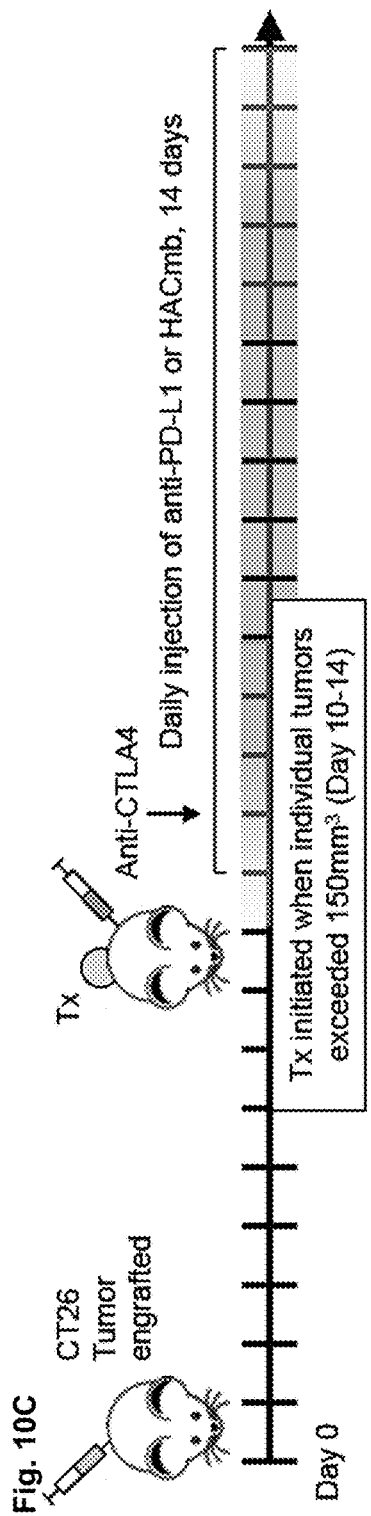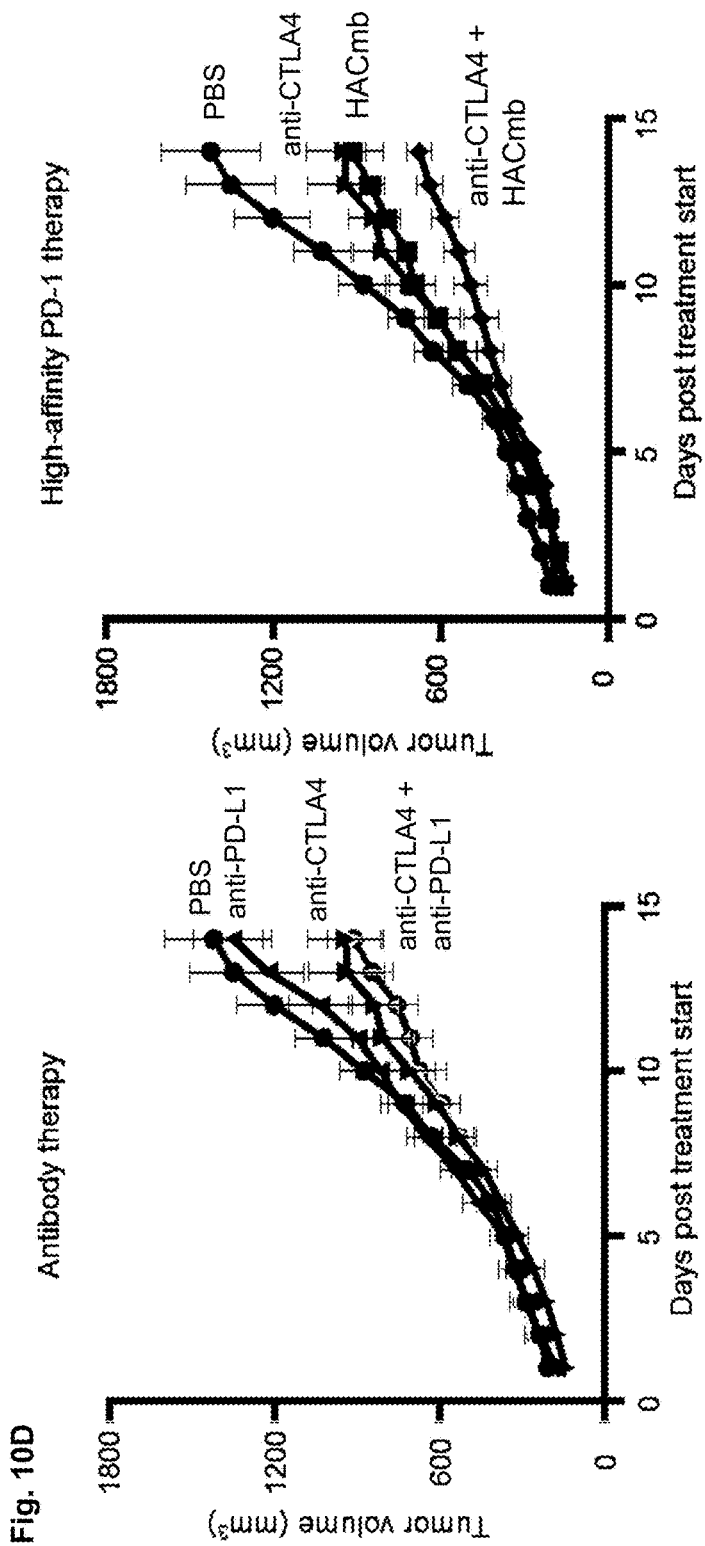
Fig. 10C
Fig. 10D

Fig. 12A

| Position | Codon | Possible replacement residues |
|---|---|---|
| V39 | NDT | C,D,F,G,H,I,L,N,R,S,V, or Y |
| N41 | RWT | N,I,V, or D |
| Y43 | HWT | F,Y,L,H,I, or N |
| M45 | VWG | E,K,L,M,Q, or V |
| S48 | VNT | A,D,G,H,I,L,N,P,R,S,T, or V |
| N49 | NDT | C,D,F,G,H,I,L,N,R,S,V, or Y |
| Q50 | VWW | H,Q,N,K,D,E,L,I, or V |
| T51 | VYT | A,I,L,P,T, or V |
| D52 | NDT | C,D,F,G,H,I,L,N,R,S,V, or Y |
| K53 | VNA | A,E,G,I,K,L,P,Q,T,V, or R |
| A56 | NHT | A,D,F,H,I,L,N,P,S,T,V, or Y |
| Q63 | VNA | A,E,G,I,K,L,P,Q,T,V, or R |
| G65 | NDT | C,D,F,G,H,I,L,N,R,S,V, or Y |
| Q66 | CMA | Q or P |
| L97 | NWT | F,I,L,V,Y,H,N, or D |
| S102 | NCT | S,T,A, or P |
| L103 | NDT | C,D,F,G,H,I,L,N,R,S,V, or Y |
| A104 | NHT | A,D,F,H,I,L,N,P,S,T,V, or Y |
| P105 | SCT | A or P |
| K106 | VNA | A,E,G,I,K,L,P,Q,T,V, or R |
| A107 | NYT | F,I,L,V,S,P,T, or A |
| E111 | VRW | D,E,H,K,N,Q,S,G, or R |

Fig. 12B

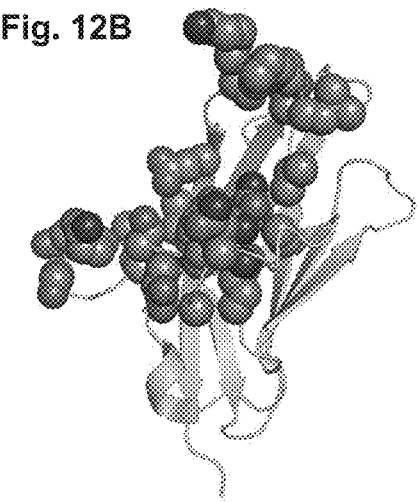

| Position | Codon | Possible replacement residues |
|---|---|---|
| V39 | VRT | D,G,H,N,R, or S |
| L40 | NTT | F,I,L, or V |
| N41 | NWT | F,I,L,V,D,H,N, or Y |
| Y43 | YWT | F,H,L, or Y |
| R44 | YDT | F,H,L,R,Y, or C |
| M45 | SAW | D,E,H, or Q |
| N49 | DRT | C,D,G,N,S, or Y |
| K53 | AMA | K or T |
| Q66 | CMA | Q or P |
| V72 | RYT | V,A,I, or T |
| M83 | NTS | F,I,L,V, or M |
| Y96 | YWT | F,H,L, or Y |
| L97 | NTT | F,I,L, or V |
| A100 | RYT | V,A,I, or T |
| L103 | YWT | F,H,L, or Y |
| A107 | NTT | F,I,L, or V |

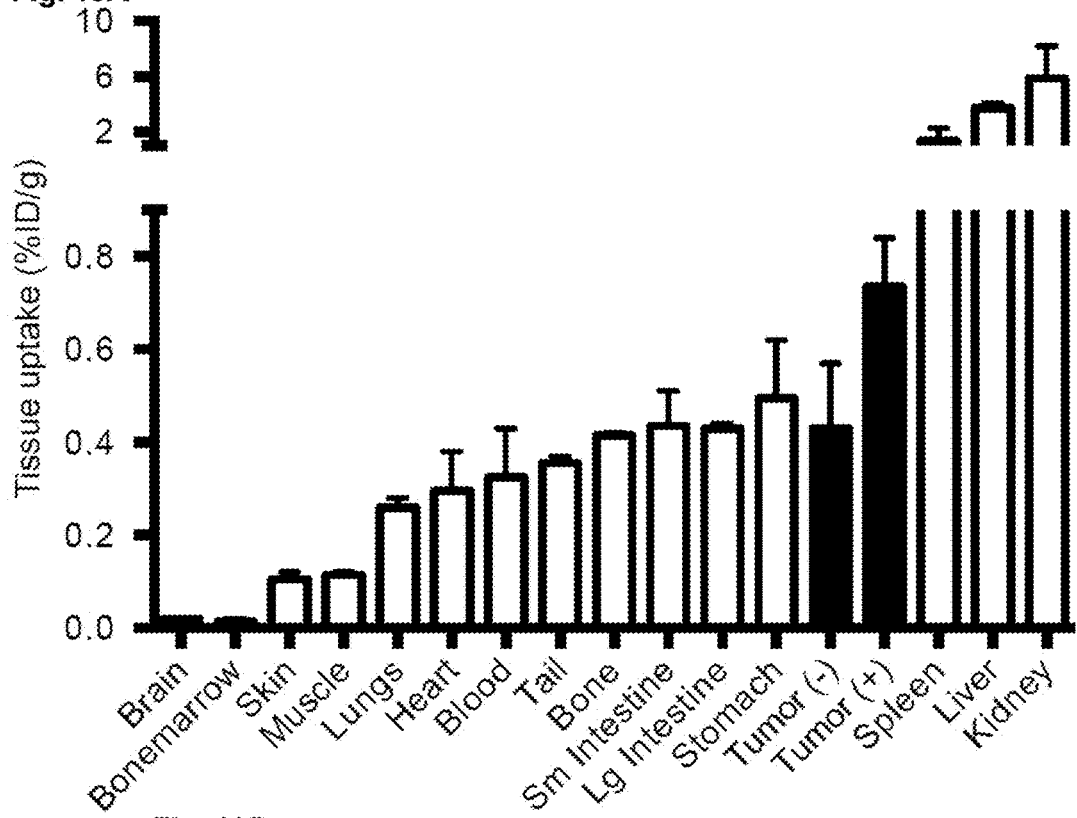
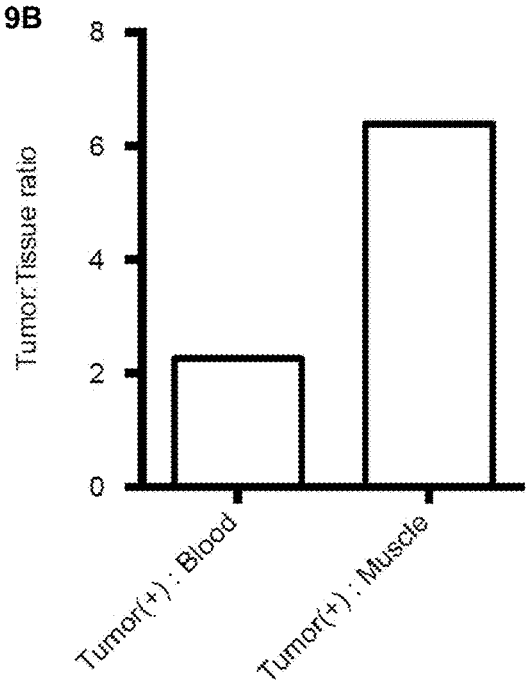

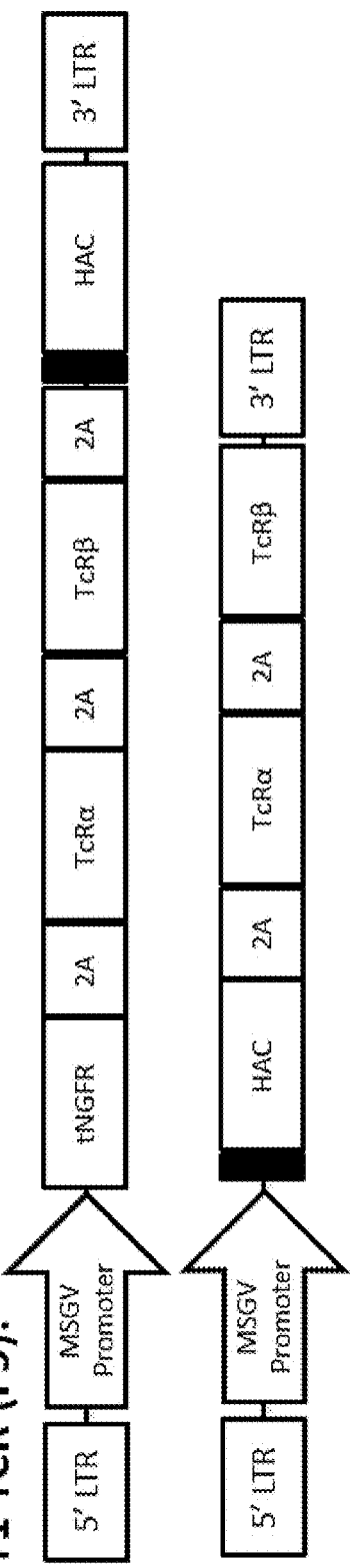
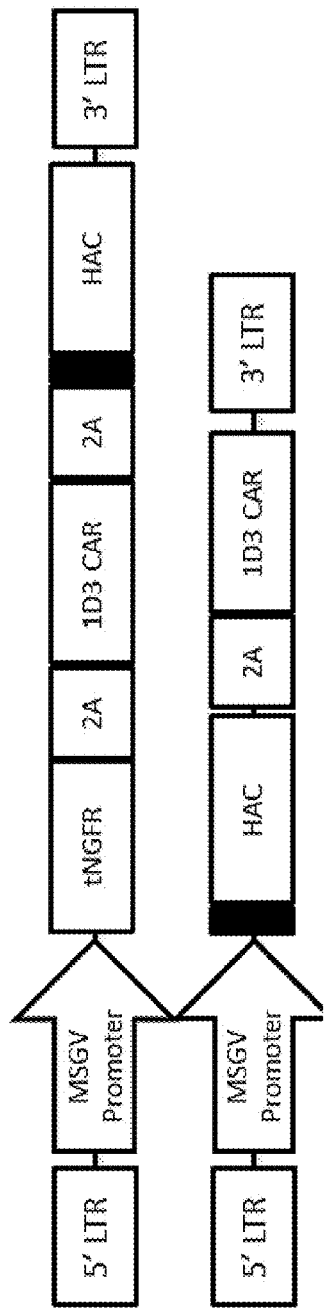
Fig. 20B

Fig. 20C
Single promoter vector:
Engineered TCR
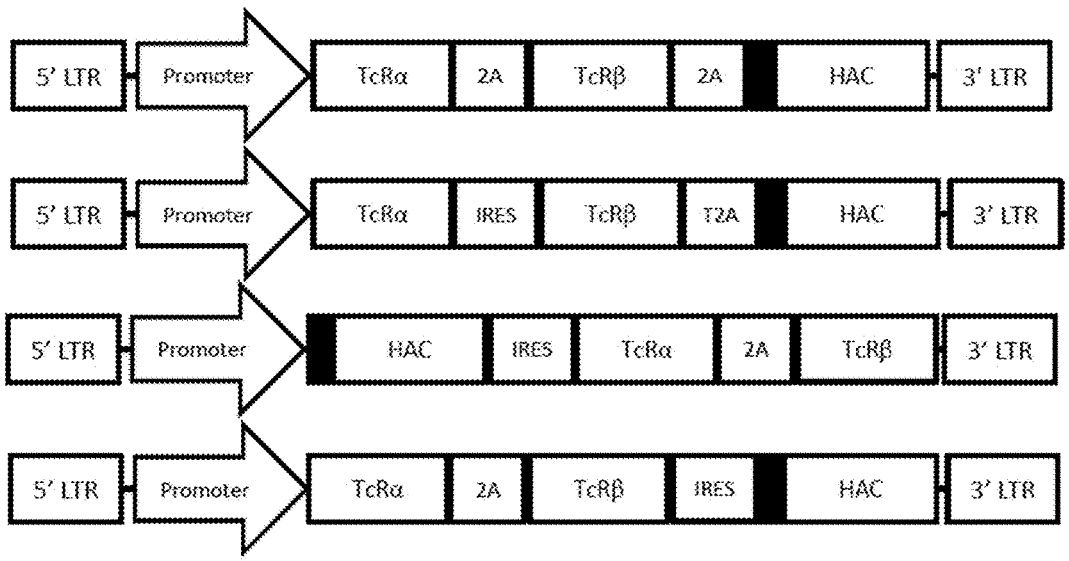
Engineered CAR
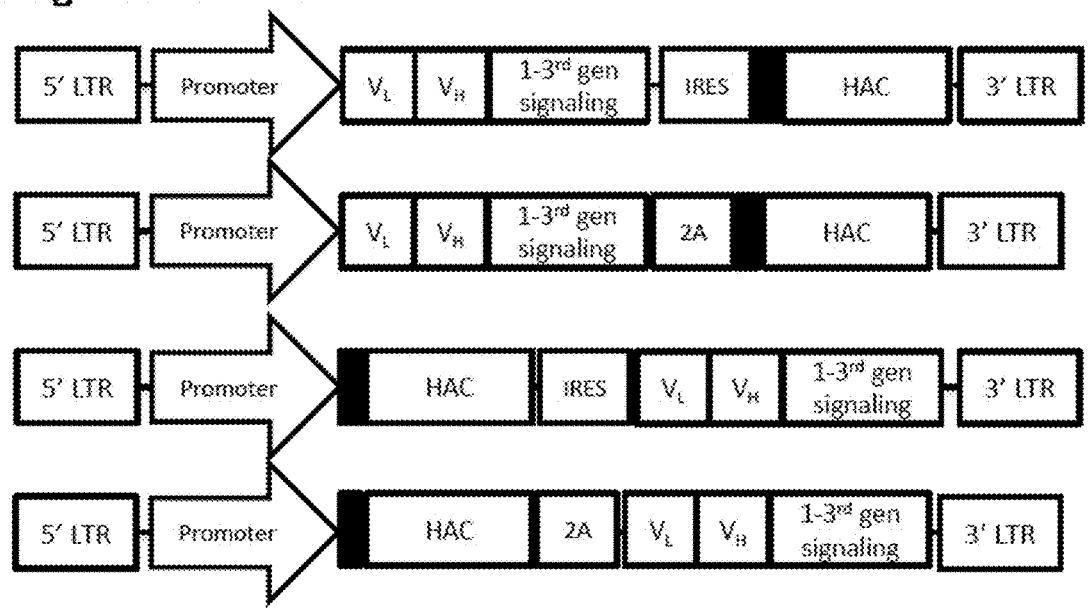

Fig. 20D
Separate promoter vectors:
Engineered TCR
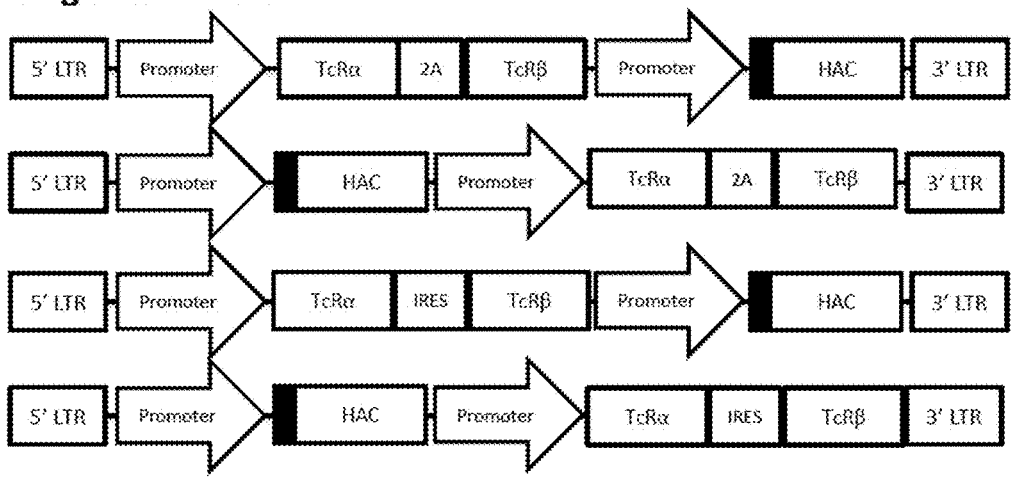
Engineered CAR
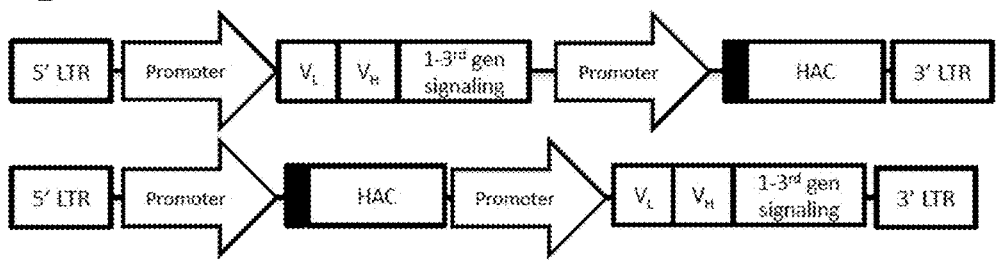

Fig. 20E
Bidirectional separate promoter vectors:
Engineered TCR
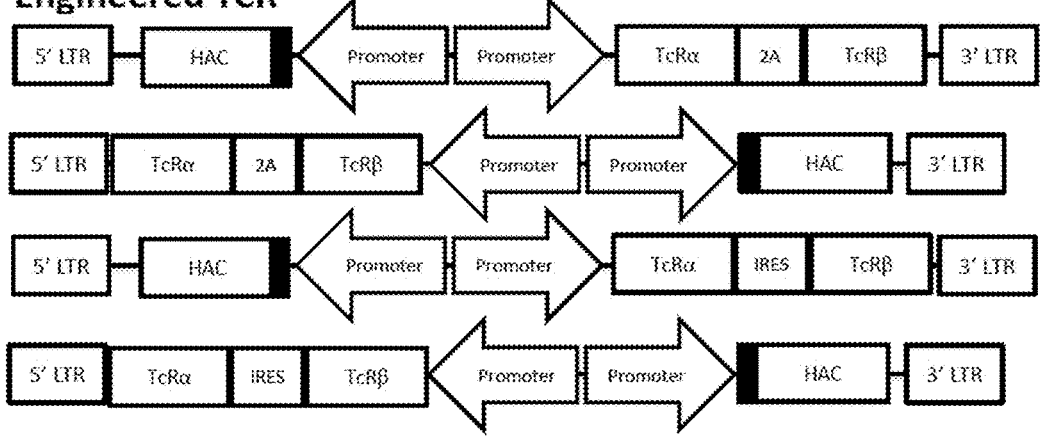
Engineered CAR
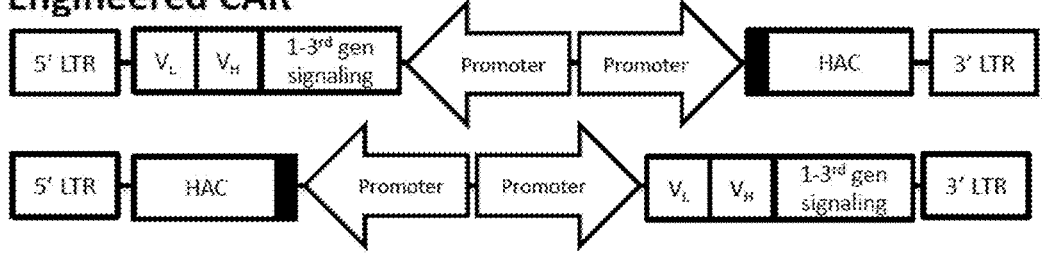

MSGV-HAC-M5
(sequence is SEQ ID NO: 101)

MSGV-HACmb-1D3 CAR
(sequence is SEQ ID NO: 103)

MSGV-NGFR-1D3 CAR-HACmb
(sequence is SEQ ID NO: 104)

HIGH AFFINITY PD-1 AGENTS AND METHODS OF USE

CROSS-REFERENCE

This application is a 371 application and claims the benefit of PCT Application No. PCT/US2015/044356, filed Aug. 7, 2015, which claims the benefit of U.S. Provisional Patent Application Nos. 62/035,316 filed Aug. 8, 2014, and 62/150,789, filed Apr. 21, 2015, which applications are incorporated herein by reference in its theft entirety.

INCORPORATION BY REFERENCE OF SEQUENCE LISTING PROVIDED AS A TEXT FILE

A Sequence Listing is provided herewith as a text file, "STAN-1136WO2_SeqList_ST25.txt" created on Aug. 7, 2015 and having a size of 119 KB. The contents of the text file are incorporated by reference herein in their entirety.

INTRODUCTION

T cell activation depends on an antigen specific signal provided to T cell receptors. Additional signals, for example costimulatory (positive) and/or coinhibitory (negative) signals, fine-tune this response, helping to determine its strength, nature, and duration. Costimulatory interactions potentiate the activation and proliferation of T cells, while coinhibitory interactions promote regulation. For example, CD28 and CTLA-4 coreceptors both bind to the B7-1 (CD80) and B7-2 (CD86) molecules. CD28 acts as a strong positive costimulatory receptor and CTLA-4 as a potent coinhibitory receptor.

A receptor known as the programmed death-1 (PD-1) receptor is expressed on T cells, B cells and myeloid cells, and binds to the programmed death ligand (PD-L). This receptor-ligand pair functions primarily to provide inhibitory signals (e.g., through the recruitment of phosphatases, such as SHP-2, to the immunoreceptor tyrosin-based switch motif (ITSM) of the cytoplasmic tail of PD-1).

PD-1 signaling plays an important role in inducing and maintaining peripheral tolerance. PD-1 ligands (PD-Ls) on antigen presenting cells have been shown to inhibit autoreactive T cells and induce peripheral tolerance, whereas those on parenchymal cells prevent tissue destruction by suppressing effector T cells to maintain tolerance. The inhibitory role of PD-1 is highlighted by the phenotype of PD-1 deficient mice, which develop various autoimmune diseases, depending on the genetic background. The PD-1/PD-L pathway is frequently exploited as a target for immune evasion by tumor cells and by a wide range of pathogens For example, the PD1:PD-L pathway can be exploited (e.g., hyperactivated) by tumors and viruses (e.g., viruses that cause chronic infection), which can express PD-L proteins to stimulate PD-1 (e.g., on T-cells), thereby reducing immune cell (e.g., T-cell) responses and evading eradication by the immune system.

The present disclosure provides high affinity PD-1 mimic polypeptides that mimic PD-1 by specifically binding to PD-L1, blocking/reducing the interaction of PD-L1 with PD-1 on the surface of cells (e.g., immune cells such as T cells), and thereby blocking/reducing PD-L1 stimulated PD-1 activity. Also disclosed are methods of using high affinity PD-1 mimic polypeptides to reduce PD-1 activity.

SUMMARY

High affinity PD-1 variant (mimic) polypeptides are provided. The polypeptides are sequence variants of a wild type PD-1 protein (e.g., the wild type human PD-1 protein), and have utility for in vivo and in vitro methods that block the interaction between a wild type PD-1 protein and its ligand PD-L (PD-L1 and/or PD-L2). A high affinity PD-1 mimic polypeptide includes at least one amino acid change relative to a wild-type PD-1 protein, has an increased affinity for PD-L (PD-L1 and/or PD-L2) relative to the wild-type PD-1 protein, and lacks a transmembrane domain of a wild type PD-1 protein. The amino acid changes that provide for increased affinity can be localized to amino acid positions of contact between PD-1 and PD-L, and/or can be located in the immunoglobulin domain of PD-1 protein from which it was derived.

A high affinity PD-1 mimic polypeptide can be post-translationally modified, for example by glycosylation, PEGylation, etc. A high affinity PD-1 mimic polypeptide can be a fusion protein (i.e., can include additional amino acid sequences), for example a fusion with antibody Fc sequences and/or a variable region of an antibody that provides for specific binding to an antigen of interest; and the like. High affinity PD-1 mimic polypeptides may be monomeric or multimeric, i.e. dimer, trimer, tetramer, etc.

In some embodiments, methods are provided for modulating the activity of immune cells (T cells, NK cells, etc.) in a mammal by administering a therapeutic dose of a pharmaceutical composition comprising a high affinity PD-1 mimic polypeptide, which blocks the physiological binding interaction between PD-1 and its ligand PD-L1 and/or PD-L2.

The disclosure also includes pharmaceutical formulations having a high affinity PD-1 mimic polypeptide in combination with a pharmaceutically acceptable excipient. Such formulations may be provided as a unit dose, e.g., a dose effective to block the interaction of PD-1 on a first cell with PD-L (PD-L1 and/or PD-L2) on a second cell within an individual. Pharmaceutical formulations also include lyophilized or other preparations of the high affinity PD-1 mimic polypeptides, which may be reconstituted for use.

In some embodiments, methods are provided to stimulate an immune response towards target cells, e.g., targeting the destruction of living cancer cells by the immune system. In such methods, a cell expressing PD-L1 is contacted with a high affinity PD-1 mimic polypeptide in a dose effective to block the interaction between endogenous PD-1 (e.g., on a first cell) and PD-L (PD-L1 and/or PD-L2, e.g., on a second cell). Blocking this interaction allows the immune-based destruction of target cells that are not destroyed in the absence of the high affinity PD-1 mimic polypeptide. The contacting may be performed in vivo, e.g., for therapeutic purposes, and in vitro, e.g., for screening assays and the like. The high affinity PD-1 mimic polypeptide for these purposes may be multimeric; or monomeric. Monomeric reagents find particular use for administration in combination with an antibody that selectively binds to the targeted cell.

Inflicted individuals that can be treated with a high affinity PD-1 mimic polypeptide include individuals that have cancer, individuals that harbor an infection (e.g., a chronic infection, a viral infection, etc.), individuals that have an immunological disorder (e.g., a disorder associated with immunosuppression), individuals that have an inflammatory disorder, and/or individuals that have other hyper-proliferative conditions, for example sclerosis, fibrosis, and the like, etc. In some cases, cancer cells, e.g., tumor cells, are targeted for elimination by contacting the cells of the immune system with a dose of a high affinity PD-1 mimic polypeptide that is effective to block, or mask the interaction of PD-1 with PD-L, allowing for increased stimulation of the immune system. In some cases, the targeted cell (e.g., an inflicted cell such as a cancer cell, a tumor cell, an infected cell, etc.) expresses PD-L1 and/or PD-L2, and a high affinity PD-1 mimic polypeptide blocks the interaction of PD-L on the targeted cell with PD-1 on an immune cell (e.g., a T cell, an NK cell, etc.), which can block the ability of the targeted cell to suppress an immune response against the targeted cell.

Administration of an effective dose of high affinity PD-1 mimic polypeptide to a patient prevents interaction between PD-1 and PD-L1, which can increase the clearance of tumor cells and/or infected cells (e.g., chronically infected cells). In some cases, the high affinity PD-1 mimic polypeptide can be combined with monoclonal antibodies directed against one or more tumor cell markers, which combination therapy can be synergistic in enhancing elimination of cancer cells as compared to the administration of either agent as a single entity. In other embodiments the high affinity PD-1 mimic polypeptide comprises a detectable label. Such a labeled reagent can be used for imaging purposes in vitro or in vivo, e.g., in the imaging of a tumor. In some cases, a high affinity PD-1 mimic polypeptide can be used as a diagnostic tool for the detection of PD-L (e.g, cells expressing PD-L1), and can be used as a companion diagnostic to assess whether a particular treatment regimen has been successful.

Provided are high affinity PD-1 mimic polypeptides. In some cases, a high affinity PD-1 mimic polypeptide is a variant of a wild-type PD-1 sequence, but lacks the PD-1 transmembrane domain, and comprises one or more amino acid changes relative to a corresponding sequence of the wild type PD-1 polypeptide, where the one or more amino acid changes increases the affinity of the polypeptide for PD-L1 as compared to the affinity for PD-L1 of the corresponding wild type PD-1 polypeptide. In some cases, the PD-1 mimic polypeptide has a $K_d$ of $1 \times 10^{-7}$ M or less for PD-L1. In some cases, the affinity for PD-L1 of the high affinity PD-1 mimic polypeptide is 5-fold or more greater than the affinity for PD-L1 of said PD-1 mimic polypeptide that does not have an amino acid change relative to a corresponding sequence of a wild type PD-1 polypeptide. In some cases, the high affinity PD-1 mimic polypeptide has a decreased affinity for PD-L2 as compared to the affinity for PD-L2 of said PD-1 mimic polypeptide that does not have an amino acid change relative to a corresponding sequence of a wild type PD-1 polypeptide. In some cases, the one or more amino acid changes is located at an amino acid position of PD-1 that contacts PD-L1. In some cases, the one or more amino acid changes is located at an amino acid position, relative to the protein fragment set forth in SEQ ID NO: 2, selected from: V39, N41, Y43, M45, S48, N49, Q50, T51, D52, K53, A56, Q63, G65, Q66, L97, S102, L103, A104, P105, K106, and A107; or the corresponding amino acid position relative to another wild type PD-1 protein. In some cases, the one or more amino acid changes is located at an amino acid position, relative to the protein fragment set forth in SEQ ID NO: 2, selected from: V39, L40, N41, Y43, R44, M45, S48, N49, Q50, T51, D52, K53, A56, Q63, G65, Q66, V72, H82, M83, R90, Y96, L97, A100, S102, L103, A104, P105, K106, and A107; or the corresponding amino acid position relative to another wild type PD-1 protein. In some cases, the one or more amino acid changes is 5 or more amino acid changes.

Also provided are high affinity PD-1 mimic polypeptides comprising one or more amino acid changes to the PD-1 protein fragment set forth in SEQ ID NO: 2, selected from: (1) V39I or V39R; (2) L40V or L40I; (3) N41I or N41V; (4) Y43F or Y43H; (5) R44Y or R44L; (6) M45Q, M45E, M45L, or M45D; (7) S48D, S48L, S48N, S48G, or S48V; (8) N49C, N49G, N49Y, or N49S; (9) Q50K, Q50E, or Q50H; (10) T51V, T51L, or T51A; (11) D52F, D52R, D52Y, or D52V; (12) K53T or K53L; (13) A56S or A56L; (14) Q63T, Q63I, Q63E, Q63L, or Q63P; (15) G65N, G65R, G65I, G65L, G65F, or G65V; (16) Q66P; (17) V72I; (18) H82Q; (19) M83L or M83F; (20) R90K; (21) Y96F; (22) L97Y, L97V, or L97I; (23) A100I or A100V; (24) S102T or S102A; (25) L103I, L103Y, or L103F; (26) A104S, A104H, or A104D; (27) P105A; (28) K106G, K106E, K106I, K106V, K106R, or K106T; and (29) A107P, A107I, or A107V; or a change that results in the same amino acid at the corresponding position relative to another wild type PD-1 protein.

Also provided are high affinity PD-1 mimic polypeptides comprising amino acid changes located at amino acid positions, relative to the protein fragment set forth in SEQ ID NO: 2, selected from: (a) V39, N41, Y43, M45, S48, N49, Q50, K53, A56, Q63, G65, Q66, L97, S102, L103, A104, K106, and A107, or the corresponding amino acid positions relative to another wild type PD-1 protein; (b) V39, N41, Y43, M45, S48, Q50, T51, D52F, K53, A56, Q63, G65, Q66, L97, S102, L103, A104, K106, and A107, or the corresponding amino acid positions relative to another wild type PD-1 protein; (c) V39, L40, N41, Y43, R44, M45, N49, K53, M83, L97, A100, and A107, or the corresponding amino acid positions relative to another wild type PD-1 protein; (d) V39, L40, N41, Y43, M45, N49, K53, Q66P, M83, L97, and A107, or the corresponding amino acid positions relative to another wild type PD-1 protein; (e) V39, L40, N41, Y43, M45, N49, K53, Q66P, H82, M83, L97, A100, and A107, or the corresponding amino acid positions relative to another wild type PD-1 protein; (f) V39, L40, N41, Y43, M45, N49, K53, M83, L97, A100, and A107, or the corresponding amino acid positions relative to another wild type PD-1 protein; (g) V39, L40, N41, Y43, R44, M45, N49, K53, L97, A100, and A107, or the corresponding amino acid positions relative to another wild type PD-1 protein; and (h) V39, L40, N41, Y43, M45, N49, K53, L97, A100, and A107, or the corresponding amino acid positions relative to another wild type PD-1 protein.

Also provided are high affinity PD-1 mimic polypeptides comprising amino acid changes, relative to the PD-1 protein fragment set forth in SEQ ID NO: 2, selected from: (a) {V39H or V39R}, {N41I or N41V}, {Y43F or Y43H}, {M45Q, M45E, M45L, or M45D}, {S48D, S48L, S48N, S48G, or S48V}, {N49C, N49G, N49Y, or N49S}, {Q50K, Q50E, or Q50H}, {K53T or K53L}, {A56S or A56L}, {Q63T, Q63I, Q63E, Q63L, or Q63P}, {G65N, G65R, G65I, G65L, G65F, or G65V}, {Q66P}, {L97Y, L97V, or L97I}, {S102T or S102A}, {L103I, L103Y, or L103F}, {A104S, A104H, or A104D}, {K106G, K106E, K106I, K106V, K106R, or K106T}, and {A107P, A107I, or A107V}; or changes that result in the same amino acids at the corresponding positions relative to another wild type PD-1 protein; (b){V39H or V39R}, {N41I or N41V}, {Y43F or Y43H}, {M45Q, M45E, M45L, or M45D}, {S48D, S48L, S48N, S48G, or S48V}, {Q50K, Q50E, or Q50H}, {T51V, T51L, or T51A}, {D52F, D52R, D52Y, or D52V}, {K53T or K53L}, {A56S or A56L}, {Q63T, Q63I, Q63E, Q63L, or Q63P}, {G65N, G65R, G65I, G65L, G65F, or G65V}, {Q66P}, {L97Y, L97V, or L97I}, {S102T or S102A}, {L103I, L103Y, or L103F}, {A104S, A104H, or A104D}, {K106G, K106E, K106I, K106V, K106R, or K106T}, and {A107P, A107I, or A107V}; or changes that result in the same amino acids at the corresponding positions relative to another wild type PD-1 protein; (c){V39H or V39R}, {L40V or L40I}, {N41I or N41V}, {Y43F or Y43H}, {R44Y or R44L}, {M45Q, M45E, M45L, or M45D}, {N49C, N49G, N49Y, or N49S}, {K53T or K53L}, {M83L or M83F}, {L97Y, L97V, or L97I}, {A100I or A100V}, and {A107P, A107I, or A107V}; or changes that result in the same amino acids at the corresponding positions relative to another wild type PD-1 protein; (d) {V39H or V39R}, {L40V or L40I}, {N41I or N41V}, {Y43F or Y43H}, {M45Q, M45E, M45L, or M45D}, {N49C, N49G, N49Y, or N49S}, {K53T or K53L}, {Q66P}, {M83L or M83F}, {L97Y, L97V, or L97I}, and {A107P, A107I, or A107V}; or changes that result in the same amino acids at the corresponding positions relative to another wild type PD-1 protein; (e){V39H or V39R}, {L40V or L40I}, {N41I or N41V}, {Y43F or Y43H}, {M45Q, M45E, M45L, or M45D}, {N49C, N49G, N49Y, or N49S}, {K53T or K53L}, {Q66P}, {H82Q}, {M83L or M83F}, {L97Y, L97V, or L97I}, {A100I or A100V}, and {A107P, A107I, or A107V}; or changes that result in the same amino acids at the corresponding positions relative to another wild type PD-1 protein; (f) {V39H or V39R}, {L40V or L40I}, {N41I or N41V}, {Y43F or Y43H}, {M45Q, M45E, M45L, or M45D}, {N49C, N49G, N49Y, or N49S}, {K53T or K53L}, {M83L or M83F}, {L97Y, L97V, or L97I}, {A100I or A100V}, and {A107P, A107I, or A107V}; or changes that result in the same amino acids at the corresponding positions relative to another wild type PD-1 protein; (g) {V39H or V39R}, {L40V or L40I}, {N41I or N41V}, {Y43F or Y43H}, {R44Y or R44L}, {M45Q, M45E, M45L, or M45D}, {N49C, N49G, N49Y, or N49S}, {K53T or K53L}, {L97Y, L97V, or L97I}, {A100I or A100V}, and {A107P, A107I, or A107V}; or changes that result in the same amino acids at the corresponding positions relative to another wild type PD-1 protein; and (h) {V39H or V39R}, {L40V or L40I}, {N41I or N41V}, {Y43F or Y43H}, {M45Q, M45E, M45L, or M45D}, {N49C, N49G, N49Y, or N49S}, {K53T or K53L}, {L97Y, L97V, or L97I}, {A100I or A100V}, and {A107P, A107I, or A107V}; or changes that result in the same amino acids at the corresponding positions relative to another wild type PD-1 protein.

Also provided are high affinity PD-1 mimic polypeptides comprising the amino acid changes, relative to the PD-1 protein fragment set forth in SEQ ID NO: 2, selected from: (a) V39R, N41V, Y43H, M45E, S48G, N49Y, Q50E, K53T, A56S, Q63T, G65L, Q66P, L97V, S102A, L103F, A104H, K106V, and A107I; or changes that result in the same amino acids at the corresponding positions relative to another wild type PD-1 protein; (b) V39R, N41V, Y43H, M45E, S48N, Q50H, T51A, D52Y, K53T, A56L, Q63L, G65F, Q66P, L97I, S102T, L103F, A104D, K106R, and A107I; or changes that result in the same amino acids at the corresponding positions relative to another wild type PD-1 protein; (c) V39H, L40V, N41V, Y43H, R44Y, M45E, N49G, K53T, M83L, L97V, A100I, and A107I; or changes that result in the same amino acids at the corresponding positions relative to another wild type PD-1 protein; (d) V39H, L40V, N41V, Y43H, M45E, N49G, K53T, Q66P, M83L, L97V, and A107I; or changes that result in the same amino acids at the corresponding positions relative to another wild type PD-1 protein; (e) V39H, L40V, N41V, Y43H, M45E, N49S, K53T, Q66P, H82Q, M83L, L97V, A100V, and A107I; or changes that result in the same amino acids at the corresponding positions relative to another wild type PD-1 protein; (f) V39H, L40I, N41I, Y43H, M45E, N49G, K53T, M83L, L97V, A100V, and A107I; or changes that result in the same amino acids at the corresponding positions relative to another wild type PD-1 protein; (g) V39H, L40V, N41I, Y43H, R44L, M45E, N49G, K53T, L97V, A100V, and A107I; or changes that result in the same amino acids at the corresponding positions relative to another wild type PD-1 protein; (h) V39H, L40V, N41I, Y43H, M45E, N49G, K53T, L97V, A100V, and A107I; or changes that result in the same amino acids at the corresponding positions relative to another wild type PD-1 protein; and (i) V39H, L40V, N41V, Y43H, M45E, N49G, K53T, L97V, A100V, and A107I or changes that result in the same amino acids at the corresponding positions relative to another wild type PD-1 protein.

In some cases, the high affinity PD-1 mimic polypeptide includes (e.g., is fused to) a fusion partner. In some cases, the fusion partner is a fragment of a human immunoglobulin polypeptide sequence (e.g., a fragment is selected from: (a) a CH3 domain; and (b) part or whole of an Fc region). In some cases the fusion partner is selected from: a multimerization domain; a cytokine; an attenuated cytokine; a 41 BB-agonist; CD40-agonist; an inhibitor of BTLA and/or CD160; and an inhibitor of TIM3 and/or CEACAM1.

In some cases, the high affinity PD-1 mimic polypeptide is multimeric (e.g., dimeric). In some such cases, the high affinity PD-1 mimic polypeptide includes (e.g., is fused to) a fusion partner and the fusion partner includes a multimerization (e.g., a dimerization) domain. For example, in some cases, the fusion partner is a CH3 domain (from a immunoglobulin polypeptide sequence, e.g., a human immunoglobulin polypeptide sequence).

In some cases, a subject high affinity PD-1 mimic polypeptide includes one or more mutations corresponding to R87C, N91C, and/or R122C relative to the PD-1 protein fragment set forth in SEQ ID NO: 2. In some cases, a subject high affinity PD-1 mimic polypeptide includes the amino acid sequence set forth in any of SEQ ID NOs: 3-25 and 39-46. In some cases, the high affinity PD-1 mimic polypeptide includes a detectable label (e.g., a positron-emission tomography (PET) imaging label). In some cases, a subject high affinity PD-1 mimic polypeptide includes one or more mutations corresponding to R87C, N91C, and/or R122C relative to the PD-1 protein fragment set forth in SEQ ID NO: 2, and also includes a detectable label (e.g., a positron-emission tomography (PET) imaging label).

Also provided is a pharmaceutical formulation comprising a subject high affinity PD-1 mimic polypeptide.

Also provided are nucleic acids. A subject nucleic acid includes a nucleotide sequence that encodes a high affinity PD-1 mimic polypeptide. In some cases, the nucleic acid further includes (i) a nucleotide sequence encoding a TCR (e.g., nucleotide sequences encoding a TCR alpha polypeptide and a TCR beta polypeptide of a TCR); and/or (ii) a nucleotide sequence encoding a chimeric antigen receptor (CAR). In some cases, the nucleic acid is an expression vector (e.g., a linear vector, a circular vector, a plasmid, a viral vector, etc.).

Also provided are cells that include such a nucleic acid (e.g., human cell, primate cell, mouse cell, mammalian cell)(e.g., an immune cell, a leukocyte, a T cell, a CD8 T cell, a CD4 T cell, a memory/effector T cell, a B cell, an antigen presenting cell (APC), a dendritic cell, a macrophage, a monocyte, an NK cell, a stem cell, a hematopoietic stem cell, a pluripotent stem cell, a multipotent stem cell, a tissue restricted stem cell, etc). In some cases, the cell is an immune cell. In some cases, the cell is a stem or progenitor cell. In some cases the cell is a hematopoietic stem cell. In some cases, the cell is a T cell (e.g., a T cell with an engineered T cell receptor (TCR), e.g., a chimeric antigen receptor (CAR) T cell).

Also provided are methods of imaging. In some cases, the method includes contacting cells expressing PD-L1 (e.g., in vitro, ex vivo, in vivo) with a subject high affinity PD-1 mimic polypeptide. In some cases, said contacting comprises administering the high affinity PD-1 mimic polypeptide to an individual. In some cases, the method is a method of diagnosing and/or prognosing cancer in an individual. Thus, in some cases, the imaging is used for diagnosing and/or prognosing cancer in an individual.

Also provided are methods of inhibiting the interaction of PD-1 on a first cell with PD-L1 and/or PD-L2 on a second cell. In some cases, the method includes contacting the second cell with a high affinity PD-1 mimic polypeptide. In some cases, the second cell is a cancer cell or a chronically infected cell. In some cases, the contacting is in vitro. In some cases, the contacting is ex vivo (e.g., one or more cells can be autologous to an individual into whom one or more cells will be introduced). In some cases, the contacting is in vivo. In some cases, the method includes contacting the second cell with an agent selected from: an immune stimulant, an agent to treat chronic infection, a cytotoxic agent, a chemotherapeutic agent, a cell-specific antibody, an antibody selective for a tumor cell marker, and a T cell with an engineered T cell receptor (TCR). In some cases, the method includes contacting the second cell with a tumor specific antibody.

Also provided are methods of treating an individual having cancer, having a chronic infection, or having an immunological disorder associated with immunosuppression. For example, methods can include administering to the individual (e.g., in an amount effective for reducing the binding of PD-1 on a first cell with PD-L1 on a second cell) a subject high affinity PD-1 mimic polypeptide. In some cases, the administering includes introducing a nucleic acid encoding the PD-1 mimic polypeptide into a third cell. In some cases, the third cell is in vivo. In some cases, the nucleic acid encoding the PD-1 mimic polypeptide is introduced into the third cell in vitro or ex vivo, and the third cell is then introduced into the individual. In some cases, the third cell is an immune cell. In some cases, the immune cell is a T cell with an engineered T cell receptor (TCR). In some cases, the engineered TCR is a chimeric antigen receptor (CAR). In some cases, the individual has an advanced tumor. In some cases, the method includes administering to the individual an agent selected from: an immune stimulant, an agent to treat chronic infection, a cytotoxic agent, a chemotherapeutic agent, a cell-specific antibody, an antibody selective for a tumor cell marker, and a T cell with an engineered T cell receptor (TCR).

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

(FIG. 1A) Schematic illustrating PD-L1 on the surface of a tumor cell specifically binding to PD-1 on the surface of a T cell to inhibit activation of the T cell, thereby allowing the tumor cell to evade destruction by the immune system. (FIG. 1B) Schematic illustrating a subject high affinity PD-1 mimic polypeptide specifically binding to PD-L1 on the surface of a cancer cell, thereby reducing the ability of the cancer cell to inhibit T cell activation, which in turn reduces the cancer cell's ability to evade the immune response.

FIG. 2A-2B. (FIG. 2A) Structural representation of the interaction of PD-1 (upper right) with PD-L1 (lower left). Residues of PD-1 located at the contact site with PD-L1 are represented as spheres. (FIG. 2B) A PD-1 mimic polypeptide (comprising wild type amino acid residues) was mutagenized at the residues that contact PD-L1 to generate a first generation library (Generation 1), which was displayed on yeast. Selections based on binding were then performed using biotinylated human PD-L1 (100 nM). A second generation library (Generation 2) that focused on converging positions was created to screen for PD-1 mimic polypeptides having even greater affinity for PD-L1 (using 1 nM biotinylated human PD-L1).

FIG. 3. The table reflects the sequences of the engineered variants (subject high affinity PD-1 mimic polypeptides). "G1" variants are from Generation 1 while "G2" variants are from Generation 2 (see FIG. 2A-2B). Each numbered column represents the amino acid position for each shown residue relative to the PD-1 polypeptide set forth SEQ ID NO: 2 (The polypeptide of SEQ ID NO: 2 is a PD-1 mimic polypeptide that includes a wild type PD-1 sequence, but lacks a transmembrane domain and lacks the first 25 amino acids of wild type PD-1). Divergence from the wild-type amino acid residue is indicated with the single-letter code for the resulting mutation for each variant. The measured Surface Plasmon Resonance (SPR) affinity for PD-L1 is indicated (when measured) at the right. HAC: High Affinity Consensus.

(FIG. 5A) human PD-L1, (FIG. 5B) human PD-L2, or (FIG. 5C) mouse PD-L1, were stained with labeled native PD-1 mimic polypeptide streptavidin tetramers (a control PD-1 mimic polypeptide having wild-type human PD-1 sequences and conjugated to Alexa647). The binding of the labeled native PD-1 mimic polypeptide to PD-L1 was competed with variable concentrations of unlabeled high affinity PD-1 mimic polypeptides (concentrations indicated on the x-axis). (FIG. 5A) An unlabeled native PD-1 mimic polypeptide (having wild-type human PD-1 sequences) antagonized the PD-1/PD-L1 interaction. High-affinity PD-1 mimic polypeptides (HAC-V PD-1, G2 4-1, and G2 4-2) potently antagonized the PD-1/PD-L1 interaction. (FIG. 5B) The high-affinity PD-1 mimic polypeptides did not demonstrate any antagonism of the PD-1:PD-L2 interaction, while a native PD-1 mimic polypeptide did antagonize the PD-1:PD-L2 interaction. (FIG. 5C) Subject high-affinity PD-1 mimic polypeptides were also able to compete for binding to mouse PD-L1.

(FIG. 6A) Expression of PD-L1 on human melanoma cell line SKMEL28. PD-L1 expression was induced on SKMEL28 cells by stimulation with 2000 U/mL human interferon-gamma (IFNγ) for 24 hours. PD-L1 staining was assessed by flow cytometry under induced (plus IFNγ) versus non-induced (minus IFNγ) conditions. (FIG. 6B) IFNγ-stimulated SKMEL28 cells were stained with labeled native PD-1 mimic polypeptide streptavidin tetramers (a control PD-1 mimic polypeptide having wild-type human PD-1 sequences and conjugated to Alexa647) with variable concentrations of unlabeled high-affinity PD-1 mimic polypeptides (concentrations indicated on the x-axis). An unlabeled native PD-1 mimic polypeptide (having wild-type human PD-1 sequences) was ineffective at preventing binding of the labeled native PD-1 mimic polypeptide to the SKMEL28 cells (IC50=8.2 µM). By contrast, HAC-V (a high-affinity PD-1 mimic polypeptide) potently inhibited binding of the labeled native PD-1 mimic polypeptide (IC50 of 210 pM). HAC-MBH (HAC-V, a high-affinity PD-1 mimic polypeptide, fused to the CH3 domain of human IgG1) inhibited binding of the labeled native PD-1 mimic polypeptide with additionally enhanced potency (IC50 of 55 pM).

FIG. 7A-7C. Directed evolution of high-affinity PD-1 with yeast surface display. (FIG. 7A) Model of hPD-1 complexed with hPD-L1 constructed by structural alignment of mPD-1:hPD-L1 complex (PDB ID 3BIK) with hPD-1 (PDB ID 3RRQ). Randomized residues of PD-1 are depicted as "blue spheres" for PD-L1 contact residues and "red spheres" for core residues. (FIG. 7B) Histogram overlays assessing yeast hPD-L1 staining at each round of selection. For the first generation selections (left panel), all rounds were stained with 100 nM biotinylated hPD-L1. For the second generation selections (right panel), yeast were stained with 1 nM biotinylated hPD-L1. (FIG. 7C) Summary of sequences and hPD-L1 affinities for selected PD-1 variants. From top ("hPD-1") to bottom ("Consensus 2 (HAC-V)"), the sequences correspond to SEQ ID NOs: 2, 10-15, 9, 5, 8, 16-22, 6, 23, 7, and 3-4. The position of each mutated position and the corresponding residue in wild-type PD-1 is indicated at the top of the table. Italic font indicates mutations that occurred at non-randomized sites. Residues indicated as 39, 41, 43, 45, 49, 53, 97, and 107 are PD-L1 contact positions that converged in the HAC consensus sequence ("Contact consensus sites"), while residues indicated as 40 and 100 are converging core positions ("Core consensus sites"). The affinities for some sequences to hPD-L1 were determined (as indicated, far right column) by surface plasmon resonance (SPR).

FIG. 8A-8B. HAC-PD-1 binds and antagonizes human and murine PD-L1, but not PD-L2. (FIG. 8A) Representative surface plasmon resonance (SPR) sensorgrams of wild-type PD-1 (left) and HAC-V PD-1 (right) binding to immobilized hPD-L1. (FIG. 8B) Competition binding assays of wild-type hPD-1, HAC-V PD-1, or HAC 'microbody' (HACmb) on human SK-MEL-28 cells (left), mouse B16-F10 cells, or yeast displaying hPD-L2. 100 nM hPD-1/streptavidin-AlexaFluor 647 tetramer was used as the probe ligand. Error bars represent s.e.m.

FIG. 9A-9D. HAC-PD-1 yields enhanced tumor penetration and does not deplete peripheral T cells. (FIG. 9A) Representative fluorescence microscopy images of sectioned CT26 tumors deficient in PD-L1 (top) or transgenic for hPD-L1 (bottom) four hours post intraperitoneal injection of anti-hPD-L1-AlexaFluor488 (green when presented in color) and HAC-AlexaFluor 594 (red when presented in color). Nuclei (blue when presented in color) were labeled with DAPI. Scale bars represent 500 µm. (FIG. 9B) Representative flow cytometry of dissociated tumors from FIG. 9A showing relative HAC-AlexaFluor 594 staining versus anti-hPD-L1-AlexaFluor 488 staining. Percentages are given in each positive quadrant. (FIG. 9C) Summary of flow cytometry studies from 4 PD-L1 deficient tumors and 4 hPD-L1 transgenic tumors. n.s., not significant. ***, $p<0.0001$, Two-way ANOVA. Error bars represent s.e.m. (FIG. 9D) Relative abundance of peripheral CD8+ T cells (left-most panel), peripheral CD4+ T cells (second from left panel), lymph node CD8+ T cells (second from right panel), and lymph node CD4+ T cells (right-most panel) after 3 days of administration of vehicle (PBS), anti-mPD-L1, or HACmb to mice engrafted with CT26 tumors. ns, not significant *, $p<0.05$; ***, $p<0.001$, One-way ANOVA.

FIG. 10A-10D. Anti-tumor efficacy of HACmb and anti-PD-L1 antibodies in small and large CT26 syngeneic tumor models. (FIG. 10A) Schematic illustrating experimental design of small tumor experiment. Treatment was initiated for all cohorts 7 days after engraftment of tumors. Mice were injected with daily doses of vehicle (PBS), 250 µg anti-PD-L1 (clone 10F.9G2), or 250 µg of HACmb for 14 days. (FIG. 10B) Relative growth rates of engrafted tumors, calculated as fold-change from displayed for individual tumors (left three panels) or as summary data (right-most panel) over the course of the treatment period. Error bars represent s.e.m. n.s., not significant. *, $p<0.0001$. (FIG. 10C) Schematic illustrating experimental design of large tumor experiment. Mice were engrafted with CT26 tumors, and monitored daily. When an individual tumor exceeded 150 mm$^3$, the mouse was randomized to a treatment cohort. Tumors were measured daily, and received daily treatment with vehicle (PBS), 250 µg anti-PD-L1 (clone 10F.9G2), or 250 µg of HACmb for 14 days. Anti-CTLA4 (clone 9D9) was administered as a single dose of 250 µg. (FIG. 10D) Summary data for average tumor growth over the 14-day period of treatment. Error bars represent s.e.m. The PBS-treated tumor growth (black) and anti-CTLA4-treated tumor growth (purple) on the left and right panels are identical; they are represented twice for clarity. n.s., not significant. *, $p<0.001$, Two-way ANOVA. Complete statistical analysis at day 14 post-treatment is shown in Table 4.

(FIG. 11A) PET-CT images one hour post injection of $^{64}$Cu-DOTA-HAC (230 µCi/25 µg/200 µl) in NSG mice bearing subcutaneous hPD-L1(+) or hPD-L1(−) CT26 tumors. Blocking was performed with 500 µg/200 µl of unlabeled HAC-PD1, 2 hours prior to PET tracer. T-tumor, L-liver, K-kidneys, B-bladder, SG-salivary glands. (FIG. 11B) Quantification of tumor uptake one hour post-injection by region of interest (ROI) analysis, indicated as a percent of injected dose per gram of tissue (% ID/g). *, $p<0.05$.

FIG. 12A-12B. Design of the "First Generation" PD-1 library. (FIG. 12A) Table of randomized positions of hPD-1 (as set forth in SEQ ID NO: 2) are given in the table, with the corresponding degenerate codon and the potential amino acids possible at each site. (FIG. 12B) Structural depiction of the "First Generation" library; hPD-1 is in green (when presented in color) with randomized side chains indicated as space-filling spheres.

(FIG. 13A) Table of randomized positions of hPD-1 (as set forth in SEQ ID NO: 2) are given in the table, with the corresponding degenerate codon and the potential amino acids possible at each site. (FIG. 13B) Structural depiction of the "Second Generation" library; hPD-1 is in green (when presented in color) with randomized side chains indicated as space-filling spheres.

(FIG. 15A) FACS plot of CT26-Tg(hPD-L1)-Δ(mPDL1) either unstained, stained with AlexaFluor594-labeled HAC monomer, or AlexaFluor488-labeled anti-PD-L1 antibody (clone 29E.2A3, Biolegend). (FIG. 15B) Histological section taken from the same tumor as depicted in FIG. 9A, but from the center of the tumor rather than at the periphery. Image is from tumors dissected four hours after intraperitoneal injection of anti-hPD-L1-Alexa Fluor488 (green when presented in color) and HAC-Alexa Fluor 594 (red when presented in color). Nuclei (blue when presented in color) were labeled with DAPI. Scale bars represent 500 µm.

(FIG. 17A) Competition binding assays of wild-type hPD-1, HAC-V, or DOTA-HAC on human SK-MEL-28 cells. 100 nM hPD-1/streptavidin-Alexa Fluor 647 tetramer was used as the probe ligand. Error bars represent s.e.m. (FIG. 17B) Immunoreactivity of anti-hPD-L1 radiotracer. hPD-L1(+), hPD-L1(−) and hPD-L1(+) cells blocked with excess HAC-N91C prior to the addition of tracer were tested for binding specificity. 5 nM $^{64}$Cu-DOTA-HAC readily bound to hPD-L1(+) cells (80.5%±1.9%), while control hPD-L1(−) cells only exhibited minimal immunoreactivity (8.3%±0.5%). Binding was blocked in hPD-L1(+) cells by the addition of HAC-N91C to 1 µM (8.9%±0.1%). n.s., not significant. ****, $p<0.0001$, Two-way ANOVA.

(FIG. 18A) Tumor uptake computed by region of interest (ROI) analysis over 24 hours. (FIG. 18B) Renal uptake in hPD-L1 (+) and (−) tumor bearing mice assessed by ROI analysis. (FIG. 18C) PET-CT image 24 hours post-injection of $^{64}$Cu-DOTA-HAC (230 µCi/25 µg/200 µl) in NSG mouse bearing dual subcutaneous hPD-L1(+) (dashed) and hPD-L1(−) (solid) CT26 tumors. (FIG. 18D) Tumor uptake computed by region of interest (ROI). (FIG. 18E) Renal clearance over 24 h. Uptake values given as percentage of injected dose per gram of tissue (% ID/g).

FIG. 19A-19B. 24 hour biodistribution of $^{64}$Cu-DOTA-HAC. (FIG. 19A) After completion of micro-PET/CT imaging, mice were euthanized and dissected for biodistribution. Uptake in the indicated organs and tissues are given as the percentage of injected dose per gram of tissue (% ID/g). (FIG. 19B) Relative amount of hPD-L1(+) tumor radiotracer uptake compared to blood and muscle.

FIG. 20A-20E. Schematic depiction of examples of viral vector constructs encoding a subject high affinity PD-1 mimic polypeptide as well as (i) a heterologous TCR (that binds to an antigen)(e.g., encodes the TCR-alpha and TCR-beta polypeptides) or (ii) a chimeric antigen receptor (CAR). FIG. 20A provides a legend for FIG. 20B-20E.

DETAILED DESCRIPTION

Figure 1A:
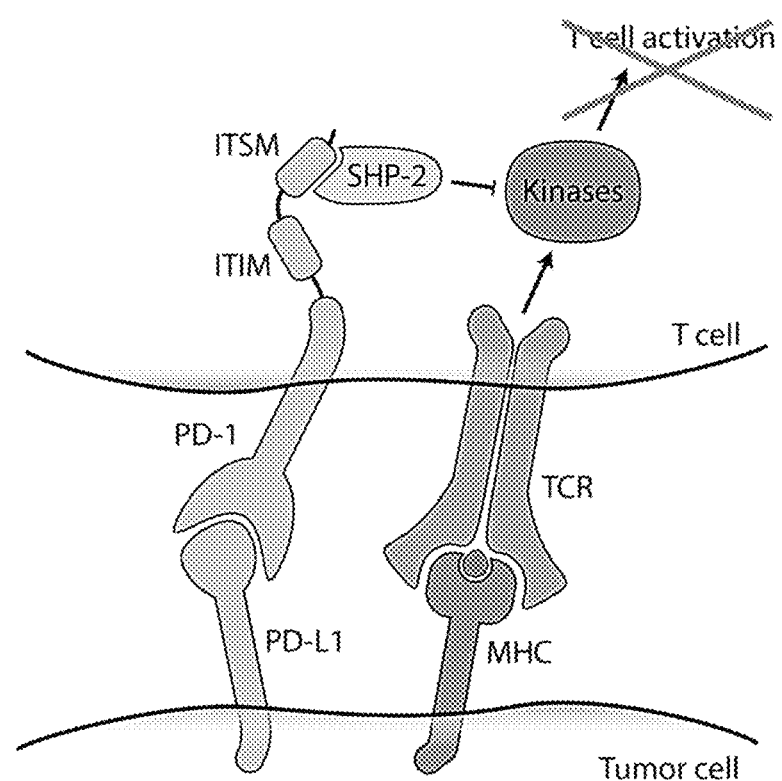
FIG. 1A-1B.

High affinity PD-1 mimic polypeptides, and methods of their use, are provided. The high affinity PD-1 mimic polypeptides are sequence variants of a wild type PD-1 protein (e.g., the wild type human PD-1 protein), and have utility for in vivo and in vitro methods that block the interaction between a wild type PD-1 protein and its ligand PD-L (PD-L1 and/or PD-L2). A high affinity PD-1 mimic polypeptide includes at least one amino acid change relative to a wild-type PD-1 protein, has an increased affinity for PD-L (PD-L1 and/or PD-L2) relative to the wild-type PD-1 protein, and lacks a transmembrane domain of a wild type PD-1 protein. The amino acid changes that provide for increased affinity can be localized to amino acid positions of contact between PD-1 and PD-L, and/or can be located in the immunoglobulin domain of PD-1 protein from which it was derived.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order that is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

In the description that follows, a number of terms conventionally used in the field are utilized. In order to provide a clear and consistent understanding of the specification and claims, and the scope to be given to such terms, the following definitions are provided.

The terms "inhibitors," "blocking agents" and "masking agents" of the interaction between PD-1 and its ligand PD-L1 refer to molecules that prevent the binding of PD-1 and PD-L1. For development purposes the binding may be performed under experimental conditions, e.g., using isolated proteins as binding partners, using portions of proteins as binding partners, using yeast display of proteins or portions of proteins as binding partners, and the like.

For physiologically relevant purposes the binding of PD-1 and PD-L1 is usually an event between two cells, where each cell expresses one of the binding partners. In some cases, PD-1 is expressed on the surface of immune cells (e.g., T cells), and PD-L1 is expressed on cells that could be targets for destruction by the immune system (e.g., tumor cells, cells harboring an infection such as a chronic infection, and the like). Inhibitors may be identified using in vitro and in vivo assays for receptor or ligand binding or signaling.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is human.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g., clone of a cancer cell. Many types of cancers are known to those of skill in the art, including solid tumors such as carcinomas, sarcomas, glioblastomas, melanomas, lymphomas, myelomas, etc., and circulating cancers such as leukemias.

As used herein "cancer" includes any form of cancer, including but not limited to solid tumor cancers (e.g., lung, prostate, breast, bladder, colon, ovarian, pancreas, kidney, liver, glioblastoma, medulloblastoma, leiomyosarcoma, head & neck squamous cell carcinomas, melanomas, neuroendocrine; etc.) and liquid cancers (e.g., hematological cancers); carcinomas; soft tissue tumors; sarcomas; teratomas; melanomas; leukemias; lymphomas; and brain cancers, including minimal residual disease, and including both primary and metastatic tumors. Any cancer is a suitable cancer to be treated by the subject methods and compositions. In some cases, the cancer cells express PD-L1. In some cases, the cancer cells do not express PD-L1 (e.g., in such cases, cells of the immune system of the individual being treated express PD-L1).

Carcinomas are malignancies that originate in the epithelial tissues. Epithelial cells cover the external surface of the body, line the internal cavities, and form the lining of glandular tissues. Examples of carcinomas include, but are not limited to: adenocarcinoma (cancer that begins in glandular (secretory) cells), e.g., cancers of the breast, pancreas, lung, prostate, and colon can be adenocarcinomas; adrenocortical carcinoma; hepatocellular carcinoma; renal cell carcinoma; ovarian carcinoma; carcinoma in situ; ductal carcinoma; carcinoma of the breast; basal cell carcinoma; squamous cell carcinoma; transitional cell carcinoma; colon carcinoma; nasopharyngeal carcinoma; multilocular cystic renal cell carcinoma; oat cell carcinoma; large cell lung carcinoma; small cell lung carcinoma; non-small cell lung carcinoma; and the like. Carcinomas may be found in prostrate, pancreas, colon, brain (usually as secondary metastases), lung, breast, skin, etc.

Soft tissue tumors are a highly diverse group of rare tumors that are derived from connective tissue. Examples of soft tissue tumors include, but are not limited to: alveolar soft part sarcoma; angiomatoid fibrous histiocytoma; chondromyoxid fibroma; skeletal chondrosarcoma; extraskeletal myxoid chondrosarcoma; clear cell sarcoma; desmoplastic small round-cell tumor; dermatofibrosarcoma protuberans; endometrial stromal tumor; Ewing's sarcoma; fibromatosis (Desmoid); fibrosarcoma, infantile; gastrointestinal stromal tumor; bone giant cell tumor; tenosynovial giant cell tumor; inflammatory myofibroblastic tumor; uterine leiomyoma; leiomyosarcoma; lipoblastoma; typical lipoma; spindle cell or pleomorphic lipoma; atypical lipoma; chondroid lipoma; well-differentiated liposarcoma; myxoid/round cell liposarcoma; pleomorphic liposarcoma; myxoid malignant fibrous histiocytoma; high-grade malignant fibrous histiocytoma; myxofibrosarcoma; malignant peripheral nerve sheath tumor; mesothelioma; neuroblastoma; osteochondroma;

osteosarcoma; primitive neuroectodermal tumor; alveolar rhabdomyosarcoma; embryonal rhabdomyosarcoma; benign or malignant schwannoma; synovial sarcoma; Evan's tumor; nodular fasciitis; desmoid-type fibromatosis; solitary fibrous tumor; dermatofibrosarcoma protuberans (DFSP); angiosarcoma; epithelioid hemangioendothelioma; tenosynovial giant cell tumor (TGCT); pigmented villonodular synovitis (PVNS); fibrous dysplasia; myxofibrosarcoma; fibrosarcoma; synovial sarcoma; malignant peripheral nerve sheath tumor; neurofibroma; and pleomorphic adenoma of soft tissue; and neoplasias derived from fibroblasts, myofibroblasts, histiocytes, vascular cells/endothelial cells and nerve sheath cells.

A sarcoma is a rare type of cancer that arises in cells of mesenchymal origin, e.g., in bone or in the soft tissues of the body, including cartilage, fat, muscle, blood vessels, fibrous tissue, or other connective or supportive tissue. Different types of sarcoma are based on where the cancer forms. For example, osteosarcoma forms in bone, liposarcoma forms in fat, and rhabdomyosarcoma forms in muscle. Examples of sarcomas include, but are not limited to: askin's tumor; sarcoma botryoides; chondrosarcoma; ewing's sarcoma; malignant hemangioendothelioma; malignant schwannoma; osteosarcoma; and soft tissue sarcomas (e.g., alveolar soft part sarcoma; angiosarcoma; cystosarcoma phyllodesdermatofibrosarcoma protuberans (DFSP); desmoid tumor; desmoplastic small round cell tumor; epithelioid sarcoma; extraskeletal chondrosarcoma; extraskeletal osteosarcoma; fibrosarcoma; gastrointestinal stromal tumor (GIST); hemangiopericytoma; hemangiosarcoma (more commonly referred to as "angiosarcoma"); kaposi's sarcoma; leiomyosarcoma; liposarcoma; lymphangiosarcoma; malignant peripheral nerve sheath tumor (MPNST); neurofibrosarcoma; synovial sarcoma; undifferentiated pleomorphic sarcoma, and the like).

A teratoma is a type of germ cell tumor that may contain several different types of tissue (e.g., can include tissues derived from any and/or all of the three germ layers: endoderm, mesoderm, and ectoderm), including for example, hair, muscle, and bone. Teratomas occur most often in the ovaries in women, the testicles in men, and the tailbone in children.

Melanoma is a form of cancer that begins in melanocytes (cells that make the pigment melanin). It may begin in a mole (skin melanoma), but can also begin in other pigmented tissues, such as in the eye or in the intestines.

Leukemias are cancers that start in blood-forming tissue, such as the bone marrow, and causes large numbers of abnormal blood cells to be produced and enter the bloodstream. For example, leukemias can originate in bone marrow-derived cells that normally mature in the bloodstream. Leukemias are named for how quickly the disease develops and progresses (e.g., acute versus chronic) and for the type of white blood cell that is affected (e.g., myeloid versus lymphoid). Myeloid leukemias are also called myelogenous or myeloblastic leukemias. Lymphoid leukemias are also called lymphoblastic or lymphocytic leukemia. Lymphoid leukemia cells may collect in the lymph nodes, which can become swollen. Examples of leukemias include, but are not limited to: Acute myeloid leukemia (AML), Acute lymphoblastic leukemia (ALL), Chronic myeloid leukemia (CML), and Chronic lymphocytic leukemia (CLL).

Lymphomas are cancers that begin in cells of the immune system. For example, lymphomas can originate in bone marrow-derived cells that normally mature in the lymphatic system. There are two basic categories of lymphomas. One kind is Hodgkin lymphoma (HL), which is marked by the presence of a type of cell called the Reed-Sternberg cell. There are currently 6 recognized types of HL. Examples of Hodgkin lymphomas include: nodular sclerosis classical Hodgkin lymphoma (CHL), mixed cellularity CHL, lymphocyte-depletion CHL, lymphocyte-rich CHL, and nodular lymphocyte predominant HL.

The other category of lymphoma is non-Hodgkin lymphomas (NHL), which includes a large, diverse group of cancers of immune system cells. Non-Hodgkin lymphomas can be further divided into cancers that have an indolent (slow-growing) course and those that have an aggressive (fast-growing) course. There are currently 61 recognized types of NHL. Examples of non-Hodgkin lymphomas include, but are not limited to: AIDS-related Lymphomas, anaplastic large-cell lymphoma, angioimmunoblastic lymphoma, blastic NK-cell lymphoma, Burkitt's lymphoma, Burkitt-like lymphoma (small non-cleaved cell lymphoma), chronic lymphocytic leukemia/small lymphocytic lymphoma, cutaneous T-Cell lymphoma, diffuse large B-Cell lymphoma, enteropathy-type T-Cell lymphoma, follicular lymphoma, hepatosplenic gamma-delta T-Cell lymphomas, T-Cell leukemias, lymphoblastic lymphoma, mantle cell lymphoma, marginal zone lymphoma, nasal T-Cell lymphoma, pediatric lymphoma, peripheral T-Cell lymphomas, primary central nervous system lymphoma, transformed lymphomas, treatment-related T-Cell lymphomas, and Waldenstrom's macroglobulinemia.

Brain cancers include any cancer of the brain tissues. Examples of brain cancers include, but are not limited to: gliomas (e.g., glioblastomas, astrocytomas, oligodendrogliomas, ependymomas, and the like), meningiomas, pituitary adenomas, vestibular schwannomas, primitive neuroectodermal tumors (medulloblastomas), etc.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of disease progression (e.g., cancer-attributable death or progression), including recurrence, metastatic spread of cancer, and drug resistance. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides). In some embodiments, the affinity of one molecule for another molecule to which it specifically binds is characterized by a $K_d$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_d$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member).

The terms "co-administration", "co-administer", and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

For example, "Concomitant administration" of a cancer therapeutic drug, therapeutic drug to treat an infection, or tumor-directed antibody, with a pharmaceutical composition of the present disclosure means administration with the high affinity PD-1 mimic polypeptide at such time that both the drug/antibody and the composition of the present disclosure will have a therapeutic effect. Such concomitant administration may involve concurrent (i.e. at the same time), prior, or subsequent administration of the drug/antibody with respect to the administration of a compound of the disclosure. A person of ordinary skill in the art would have no difficulty determining the appropriate timing, sequence and dosages of administration for particular drugs and compositions of the present disclosure.

In some embodiments, treatment is accomplished by administering a combination of a high affinity PD-1 mimic polypeptide of the disclosure with another agent (e.g., an immune stimulant, an agent to treat chronic infection, a cytotoxic agent, etc.). One exemplary class of cytotoxic agents are chemotherapeutic agents. Exemplary chemotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, duocarmycin, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol™), pilocarpine, prochloroperazine, rituximab, saproin, tamoxifen, taxol, topotecan hydrochloride, trastuzumab, vinblastine, vincristine and vinorelbine tartrate.

Other combination therapies include administration with cell-specific antibodies, for example antibodies selective for tumor cell markers, radiation, surgery, and/or hormone deprivation (Kwon et al., Proc. Natl. Acad. Sci U.S.A., 96: 15074-9, 1999). Angiogenesis inhibitors can also be combined with the methods of the disclosure. A number of antibodies are currently in clinical use for the treatment of cancer, and others are in varying stages of clinical development. For example, there are a number of antigens and corresponding monoclonal antibodies for the treatment of B cell malignancies. One target antigen is CD20. Rituximab is a chimeric unconjugated monoclonal antibody directed at the CD20 antigen. CD20 has an important functional role in B cell activation, proliferation, and differentiation. The CD52 antigen is targeted by the monoclonal antibody alemtuzumab, which is indicated for treatment of chronic lymphocytic leukemia. CD22 is targeted by a number of antibodies, and has recently demonstrated efficacy combined with toxin in chemotherapy-resistant hairy cell leukemia. Two new monoclonal antibodies targeting CD20, tositumomab and ibritumomab, have been submitted to the Food and Drug Administration (FDA). These antibodies are conjugated with radioisotopes. Alemtuzumab (Campath) is used in the treatment of chronic lymphocytic leukemia; Gemtuzumab (Mylotarg) finds use in the treatment of acute myelogenous leukemia; Ibritumomab (Zevalin) finds use in the treatment of non-Hodgkin's lymphoma; Panitumumab (Vectibix) finds use in the treatment of colon cancer.

Monoclonal antibodies, including humanized and chimeric variants, useful in the methods of the disclosure that have been used in solid tumors include, without limitation, edrecolomab and trastuzumab (herceptin). Edrecolomab targets the 17-1A antigen seen in colon and rectal cancer, and has been approved for use in Europe for these indications. Trastuzumab targets the HER-2/neu antigen. This antigen is seen on 25% to 35% of breast cancers. Cetuximab (Erbitux) is also of interest for use in the methods of the disclosure. The antibody binds to the EGF receptor (EGFR), and has been used in the treatment of solid tumors including colon cancer and squamous cell carcinoma of the head and neck (SCCHN).

As such, in some cases, a subject high affinity PD-1 mimic polypeptide is co-administered with an agent (e.g., an antibody) that specifically binds an antigen other than PD-L1 (e.g., CD19, CD20, CD22, CD24, CD25, CD30, CD33, CD38, CD44, CD52, CD56, CD70, CD96, CD97, CD99, CD123, CD279 (PD-1), EGFR, HER2, CD117, C-Met, PTHR2, HAVCR2 (TIM3), etc.) Examples of antibodies with CDRs that provide specific binding to a cancer cell marker (and therefore can be used in a combination therapy (co-administered with a subject high affinity PD-1 mimic polypeptide) include, but are not limited to: CETUXIMAB (binds EGFR), PANITUMUMAB (binds EGFR), RITUXIMAB (binds CD20), TRASTUZUMAB (binds HER2), PERTUZUMAB (binds HER2), ALEMTUZUMAB (binds CD52), and BRENTUXIMAB (binds CD30).

In some cases, a subject high affinity PD-1 mimic polypeptide is co-administered with a T cell with an engineered T cell receptor (TCR) (such a cell is also referred to herein as a "TCR-engineered T cell"). Non-limiting suitable examples of a TCR-engineered T cell are: (i) a T cell that includes a chimeric antigen receptor (CAR); and (ii) a T cell that includes a heterologous TCR that binds to an antigen such as a cancer antigen. (TCR-engineered T cells are described in more detail below in the section on introducing nucleic acids).

A subject high affinity PD-1 mimic polypeptide can be co-administered with any convenient immunomodulatory agent (e.g., an anti-CTLA4 antibody, an anti-PD-1 antibody, a CD40 agonist, a 4-1BB modulator (e.g., a 41BB-agonist), and the like). In some cases, a subject high affinity PD-1 mimic polypeptide is co-administered with an inhibitor of BTLA and/or CD160. In some cases, a subject high affinity PD-1 mimic polypeptide is co-administered with an inhibitor of TI M3 and/or CEACAM1.

As used herein, the phrase "disease-free survival," refers to the lack of such tumor recurrence and/or spread and the fate of a patient after diagnosis, with respect to the effects of the cancer on the life-span of the patient. The phrase "overall survival" refers to the fate of the patient after diagnosis, despite the possibility that the cause of death in a patient is not directly due to the effects of the cancer. The phrases, "likelihood of disease-free survival", "risk of recurrence" and variants thereof, refer to the probability of tumor recurrence or spread in a patient subsequent to diagnosis of cancer, wherein the probability is determined according to the process of the disclosure.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

The term "target cell" as used herein refers to a cell targeted for destruction by the immune system after administration of a subject high affinity PD-1 mimic polypeptide. In some cases, the target cell expresses a PD-L protein (e.g., PD-L1 and/or PD-L2). A subject high affinity PD-1 mimic polypeptide can bind to a target cell by virtue of binding to the PD-L protein expressed on the surface of the target cell. Thus, the term "target cell" can refer to a PD-L1-expressing cell because a subject high affinity PD-1 mimic polypeptide, by inhibiting the interaction between the PD-L1 expressing cell and the PD-1 expressing cell, facilitates decreased PD-1 signaling in the PD-1 expressing cell.

However, a target cell need not express PD-L1. In some cases a target cell (e.g., an infected cell, a cancer cell, etc.) does not express PD-L1. In some such cases, administration of a subject high affinity PD-1 mimic polypeptide leads to stimulation of the immune system, thereby leading to the destruction of the target cell.

In some cases, a target cell is an "inflicted" cell (e.g., a cell from an "inflicted" individual), where the term "inflicted" is used herein to refer to a subject with symptoms, an illness, or a disease that can be treated with a subject high affinity PD-1 mimic polypeptide. An "inflicted" individual can have cancer, can harbor an infection (e.g., a chronic infection), can have an immunological disorder (e.g., a disorder associated with immunosuppression), can have an inflammatory disorder, and/or can have other hyper-proliferative conditions, for example sclerosis, fibrosis, and the like, etc. "Inflicted cells" can be those cells that cause the symptoms, illness, or disease. As non-limiting examples, the inflicted cells of an inflicted patient can be PD-L1 expressing cancer cells, infected cells, inflammatory cells, and the like. In some cases, one indication that an illness or disease can be treated with a subject high affinity PD-1 mimic polypeptide is that the involved cells (i.e., the inflicted cells, e.g., the cancerous cells, the infected cells, the inflammatory cells, the immune cells, etc.) express PD-L1. In some cases, the inflicted cell (e.g., cancer cells) do not express PD-L1, but the disease (e.g., cancer) can still be treated using a subject high affinity PD-1 mimic polypeptide.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with cancer, those with an infection, those with an immune disorder, etc.) as well as those in which prevention is desired (e.g., those with increased susceptibility to cancer, those with an increased likelihood of infection, those suspected of having cancer, those suspected of harboring an infection, etc.).

A therapeutic treatment is one in which the subject is inflicted prior to administration and a prophylactic treatment is one in which the subject is not inflicted prior to administration. In some embodiments, the subject has an increased likelihood of becoming inflicted or is suspected of being inflicted prior to treatment. In some embodiments, the subject is suspected of having an increased likelihood of becoming inflicted.

The word "label" when used herein refers to a detectable compound or composition which is conjugated directly or indirectly to a subject PD-1 mimic polypeptide. The label may itself be detectable by itself (e.g., radioisotope labels or fluorescent labels) or, in the case of an enzymatic label, may catalyze chemical alteration of a substrate compound or composition which is detectable.

By "solid phase" is meant a non-aqueous matrix to which a high affinity PD-1 mimic polypeptide of the present disclosure can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety (3) single chain polypeptides containing only one heavy chain variable region, or a fragment thereof containing the three CDRs of the heavy chain variable region, without an associated light chain moiety and (4) nanobodies comprising single Ig domains from non-human species or other specific single-domain binding modules; and multispecific or multivalent structures formed from antibody fragments. In an antibody fragment comprising one or more heavy chains, the heavy chain(s) can contain any constant domain sequence (e.g., CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., J. Mol. Biol. 186:651 (1985); Novotny and Haber, Proc. Natl. Acad. Sci. U.S.A. 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv see Pluckthun, in The Pharmacology of Monoclonal Antibodies, vol. 113, Rosenburg and Moore eds., Springer-Verlag, New York, pp. 269-315 (1994).

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

There are five major classes of immunoglobulins: IgA, IgD, IgE, IgG, and IgM, and several of these can be further divided into subclasses (isotypes), e.g., IgG$_1$, IgG$_2$, IgG$_3$, IgG$_4$, IgA$_1$, IgA$_2$. The heavy-chain constant domains that correspond to the different classes of immunoglobulins are called a, d, e, g, and m, respectively. The subunit structures and three-dimensional configurations of different classes of immunoglobulins are well known. Engineered variants of immunoglobulin subclasses, including those that increase or decrease immune effector functions, half-life, or serum-stability, are also encompassed by this terminology.

Unless specifically indicated to the contrary, the term "conjugate" as described and claimed herein is defined as a heterogeneous molecule formed by the covalent attachment of one or more antibody fragment(s) to one or more polymer molecule(s), wherein the heterogeneous molecule is water soluble, i.e. soluble in physiological fluids such as blood, and wherein the heterogeneous molecule is free of any structured aggregate. A conjugate of interest is PEG. In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

As used in this disclosure, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Compositions

High affinity PD-1 mimic polypeptides and analogs thereof are provided, which may be referred to generically as high affinity PD-1 reagents. The high affinity PD-1 mimic polypeptides are variants of the wild type human PD-1 protein. In some embodiments, the present disclosure provides a high affinity PD-1 mimic polypeptide, where the polypeptide lacks the PD-1 transmembrane domain (and can be a soluble high affinity PD-1 mimic polypeptide) and includes at least one amino acid change relative to the wild-type PD-1 sequence, and where the amino acid change increases the affinity of the PD-1 mimic polypeptide for binding to PD-L1 (e.g., by decreasing the off-rate by at least 10-fold, at least 20-fold, at least 50-fold, at least 100-fold, at least 500-fold, or more).

It is to be understood that when a subject high affinity PD-1 mimic polypeptide lacks a PD-1 transmembrane domain, some amino acids from a transmembrane domain (e.g., a PD-1 transmembrane domain) may still be present (e.g., some amino acids from the transmembrane may be retained, as long as the protein retains the desired function). In some cases, a subject high affinity PD-1 mimic polypeptide is soluble. In some cases, a subject high affinity PD-1 mimic polypeptide lacks a PD-1 transmembrane domain, but includes a heterologous transmembrane domain (i.e., a transmembrane domain form a protein other than PD-1). In some cases, a subject high affinity PD-1 mimic polypeptide includes a transmembrane domain (e.g., a heterologous transmembrane domain, a PD-1 transmembrane domain, etc.), and includes a cleavable linker between the ectodomain portion and the transmembrane domain.

Polypeptides

A "PD-1 mimic polypeptide" as used herein refers to a polypeptide having the portion of a PD-1 protein that is sufficient to bind PD-L (e.g., PD-L1 and/or PD-L2) at a recognizable affinity, but which lacks a transmembrane domain (e.g., lacks the naturally present transmembrane domain of a wild type PD-1 protein). Thus, unlike a naturally existing PD-1 polypeptide, a subject PD-1 mimic polypeptide is not permanently tethered to a cell membrane by way of a transmembrane domain. In some embodiments, a subject PD-1 mimic polypeptide is soluble. An extracellular domain of protein that is normally tethered to the plasma membrane of a cell is sometimes referred to in the art as an ectodomain. Thus, a PD-1 mimic polypeptide can be considered to be (or be derived from) an ectodomain of PD-1, or can be considered to include at least a portion of (or a portion that is derived from) the ectodomain of a PD-1 polypeptide.

A wild type PD-1 protein has a transmembrane domain, is expressed on the cell surface, and specifically binds to its PD-L ligands (PD-L1 and PD-L2), which are also expressed on the cell surface. Thus, a wild type PD-1, expressed on the surface of a first cell, specifically binds to PD-L1 and/or PD-L2, expressed on the surface of a second cell. A PD-1 protein, to which a PD-1 mimic polypeptide corresponds (e.g., from which a PD-1 mimic polypeptide is derived) can be any PD-1 protein (e.g., a wild type PD-1 protein). Example PD-1 proteins include those from any species, e.g., a mammalian PD-1 protein, a rodent PD-1 protein, a primate PD-1 protein, a rat PD-1 protein, a mouse PD-1 protein, a pig PD-1 protein, a cow PD-1 protein, a sheep PD-1 protein, a rabbit PD-1 protein, a dog PD-1 protein, a human PD-1 protein, etc. Sequences for various wild type PD-1 polypeptide sequences (e.g., canine, bovine, sheep, equine, porcine, rodent, mouse, rat, feline, primate, monkey, ape, chimpanzee, and the like) can easily be found and are readily available to one of ordinary skill in the art. For example, the human PD-1 protein (set forth as SEQ ID NO: 1) is:

Wild Type Human PD-1
(also known as "programmed cell death 1", PDCD1, CD279, PD1, SLEB2, hPD-1, hPD-I, and hSLE1)

(SEQ ID NO: 1)
MQIPQAPWPVVWAVLQLGWRPGWFLDSPDRPWNPPTFSPALLVVTEGDN

ATFTCSFSNTSESFVLNWYRMSPSNQTDKLAAFPEDRSQPGQDCRFRVTQ

LPNGRDFHMSVVRARRNDSGTYLCGAISLAPKAQIKESLRAELRVTERRA

EVPTAHPSPSPRPAGQFQTLVVGVVGGLLGSLVLLVWVLAVICSRAARGT

IGARRTGQPLKEDPSAVPVFSVDYGELDFQWREKTPEPPVPCVPEQTEYA

TIVFPSGMGTSSPARRGSADGPRSAQPLRPEDGHCSWPL bold: transmembrane domain—amino acids 168-191
underline: exemplary native PD-1 mimic polypeptide—amino acids 26-147

A PD-L protein is a membrane-bound ligand to PD-1. There are two human PD-L proteins that are referred to in the art as PD-L1 and PD-L2. Example PD-L proteins include those from any species, e.g., a mammalian PD-L protein, a rodent PD-L protein, a primate PD-L protein, a rat PD-L protein, a mouse PD-L protein, a pig PD-L protein, a cow PD-L protein, a sheep PD-L protein, a rabbit PD-L protein, a dog PD-L protein, a human PD-L protein, etc. Sequences for various wild type PD-L polypeptide sequences (e.g., canine, bovine, sheep, equine, porcine, rodent, mouse, rat, feline, primate, monkey, ape, chimpanzee, and the like) can easily be found and are readily available to one of ordinary skill in the art. For example, the human PD-L1 and PD-L2 proteins (set forth as SEQ ID NOs: 36-38, respectively) are:

Wild Type Human PD-L1
(also known as "programmed cell death 1 ligand 1", PDCD1LG1, CD274, B7-H, B7H1, PDL1, PD-L1, PDCD1L1)

(Isoform a)
(SEQ ID NO: 36)
MRIFAVFIFMTYWHLLNAFTVTVPKDLYVVEYGSNMTIECKFPVEKQLDL

AALIVYWEMEDKNIIQFVHGEEDLKVQHSSYRQRARLLKDQLSLGNAALQ

ITDVKLQDAGVYRCMISYGGADYKRITVKVNAPYNKINQRILVVDPVTSE

HELTCQAEGYPKAEVIWTSSDHQVLSGKTTTTNSKREEKLFNVTSTLRIN

TTTNEIFYCTFRRLDPEENHTAELVIPELPLAHPPNERTHLVILGAILLC

LGVALTFIFRLRKGRMMDVKKCGIQDTNSKKQSDTHLEET (Isoform b)
(SEQ ID NO: 37)
MRIFAVFIFMTYWHLLNAPYNKINQRILVVDPVTSEHELTCQAEGYPKAE

VIWTSSDHQVLSGKTTTTNSKREEKLFNVTSTLRINTTTNEIFYCTFRRL

DPEENHTAELVIPELPLAHPPNERTHLVILGAILLCLGVALTFIFRLRKG

RMMDVKKCGIQDTNSKKQSDTHLEET

Wild Type Human PD-L2
(also known as "programmed cell death 1 ligand 2", PDCD1LG2, CD273, B7DC, Btdc, PDL2, PDCD1L2, bA574F11.2)

(SEQ ID NO: 38)
MIFLLLMLSLELQLHQIAALFTVTVPKELYIIEHGSNVTLECNFDTGSHV

NLGAITASLQKVENDTSPHRERATLLEEQLPLGKASFHIPQVQVRDEGQY

QCIIIYGVAWDYKYLTLKVKASYRKINTHILKVPETDEVELTCQATGYPL

AEVSWPNVSVPANTSHSRTPEGLYQVTSVLRLKPPPGRNFSCVFWNTHVR

ELTLASIDLQSQMEPRTHPTWLLHIFIPFCIIAFIFIATVIALRKQLCQK

LYSSKDTTKRPVTTTKREVNSAI

The transmembrane domain of a wild type PD-1 is readily identifiable. As an illustrative example, three different domain prediction programs were run on the wild type human PD-1 protein set forth in SEQ ID NO: 1, and the following overlapping amino acid regions were determined to define a transmembrane domain: 168-191, 167-189, and 169-191. Thus, a transmembrane domain is present at amino acids 167-191 (e.g., 168-191, 167-189, and/or 169-191) of the wild type human PD-1 protein set forth in SEQ ID NO: 1. Thus, in some cases, a PD-1 mimic polypeptide lacks amino acids 167-191, 168-191, 167-189, and/or 169-191 of the wild type human PD-1 protein set forth in SEQ ID NO: 1, or the corresponding region of another wild type PD-1 protein. Sequences for various additional wild type PD-1 polypeptide sequences (e.g., canine, bovine, sheep, equine, porcine, rodent, mouse, rat, feline, primate, monkey, ape, chimpanzee, and the like) can easily be found and are readily available to one of ordinary skill in the art.

A suitable PD-1 mimic polypeptide specifically binds to PD-L (e.g., PD-L1 and/or PD-L2 on a target cell, e.g., on a cancer cell) and thereby reduces (e.g., blocks, prevents, etc.) the interaction between the PD-L and PD-1 (e.g., PD-1 on an immune cell, e.g., on a T cell). Thus, a subject PD-1 mimic polypeptide can be considered to be an engineered decoy receptor for PD-L (e.g., PD-L1 and/or PD-L2). By reducing the interaction between PD-L and PD-1, a subject PD-1 mimic polypeptide can decrease the immune inhibitory signals produced by the PD-L/PD-1 interaction, and therefore can increase the immune response (e.g., by increasing T cell activation).

A suitable PD-1 mimic polypeptide comprises the portion of PD-1 that is sufficient to bind PD-L1 at a recognizable affinity, e.g., high affinity, which normally lies between the signal sequence and the transmembrane domain, or a fragment thereof that retains the binding activity. Thus, a subject PD-1 mimic polypeptide can comprise an immunoglobulin domain, or a portion thereof (as described below) that is sufficient to bind PD-L1 with a recognizable affinity. A subject PD-1 mimic polypeptide (e.g., a high affinity PD-1 mimic polypeptide) can comprise portions of a wild type PD-1 protein other than the immunoglobulin domain, including, for example, contiguous amino acids of any of the sequences set forth in SEQ ID NOs: 2 and 27-34 (or the corresponding sequences of any other PD-1 protein, e.g., any other mammalian PD-1 protein).

In some cases, the portion of PD-1 that is sufficient to bind PD-L1 and/or PD-L2 includes all or a portion of the immunoglobulin domain of a wild type PD-1 polypeptide, which can readily be identified by one of ordinary skill in the art. For example, a scan of the wild type human PD-1 sequence set forth in SEQ ID NO: 1 reveals that the region from amino acids 35-146 contains an immunoglobulin domain (Table 1). A PD-1 mimic polypeptide (e.g., a high affinity PD-1 mimic polypeptide) can include all or a portion of the immunoglobulin domain of PD-1; and may further comprise one or more amino acids from PD-1 outside of the immunoglobulin domain; and may comprise amino acid sequences other than PD-1, which include without limitation immunoglobulin Fc region sequences.

TABLE 1

Immunoglobulin domains of wild type human PD-1 identified by various sequence analysis software.

| Amino acids | Domain | Database |
| --- | --- | --- |
| 35-145 | Immunoglobulin-like domain | PROSITE |
| 38-128 | Immunoglobulin V-set domain | Pfam |
| 39-145 | Immunoglobulin subtype | SMART |
| 39-146 | Immunoglobulin-like fold | GENE3D |
| 49-125 | Immunoglobulin V-Type (IGv); Immunoglobulin V-set, subgroup | SMART |
| 42-136 | IgV; Immunoglobulin variable domain (IgV) | NCBI |
| 39-125 | IG_like; Immunoglobulin like | NCBI |

In some cases, a PD-1 mimic polypeptide includes an amino acid sequence having 85% or more sequence identity (e.g., 90% or more, 95% or more, 98% or more, 99% or more, 99.2% or more, 99.5% or more, 99.8% or more, 99.9% or more, or 100% sequence identity) to a wild type PD-1 polypeptide (e.g., to the corresponding region of a wild type PD-1 polypeptide) (e.g., a mammalian wild type PD-1 polypeptide; the human wild type PD-1 protein set forth in SEQ ID NO: 1, and the like).

In some cases, a PD-1 mimic polypeptide includes an amino acid sequence having 85% or more sequence identity (e.g., 90% or more, 95% or more, 98% or more, 99% or more, 99.2% or more, 99.5% or more, 99.8% or more, 99.9% or more, or 100% sequence identity) to an immunoglobulin domain of a wild type PD-1 polypeptide (e.g., an Immunoglobulin V-set domain or Immunoglobulin V-Type domain (IGv domain); an Immunoglobulin-like fold; an Immunoglobulin variable domain; an Immunoglobulin like domain, and the like.). Sequences for various additional wild type PD-1 polypeptide sequences (e.g., canine, bovine, sheep, equine, porcine, rodent, mouse, rat, feline, primate, monkey, ape, chimpanzee, and the like) can easily be found and are readily available to one of ordinary skill in the art.

In some cases, a PD-1 mimic polypeptide includes an amino acid sequence having 85% or more sequence identity (e.g., 90% or more, 95% or more, 98% or more, 99% or more, 99.2% or more, 99.5% or more, 99.8% or more, 99.9% or more, or 100% sequence identity) to an immunoglobulin domain-containing region of the human PD-1 amino acid sequence set forth in SEQ ID NO: 1; or the corresponding region of another wild type PD-1 protein (e.g., another mammalian wild type PD-1 protein). In some cases, a PD-1 mimic polypeptide includes an amino acid sequence having 85% or more sequence identity (e.g., 90% or more, 95% or more, 98% or more, 99% or more, 99.2% or more, 99.5% or more, 99.8% or more, 99.9% or more, or 100% sequence identity) to amino acids 35-145 (SEQ ID NO: 27), 38-128 (SEQ ID NO: 28), 39-145 (SEQ ID NO: 29), 39-146 (SEQ ID NO: 30), 49-125 (SEQ ID NO: 31), 42-136 (SEQ ID NO: 32), 39-125 (SEQ ID NO: 33), 35-146 (SEQ ID NO: 34), 1-166 (SEQ ID NO: 35), and/or 26-147 (SEQ ID NO: 2) of the wild type human PD-1 polypeptide amino acid sequence set forth in SEQ ID NO: 1; or the corresponding region of another wild type PD-1 protein (e.g., another mammalian wild type PD-1 protein). In some cases, a PD-1 mimic polypeptide includes amino acids 35-145, 38-128, 39-145, 39-146, 49-125, 42-136, 39-125, 35-146, 1-166 and/or 26-147 (SEQ ID NO: 2) of the wild type human PD-1 protein sequence (amino acid sequence) set forth in SEQ ID NO: 1; or the corresponding region of another wild type PD-1 protein (e.g., another mammalian wild type PD-1 protein).

In some cases, a PD-1 mimic polypeptide includes an amino acid sequence having 85% or more sequence identity (e.g., 90% or more, 95% or more, 98% or more, 99% or more, 99.2% or more, 99.5% or more, 99.8% or more, 99.9% or more, or 100% sequence identity) to the native PD-1 mimic polypeptide amino acid sequence set forth in SEQ ID NO: 2 (i.e., the PD-1 protein fragment set forth in SEQ ID NO: 2); or the corresponding region of another wild type PD-1 protein (e.g., another mammalian wild type PD-1 protein). The polypeptide set forth in SEQ ID NO: 2 is a protein fragment (amino acids 26-147) of the wild type human PD-1 protein (SEQ ID NO: 1). The amino acid sequence set forth in SEQ ID NO: 2 includes an immunoglobulin domain of the wild type human PD-1 polypeptide. In some cases, a PD-1 mimic polypeptide includes the amino acid sequence set forth in SEQ ID NO: 2 (i.e., amino acids 26-147 of the human PD-1 protein sequence set forth in SEQ ID NO: 1)(i.e., in some cases, a PD-1 mimic polypeptide includes the PD-1 protein fragment set forth in SEQ ID NO: 2); or the corresponding region of another wild type PD-1 protein, e.g., another mammalian wild type PD-1 protein.

In some cases, a PD-1 mimic polypeptide includes an amino acid sequence having 85% or more sequence identity (e.g., 90% or more, 95% or more, 98% or more, 99% or more, 99.2% or more, 99.5% or more, 99.8% or more, 99.9% or more, or 100% sequence identity) to the amino acid sequence set forth in any of SEQ ID NOs: 2-25 (e.g., 85% or more, 90% or more, 95% or more, 98% or more, 99% or more, 99.2% or more, 99.5% or more, 99.8% or more, 99.9% or more, or 100% sequence identity to any of SEQ ID NOs: 3-25, SEQ ID NOs: 2-23, SEQ ID NOs: 3-23, SEQ ID NOs: 24-25, etc.). In some cases, a PD-1 mimic polypeptide includes the amino acid sequence set forth in any of SEQ ID NOs: 2-25 (e.g., SEQ ID NOs: 3-25, SEQ ID NOs: 2-23, SEQ ID NOs: 3-23, SEQ ID NOs: 24-25, etc.).

A PD-1 mimic polypeptide having no mutations relative to the corresponding region of a wild type PD-1 protein (i.e., where the PD-1 mimic polypeptide is a fragment of a wild type protein) is referred to herein as a "native PD-1 mimic polypeptide." A native PD-1 mimic polypeptide can be used as a control in various instances, for example, in some cases when determining whether a PD-1 mimic polypeptide is a "high affinity PD-1 mimic polypeptide."

High Affinity PD-1 Mimic Polypeptide.

A "high affinity PD-1 mimic polypeptide" is a PD-1 mimic polypeptide (as defined above, and thus lacks a transmembrane domain of a wild type PD-1 protein) that has an amino acid mutation (i.e., an amino acid change) relative to a wild type PD-1 protein, (e.g., relative to the corresponding region of a wild type PD-1 protein, relative to the ectodomain of a wild type PD-1 protein, relative to the immunoglobulin domain of a wild type PD-1 protein, relative to a native PD-1 mimic polypeptide, etc.), where the amino acid mutation increases the affinity of the PD-1 mimic polypeptide for PD-L1 such that the affinity of the high affinity PD-1 mimic polypeptide for PD-L1 is greater than that affinity of the wild type PD-1 protein (and/or the corresponding native PD-1 mimic polypeptide) for PD-L1. For example, the amino acid mutation can increase the affinity by decreasing the off-rate by at least 10-fold, at least 20-fold, at least 50-fold, at least 100-fold, at least 500-fold, or more.

According to the present disclosure, amino acid mutations (i.e., changes) include any naturally occurring or man-made amino acid modifications known or later discovered in the field. In some embodiments, amino acid changes include, e.g., substitution, deletion, addition, insertion, etc. of one or more amino acids. In some embodiments, amino acid changes include replacing an existing amino acid with another amino acid. In related embodiments, amino acid changes include replacing one or more existing amino acids with non-natural amino acids, or inserting one or more non-natural amino acids. Amino acid changes may be made in 1 or more (e.g, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, etc.) amino acid residues relative to a wild type sequence. The one or more amino acid changes can confer various properties to the high affinity PD-1 mimic polypeptide, e.g., affecting the stability, binding activity and/or specificity, etc.

In some cases, a high affinity PD-1 mimic polypeptide includes an amino acid change (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes) relative to a wild type PD-1 polypeptide (e.g., relative to the corresponding region of a wild type PD-1 polypeptide) (e.g., a mammalian wild type PD-1 polypeptide; the human wild type PD-1 protein set forth in SEQ ID NO: 1, and the like).

In some cases, a high affinity PD-1 mimic polypeptide includes an amino acid change (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes) relative to the immunoglobulin domain of a wild type PD-1 polypeptide (e.g., amino acids 35-145, 38-128, 39-145, 39-146, 49-125, 42-136, 39-125, 35-146, 1-166 and/or 26-147 (SEQ ID NO: 2) of the wild type human PD-1 polypeptide amino acid sequence set forth in SEQ ID NO: 1; or the corresponding region of another wild type PD-1 protein, e.g., another mammalian wild type PD-1 protein). In some cases, a high affinity PD-1 mimic polypeptide includes an amino acid change (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes) relative to the ectodomain of a wild type PD-1 polypeptide.

In some cases, a high affinity PD-1 mimic polypeptide includes an amino acid change (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes) relative to the amino acid sequence set forth in SEQ ID NO: 2 (which is a human "native PD-1 mimic polypeptide", as defined above); or the corresponding region of another wild type PD-1 protein, e.g., another mammalian wild type PD-1 protein. In some cases, a high affinity PD-1 mimic polypeptide includes an amino acid change (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes) relative to the amino acid sequence set forth in any of SEQ ID NOs: 2-25 (e.g., relative to any of SEQ ID NOs: 3-25, SEQ ID NOs: 2-23, SEQ ID NOs: 3-23, SEQ ID NOs: 24-25, etc.).

In some cases, a high affinity PD-1 mimic polypeptide includes an amino acid change (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes) relative to a wild type PD-1 polypeptide (e.g., to the corresponding region of a wild type PD-1 polypeptide) (e.g., a mammalian wild type PD-1 polypeptide; the human wild type PD-1 protein set forth in SEQ ID NO: 1, and the like), and includes an amino acid sequence having 85% or more sequence identity (e.g., 90% or more, 95% or more, 98% or more, 99% or more, 99.2% or more, 99.5% or more, 99.8% or more, 99.9% or more, or 100% sequence identity) to a wild type PD-1 polypeptide (e.g., to the corresponding region of a wild type PD-1 polypeptide) (e.g., a mammalian wild type PD-1 polypeptide; the human wild type PD-1 protein set forth in SEQ ID NO: 1, and the like).

In some cases, a high affinity PD-1 mimic polypeptide includes an amino acid change (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes) relative to the immunoglobulin domain of a wild type PD-1 polypeptide; or the corresponding region of another wild type PD-1 protein, e.g., another mammalian wild type PD-1 protein, and includes an amino acid sequence having 85% or more sequence identity (e.g., 90% or more, 95% or more, 98% or more, 99% or more, 99.2% or more, 99.5% or more, 99.8% or more, 99.9% or more, or 100% sequence identity) to the immunoglobulin domain of a wild type PD-1 polypeptide (e.g., amino acids 35-145, 38-128, 39-145, 39-146, 49-125, 42-136, 39-125, or 35-146 of the wild type human PD-1 polypeptide amino acid sequence set forth in SEQ ID NO: 1); or the corresponding region of another wild type PD-1 protein, e.g., another mammalian wild type PD-1 protein.

In some cases, a high affinity PD-1 mimic polypeptide includes an amino acid change (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes) relative to amino acids 35-145, 38-128, 39-145, 39-146, 49-125, 42-136, 39-125, 35-146, 1-166 and/or 26-147 (SEQ ID NO: 2) of the wild type human PD-1 polypeptide amino acid sequence set forth in SEQ ID NO: 1; or the corresponding region of another wild type PD-1 protein, e.g., another mammalian wild type PD-1 protein; and includes an amino acid sequence having 85% or more sequence identity (e.g., 90% or more, 95% or more, 98% or more, 99% or more, 99.2% or more, 99.5% or more, 99.8% or more, 99.9% or more, or 100% sequence identity) to amino acids 35-145, 38-128, 39-145, 39-146, 49-125, 42-136, 39-125, 35-146, 1-166 and/or 26-147 (SEQ ID NO: 2) of the wild type human PD-1 polypeptide amino acid sequence set forth in SEQ ID NO: 1; or the corresponding region of another wild type PD-1 protein, e.g., another mammalian wild type PD-1 protein.

In some cases, a high affinity PD-1 mimic polypeptide includes an amino acid change (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes) relative to the amino acid sequence set forth in SEQ ID NO: 2; or the corresponding region of another wild type PD-1 protein, e.g., another mammalian wild type PD-1 protein; and includes an amino acid sequence having 85% or more sequence identity (e.g., 90% or more, 95% or more, 98% or more, 99% or more, 99.2% or more, 99.5% or more, 99.8% or more, 99.9% or more, or 100% sequence identity) to the amino acid sequence set forth in SEQ ID NO: 2; or the corresponding region of another wild type PD-1 protein, e.g., another mammalian wild type PD-1 protein.

In some cases, a high affinity PD-1 mimic polypeptide includes an amino acid change (e.g., 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acid changes) relative to the amino acid sequence set forth in any of SEQ ID NOs: 2-25 (e.g., relative to any of SEQ ID NOs: 3-25, SEQ ID NOs: 2-23, SEQ ID NOs: 3-23, SEQ ID NOs: 24-25, etc.); and includes an amino acid sequence having 85% or more sequence identity (e.g., 90% or more, 95% or more, 98% or more, 99% or more, 99.2% or more, 99.5% or more, 99.8% or more, 99.9% or more, or 100% sequence identity) to the amino acid sequence set forth in any of SEQ ID NOs: 2-25 (e.g., 85% or more, 90% or more, 95% or more, 98% or more, 99% or more, 99.2% or more, 99.5% or more, 99.8% or more, 99.9% or more, or 100% sequence identity to any of SEQ ID NOs: 3-25, SEQ ID NOs: 2-23, SEQ ID NOs: 3-23, SEQ ID NOs: 24-25, etc.).

In some cases, a high affinity PD-1 mimic polypeptide of the disclosure includes one or more (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 14 or more, 15 or more) amino acid changes located at amino acid positions of PD-1 that contacts PD-L1. For example, in some cases, the one or more (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 14 or more, 15 or more) amino acid changes is located at an amino acid position, relative to the protein fragment (of human wild type PD-1) set forth in SEQ ID NO: 2 (which is a protein fragment of the human wild type PD-1 protein), selected from: V39, N41, Y43, M45, S48, N49, Q50, T51, D52, K53, A56, Q63, G65, Q66, L97, S102, L103, A104, P105, K106, and A107; or the corresponding amino acid position relative to another wild type PD-1 protein. For example, refer to FIG. 3.

In some cases, a high affinity PD-1 mimic polypeptide of the disclosure includes one or more (e.g., 2 or more, 3 or more, 4 or more, 5 or more, 6 or more, 7 or more, 8 or more, 9 or more, 10 or more, 11 or more, 12 or more, 13 or more, 14 or more, 15 or more) amino acid changes located at an amino acid position, relative to the protein fragment (of human wild type PD-1) set forth in SEQ ID NO: 2 (which is a protein fragment of the human wild type PD-1 protein), selected from: V39, L40, N41, Y43, R44, M45, S48, N49, Q50, T51, D52, K53, A56, Q63, G65, Q66, V72, H82, M83, R90, Y96, L97, A100, S102, L103, A104, P105, K106, and A107; or the corresponding amino acid position relative to another wild type PD-1 protein. For example, refer to FIG. 3.

In some cases, a high affinity PD-1 mimic polypeptide of the disclosure includes amino acid changes located at amino acid positions, relative to the protein fragment (of human wild type PD-1) set forth in SEQ ID NO: 2 (which is a protein fragment of the human wild type PD-1 protein), selected from: (a) V39, N41, Y43, M45, S48, N49, Q50, K53, A56, Q63, G65, Q66, L97, S102, L103, A104, K106, and A107, or the corresponding amino acid positions relative to another wild type PD-1 protein; (b) V39, N41, Y43, M45, S48, Q50, T51, D52F, K53, A56, Q63, G65, Q66, L97, S102, L103, A104, K106, and A107, or the corresponding amino acid positions relative to another wild type PD-1 protein; (c) V39, L40, N41, Y43, R44, M45, N49, K53, M83, L97, A100, and A107, or the corresponding amino acid positions relative to another wild type PD-1 protein; (d) V39, L40, N41, Y43, M45, N49, K53, Q66P, M83, L97, and A107, or the corresponding amino acid positions relative to another wild type PD-1 protein; (e) V39, L40, N41, Y43, M45, N49, K53, Q66P, H82, M83, L97, A100, and A107, or the corresponding amino acid positions relative to another wild type PD-1 protein; (f) V39, L40, N41, Y43, M45, N49, K53, M83, L97, A100, and A107, or the corresponding amino acid positions relative to another wild type PD-1 protein; (g) V39, L40, N41, Y43, R44, M45, N49, K53, L97, A100, and A107, or the corresponding amino acid positions relative to another wild type PD-1 protein; and (h) V39, L40, N41, Y43, M45, N49, K53, L97, A100, and A107, or the corresponding amino acid positions relative to another wild type PD-1 protein. For example, refer to FIG. 3.

In some cases, a high affinity PD-1 mimic polypeptide of the disclosure includes one or more (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 14 or more, 15 or more) amino acid changes, relative to the protein fragment (of human wild type PD-1) set forth in SEQ ID NO: 2 (which is a protein fragment of the human wild type PD-1 protein), selected from: (1) V39H or V39R; (2) L40V or L40I; (3) N41I or N41V; (4) Y43F or Y43H; (5) R44Y or R44L; (6) M45Q, M45E, M45L, or M45D; (7) S48D, S48L, S48N, S48G, or S48V; (8) N49C, N49G, N49Y, or N49S; (9) Q50K, Q50E, or Q50H; (10) T51V, T51L, or T51A; (11) D52F, D52R, D52Y, or D52V; (12) K53T or K53L; (13) A56S or A56L; (14) Q63T, Q63I, Q63E, Q63L, or Q63P; (15) G65N, G65R, G65I, G65L, G65F, or G65V; (16) Q66P; (17) V72I; (18) H82Q; (19) M83L or M83F; (20) R90K; (21) Y96F; (22) L97Y, L97V, or L97I; (23) A100I or A100V; (24) S102T or S102A; (25) L103I, L103Y, or L103F; (26) A104S, A104H, or A104D; (27) P105A; (28) K106G, K106E, K106I, K106V, K106R, or K106T; and (29) A107P, A107I, or A107V; or a change that results in the same amino acid at the corresponding position relative to another wild type PD-1 protein. For example, refer to FIG. 3.

In some cases, a high affinity PD-1 mimic polypeptide of the disclosure includes amino acid changes, relative to the protein fragment (of human wild type PD-1) set forth in SEQ ID NO: 2 (which is a protein fragment of the human wild type PD-1 protein), selected from:

(a) {V39H or V39R}, {N41I or N41V}, {Y43F or Y43H}, {M45Q, M45E, M45L, or M45D}, {S48D, S48L, S48N, S48G, or S48V}, {N49C, N49G, N49Y, or N49S}, {Q50K, Q50E, or Q50H}, {K53T or K53L}, {A56S or A56L}, {Q63T, Q63I, Q63E, Q63L, or Q63P}, {G65N, G65R, G65I, G65L, G65F, or G65V}, {Q66P}, {L97Y, L97V, or L97I}, {S102T or S102A}, {L103I, L103Y, or L103F}, {A104S, A104H, or A104D}, {K106G, K106E, K106I, K106V, K106R, or K106T}, and {A107P, A107I, or A107V}; or changes that result in the same amino acids at the corresponding positions relative to another wild type PD-1 protein;

(b) {V39H or V39R}, {N41I or N41V}, {Y43F or Y43H}, {M45Q, M45E, M45L, or M45D}, {S48D, S48L, S48N, S48G, or S48V}, {Q50K, Q50E, or Q50H}, {T51V, T51L, or T51A}, {D52F, D52R, D52Y, or D52V}, {K53T or K53L}, {A56S or A56L}, {Q63T, Q63I, Q63E, Q63L, or Q63P}, {G65N, G65R, G65I, G65L, G65F, or G65V}, {Q66P}, {L97Y, L97V, or L97I}, {S102T or S102A}, {L103I, L103Y, or L103F}, {A104S, A104H, or A104D}, {K106G, K106E, K106I, K106V, K106R, or K106T}, and {A107P, A107I, or A107V}; or changes that result in the same amino acids at the corresponding positions relative to another wild type PD-1 protein;

(c) {V39H or V39R}, {L40V or L40I}, {N41I or N41V}, {Y43F or Y43H}, {R44Y or R44L}, {M45Q, M45E, M45L, or M45D}, {N49C, N49G, N49Y, or N49S}, {K53T or K53L}, {M83L or M83F}, {L97Y, L97V, or L97I}, {A100I or A100V}, and {A107P, A107I, or A107V}; or changes that result in the same amino acids at the corresponding positions relative to another wild type PD-1 protein;

(d){V39H or V39R}, {L40V or L40I}, {N41I or N41V}, {Y43F or Y43H}, {M45Q, M45E, M45L, or M45D}, {N49C, N49G, N49Y, or N49S}, {K53T or K53L}, {Q66P}, {M83L or M83F}, {L97Y, L97V, or L97I}, and {A107P, A107I, or A107V}; or changes that result in the same amino acids at the corresponding positions relative to another wild type PD-1 protein;

(e) {V39H or V39R}, {L40V or L40I}, {N41I or N41V}, {Y43F or Y43H}, {M45Q, M45E, M45L, or M45D}, {N49C, N49G, N49Y, or N49S}, {K53T or K53L}, {Q66P}, {H82Q}, {M83L or M83F}, {L97Y, L97V, or L97I}, {A100I or A100V}, and {A107P, A107I, or A107V}; or changes that result in the same amino acids at the corresponding positions relative to another wild type PD-1 protein;

(f) {V39H or V39R}, {L40V or L40I}, {N41I or N41V}, {Y43F or Y43H}, {M45Q, M45E, M45L, or M45D}, {N49C, N49G, N49Y, or N49S}, {K53T or K53L}, {M83L or M83F}, {L97Y, L97V, or L97I}, {A100I or A100V}, and {A107P, A107I, or A107V}; or changes that result in the same amino acids at the corresponding positions relative to another wild type PD-1 protein;

(g) {V39H or V39R}, {L40V or L40I}, {N41I or N41V}, {Y43F or Y43H}, {R44Y or R44L}, {M45Q, M45E, M45L, or M45D}, {N49C, N49G, N49Y, or N49S}, {K53T or K53L}, {L97Y, L97V, or L97I}, {A100I or A100V}, and {A107P, A107I, or A107V}; or changes that result in the same amino acids at the corresponding positions relative to another wild type PD-1 protein; and (h) {V39H or V39R}, {L40V or L40I}, {N41I or N41V}, {Y43F or Y43H}, {M45Q, M45E, M45L, or M45D}, {N49C, N49G, N49Y, or N49S}, {K53T or K53L}, {L97Y, L97V, or L97I}, {A100I or A100V}, and {A107P, A107I, or A107V}; or changes that result in the same amino acids at the corresponding positions relative to another wild type PD-1 protein. For example, refer to FIG. 3.

In some cases, a high affinity PD-1 mimic polypeptide of the disclosure includes amino acid changes, relative to the protein fragment (of human wild type PD-1) set forth in SEQ ID NO: 2 (which is a protein fragment of the human wild type PD-1 protein), selected from:

(a) V39R, N41V, Y43H, M45E, S48G, N49Y, Q50E, K53T, A56S, Q63T, G65L, Q66P, L97V, S102A, L103F, A104H, K106V, and A107I; or changes that result in the same amino acids at the corresponding positions relative to another wild type PD-1 protein;

(b) V39R, N41V, Y43H, M45E, S48N, Q50H, T51A, D52Y, K53T, A56L, Q63L, G65F, Q66P, L97I, S102T, L103F, A104D, K106R, and A107I; or changes that result in the same amino acids at the corresponding positions relative to another wild type PD-1 protein;

(c) V39H, L40V, N41V, Y43H, R44Y, M45E, N49G, K53T, M83L, L97V, A100I, and A107I; or changes that result in the same amino acids at the corresponding positions relative to another wild type PD-1 protein;

(d) V39H, L40V, N41V, Y43H, M45E, N49G, K53T, Q66P, M83L, L97V, and A107I; or changes that result in the same amino acids at the corresponding positions relative to another wild type PD-1 protein;

(e) V39H, L40V, N41V, Y43H, M45E, N49S, K53T, Q66P, H82Q, M83L, L97V, A100V, and A107I; or changes that result in the same amino acids at the corresponding positions relative to another wild type PD-1 protein;

(f) V39H, L40I, N41I, Y43H, M45E, N49G, K53T, M83L, L97V, A100V, and A107I; or changes that result in the same amino acids at the corresponding positions relative to another wild type PD-1 protein;

(g) V39H, L40V, N41I, Y43H, R44L, M45E, N49G, K53T, L97V, A100V, and A107I; or changes that result in the same amino acids at the corresponding positions relative to another wild type PD-1 protein;

(h) V39H, L40V, N41I, Y43H, M45E, N49G, K53T, L97V, A100V, and A107I; or changes that result in the same amino acids at the corresponding positions relative to another wild type PD-1 protein; and (i) V39H, L40V, N41V, Y43H, M45E, N49G, K53T, L97V, A100V, and A107I or changes that result in the same amino acids at the corresponding positions relative to another wild type PD-1 protein. For example, refer to FIG. 3.

Affinity

As subject high affinity PD-1 mimic polypeptide has an increased affinity for PD-L1 as compared to the affinity for PD-L1 of a wild type PD-1 protein, and/or as compared to the affinity for PD-L1 of a PD-1 mimic polypeptide that does not have an amino acid change relative to a corresponding sequence of a wild type PD-1 polypeptide (e.g., a native PD-1 mimic polypeptide, as defined above).

In some embodiments, the high affinity PD-1 mimic polypeptide has a $K_d$ of $1\times10^{-7}$ M or less (e.g., $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less) for PD-L1. In some cases, the high affinity PD-1 mimic polypeptide has an affinity for PD-L1 in a range of from 1 fM to 1 µM (e.g., from 1 fM to 800 nM, from 10 fM to 500 nM, from 100 fM to 100 nM, from 500 fM to 50 nM, from 800 fM to 50 nM, from 1 pM to 50 nM, from 10 pM to 50 nM, from 50 pM to 50 nM, from 100 pM to 50 nM, from 500 fM to 100 nM, from 800 fM to 100 nM, from 1 pM to 100 nM, from 10 pM to 100 nM, from 50 pM to 100 nM, or from 100 pM to 100 nM). In some cases, the high affinity PD-1 mimic polypeptide binds to PD-L1 with an affinity of 1 pM or greater (e.g., 800 nM or greater, 500 nM or greater, 200 nM or greater, 100 nM or greater, 50 nM or greater, 10 nM or greater, 1 nM or greater, 900 pM or greater, 750 pM or greater, 500 pM or greater, 200 pM or greater, 100 pM or greater, 10 pM or greater, 1 pM or greater, etc.) (where the affinity increases with decreasing values).

In some embodiments, the high affinity PD-1 mimic polypeptide has an affinity for PD-L1 that is 2-fold or more (e.g., 5-fold or more, 10-fold or more, 100-fold or more, 500-fold or more, 1000-fold or more, 5000-fold or more, $10^4$-fold or more, $10^5$-fold or more, $10^6$-fold or more, $10^7$-fold or more, $10^8$-fold or more, etc.) greater than the affinity for PD-L1 of a wild type PD-1 protein; and/or 2-fold or more (e.g., 5-fold or more, 10-fold or more, 100-fold or more, 500-fold or more, 1000-fold or more, 5000-fold or more, $10^4$-fold or more, $10^5$-fold or more, $10^6$-fold or more, $10^7$-fold or more, $10^8$-fold or more, etc.) greater than the affinity for PD-L1 of a PD-1 mimic polypeptide that does not have an amino acid change relative to a corresponding sequence of a wild type PD-1 polypeptide (e.g., a native PD-1 mimic polypeptide, as defined above).

In some embodiments, the high affinity PD-1 mimic polypeptide has a dissociation half-life for PD-L1 that is 2-fold or more (e.g., 5-fold or more, 10-fold or more, 100-fold or more, 500-fold or more, 1000-fold or more, 5000-fold or more, $10^4$-fold or more, $10^5$-fold or more, $10^6$-fold or more, $10^7$-fold or more, $10^8$-fold or more, etc.) greater than the dissociation half-life for PD-L1 of a wild type PD-1 protein; and/or 2-fold or more (e.g., 5-fold or more, 10-fold or more, 100-fold or more, 500-fold or more, 1000-fold or more, 5000-fold or more, $10^4$-fold or more, $10^5$-fold or more, $10^6$-fold or more, $10^7$-fold or more, $10^8$-fold or more, etc.) greater than the dissociation half-life for PD-L1 of a PD-1 mimic polypeptide that does not have an amino acid change relative to a corresponding sequence of a wild type PD-1 polypeptide (e.g., a native PD-1 mimic polypeptide, as defined above). For example, in some cases, a native PD-1 mimic polypeptide (as defined above) has a dissociation half-life for PD-L1 of less than 1 second, while a subject high affinity PD-1 mimic polypeptide can have a dissociation half-life of 5 seconds or more (e.g., 30 seconds or more, 1 minute or more, 5 minutes or more, 10 minutes or more, 20 minutes or more, 30 minutes or more, 40 minutes or more, etc.). For example, the amino acid mutation of a subject high affinity PD-1 mimic polypeptide can increase the affinity by decreasing the off-rate by at least 10-fold, at least 20-fold, at least 50-fold, at least 100-fold, at least 500-fold, or more.

In some cases, a subject high affinity PD-1 mimic polypeptide has a decreased affinity for PD-L2 as compared to the affinity for PD-L2 of a corresponding PD-1 mimic polypeptide that does not have an amino acid change relative to the wild type PD-1 polypeptide (e.g., a decreased affinity for PD-L2 as compared to the affinity for PD-L2 of a corresponding native PD-1 mimic polypeptide, as defined above).

In some cases, a subject high affinity PD-1 mimic polypeptide has a greater affinity for PD-L1 than for PD-L2. For example, in some cases, subject high affinity PD-1 mimic polypeptide specifically binds to PD-L1, but not PD-L2. In some cases, a subject high affinity PD-1 mimic polypeptide has an affinity for PD-L2 that is characterized by a $K_d$ (dissociation constant) that is 2-fold or more (e.g., 5-fold or more, 10-fold or more, 100-fold or more, 500-fold or more, 1000-fold or more, 5000-fold or more, $10^4$-fold or more, $10^5$-fold or more, $10^6$-fold or more, $10^7$-fold or more, $10^8$-fold or more, etc.) greater than the $K_d$ that characterizes the affinity of the high affinity PD-1 mimic polypeptide for PD-L1. In other words, in some cases, the affinity of a subject high affinity PD-1 mimic polypeptide for PD-L1 can be 2-fold or more (e.g., 5-fold or more, 10-fold or more, 100-fold or more, 500-fold or more, 1000-fold or more, 5000-fold or more, $10^4$-fold or more, $10^5$-fold or more, $10^6$-fold or more, $10^7$-fold or more, $10^8$-fold or more, etc.) greater than the affinity of the subject high affinity PD-1 mimic polypeptide for PD-L2.

The affinity to bind to PD-L1 and/or PD-L2 can be determined, for example, by the ability of a high-affinity PD-1 mimic polypeptide to bind to PD-L1 and/or PD-L2 coated on an assay plate; displayed on a microbial cell surface; in solution; etc. The binding activity of high-affinity PD-1 mimic polypeptides of the present disclosure to PD-L1 and/or PD-L2 can be assayed by immobilizing the ligand (e.g., PD-L1 and/or PD-L2) or the high-affinity PD-1 mimic polypeptide, to a bead, substrate, cell, etc. Agents can be added in an appropriate buffer and the binding partners incubated for a period of time at a given temperature. After washes to remove unbound material, the bound protein can be released with, for example, SDS, buffers with a high pH, and the like and analyzed. For example, see FIG. 4 which depicts Surface Plasmon Resonance (SPR) plots (i.e., results from SPR experiments that tested the ability of a high affinity PD-1 mimic polypeptide to bind to PD-L1).

Binding can also be determined by, for example, measuring the ability of a unlabeled high affinity PD-1 mimic polypeptide to compete with a labeled PD-1 polypeptide (e.g., a labeled native PD-1 mimic polypeptide, as defined above) for binding to PD-L1 (for examples, see FIGS. 5A-5C and FIGS. 6A-6B). Accordingly, relative binding can be assessed by comparing the results using a candidate unlabeled high-affinity PD-1 mimic polypeptide to results using an unlabeled native PD-1 mimic polypeptide (as defined above, a PD-1 mimic polypeptide that does not have an amino acid change relative to the corresponding sequence of a wild type PD-1).

Any convenient method can be used to generate a subject high-affinity PD-1 mimic polypeptide. As one example non-limiting example, mutagenesis can be performed (beginning with a native PD-1 mimic polypeptide, or beginning with a high-affinity PD-1 mimic polypeptide for the purpose of generating a polypeptide with even greater affinity) to generate collections of mutated PD-1 mimic polypeptides. Mutagenesis can be targeted to produce changes at particular amino acids, or mutagenesis can be random. The mutated PD-1 mimic polypeptides can then be screen for their ability to bind a PD-L protein (e.g., PD-L1 and/or PD-L2). For example, a PD-L protein (or a variant of a PD-L protein, e.g., a version lacking a transmembrane domain) can be labeled (e.g., with a direct label such as a radioisotope, a fluorescent moiety, etc.; or with an indirect label such as an antigen, an affinity tag, biotin, etc.) and then can be used to contact the candidate high-affinity PD-1 mimic polypeptides (e.g., where the candidate high-affinity PD-1 mimic polypeptides can be attached to a solid surface or displayed on the membrane of a cell, e.g., a yeast cell). By varying the concentration of PD-L used, one can identify high-affinity PD-1 mimic polypeptides from among the candidates (i.e., from among the collection of mutated PD-1 mimic polypeptides). See FIG. 2A-2B for a non-limiting example of how one can identify a subject high-affinity PD-1 mimic polypeptide.

In some embodiments, a high-affinity PD-1 mimic polypeptide of the present disclosure is a fusion protein, e.g., fused in frame with a second polypeptide (a fusion partner). In some embodiments, the second polypeptide is capable of increasing the size of the fusion protein, e.g., so that the fusion protein will not be cleared from the circulation rapidly. As tissue penetration (i.e., the ability to penetrate tissues) can be a distinct advantage of using a subject high-affinity PD-1 mimic polypeptide due to its relatively small size (e.g., compared to a much larger protein such as an antibody, e.g., an anti-PD-1 or anti-PD-L antibody), in some cases, a high affinity PD-1 mimic polypeptide is not fused to a second polypeptide, or is fused to a second polypeptide that is small enough so as not to limit the tissue penetration of the high affinity PD-1 mimic polypeptide to an unacceptable level (which would depend on the context of the particular method and/or desired outcome). Thus, in some cases, the second polypeptide (i.e., the polypeptide to which a subject high-affinity PD-1 mimic polypeptide is fused) is 200 amino acids or less (e.g., 190 amino acids or less, 180 amino acids or less, 170 amino acids or less, 160 amino acids or less, 150 amino acids or less, 140 amino acids or less, 130 amino acids or less, 120 amino acids or less, 110 amino acids or less, 100 amino acids or less, 90 amino acids or less, 80 amino acids or less, 70 amino acids or less, 60 amino acids or less, 50 amino acids or less, 40 amino acids or less, or 30 amino acids or less). In some cases, the fusion protein has a molecular weight average of 200 kD or less, 150 kD or less, 100 kD or less, 90 kD or less, 80 kD or less, 70 kD or less, 60 kD or less, 50 kD or less, 40 kD or less, or 30 kD or less.

In some embodiments, the second polypeptide is part or whole of an immunoglobulin Fc region (e.g., a human immunoglobulin Fc region) (e.g., an antibody Fc sequence, a CH3 domain, and the like). In other embodiments, the second polypeptide is any suitable polypeptide that is substantially similar to an Fc, e.g., providing increased size, multimerization domains, and/or additional binding or interaction with Ig molecules. These fusion proteins can facilitate purification, multimerization, and show an increased half-life in vivo. Fusion proteins having disulfide-linked multimeric structures can also be more efficient in binding and neutralizing other molecules than a monomeric high-affinity PD-1 mimic polypeptide.

When fused to a heterologous polypeptide, the portion corresponding to the high affinity PD-1 mimic polypeptide can be referred to as the "high affinity PD-1 mimic polypeptide portion." High affinity PD-1 mimic polypeptides (e.g., the high affinity PD-1 mimic polypeptide portion) can be 70 amino acids or more in length (e.g., 75 amino acids or more, 80 amino acids or more, 85 amino acids or more, 90 amino acids or more, 95 amino acids or more, 100 amino acids or more, 105 amino acids or more, 110 amino acids or more, 115 amino acids or more, 120 amino acids or more, 125 amino acids or more, or 130 amino acids or more), up to the full-length of the portion of the wild-type protein that is N-terminal to the transmembrane domain (e.g., 165-170 amino acids for the human PD-1 protein), and can further be fused to a heterologous polypeptide, e.g., an immunoglobulin Fc. In some cases, a high affinity PD-1 mimic polypeptide (e.g., the high affinity PD-1 mimic polypeptide portion) has a length in a range of from 70 amino acids to 170 amino acids (e.g., from 70 amino acids to 166 amino acids, from 75 amino acids to 170 amino acids, from 80 amino acids to 170 amino acids, etc.).

In some embodiments, a high affinity PD-1 mimic polypeptide is fused or otherwise joined to an immunoglobulin sequence to form a chimeric protein. The immunoglobulin sequence can be an immunoglobulin constant domain(s). The immunoglobulin moiety in such chimeras may be obtained from any species, usually human, and includes IgG1, IgG2, IgG3 or IgG4 subtypes, IgA, IgE, IgD or IgM. The immunoglobulin moiety may comprise one or more domains, e.g., CH1, CH2, CH3, etc.

Chimeras constructed from a sequence linked to an appropriate immunoglobulin constant domain sequence are known in the art. In such fusions, the encoded chimeric polypeptide may retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. The precise site at which the fusion is made is not critical; particular sites are well known and may be selected in order to optimize the biological activity, secretion or binding characteristics of the high affinity PD-1 mimic polypeptide:immunoglobulin chimeras. In some embodiments, the high affinity PD-1 mimic polypeptide:immunoglobulin chimeras are assembled as monomers, or hetero- or homo-multimers, and in some cases as dimers or tetramers.

Although the presence of an immunoglobulin light chain is not required, an immunoglobulin light chain may be included, either covalently associated to a high affinity PD-1 mimic polypeptide:immunoglobulin heavy chain fusion polypeptide, or directly fused to the polypeptide. A single chain construct may be used to provide both heavy and light chain constant regions.

In other fusion protein constructs, the second polypeptide is a marker sequence, such as a peptide that facilitates purification of the fused polypeptide. For example, the marker amino acid sequence can be a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86: 821-824, 1989, for instance, hexa-histidine provides for convenient purification of the fusion protein. Another peptide tag useful for purification, the "HA" tag, corresponds to an epitope derived from the influenza hemagglutinin protein. Wilson et al., Cell 37: 767, 1984. The addition of peptide moieties to facilitate handling of polypeptides are familiar and routine techniques in the art.

In some cases, a subject high affinity PD-1 mimic polypeptide is multivalent (e.g., tetravalent).

High affinity PD-1 mimic polypeptides can be monomeric or multimeric, i.e. dimer, trimer, tetramer, etc. For example, one or more PD-L1 (and/or PD-L2) binding domains can be covalently or non-covalently linked, e.g., as a fusion protein; disulfide bonded; through biotin binding to avidin, streptavidin, etc. Such monomeric or multimeric high-affinity PD-1 mimic polypeptides are useful as single agents to stimulate an immune response (e.g., to stimulate a general immune response and/or to stimulate a response directed to a cell expressing PD-L1, e.g., a cancer cell); or in combination with other binding agents, e.g., monoclonal antibodies.

For example, a subject high affinity PD-1 mimic polypeptide can have a fusion partner where the fusion partner provides a multimerization domain (i.e., a domain that facilitates multimerization, e.g., a domain the facilitates dimerization). For example, a fusion partner can be any convenient protein-protein interaction domain (e.g., a leucine zipper motif, a synzip polypeptide (a polypeptide pair), a CH 3 domain, and the like).

High affinity PD-1 mimic polypeptides of the present disclosure can be modified, e.g., joined to a wide variety of other oligopeptides or proteins for a variety of purposes. For example, post-translationally modified, for example by prenylation, acetylation, amidation, carboxylation, glycosylation, PEGylation (covalent attachment of polyethylene glycol (PEG) polymer chains), etc. Such modifications can also include modifications of glycosylation, e.g., those made by modifying the glycosylation patterns of a polypeptide during its synthesis and processing or in further processing steps; e.g., by exposing the polypeptide to enzymes which affect glycosylation, such as mammalian glycosylating or deglycosylating enzymes. In some embodiments, a subject high affinity PD-1 mimic polypeptide has one or more phosphorylated amino acid residues, e.g., phosphotyrosine, phosphoserine, or phosphothreonine.

In some other embodiments, high affinity PD-1 mimic polypeptides of the disclosure include reagents further modified to improve their resistance to proteolytic degradation or to optimize solubility properties or to render them more suitable as a therapeutic agent. For example, variants of the present disclosure further include analogs containing residues other than naturally occurring L-amino acids, e.g., D-amino acids or non-naturally occurring synthetic amino acids. D-amino acids may be substituted for some or all of the amino acid residues.

In addition to use as a treatment for various disorders and diseases, high affinity PD-1 mimic polypeptides are useful, for example, as an adjuvant to increase immune function, (e.g., when combined with a specific binding agent, e.g., an antibody, in some cases to a tumor cell specific antibody as defined herein)(e.g., by stimulating, or reducing inhibition, of a number of immune cells, such as macrophages, dendritic cells, neutrophils, granulocytes, antigen presenting cells, T cells, and the like).

High affinity PD-1 mimic polypeptides are also useful as imaging agents, e.g., when conjugated to a detectable label, which can be used for various purposes, e.g., as diagnostic reagents. For example, in some cases a subject method is a method of diagnosing or prognosing cancer in an individual (e.g., a cancer in which the presence, level, and/or location of detectable PD-L1 can be diagnostic and/or prognostic).

In some embodiments of the disclosure, the high affinity PD-1 mimic polypeptide is coupled or conjugated to one or more imaging moieties, i.e. a detectable label. As used herein, "cytotoxic moiety" refers to a moiety that inhibits cell growth or promotes cell death when proximate to or absorbed by the cell. Suitable cytotoxic moieties in this regard include radioactive isotopes (radionuclides), chemotoxic agents such as differentiation inducers and small chemotoxic drugs, toxin proteins, and derivatives thereof.

As utilized herein, "imaging moiety", or detectable label, refers to a moiety that can be utilized to increase contrast between a tumor and the surrounding healthy tissue in a visualization technique, e.g., radiography, positron-emission tomography (PET), magnetic resonance imaging (MRI), direct or indirect visual inspection. Thus, suitable imaging moieties include radiography moieties, e.g., heavy metals and radiation emitting moieties, positron emitting moieties, magnetic resonance contrast moieties, and optically visible moieties (e.g., fluorescent or visible-spectrum dyes, visible particles, etc. It will be appreciated by one of ordinary skill that some overlap exists between what is a therapeutic moiety and what is an imaging moiety.

In general, therapeutic or imaging agents can be conjugated to a high affinity PD-1 mimic polypeptide moiety by any suitable technique, with appropriate consideration of the need for pharmacokinetic stability and reduced overall toxicity to the patient. A direct reaction between an agent and PD-L1 is possible when each possesses a functional group capable of reacting with the other. For example, a nucleophilic group, such as an amino or sulfhydryl group, may be capable of reacting with a carbonyl-containing group, such as an anhydride or an acid halide, or with an alkyl group containing a good leaving group (e.g., a halide). Alternatively, a suitable chemical linker group may be used. A linker group can function as a spacer in order to avoid interference with binding capabilities.

It will be evident to those skilled in the art that a variety of bifunctional or polyfunctional reagents, both homo- and hetero-functional (such as those described in the catalog of the Pierce Chemical Co., Rockford, Ill.), may be employed as a linker group. Coupling may be effected, for example, through amino groups, carboxyl groups, sulfhydryl groups or oxidized carbohydrate residues. There are numerous references describing such methodology. Alternatively a high affinity PD-1 mimic polypeptide is linked to the cytotoxic or imaging moiety by the use of a non-covalent binding pair, such as streptavidin/biotin, or avidin/biotin. In these embodiments, one member of the pair is covalently coupled to a high affinity PD-1 mimic polypeptide and the other member of the binding pair is covalently coupled to the cytotoxic or imaging moiety. It may be desirable to couple more than one cytotoxic and/or imaging moiety. By polyderivatizing the high affinity PD-1 mimic polypeptide, several strategies may be simultaneously implemented, an antibody may be made useful as a contrasting agent for several visualization techniques, or a therapeutic antibody may be labeled for tracking by a visualization technique.

A carrier may bear the agents in a variety of ways, including covalent bonding either directly or via a linker group, and non-covalent associations. Suitable covalent-bond carriers include proteins such as albumins, peptides, and polysaccharides such as aminodextran, each of which have multiple sites for the attachment of moieties. A carrier may also bear an agent by non-covalent associations, such as non-covalent bonding or by encapsulation Carriers and linkers specific for radionuclide agents include radiohalogenated small molecules and chelating compounds. A radionuclide chelate may be formed from chelating compounds that include those containing nitrogen and sulfur atoms as the donor atoms for binding the metal, or metal oxide, radionuclide.

Radiographic moieties for use as imaging moieties in the present disclosure include compounds and chelates with relatively large atoms, such as gold, iridium, technetium, barium, thallium, iodine, and their isotopes. In some cases, less toxic radiographic imaging moieties, such as iodine or iodine isotopes, can be utilized in the compositions and methods of the disclosure. Such moieties may be conjugated to the high affinity PD-1 mimic polypeptide through an acceptable chemical linker or chelation carrier. Positron emitting moieties for use in the present disclosure include $^{18}$F, which can be easily conjugated by a fluorination reaction with the high affinity PD-1 mimic polypeptide. Examples of PET emitters include $^{64}$Cu, $^{68}$Ga, $^{89}$Zr, and $^{18}$F.

PET imaging can include coupling a positron emitter to the protein. Examples of PET emitters include $^{64}$Cu, $^{68}$Ga, $^{89}$Zr, and $^{18}$F. These agents can be coupled to the protein using any convenient method, e.g., via chelating groups, e.g., 1,4,7,10-tetraazacyclododecane-1,4,7,10-tetraacetic acid (DOTA), 1,4,7-Triazacyclononane-1,4,7-triacetic acid (NOTA), and Desferoxamine (DFO). Such chelators can be covalently and site-specifically attached to the protein using any convenient method, e.g., by maleimide chemistry at free cysteine residues, e.g., engineered free cysteine residues such as at cysteines R87C, N91C, and/or R122C (mutations corresponding to R87C, N91C, and/or R122C relative to the PD-1 protein fragment set forth in SEQ ID NO: 2).

Single-photon emission computed tomography (SPECT) moieties for use as imaging moieties in the present disclosure. SPECT is similar to positron emission tomography (PET) in its use of radioactive tracer material and detection of gamma rays. In contrast with PET, however, the tracers used in SPECT emit gamma radiation that is measured directly, whereas PET tracers emit positrons that annihilate with electrons up to a few millimeters away, causing two gamma photons to be emitted in opposite directions.

Magnetic resonance contrast moieties can include chelates of chromium(III), manganese(II), iron(II), nickel(II), copper(II), praseodymium(III), neodymium(III), samarium (III) and ytterbium(III) ion. Because of their very strong magnetic moment, the gadolinium(III), terbium(III), dysprosium(III), holmium(III), erbium(III), and iron(III) ions are also considered as contrast moieties.

Optically visible moieties for use as imaging moieties include fluorescent dyes, or visible-spectrum dyes, visible particles, and other visible labeling moieties. Fluorescent dyes such as fluorescein, coumarin, rhodamine, bodipy Texas red, and cyanine dyes, are useful when sufficient excitation energy can be provided to the site to be inspected visually. Endoscopic visualization procedures may be more compatible with the use of such labels. Acceptable dyes include FDA-approved food dyes and colors, which are non-toxic, although pharmaceutically acceptable dyes which have been approved for internal administration are preferred.

The effective amount of an imaging conjugate composition to be given to a particular patient can depend on a variety of factors, several of which will be different from patient to patient. A competent clinician will be able to determine an effective amount to facilitate the visualization of, for example, a tumor. Dosage will depend on the treatment of the tumor, route of administration, the nature of the therapeutics, sensitivity of the tumor to the therapeutics, etc. Utilizing ordinary skill, the competent clinician will be able to optimize the dosage of a particular therapeutic or imaging composition in the course of routine clinical trials.

A typical dose may be from 0.001 to 100 milligrams of conjugate per kilogram subject body weight. Relatively large doses, in the range of 0.1 to 10 mg per kilogram of patient body weight may be used for imaging conjugates with a relatively non-toxic imaging moiety. The amount utilized will depend on the sensitivity of the imaging method, and the relative toxicity of the imaging moiety.

High affinity PD-1 mimic polypeptides of the present disclosure can be produced by any suitable means known or later discovered in the field, e.g., produced from eukaryotic or prokaryotic cells, synthesized in vitro, etc. Where the protein is produced by prokaryotic cells, it may be further processed by unfolding, e.g., heat denaturation, DTT reduction, etc. and may be further refolded, using methods known in the art.

In some cases, a subject high affinity PD-1 mimic polypeptide includes one or more mutations corresponding to R87C, N91C, and/or R122C relative to the PD-1 protein fragment set forth in SEQ ID NO: 2. In some cases, a subject high affinity PD-1 mimic polypeptide includes the amino acid sequence set forth in any of SEQ ID NOs: 3-25 and 39-46. As noted above, in some cases, the high affinity PD-1 mimic polypeptide includes a detectable label (e.g., a positron-emission tomography (PET) imaging label). In some cases, a subject high affinity PD-1 mimic polypeptide includes one or more mutations corresponding to R87C, N91C, and/or R122C relative to the PD-1 protein fragment set forth in SEQ ID NO: 2, and also includes a detectable label (e.g., a positron-emission tomography (PET) imaging label). In some cases, a subject high affinity PD-1 mimic polypeptide (e.g., a subject high affinity PD-1 mimic polypeptide that includes one or more mutations corresponding to R87C, N91C, and/or R122C relative to the PD-1 protein fragment set forth in SEQ ID NO: 2) includes an imaging moiety for positron-emission tomography (PET) imaging (e.g., a PET emitters such as $^{64}Cu$, $^{68}Ga$, $^{89}Zr$, and $^{18}F$), SPECT (e.g., a gamma ray emitter), and/or Fluorescencse imaging (e.g., a fluorescent dye such as fluorescein, coumarin, rhodamine, bodipy Texas red, a cyanine dyes, and the like).

The polypeptides may be prepared by cell-free translation systems, or synthetic in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized. One of skill in the art can readily utilize well-known codon usage tables and synthetic methods to provide a suitable coding sequence for any of the polypeptides of the disclosure. The nucleic acids may be isolated and obtained in substantial purity. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome. The nucleic acids of the disclosure can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the disclosure can be introduced into suitable host cells using a variety of techniques available in the art.

According to the present disclosure, high affinity PD-1 mimic polypeptides can be provided in pharmaceutical compositions (pharmaceutical formulations) suitable for therapeutic use, e.g., for human treatment. In some embodiments, pharmaceutical compositions of the present disclosure include one or more therapeutic entities of the present disclosure or pharmaceutically acceptable salts, esters or solvates thereof. In some other embodiments, pharmaceutical compositions of the present disclosure include one or more therapeutic entities of the present disclosure in combination with another therapeutic agent, e.g., another anti-tumor agent.

Therapeutic entities of the present disclosure are often administered as pharmaceutical compositions (pharmaceutical formulations) comprising an active therapeutic agent and a other pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like In still some other embodiments, pharmaceutical compositions of the present disclosure can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

In some embodiments, a subject high affinity PD-1 mimic polypeptide is multispecific (e.g., bispecific). The terms "multispecific" or "bispecific" are commonly used in the art to refer to antibodies that recognize two or more different antigens by virtue of possessing at least one region (e.g., derived from a variable region of a first antibody) that is specific for a first antigen, and at least a second region (e.g., derived from a variable region of a second antibody) that is specific for a second antigen (These antibodies are also known as bifunctional antibodies or multifunctional antibodies). A bispecific antibody specifically binds to two target antigens and is thus one type of multispecific antibody. Multispecific antibodies can be produced by recombinant DNA methods or include, but are not limited to, antibodies produced chemically by any convenient method. Bispecific antibodies include all antibodies or conjugates of antibodies, or polymeric forms of antibodies which are capable of recognizing two different antigens. Bispecific antibodies include antibodies that have been reduced and reformed so as to retain their bivalent characteristics and to antibodies that have been chemically coupled so that they can have several antigen recognition sites for each antigen.

In some embodiments, a subject high affinity PD-1 mimic polypeptide is multispecific (e.g., bispecific). For example, a subject high affinity PD-1 mimic polypeptide can be multispecific (e.g., bispecific) such that a first region of the polypeptide corresponds to a subject high affinity PD-1 mimic polypeptide sequence (which specifically binds PD-L1), and a second region (the fusion partner) (e.g., an antibody derived sequence, e.g., a binding region of an antibody comprising that CDRs of the antibody; a specific binding polypeptide; a binding portion of a ligand; a binding portion of a receptor, etc.) that specifically binds to another target (e.g., antigen, a receptor, a ligand, etc.). For example, in some cases, a high affinity PD-1 mimic polypeptide is fused to a second polypeptide (a fusion partner) that binds specifically to a target sequence other than PD-L1. In some cases, a high affinity PD-1 mimic polypeptide is fused to a second polypeptide (a fusion partner) that binds specifically to a target other than PD-L1 (thus, such a multimeric high affinity PD-1 mimic polypeptide can be bispecific, and would therefore bind 2 different targets/moieties).

In some cases, a subject multimeric high affinity PD-1 mimic polypeptide alters signaling as a result of the fusion partner binding to its target. For example, in some cases, the fusion partner includes, as a fusion partner, a ligand or a binding region of a ligand (e.g., a cytokine, an attenuated cytokine, etc.), and the multimeric high affinity PD-1 mimic polypeptide alters signaling when the ligand binds to its target (e.g., a receptor). Likewise, in some cases, the fusion partner includes, as a fusion partner, a receptor or a binding region of a receptor, and the multimeric high affinity PD-1 mimic polypeptide alters signaling when the receptor binds to its target (e.g., a ligand).

Examples of suitable fusion partners include, but are not limited to the binding sequences from antibodies against cancer cell markers such as CD19, CD20, CD22, CD24, CD25, CD30, CD33, CD38, CD44, CD52, CD56, CD70, CD96, CD97, CD99, CD123, CD279 (PD-1), EGFR, HER2, CD117, C-Met, PTHR2, HAVCR2 (TIM3), etc. Examples of antibodies with CDRs that provide specific binding to a cancer cell marker include, but are not limited to: CETUX-IMAB (binds EGFR), PANITUMUMAB (binds EGFR), RITUXIMAB (binds CD20), TRASTUZUMAB (binds HER2), PERTUZUMAB (binds HER2), ALEMTUZUMAB (binds CD52), BRENTUXIMAB (binds CD30), and the like.

Examples of suitable fusion partners include a cytokine; an attenuated cytokine; a 41BB-agonist; CD40-agonist; an inhibitor of BTLA and/or CD160; and an inhibitor of TIM3 and/or CEACAM1. For example, in some cases, a high affinity PD-1 mimic polypeptide is a multispecific high affinity PD-1 mimic polypeptide, and is fused to one or more fusion partners selected from: a cytokine; an attenuated cytokine; a 41 BB-agonist; CD40-agonist; an inhibitor of BTLA and/or CD160; and an inhibitor of TIM3 and/or CEACAM1. For example, a multispecific high affinity PD-1 mimic polypeptide can be fused to a fusion partner that is a modified cytokine that has a decreased affinity (reduced relative to a corresponding wild type cytokine) for its ligand/receptor. Such a modified cytokine is referred to herein as an 'attenuated cytokine'. An example of an attenuated cytokine (one example of a possible fusion partner) is an IL-2 protein that has mutations that decrease affinity for two of the IL-2 receptor subunits (e.g., F42A to decrease binding to CD25 and D20T to decrease binding to CD122) (e.g., see SEQ ID NO: 39).

In some cases a high affinity PD-1 mimic polypeptide is a multispecific high affinity PD-1 mimic polypeptide, and has a fusion partner that is a 41BB-agonist (e.g., 41BBL, e.g., see SEQ ID NO: 40). In some cases a high affinity PD-1 mimic polypeptide is a multispecific high affinity PD-1 mimic polypeptide, and has a fusion partner that is a CD40-agonist (e.g., CD40L, e.g., see SEQ ID NO: 41). In some cases a high affinity PD-1 mimic polypeptide is a multispecific high affinity PD-1 mimic polypeptide, and has a fusion partner that is an inhibitor of BTLA and/or CD160 (e.g., see SEQ ID NO: 42). In some cases a high affinity PD-1 mimic polypeptide is a multispecific high affinity PD-1 mimic polypeptide, and has a fusion partner that is an inhibitor of TIM3 and/or CEACAM1 (e.g., see SEQ ID NO: 43).

In some embodiments, a subject high affinity PD-1 mimic polypeptide and a fusion partner are separated by a linker (e.g., a linker polypeptide). A linker polypeptide may have any of a variety of amino acid sequences. Proteins can be joined by a linker polypeptide can be of a flexible nature (e.g., a flexible linker polypeptide), although other chemical linkages are not excluded. Suitable linkers include polypeptides of between about 6 amino acids and about 40 amino acids in length, or between about 6 amino acids and about 25 amino acids in length. These linkers can be produced by using synthetic, linker-encoding oligonucleotides to couple the proteins. Peptide linkers with a degree of flexibility can be used. The linking peptides may have virtually any amino acid sequence, bearing in mind that the in some case, linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

Examples of linker polypeptides include glycine polymers $(G)_n$, glycine-serine polymers (including, for example, $(GS)_n$, $GSGGS_n$ (SEQ ID NO: 47), $GGSGGS_n$ (SEQ ID NO: 48), and $GGGS_n$ (SEQ ID NO: 49), where n is an integer of at least one (e.g., where n is an integer of one, two, three, four, five, six, seven, eight, nine, ten, or greater than ten), glycine-alanine polymers, alanine-serine polymers. Exemplary linkers can comprise amino acid sequences including, but not limited to, GGSG (SEQ ID NO: 50), GGSGG (SEQ ID NO: 51), GSGSG (SEQ ID NO: 52), GSGGG (SEQ ID NO: 53), GGGSG (SEQ ID NO: 54), GSSSG (SEQ ID NO: 55), and the like. The ordinarily skilled artisan will recognize that design of a peptide conjugated to any elements described above can include linkers that are all or partially flexible, such that the linker can include a flexible linker as well as one or more portions that confer less flexible structure.

Nucleic Acids.

The disclosure also provides isolated nucleic acids encoding a subject high affinity PD-1 mimic polypeptide, vectors and host cells comprising the nucleic acid, and recombinant techniques for the production of the high affinity PD-1 mimic polypeptide.

For recombinant production of the high affinity PD-1 mimic polypeptide, the nucleic acid encoding the high affinity PD-1 mimic polypeptide can be inserted into a replicable vector for further cloning (amplification of the DNA) or for expression. DNA encoding a subject high affinity PD-1 mimic polypeptide can be readily isolated and sequenced using conventional procedures. Many vectors are available. The vector components generally include, but are not limited to, one or more of the following: a signal sequence, an origin of replication, one or more marker genes, an enhancer element, a promoter, and a transcription termination sequence.

A subject high affinity PD-1 mimic polypeptide of this disclosure may be produced recombinantly not only directly, but also as a fusion polypeptide with a heterologous or homologous polypeptide, which can include a signal sequence or other polypeptide having a specific cleavage site at the N-terminus of the mature protein or polypeptide, an immunoglobulin constant region sequence, and the like. A heterologous signal sequence selected preferably may be one that is recognized and processed (i.e., cleaved by a signal peptidase) by the host cell. For prokaryotic host cells that do not recognize and process the native antibody signal sequence, the signal sequence is substituted by a prokaryotic signal sequence selected.

An "isolated" nucleic acid molecule is a nucleic acid molecule that is identified and separated from at least one contaminant nucleic acid molecule with which it is ordinarily associated prior to isolation. An isolated nucleic acid molecule is other than in the form or setting in which it can be found in nature. Isolated nucleic acid molecules therefore are distinguished from the nucleic acid molecule as it exists in natural cells.

Examples of suitable host cells for cloning or expressing subject nucleic acids include, but are not necessary limited to prokaryote, yeast, or higher eukaryote cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1.982)); MRC 5 cells; FS4 cells; and a human hepatoma line (Hep G2). Host cells are transformed with the above-described expression or cloning vectors for high affinity PD-1 mimic polypeptide production and cultured in conventional nutrient media modified as appropriate for inducing promoters, selecting transformants, or amplifying the genes encoding the desired sequences.

Introduction of Nucleic Acids.

In some cases, as subject high affinity PD-1 mimic polypeptide is administered to an individual by providing the high affinity PD-1 mimic polypeptide as a nucleic acid (e.g., an RNA, e.g., an mRNA; or a DNA, e.g., a recombinant expression vector, a linear DNA, a circular DNA, a plasmid, a viral vector, etc.) encoding the high affinity PD-1 mimic polypeptide. This disclosure provides such methods and also the nucleic acids for such methods.

For example, an mRNA encoding a subject high affinity PD-1 mimic polypeptide can be introduced into a cell, and the cell can then secret the translated protein. As another example, a DNA (e.g., a recombinant expression vector, a linear DNA, a circular DNA, a plasmid, a viral vector, etc.) encoding a subject high affinity PD-1 mimic polypeptide can be introduced into a cell and the cell can then produce and secret the encoded protein. Therefore, in some cases, a nucleic acid encoding a subject high affinity PD-1 mimic polypeptide includes a nucleotide sequence encoding a signal sequence (e.g., upstream of and in frame with the nucleotide sequence that encodes the high affinity PD-1 mimic polypeptide). As would be readily recognized by one of ordinary skill in the art, a signal sequence as referred to here is an amino acid sequence at or near the amino terminus of a nascent protein that can be recognized by the signal recognition particle of a eukaryotic cell, resulting in transport of the protein into the secretory pathway of the cell, thus facilitating secretion of a protein from the cell (e.g., the signal sequence can be cleaved from the protein). Any convenient signal sequence can be used.

In some cases, a nucleic acid encoding a subject high affinity PD-1 mimic polypeptide is introduced into a cell (e.g., in vivo, ex vivo, in vitro) and the cell can then produce and secret the encoded protein. In some cases, the cell is in vitro. In some cases, the cell is ex vivo. In some cases, the cell is in vivo. For example, in some cases, a nucleic acid encoding a high affinity PD-1 mimic polypeptide is introduced into a cell that is in vivo (e.g., in some cases, a nucleic acid encoding a high affinity PD-1 mimic polypeptide is introduced into a cell in vivo by administering the nucleic acid to an individual). In some cases, a nucleic acid encoding a subject high affinity PD-1 mimic polypeptide is introduced into a cell (e.g., ex vivo, in vitro) and the cell is then introduced into an individual. In some cases, the cell is autologous to the individual (e.g., the cell was isolated from the individual or is the progeny of a cell that was isolated from the individual).

In some cases (e.g., in any of the above scenarios, e.g., in vitro, ex vivo, in vivo), the cell into which a nucleic acid encoding a subject high affinity PD-1 mimic polypeptide is introduced is an immune cell (e.g., a leukocyte, a T cell, a CD8 T cell, a CD4 T cell, a memory/effector T cell, a B cell, an antigen presenting cell (APC), a dendritic cell, a macrophage, a monocyte, an NK cell, and the like). In some cases (e.g., in any of the above scenarios, e.g., in vitro, ex vivo, in vivo), the cell into which a nucleic acid encoding a subject high affinity PD-1 mimic polypeptide is introduced is a stem cell (e.g., a hematopoietic stem cell, a pluripotent stem cell, a multipotent stem cell, a tissue restricted stem cell, etc.). In some cases (e.g., in any of the above scenarios, e.g., in vitro, ex vivo, in vivo), the cell into which a nucleic acid encoding a subject high affinity PD-1 mimic polypeptide is introduced is an immune cell (e.g., a leukocyte, a T cell, a CD8 T cell, a CD4 T cell, a memory/effector T cell, a B cell, an antigen presenting cell (APC), a dendritic cell, a macrophage, a monocyte, an NK cell, and the like) or a stem cell (e.g., a hematopoietic stem cell, a pluripotent stem cell, a multipotent stem cell, a tissue restricted stem cell, etc.).

In some cases (e.g., in any of the above scenarios, e.g., in vitro, ex vivo, in vivo), the cell into which a nucleic acid encoding a subject high affinity PD-1 mimic polypeptide is introduced is a T cell with an engineered T cell receptor (TCR) (such a cell is also referred to herein as a "TCR-engineered T cell"). As used herein the term "TCR-engineered T cell" refers to any T-cell having a T cell receptor that is heterologous to the T cell. Suitable examples include, but are not limited to (i) a T cell that includes a chimeric antigen receptor (CAR) (such a cell is also referred to herein as a "CAR-T cell" or an "engineered CAR-T cell"); and (ii) a T cell that includes a heterologous TCR that binds to an antigen such as a cancer antigen, e.g., MART1, NY-ESO-1, p53, and the like (e.g., such a cell can include a nucleic acid encoding the TcR-alpha and TcR-beta polypeptides of a heterologous TCR, such as a TCR that binds to an antigen such as a cancer antigen, e.g., MART1, NY-ESO-1, p53, and the like).

In some cases, a suitable TCR-engineered T cell can have an engineered TCR (e.g., a heterologous TCR that binds to an antigen, a CAR, etc.) that binds to a cancer marker (e.g., CD19, CD20, CD22, CD24, CD25, CD30, CD33, CD38, CD44, CD52, CD56, CD70, CD96, CD97, CD99, CD123, CD279 (PD-1), EGFR, HER2, CD117, C-Met, PTHR2, and/or HAVCR2 (TIM3)). In some cases, a suitable TCR-engineered T cell can have an engineered TCR (e.g., a heterologous TCR that binds to an antigen, a CAR, etc.) that binds to a target antigen selected from PD-L1 (e.g., a CAR derived from an anti-PD-L1 antibody) and PD-1 (e.g., a CAR derived from an anti-PD-1 antibody). In some cases, a suitable TCR-engineered T cell can have an engineered TCR (e.g., a heterologous TCR that binds to an antigen, a CAR, etc.) that binds to PD-L1 (e.g., a CAR derived from an anti-PD-L1 antibody). In some cases, a suitable TCR-engineered T cell can have an engineered TCR (e.g., a heterologous TCR that binds to an antigen, a CAR, etc.) that binds to PD-1 (e.g., a CAR derived from an anti-PD-1 antibody). In some cases, a suitable TCR-engineered T cell can have an engineered TCR (e.g., a heterologous TCR that binds to an antigen, a CAR, etc.) that binds to CD19 (e.g., the 1 D3 CAR).

In some cases, a nucleic acid encoding a subject high affinity PD-1 mimic polypeptide also includes a nucleotide sequence encoding a T cell receptor (TCR). In some such case, the nucleic acid includes nucleotide sequences encoding both a TCR alpha polypeptide, and a TCR beta polypeptide of the TCR. In some cases, a nucleic acid encoding a subject high affinity PD-1 mimic polypeptide also includes a nucleotide sequence encoding the TcR-alpha and TcR-beta polypeptides of a heterologous TCR (such as a TCR that binds to an antigen such as a cancer antigen, e.g., MART1, NY-ESO-1, p53, and the like) and/or encodes a CAR (e.g., a first generation CAR, a second generation CAR, a third generation CAR, and the like). The various components, including the sequence encoding a subject high affinity PD-1 mimic polypeptide as well as the sequences encoding the TcR-alpha and TcR-beta polypeptides of a heterologous TCR and the sequence encoding a CAR are modular. Thus, the various sequences can each be operably linked to the same or different promoters. Those components that are operably linked to a same promoter can be separated by sequences that allow for the proteins to eventually exist as separate polypeptides (e.g., an internal ribosome entry site (IRES), 2A peptide sequences, etc.). Examples of various possible arrangements include, but are not limited to those depicted in FIGS. 20A-20E and FIGS. 21A-21D. Thus, examples of nucleic acids encoding a subject high affinity PD-1 mimic polypeptide include, but are not limited to, those depicted in FIGS. 20A-20E and FIGS. 21A-21D.

A "vector" or "expression vector" is a replicon, such as plasmid, phage, virus, or cosmid, to which another DNA segment, i.e. an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence if the promoter affects its transcription or expression.

The terms "recombinant expression vector," or "DNA construct" or "expression vector" and similar terms of the art are used interchangeably herein to refer to a DNA molecule comprising a vector and at least one insert. Recombinant expression vectors can be generated for the purpose of expressing and/or propagating the insert(s), or for the construction of other recombinant nucleotide sequences. The insert(s) (e.g., a nucleotide sequence encoding a subject high affinity PD-1 mimic polypeptide) may or may not be operably linked to a promoter sequence and may or may not be operably linked to DNA regulatory sequences. Thus in some cases, a nucleotide sequence encoding a subject high affinity PD-1 mimic polypeptide is operably linked to a promoter (e.g., one that is operable in a desired cell type, e.g., a eukaryotic cell, a mammalian cell, a primate cell, a human cell, an immune cell, a leukocyte, a T cell, a CD8 T cell, a CD4 T cell, a memory/effector T cell, a B cell, an antigen presenting cell (APC), a dendritic cell, a macrophage, a monocyte, an NK cell, a stem cell, a hematopoietic stem cell, a pluripotent stem cell, a multipotent stem cell, a tissue restricted stem cell, etc.).

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; etc.

In some embodiments, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used and the choice of suitable promoter (e.g., a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) will depend on the organism. For example, various spatially restricted promoters are known for plants, flies, worms, mammals, mice, etc. Thus, a spatially restricted promoter can be used to regulate the expression of a nucleic acid encoding a subject site-directed modifying polypeptide in a wide variety of different tissues and cell types, depending on the organism. Some spatially restricted promoters are also temporally restricted such that the promoter is in the "ON" state or "OFF" state during specific stages of embryonic development or during specific stages of a biological process (e.g., hair follicle cycle in mice).

For illustration purposes, examples of spatially restricted promoters include, but are not limited to, neuron-specific promoters, adipocyte-specific promoters, cardiomyocyte-specific promoters, smooth muscle-specific promoters, photoreceptor-specific promoters, etc. Neuron-specific spatially restricted promoters include, but are not limited to, a neuron-specific enolase (NSE) promoter (see, e.g., EMBL HSENO2, X51956); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19; and Llewellyn, et al. (2010) Nat. Med. 16(10):1161-1166); a serotonin receptor promoter (see, e.g., GenBank S62283); a tyrosine hydroxylase promoter (TH) (see, e.g., Oh et al. (2009) Gene Ther 16:437; Sasaoka et al. (1992) Mol. Brain Res. 16:274; Boundy et al. (1998) J. Neurosci. 18:9989; and Kaneda et al. (1991) Neuron 6:583-594); a GnRH promoter (see, e.g., Radovick et al. (1991) Proc. Natl. Acad. Sci. USA 88:3402-3406); an L7 promoter (see, e.g., Oberdick et al. (1990) Science 248:223-226); a DNMT promoter (see, e.g., Bartge et al. (1988) Proc. Natl. Acad. Sci. USA 85:3648-3652); an enkephalin promoter (see, e.g., Comb et al. (1988) EMBO J. 17:3793-3805); a myelin basic protein (MBP) promoter; a Ca2+-calmodulin-dependent protein kinase II-alpha (CamKIIα) promoter (see, e.g., Mayford et al. (1996) Proc. Natl. Acad. Sci. USA 93:13250; and Casanova et al. (2001) Genesis 31:37); a CMV enhancer/platelet-derived growth factor-β promoter (see, e.g., Liu et al. (2004) Gene Therapy 11:52-60); and the like.

Adipocyte-specific spatially restricted promoters include, but are not limited to aP2 gene promoter/enhancer, e.g., a region from −5.4 kb to +21 bp of a human aP2 gene (see, e.g., Tozzo et al. (1997) Endocrinol. 138:1604; Ross et al. (1990) Proc. Natl. Acad. Sci. USA 87:9590; and Pavjani et al. (2005) Nat. Med. 11:797); a glucose transporter-4 (GLUT4) promoter (see, e.g., Knight et al. (2003) Proc. Natl. Acad. Sci. USA 100:14725); a fatty acid translocase (FAT/CD36) promoter (see, e.g., Kuriki et al. (2002) Biol. Pharm. Bull. 25:1476; and Sato et al. (2002) J. Biol. Chem. 277:15703); a stearoyl-CoA desaturase-1 (SCD1) promoter (Tabor et al. (1999) J. Biol. Chem. 274:20603); a leptin promoter (see, e.g., Mason et al. (1998) Endocrinol. 139: 1013; and Chen et al. (1999) Biochem. Biophys. Res. Comm. 262:187); an adiponectin promoter (see, e.g., Kita et al. (2005) Biochem. Biophys. Res. Comm. 331:484; and Chakrabarti (2010) Endocrinol. 151:2408); an adipsin promoter (see, e.g., Platt et al. (1989) Proc. Natl. Acad. Sci. USA 86:7490); a resistin promoter (see, e.g., Seo et al. (2003) Molec. Endocrinol. 17:1522); and the like.

Cardiomyocyte-specific spatially restricted promoters include, but are not limited to control sequences derived from the following genes: myosin light chain-2, α-myosin heavy chain, AE3, cardiac troponin C, cardiac actin, and the like. Franz et al. (1997) Cardiovasc. Res. 35:560-566; Robbins et al. (1995) Ann. N.Y. Acad. Sci. 752:492-505; Linn et al. (1995) Circ. Res. 76:584-591; Parmacek et al. (1994) Mol. Cell. Biol. 14:1870-1885; Hunter et al. (1993) Hypertension 22:608-617; and Sartorelli et al. (1992) Proc. Natl. Acad. Sci. USA 89:4047-4051.

Smooth muscle-specific spatially restricted promoters include, but are not limited to an SM22α promoter (see, e.g., Akyürek et al. (2000) Mol. Med. 6:983; and U.S. Pat. No.

7,169,874); a smoothelin promoter (see, e.g., WO 2001/018048); an α-smooth muscle actin promoter; and the like. For example, a 0.4 kb region of the SM22α promoter, within which lie two CArG elements, has been shown to mediate vascular smooth muscle cell-specific expression (see, e.g., Kim, et al. (1997) Mol. Cell. Biol. 17, 2266-2278; Li, et al., (1996) J. Cell Biol. 132, 849-859; and Moessler, et al. (1996) Development 122, 2415-2425).

Photoreceptor-specific spatially restricted promoters include, but are not limited to, a rhodopsin promoter; a rhodopsin kinase promoter (Young et al. (2003) Ophthalmol. Vis. Sci. 44:4076); a beta phosphodiesterase gene promoter (Nicoud et al. (2007) J. Gene Med. 9:1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) Exp Eye Res. 55:225); and the like.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., DNA-targeting RNA) or a coding sequence (e.g., site-directed modifying polypeptide, or Cas9/Csn1 polypeptide) and/or regulate translation of an encoded polypeptide.

Suitable expression vectors include, but are not limited to, viral vectors (e.g., viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

Also provided in this disclosure are cells that include a nucleic acid (e.g., as described above) that includes a nucleotide sequence encoding a subject high affinity PD-1 mimic polypeptide. Such a cell can be a cell from any organism (e.g., a bacterial cell, an archaeal cell, a cell of a single-cell eukaryotic organism, a plant cell, an algal cell, a fungal cell (e.g., a yeast cell), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.).

Methods of Use

Methods are provided for treating, reducing and/or or preventing cancer; treating, reducing and/or or preventing infection (e.g., chronic infection); and/or for treating, reducing and/or or preventing an immunological disease or disorder (e.g., an inflammatory disease, a condition associated with immunosuppression, etc.)(e.g., multiple sclerosis, arthritis, and the like). For example, in some cases, a subject high affinity PD-1 mimic polypeptide can be used as an immune stimulant (e.g., used for immunopotentiation).

In some cases, subject methods result in the reduction in the number of cancer cells in an individual. In some cases, subject methods result in a reduction of tumor size. In some cases, subject methods result in a reduction of tumor size. In some cases, subject methods reduce the binding of PD-1 on a first cell with PD-L1 on a second cell.

In some cases, a subject method is a method of diagnosing and/or prognosing for an individual (e.g., diagnosing and/or prognosing cancer in an individual). For example, hiigh affinity PD-1 mimic polypeptides are useful as imaging agents, e.g., when conjugated to a detectable label such as a PET label and/or fluorescent label (e.g., as described elsewhere in this disclosure), which can be used for various purposes such as diagnostic/prognostic reagents. For example, in some cases a subject method is a method of diagnosing or prognosing cancer in an individual (e.g., a cancer in which the presence, level, and/or location of detectable PD-L1 can be diagnostic and/or prognostic).

Inhibition of PD-1 mediated cellular signaling by therapeutic agents (e.g., a subject high-affinity PD-1 mimic polypeptide) can activate immune cells (e.g., T cells, B cells, NK cells, etc.), and therefore enhance immune cell functions such as inhibiting cancer cell growth and/or viral infection, and restore immune surveillance and immune memory function to treat human disease. Examples of symptoms, illnesses, and/or diseases that can be treated with a subject high-affinity PD-1 mimic polypeptide include, but are not limited to cancer (any form of cancer, including but not limited to: carcinomas, soft tissue tumors, sarcomas, teratomas, melanomas, leukemias, lymphomas, brain cancers, solid tumors, mesothelioma (MSTO), etc.); infection (e.g., chronic infection); and/or an immunological disease or disorder (e.g., an inflammatory disease)(e.g., multiple sclerosis, arthritis, and the like). For example, in some cases, a subject high affinity PD-1 mimic polypeptide can be used as an immune stimulant (e.g., used for immunopotentiation). Any disease, disorder or ailment that involves immunosuppression (e.g., caused by an immunosuppressive signal induced by PD-1, PD-L1, or PD-L2 signaling) can be treated using a subject high affinity PD-1 mimic polypeptide.

Any cancer is a suitable cancer to be treated by the subject methods and compositions. In some cases, cancer cells of the cancer express PD-L1 (i.e. are positive for PD-L1 expression). In some cases, cancer cells of the cancer do not express PD-L1, however such cancers can still be treated with a subject high-affinity PD-1 mimic polypeptide (e.g., due to immunopotentiation by the high-affinity PD-1 mimic polypeptide).

As used herein "cancer" includes any form of cancer, including but not limited to solid tumor cancers (e.g., lung, prostate, breast, bladder, colon, ovarian, pancreas, kidney, liver, glioblastoma, medulloblastoma, leiomyosarcoma, head & neck squamous cell carcinomas, melanomas, neuroendocrine; etc.) and liquid cancers (e.g., hematological cancers); carcinomas; soft tissue tumors; sarcomas; teratomas; melanomas; leukemias; lymphomas; and brain cancers, including minimal residual disease, and including both primary and metastatic tumors. Any cancer is a suitable cancer to be treated by the subject methods and compositions. In some cases, the cancer cells express PD-L1. In some cases, the cancer cells do not express PD-L1 (e.g., in such cases, cells of the immune system of the individual being treated express PD-L1).

Carcinomas are malignancies that originate in the epithelial tissues. Epithelial cells cover the external surface of the body, line the internal cavities, and form the lining of glandular tissues. Examples of carcinomas include, but are not limited to: adenocarcinoma (cancer that begins in glandular (secretory) cells), e.g., cancers of the breast, pancreas, lung, prostate, and colon can be adenocarcinomas; adrenocortical carcinoma; hepatocellular carcinoma; renal cell carcinoma; ovarian carcinoma; carcinoma in situ; ductal carcinoma; carcinoma of the breast; basal cell carcinoma; squamous cell carcinoma; transitional cell carcinoma; colon carcinoma; nasopharyngeal carcinoma; multilocular cystic renal cell carcinoma; oat cell carcinoma; large cell lung carcinoma; small cell lung carcinoma; non-small cell lung carcinoma; and the like. Carcinomas may be found in prostate, pancreas, colon, brain (usually as secondary metastases), lung, breast, skin, etc.

Soft tissue tumors are a highly diverse group of rare tumors that are derived from connective tissue. Examples of soft tissue tumors include, but are not limited to: alveolar soft part sarcoma; angiomatoid fibrous histiocytoma; chondromyoxid fibroma; skeletal chondrosarcoma; extraskeletal myxoid chondrosarcoma; clear cell sarcoma; desmoplastic small round-cell tumor; dermatofibrosarcoma protuberans; endometrial stromal tumor; Ewing's sarcoma; fibromatosis (Desmoid); fibrosarcoma, infantile; gastrointestinal stromal tumor; bone giant cell tumor; tenosynovial giant cell tumor; inflammatory myofibroblastic tumor; uterine leiomyoma; leiomyosarcoma; lipoblastoma; typical lipoma; spindle cell or pleomorphic lipoma; atypical lipoma; chondroid lipoma; well-differentiated liposarcoma; myxoid/round cell liposarcoma; pleomorphic liposarcoma; myxoid malignant fibrous histiocytoma; high-grade malignant fibrous histiocytoma; myxofibrosarcoma; malignant peripheral nerve sheath tumor; mesothelioma; neuroblastoma; osteochondroma; osteosarcoma; primitive neuroectodermal tumor; alveolar rhabdomyosarcoma; embryonal rhabdomyosarcoma; benign or malignant schwannoma; synovial sarcoma; Evan's tumor; nodular fasciitis; desmoid-type fibromatosis; solitary fibrous tumor; dermatofibrosarcoma protuberans (DFSP); angiosarcoma; epithelioid hemangioendothelioma; tenosynovial giant cell tumor (TGCT); pigmented villonodular synovitis (PVNS); fibrous dysplasia; myxofibrosarcoma; fibrosarcoma; synovial sarcoma; malignant peripheral nerve sheath tumor; neurofibroma; and pleomorphic adenoma of soft tissue; and neoplasias derived from fibroblasts, myofibroblasts, histiocytes, vascular cells/endothelial cells and nerve sheath cells.

A sarcoma is a rare type of cancer that arises in cells of mesenchymal origin, e.g., in bone or in the soft tissues of the body, including cartilage, fat, muscle, blood vessels, fibrous tissue, or other connective or supportive tissue. Different types of sarcoma are based on where the cancer forms. For example, osteosarcoma forms in bone, liposarcoma forms in fat, and rhabdomyosarcoma forms in muscle. Examples of sarcomas include, but are not limited to: askin's tumor; sarcoma botryoides; chondrosarcoma; ewing's sarcoma; malignant hemangioendothelioma; malignant schwannoma; osteosarcoma; and soft tissue sarcomas (e.g., alveolar soft part sarcoma; angiosarcoma; cystosarcoma phyllodesdermatofibrosarcoma protuberans (DFSP); desmoid tumor; desmoplastic small round cell tumor; epithelioid sarcoma; extraskeletal chondrosarcoma; extraskeletal osteosarcoma; fibrosarcoma; gastrointestinal stromal tumor (GIST); hemangiopericytoma; hemangiosarcoma (more commonly referred to as "angiosarcoma"); kaposi's sarcoma; leiomyosarcoma; liposarcoma; lymphangiosarcoma; malignant peripheral nerve sheath tumor (MPNST); neurofibrosarcoma; synovial sarcoma; undifferentiated pleomorphic sarcoma, and the like).

A teratoma is a type of germ cell tumor that may contain several different types of tissue (e.g., can include tissues derived from any and/or all of the three germ layers: endoderm, mesoderm, and ectoderm), including for example, hair, muscle, and bone. Teratomas occur most often in the ovaries in women, the testicles in men, and the tailbone in children.

Melanoma is a form of cancer that begins in melanocytes (cells that make the pigment melanin). It may begin in a mole (skin melanoma), but can also begin in other pigmented tissues, such as in the eye or in the intestines.

Leukemias are cancers that start in blood-forming tissue, such as the bone marrow, and causes large numbers of abnormal blood cells to be produced and enter the bloodstream. For example, leukemias can originate in bone marrow-derived cells that normally mature in the bloodstream. Leukemias are named for how quickly the disease develops and progresses (e.g., acute versus chronic) and for the type of white blood cell that is effected (e.g., myeloid versus lymphoid). Myeloid leukemias are also called myelogenous or myeloblastic leukemias. Lymphoid leukemias are also called lymphoblastic or lymphocytic leukemia. Lymphoid leukemia cells may collect in the lymph nodes, which can become swollen. Examples of leukemias include, but are not limited to: Acute myeloid leukemia (AML), Acute lymphoblastic leukemia (ALL), Chronic myeloid leukemia (CML), and Chronic lymphocytic leukemia (CLL).

Lymphomas are cancers that begin in cells of the immune system. For example, lymphomas can originate in bone marrow-derived cells that normally mature in the lymphatic system. There are two basic categories of lymphomas. One kind is Hodgkin lymphoma (HL), which is marked by the presence of a type of cell called the Reed-Sternberg cell. There are currently 6 recognized types of HL. Examples of Hodgkin lymphomas include: nodular sclerosis classical Hodgkin lymphoma (CHL), mixed cellularity CHL, lymphocyte-depletion CHL, lymphocyte-rich CHL, and nodular lymphocyte predominant HL.

The other category of lymphoma is non-Hodgkin lymphomas (NHL), which includes a large, diverse group of cancers of immune system cells. Non-Hodgkin lymphomas can be further divided into cancers that have an indolent (slow-growing) course and those that have an aggressive (fast-growing) course. There are currently 61 recognized types of NHL. Examples of non-Hodgkin lymphomas include, but are not limited to: AIDS-related Lymphomas, anaplastic large-cell lymphoma, angioimmunoblastic lymphoma, blastic NK-cell lymphoma, Burkitt's lymphoma, Burkitt-like lymphoma (small non-cleaved cell lymphoma), chronic lymphocytic leukemia/small lymphocytic lymphoma, cutaneous T-Cell lymphoma, diffuse large B-Cell lymphoma, enteropathy-type T-Cell lymphoma, follicular lymphoma, hepatosplenic gamma-delta T-Cell lymphomas, T-Cell leukemias, lymphoblastic lymphoma, mantle cell lymphoma, marginal zone lymphoma, nasal T-Cell lymphoma, pediatric lymphoma, peripheral T-Cell lymphomas, primary central nervous system lymphoma, transformed lymphomas, treatment-related T-Cell lymphomas, and Waldenstrom's macroglobulinemia.

Brain cancers include any cancer of the brain tissues. Examples of brain cancers include, but are not limited to: gliomas (e.g., glioblastomas, astrocytomas, oligodendrogliomas, ependymomas, and the like), meningiomas, pituitary adenomas, vestibular schwannomas, primitive neuroectodermal tumors (medulloblastomas), etc.

As used herein, the term "infection" refers to any state in at least one cell of an organism (i.e., a subject) is infected by an infectious agent (e.g., a subject has an intracellular pathogen infection, e.g., a chronic intracellular pathogen infection). As used herein, the term "infectious agent" refers to a foreign biological entity (i.e. a pathogen) that induces PD-L (PD-L1 and/or PD-L2) expression (e.g., increased PD-L expression) in at least one cell of the infected organism. For example, infectious agents include, but are not limited to bacteria, viruses, protozoans, and fungi. Intracellular pathogens are of particular interest. Infectious diseases are disorders caused by infectious agents. Some infectious agents cause no recognizable symptoms or disease under certain conditions, but have the potential to cause symptoms or disease under changed conditions. The subject methods can be used in the treatment of chronic pathogen infections, for example including but not limited to viral infections, e.g., retrovirus, lentivirus, hepadna virus, herpes viruses, pox viruses, human papilloma viruses, etc.; intracellular bacterial infections, e.g., *Mycobacterium*, *Chlamydophila*, *Ehrlichia*, *Rickettsia*, *Brucella*, *Legionella*, *Francisella*, *Listeria*, *Coxiella*, *Neisseria*, *Salmonella*, *Yersinia* sp, *Helicobacter pylori* etc.; and intracellular protozoan pathogens, e.g., *Plasmodium* sp, *Trypanosoma* sp., *Giardia* sp., *Toxoplasma* sp., *Leishmania* sp., etc.

Infectious diseases that can be treated using a subject high affinity PD-1 mimic polypeptide include but are not limited to: HIV, Influenza, Herpes, *Giardia*, Malaria, *Leishmania*, the pathogenic infection by the virus Hepatitis (A, B, & C), herpes virus (e.g., VZV, HSV-I, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, pathogenic infection by the bacteria *chlamydia*, rickettsial bacteria, *mycobacteria*, *staphylococci*, *streptococci*, *pneumonococci*, *meningococci* and *conococci*, *klebsiella*, *proteus*, *serratia*, *pseudomonas*, *E. coli*, *legionella*, diphtheria, *salmonella*, bacilli, cholera, tetanus, botulism, anthrax, plague, leptospirosis, and Lyme's disease bacteria, pathogenic infection by the fungi *Candida* (*albicans*, *krusei*, *glabrata*, *tropicalis*, etc.), *Cryptococcus neoformans*, *Aspergillus* (*fumigatus*, *niger*, etc.), Genus *Mucorales* (*mucor*, *absidia*, *rhizophus*), *Sporothrix schenkii*, *Blastomyces dermatitidis*, *Paracoccidioides brasiliensis*, *Coccidioides immitis* and *Histoplasma capsulatum*, and pathogenic infection by the parasites *Entamoeba histolytica*, *Balantidium coli*, *Naegleriafowleri*, *Acanthamoeba* sp., *Giardia lambia*, *Cryptosporidium* sp., *Pneumocystis carinii*, *Plasmodium vivax*, *Babesia microti*, *Trypanosoma brucei*, *Trypanosoma cruzi*, *Leishmania donovani*, *Toxoplasma gondi*, and/or *Nippostrongylus brasiliensis*.

In some embodiments, a subject high affinity PD-1 mimic polypeptide can block the inhibitory signals induced by PD-L (e.g., PD-L1 and/or PD-L2), and thereby allow for the activation of an immune cell. Thus, a subject high affinity PD-1 mimic polypeptide can facilitate and/or stimulate cytokine and/or chemokine production by immune cells, particularly immune cells that express PD-1 on the cell surface. For example, the presence of an immune complex (i.e., an antigen-antibody complex) interacting with an immune cell activates the immune cell and induces cytokine production by the immune cell, but this activation (stimulation) can be inhibited by PD-L on the surface of a second cell. A subject high affinity PD-1 mimic polypeptide can be used for altering immunoresponsiveness of an immune cell and thereby may be useful for treating or preventing an immunological disease or disorder (e.g., a disorder associated with immunosuppression). In other words, a subject high affinity PD-1 mimic polypeptide can be used for immunopotentiation (stimulation of the immune system) as an agent that simulates the immune system.

The methods above include administering to an individual in need of treatment a therapeutically effective amount or an effective dose of a subject high affinity PD-1 mimic polypeptide, including without limitation combinations of a high affinity PD-1 mimic polypeptide with a drug (e.g., a chemotherapeutic drug, a tumor-specific antibody, an anti-inflammatory drug, a drug to treat infection, an immunostimulant, i.e., an immunopotentiator, an agent that simulates the immune system, etc.).

Effective doses of the therapeutic entity of the present disclosure, e.g., for the treatment of cancer, vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g., companion animals such as dogs, cats, horses, etc., laboratory mammals such as rabbits, mice, rats, etc., and the like. Treatment dosages can be titrated to optimize safety and efficacy.

In some embodiments, the therapeutic dosage may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once every two weeks or once a month or once every 3 to 6 months. Therapeutic entities of the present disclosure are usually administered on multiple occasions. Intervals between single dosages can be weekly, monthly or yearly. Intervals can also be irregular as indicated by measuring blood levels of the therapeutic entity in the patient. Alternatively, therapeutic entities of the present disclosure can be administered as a sustained release formulation, in which case less frequent administration is required. Dosage and frequency vary depending on the half-life of the polypeptide in the patient.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still other embodiments, methods of the present disclosure include treating, reducing or preventing any of the above discussed conditions, ailments, and/or diseases (e.g., tumor growth, tumor metastasis or tumor invasion of cancers including lymphomas, leukemias, carcinomas, melanomas, glioblastomas, sarcomas, myelomas, etc.). For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

Subject high affinity PD-1 mimic polypeptides can be used in vitro and in vivo to monitor the course of disease therapy, for example, by measuring the increase or decrease in the number of cells expressing PD-L (PD-L1 and/or PD-L2), particularly chronically infected cells and/or cancer cells expressing PD-L1, it can be determined whether a particular therapeutic regimen aimed at ameliorating disease is effective. For such purposes, high affinity PD-1 mimic polypeptides can be detectably labeled.

Subject high affinity PD-1 mimic polypeptides can be used in vitro in binding assays in which they can be utilized in liquid phase or bound to a solid phase carrier. In addition, the polypeptides in these immunoassays can be detectably labeled in various ways. Examples of types of assays which can utilize high affinity PD-1 mimic polypeptides are flow cytometry, e.g., FACS, MACS, histochemistry, competitive and non-competitive immunoassays in either a direct or indirect format; and the like. Detection of PD-L using a high affinity PD-1 mimic polypeptide can be done with assays which are run in either the forward, reverse, or simultaneous modes, including histochemical assays on physiological samples.

Subject high affinity PD-1 mimic polypeptides can be bound to many different carriers and used to detect the presence of PD-L (PD-L1 and/or PD-L2) expressing cells. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the disclosure. Those skilled in the art will know of other suitable carriers for binding proteins, or will be able to ascertain such, using routine experimentation.

There are many different labels and methods of labeling known to those of ordinary skill in the art. Examples of the types of labels which can be used in the present disclosure include but are not limited to enzymes, radioisotopes, fluorescent compounds, colloidal metals, nanoparticles, chemiluminescent compounds, and bio-luminescent compounds. Those of ordinary skill in the art will know of other suitable labels for binding to the polypeptides of the disclosure, or will be able to ascertain such, using routine experimentation. Furthermore, the binding of these labels to the polypeptides of the disclosure can be done using standard techniques common to those of ordinary skill in the art.

PD-L may be detected by subject high affinity PD-1 mimic polypeptides when present in biological fluids and tissues. Any sample containing a detectable amount of PD-L can be used. A sample can be a liquid such as urine, saliva, cerebrospinal fluid, blood, serum and the like, or a solid or semi-solid such as tissues, feces, biopsy, and the like, or, alternatively, a solid tissue such as those commonly used in histological diagnosis.

Another labeling technique which may result in greater sensitivity consists of coupling the polypeptides to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

The imaging conjugates of high affinity PD-1 mimic polypeptides can be administered to the subject in a series of more than one administration. The imaging conjugate compositions may be administered at an appropriate time before the visualization technique. For example, administration within an hour before direct visual inspection may be appropriate, or administration within twelve hours before a PET or MRI scan may be appropriate. Care should be taken, however, to not allow too much time to pass between administration and visualization, as the imaging compound may eventually be cleared from the patient's system.

Compositions for treatment (e.g., for the treatment of cancer, chronic infection, immunosuppression, inflammation, etc.) can be administered by parenteral, topical, intravenous, intratumoral, oral, subcutaneous, intraarterial, intracranial, intraperitoneal, intranasal or intramuscular means. A typical route of administration is intravenous or intratumoral, although other routes can be equally effective.

Compositions can be prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this disclosure can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the high affinity PD-1 mimic polypeptides described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

Also within the scope of the disclosure are kits comprising the compositions (e.g., high affinity PD-1 mimic polypeptides and formulations thereof) of the disclosure and instructions for use. The kit can further contain a least one additional reagent, e.g., a chemotherapeutic drug, anti-tumor antibody, and anti-infection drug, e.g, an anti-viral drug, etc. Kits typically include a label indicating the intended use of the contents of the kit. The term label includes any writing, or recorded material supplied on or with the kit, or which otherwise accompanies the kit.

```
                       KEY TO THE SEQUENCE LISTING

Wild type human PD-1 protein
(also known as PDCD1, 0D279, PD1, SLEB2, hPD-1, hPD-I, and hSLE1)
(bold: transmembrane domain, amino acids 168-191; underline: amino
acids 26-147)
MQIPQAPWPVVWAVLQLGWRPGWFLDSPDRPWNPPTFSPALLVVTEGDNATFTCSFSNTSE
SFVLNWYRMSPSNQTDKLAAFPEDRSQPGQDCRFRVTQLPNGRDFHMSVVRARRNDSGTYL
CGAISLAPKAQIKESLRAELRVTERRAEVPTAHPSPSPRPAGQFQTLVVGVVGGLLGSLVLLV
WVLAVICSRAARGTIGARRTGQPLKEDPSAVPVFSVDYGELDFQWREKTPEPPVPCVPEQTE
YATIVFPSGMGTSSPARRGSADGPRSAQPLRPEDGHCSWPL
(SEQ ID NO: 1)

Fragment of wild type human PD-1 polypeptide (R87, N91, and R122 are
underlined) (example of a subject PD-1 mimic polypeptide; a "wild type
fragment PD-1 mimic polypeptide")
DSPDRPWNPPTFSPALLVVTEGDNATFTCSFSNTSESFVLNWYRMSPSNQTDKLAAFPEDRS
QPGQDCRFRVTQLPNGRDFHMSVVRARRNDSGTYLCGAISLAPKAQIKESLRAELRVTER
(SEQ ID NO: 2)

HAC-I PD-1 (High affinity consensus with isoleucine at position 41)
DSPDRPWNPPTFSPALLVVTEGDNATFTCSFSNTSESFHVIWHRESPSGQTDTLAAFPEDRS
QPGQDARFRVTQLPNGRDFHMSVVRARRNDSGTYVCGVISLAPKIQIKESLRAELRVTER
(SEQ ID NO: 3)

HAC-V PD-1 (High affinity consensus with valine at position 41)
DSPDRPWNPPTFSPALLVVTEGDNATFTCSFSNTSESFHVVWHRESPSGQTDTLAAFPEDRS
QPGQDARFRVTQLPNGRDFHMSVVRARRNDSGTYVCGVISLAPKIQIKESLRAELRVTER
(SEQ ID NO: 4)

G2 4-1 (Generation 2, clone 4-1)
DSPDRPWNPPTFSPALLVVTEGDNATFTCSFSNTSESFHVVWHRESPSGQTDTLAAFPEDRS
QPGPDARFRVTQLPNGRDFHLSVVRARRNDSGTYVCGAISLAPKIQIKESLRAELRVTER
(SEQ ID NO: 5)

G2 4-2
DSPDRPWNPPTFSPALLVVTEGDNATFTCSFSNTSESFHIIWHRESPSGQTDTLAAFPEDRSQ
PGQDARFRVTQLPNGRDFHLSVVRARRNDSGTYVCGVISLAPKIQIKESLRAELRVTER
(SEQ ID NO: 6)

G2 4-3
DSPDRPWNPPTFSPALLVVTEGDNATFTCSFSNTSESFHVIWHLESPSGQTDTLAAFPEDRSQ
PGQDARFRVTQLPNGRDFHMSVVRARRNDSGTYVCGVISLAPKIQIKESLRAELRVTER
(SEQ ID NO: 7)

G2 4-5
DSPDRPWNPPTFSPALLVVTEGDNATFTCSFSNTSESFHVVVVHRESPSSQTDTLAAFPEDRS
QPGPDARFRVTQLPNGRDFQLSVVRARRNDSGTYVCGVISLAPKIQIKESLRAELRVTER
(SEQ ID NO: 8)

G2 4-12
DSPDRPWNPPTFSPALLVVTEGDNATFTCSFSNTSESFHVVVVHYESPSGQTDTLAAFPEDRS
QPGQDARFRVTQLPNGRDFHLSVVRARRNDSGTYVCGIISLAPKIQIKESLRAELRVTER
(SEQ ID NO: 9)

G1 4-12
DSPDRPWNPPTFSPALLVVTEGDNATFTCSFSNTSESFHLNWYRQSPDCKVFKLAAFPEDRS
TPNPDCRFRVTQLPNGRDFHMSVVRARRNDSGTYYCGAITISPGPQIKESLRAELRVTER
(SEQ ID NO: 10)

G1 4-2
DSPDRPWNPPTFSPALLVVTEGDNATFTCSFSNTSESFHLIWFRQSPLGQLFKLAAFPEDRSIP
RQDCRFRVTQLPNGRDFHMSVVRARRNDSGTYVCGAISYSPEIQIKESLRAELRVTER
(SEQ ID NO: 11)

G1 4-5
DSPDRPWNPPTFSPALLVVTEGDNATFTCSFSNTSESFHLVWFRQSPNGQVRKLAAFPEDRS
EPIPDCRFRVTQLPNGRDFHMSVVRARRNDSGTYVCGAISYAAIVQIKESLRAELRVTER
(SEQ ID NO: 12)

G1 4-1
DSPDRPWNPPTFSPALLVVTEGDNATFTCSFSNTSESFRLVWHRESPGYETDTLASFPEDRS
TPLPDCRFRVTQLPNGRDFHMSVVRARRNDSGTYVCGAIAFHPVIQIKESLRAELRVTER
(SEQ ID NO: 13)

G1 4-4
DSPDRPWNPPTFSPALLVVTEGDNATFTCSFSNTSESFRLVWHRESPNNHAYTLALFPEDRSL
PFPDCRFRVTQLPNGRDFHMSVVRARRNDSGTYICGAITFDPRIQIKESLRAELRVTER
(SEQ ID NO: 14)
```

KEY TO THE SEQUENCE LISTING

G1 4-10
DSPDRPWNPPTFSPALLVVTEGDNATFTCSFSNTSESFHLVWHRLSPVYQTVLLAAFPEDRSP
PVQDCRFRVTQLPNGRDFHMSVVRARRNDSGTYLCGAISYDPTIQIKESLRAELRVTER
(SEQ ID NO: 15)

G2 4-10
DSPDRPWNPPTFSPALLVVTEGDNATFTCSFSNTSESFHVVWHYDSPSGQTDTLAAFPEDRS
QPGPDCRFRITQLPNGRDFHFSVVRARRNDSGTYICGVISLAPKIQIKESLRAELRVTER
(SEQ ID NO: 16)

G2 4-14
DSPDRPWNPPTFSPALLVVTEGDNATFTCSFSNTSESFHVVWHYESPSGQTDTLAAFPEDRS
QPGPDCRFRVTQLPNGRDFHFSVVRARRNDSGTYICGVISLAPKIQIKESLRAELRVTER
(SEQ ID NO: 17)

G2 4-4
DSPDRPWNPPTFSPALLVVTEGDNATFTCSFSNTSESFHIIWHRESPSCQTDTLAAFPEDRSQ
PGQDCRFRITQLPNGRDFHFSVVRARRNDSGTFVCGVISLAPKIQIKESLRAELRVTER
(SEQ ID NO: 18)

G2 4-22
DSPDRPWNPPTFSPALLVVTEGDNATFTCSFSNTSESFHIIWHRESPSGQTDTLAAFPEDRSQ
PGQDCRFRITQLPNGRDFHFSVVRARRNDSGTFVCGVISLAPKIQIKESLRAELRVTER
(SEQ ID NO: 19)

G2 4-6
DSPDRPWNPPTFSPALLVVTEGDNATFTCSFSNTSESFRLVWHRESPSGQTDTLAAFPEDRS
QPGQDCRFRITQLPNGRDFHFSVVRARRNDSGTFVCGAISFAPKIQIKESLRAELRVTER
(SEQ ID NO: 20)

G2 4-7
DSPDRPWNPPTFSPALLVVTEGDNATFTCSFSNTSESFHVVWHRESPSGQTDTLAAFPEDRS
QPGQDCRFRITQLPNGRDFHLSVVRARRNDSGTFVCGVISLAPKIQIKESLRAELRVTER
(SEQ ID NO: 21)

G2 4-18
DSPDRPWNPPTFSPALLVVTEGDNATFTCSFSNTSESFHVIWHRESPSGQTDTLAAFPEDRS
QPGPDCRFRITQLPNGRDFHMSVVRARKNDSGTYVCGIISLAPKIQIKESLRAELRVTER
(SEQ ID NO: 22)

G2 4-23
DSPDRPWNPPTFSPALLVVTEGDNATFTCSFSNTSESFHIIWHRESPSGQTDTLAAFPEDRSQ
PGPDCRFRVTQLPNGRDFHMSVVRARRNDSGTYVCGVISLAPKIQIKESLRAELRVTER
(SEQ ID NO: 23)

Multimerized high affinity PD-1 mimic polypeptides (e.g., for
improved pharmacokinetics) (i.e., fusion to a multimerization domain)
HAC-V 'microbody'
(HAC-V PD-1 fused to human IgG1 CH3 domain including hinge region)
DSPDRPWNPPTFSPALLVVTEGDNATFTCSFSNTSESFHVVWHRESPSGQTDTLAAFPEDRS
QPGQDARFRVTQLPNGRDFHMSVVRARRNDSGTYVCGVISLAPKIQIKESLRAELRVTEREPK
SCDKTHTCPPCGGGSSGGGSGGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSL
SLSPGK (SEQ ID NO: 24)

HAC-V Fc fusion
(HAC-V PD-1 fused to human IgG Fc; here human IgG4 for reduced effector
functions (compared to other Fc regions) and s228P mutation to prevent
fab arm exchange; AAA linker between PD-1 variant and Fc is included)
DSPDRPWNPPTFSPALLVVTEGDNATFTCSFSNTSESFHVVWHRESPSGQTDTLAAFPEDRS
QPGQDARFRVTQLPNGRDFHMSVVRARRNDSGTYVCGVISLAPKIQIKESLRAELRVTERAAA
PPCPPCPAPEFLGGPSVFLFPPKPKDTLMISRTPEVTCVVVDVSQEDPEVQFNWYVDGVEVH
NAKTKPREEQFNSTYRVVSVLTVLHQDWLNGKEYKCKVSNKGLPSSIEKTISKAKGQPREPQV
YTLPPSQEEMTKNQVSLTCLVKGFYPSDIAVEWESNGQPENNYKTTPPVLDSDGSFFLYSRLT
VDKSRWQEGNVFSCSVMHEALHNHYTQKSLSLSPGK (SEQ ID NO: 25)

Fusions to "attenuated" cytokines
Example: HAC-1L2 (F42A/D20T)
DSPDRPWNPPTFSPALLVVTEGDNATFTCSFSNTSESFHVVWHRESPSGQTDTLAAFPEDRS
QPGQDARFRVTQLPNGRDFHMSVVRARRNDSGTYVCGVISLAPKIQIKESLRAELRVTERGG
GGSGGGGSAPTSSSTKKTQLQLEHLLLTLQMILNGINNYKNPKLTRMLTAKFYMPKKATELKHL
QCLEEELKPLEEVLNLAQSKNFHLRPRDLISNINVIVLELKGSETTFMCEYADETATIVEFLNRWI
TFCQSIISTLT (SEQ ID NO: 39)

Fusions to 41BB-agonists
Example: HAC-41BBL

KEY TO THE SEQUENCE LISTING

```
DSPDRPWNPPTFSPALLVVTEGDNATFTCSFSNTSESFHVVWHRESPSGQTDTLAAFPEDRS
QPGQDARFRVTQLPNGRDFHMSVVRARRNDSGTYVCGVISLAPKIQIKESLRAELRVTERGG
GGSGGGGSDPAGLLDLRQGMFAQLVAQNVLLIDGPLSWYSDPGLAGVSLTGGLSYKEDTKEL
VVAKAGVYYVFFQMELRRVVAGEGSGSVSLALHLMPLRSAAGAAALALTVDLPPASSEARNSA
FGFQGRLLHLSAGQRLGVHLHTEARARHAWQLTQGATVLGLFRVTPEIPA (SEQ ID NO: 40)

Fusions to CD40-agonists
Example: HAC-CD40L
DSPDRPWNPPTFSPALLVVTEGDNATFTCSFSNTSESFHVVWHRESPSGQTDTLAAFPEDRS
QPGQDARFRVTQLPNGRDFHMSVVRARRNDSGTYVCGVISLAPKIQIKESLRAELRVTERGG
GGSGGGGSGDQNPQIAAHVISEASSKTTSVLQWAEKGYYTMSNNLVTLENGKQLTVKRQGLY
YIYAQVTFCSNREASSQAPFIASLCLKSPGRFERILLRAANTHSSAKPCGQQSIHLGGVFELQP
GASVFVNVTDPSQVSHGTGFTSFGLLKL (SEQ ID NO: 41)

Fusions to inhibitors of BTLA and/or CD160
Example: HAC-BTLA decoy:
DSPDRPWNPPTFSPALLVVTEGDNATFTCSFSNTSESFHVVWHRESPSGQTDTLAAFPEDRS
QPGQDARFRVTQLPNGRDFHMSVVRARRNDSGTYVCGVISLAPKIQIKESLRAELRVTERGG
GGSGGGGSWNIHGKESCDVQLYIKRQSEHSILAGDPFELECPVKYCANRPHVTWCKLNGTTC
VKLEDRQTSWKEEKNISFFILHFEPVLPNDNGSYRCSANFQSNLIESHSTTLYVTDVK (SEQ ID
NO: 42)

Fusions to inhibitors of TIM3 and/or CEACAM1
Example: HAC-TIM3 decoy:
DSPDRPWNPPTFSPALLVVTEGDNATFTCSFSNTSESFHVVWHRESPSGQTDTLAAFPEDRS
QPGQDARFRVTQLPNGRDFHMSVVRARRNDSGTYVCGVISLAPKIQIKESLRAELRVTERGG
GGSGGGGSEVEYRAEVGQNAYLPCFYTPAAPGNLVPVCWGKGACPVFECGNVVLRTDERD
VNYWTSRYWLNGDFRKGDVSLTIENVTLADSGIYCCRIQIPGIMNDEKFNLK (SEQ ID NO: 43)

Cysteine mutants (e.g., for PET labeling)
HAC-V N91C
DSPDRPWNPPTFSPALLVVTEGDNATFTCSFSNTSESFHVVWHRESPSGQTDTLAAFPE
DRSQPGQDARFRVTQLPNGRDFHMSVVRARRCDSGTYVCGVISLAPKIQIKESLRAELR
VTER (SEQ ID NO: 44)

HAC-V R87C
DSPDRPWNPPTFSPALLVVTEGDNATFTCSFSNTSESFHVVWHRESPSGQTDTLAAFPE
DRSQPGQDARFRVTQLPNGRDFHMSVVCARRNDSGTYVCGVISLAPKIQIKESLRAELR
VTER (SEQ ID NO: 45)

HAC-V R122C
DSPDRPWNPPTFSPALLVVTEGDNATFTCSFSNTSESFHVVWHRESPSGQTDTLAAFPE
DRSQPGQDARFRVTQLPNGRDFHMSVVRARRNDSGTYVCGVISLAPKIQIKESLRAELR
VTEC (SEQ ID NO: 46)
```

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

The following example demonstrates the creation of high affinity PD-1 mimic polypeptides that effectively antagonize the interaction between PD-1 and its ligand PD-L1. The high affinity PD-1 mimic polypeptides can be used as therapeutics for the same indications as PD-1 and PD-L1 antibodies (e.g., those that are currently in clinical trials).

Figure 1B:
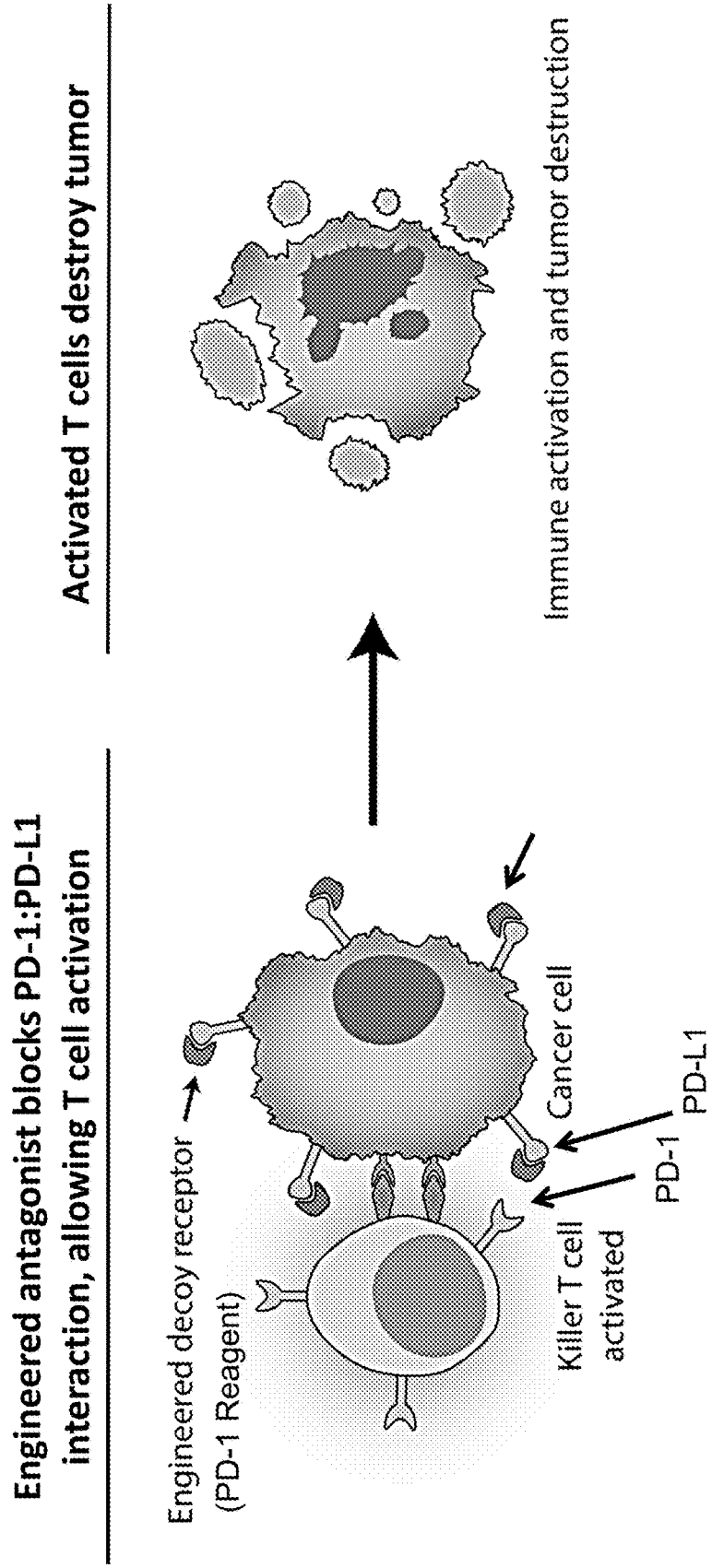

FIG. 1A depicts a schematic illustrating PD-L1 on the surface of a tumor cell specifically binding to PD-1 on the surface of a T cell to inhibit activation of the T cell, thereby allowing the tumor cell to evade destruction by the immune system. FIG. 1B depicts a schematic illustrating a subject high affinity PD-1 mimic polypeptide specifically binding to PD-L1 on the surface of a cancer cell, thereby reducing the ability of the cancer cell to inhibit T cell activation, which in turn reduces the cancer cell's ability to evade the immune response.

Figure 2A:
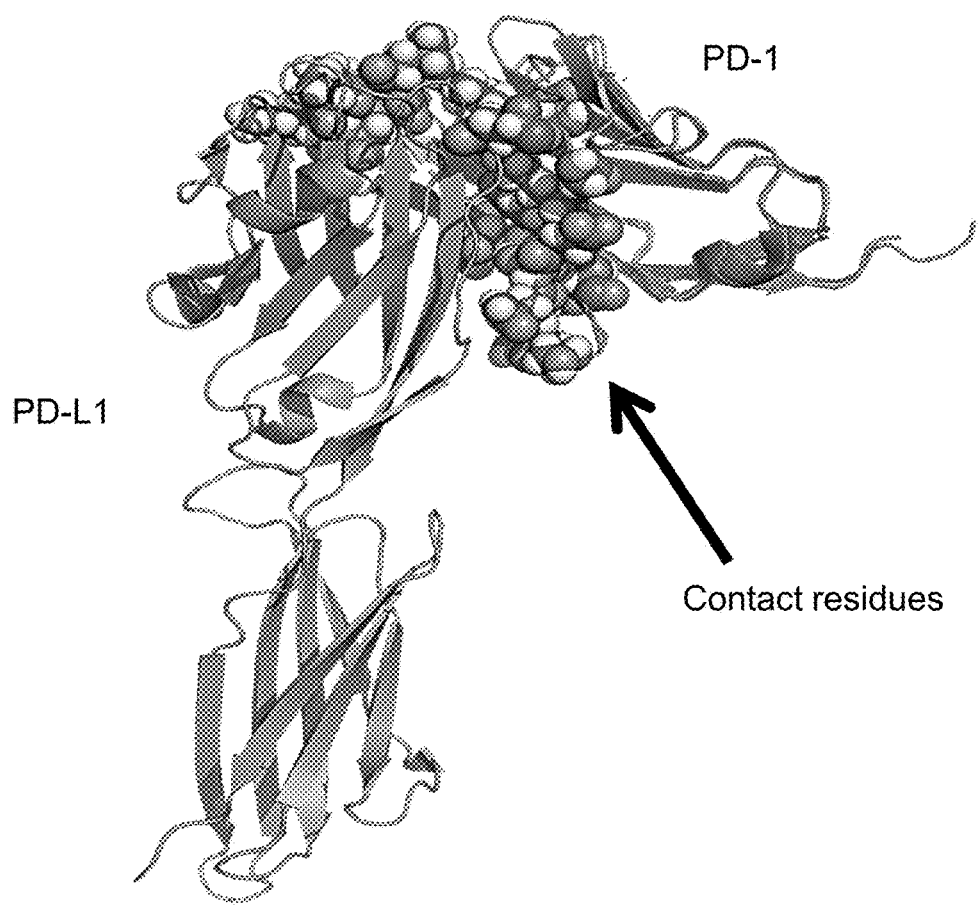

FIG. 2A depicts a structural representation of the interaction of PD-1 (upper right) with PD-L1 (lower left). Residues of PD-1 located at the contact site with PD-L1 are represented as spheres. A PD-1 mimic polypeptide (comprising wild type amino acid residues) was mutagenized at the residues that contact PD-L1 to generate a first generation library (Generation 1) of mutated polypeptides, which were displayed on the surface of yeast cells. Selections based on binding were then performed using 100 nM biotinylated human PD-L1. To screen for PD-1 mimic polypeptides having even greater affinity for PD-L1, a second generation library (Generation 2) of mutated polypeptides was generated, focusing the mutagenesis on converging positions. 1 nM biotinylated human PD-L1 was used to screen the Generation 2 library. See FIG. 2B for results from the screens.

The table of FIG. 3 reflects the sequences of the engineered variants (subject high affinity PD-1 mimic polypeptides) that were produced. "G1" variants are from the Generation 1 library while the "G2" variants are from Generation 2 library (see FIG. 2A-2B). Each numbered column represents the amino acid position for each shown residue relative to the native PD-1 mimic polypeptide set forth as SEQ ID NO: 2 (The polypeptide of SEQ ID NO: 2 is a PD-1 mimic polypeptide that includes a wild type PD-1 sequence, but lacks a transmembrane domain and lacks the first 25 amino acids of wild type PD-1). For each PD-1 mimic polypeptide recovered, divergence from the wild-type amino acid residue is indicated with the single-letter code for the resulting mutation for each variant. The measured Surface Plasmon Resonance (SPR) affinity for PD-L1 is indicated (when measured) at the right. Based on the recovered sequences, high affinity PD-1 mimic polypeptides were generated that contain consensus amino acid mutations, and are referred to as "HAC" (High Affinity Consensus).

Figure 4:
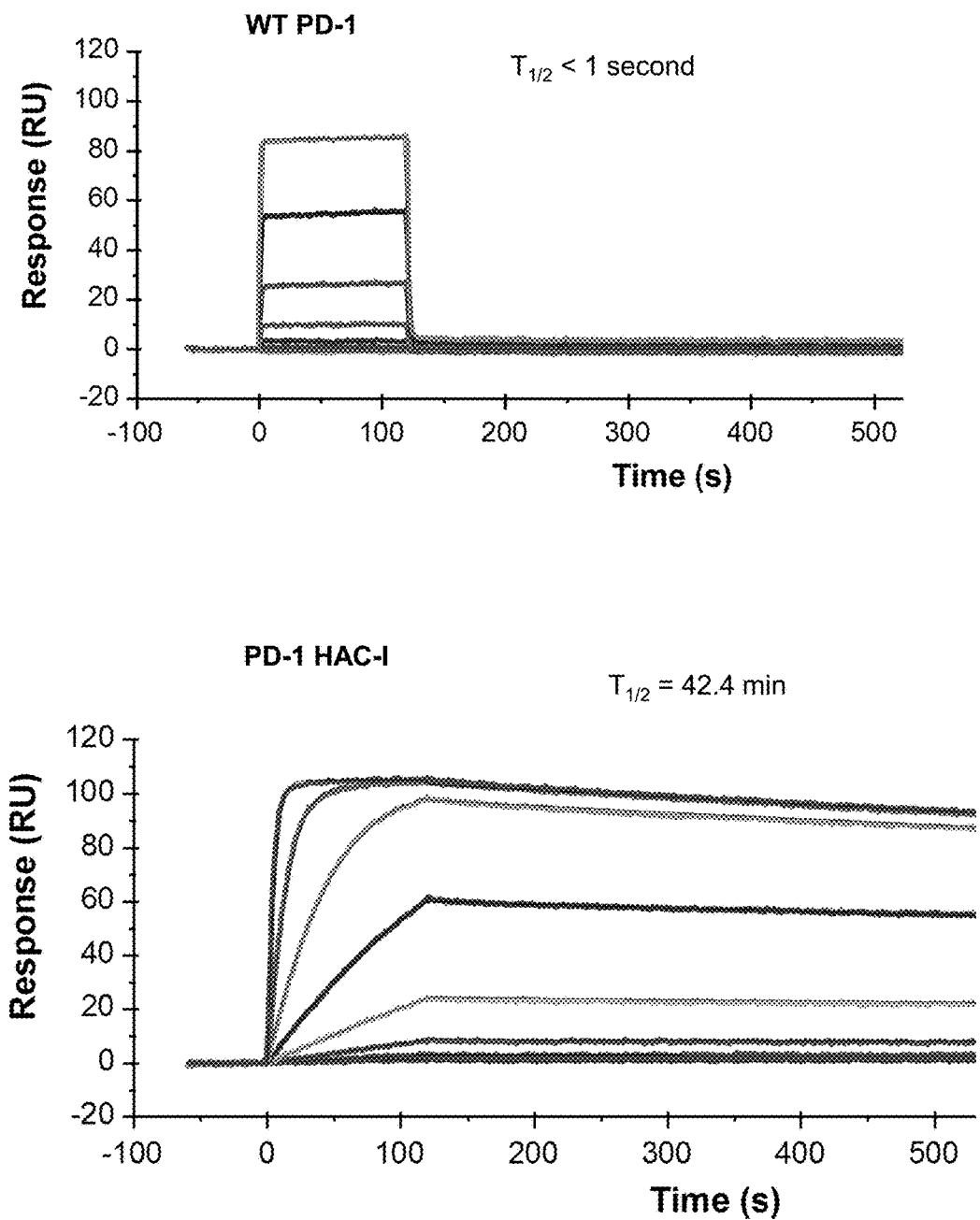
FIG. 4. Two representative Surface Plasmon Resonance (SPR) plots are shown. The dissociation half-life for a native PD-1 mimic polypeptide (having wild-type human PD-1 sequences) was less than one second. By contrast, the dissociation half-life for a high-affinity consensus PD-1 variant HAC-I (a subject high affinity PD-1 mimic polypeptide) was 42.4 minutes.

FIG. 4 depicts two representative Surface Plasmon Resonance (SPR) plots from binding experiments (for binding to PD-L1) that were performed. The dissociation half-life for a native PD-1 mimic polypeptide (having wild-type human PD-1 sequences) was less than one second. By contrast, the dissociation half-life for a high-affinity consensus PD-1 variant HAC-I (a subject high affinity PD-1 mimic polypeptide) was 42.4 minutes, thus demonstrating that the high-affinity PD-1 mimic polypeptide bound with much higher affinity to PD-L1 than did the native PD-1 mimic polypeptide.

Figure 5A:
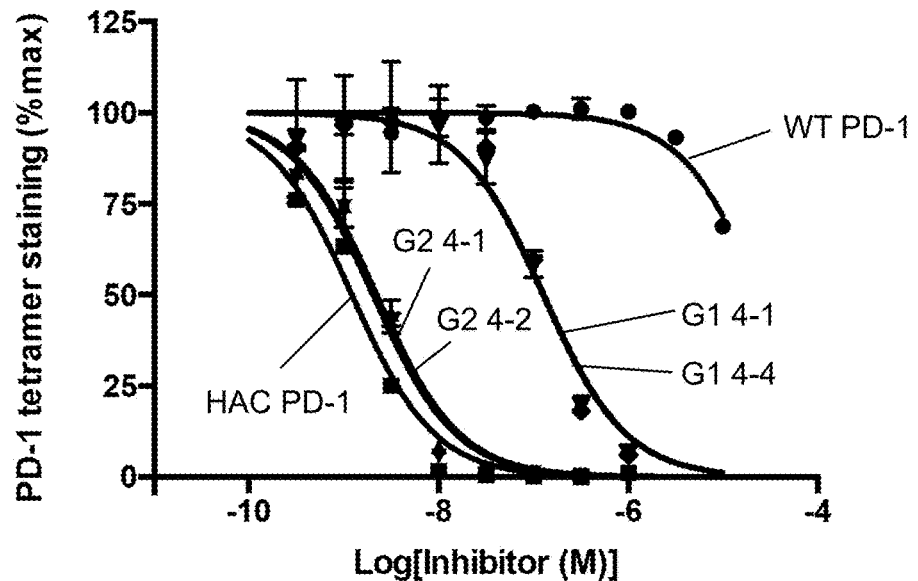
FIG. 5A-5C. Subject high affinity PD-1 mimic polypeptides potently and specifically antagonized PD-L1. Yeast displaying.
Figure 5B:
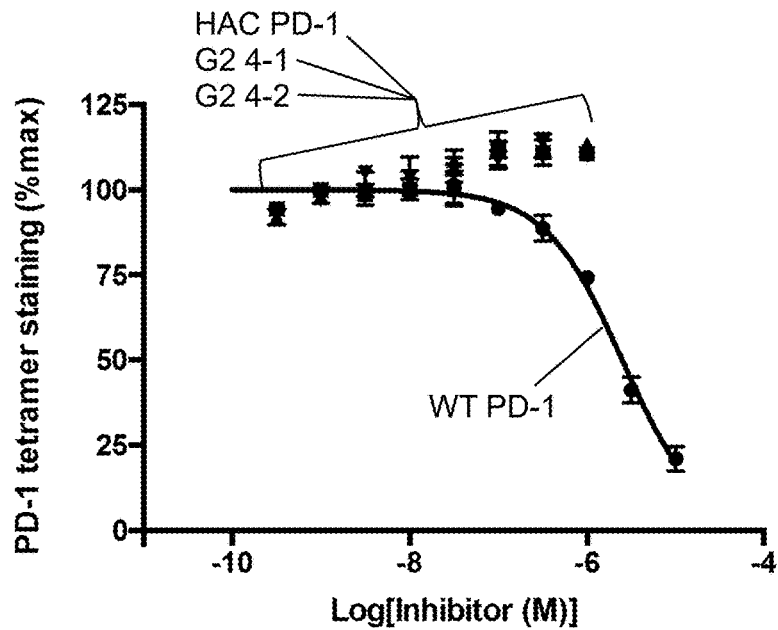
Figure 5C:
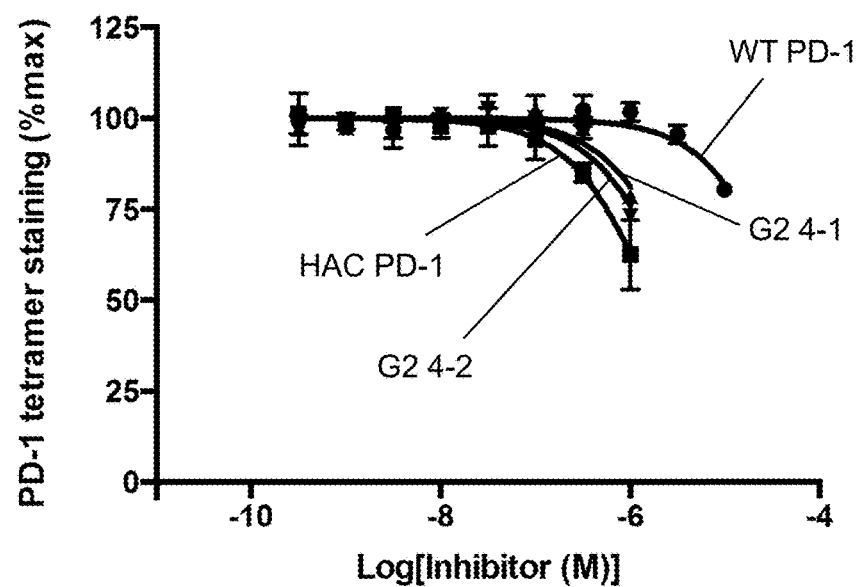

Experiments were then performed to further test the binding characteristics of some of the produced high-affinity PD-1 mimic polypeptides compared to a native PD-1 mimic polypeptide. FIG. 5A-5C show that produced high affinity PD-1 mimic polypeptides potently and specifically bound to PD-L1. Yeast displaying: (FIG. 5A) human PD-L1, (FIG. 5B) human PD-L2, or (FIG. 5C) mouse PD-L1, were stained with labeled native PD-1 mimic polypeptide streptavidin tetramers (a control PD-1 mimic polypeptide having wild-type human PD-1 sequences and conjugated to Alexa647). The binding of the labeled native PD-1 mimic polypeptide to PD-L1 was competed with variable concentrations of unlabeled high affinity PD-1 mimic polypeptides (concentrations indicated on the x-axis).

An unlabeled native PD-1 mimic polypeptide (having wild-type human PD-1 sequences) antagonized the PD-1/PD-L1 interaction. High-affinity PD-1 mimic polypeptides (HAC-V PD-1, G2 4-1, and G2 4-2) potently antagonized the PD-1/PD-L1 interaction at much lower concentrations than did the native PD-1 mimic polypeptide, thus demonstrating that they are in fact high affinity PD-1 mimic polypeptides (FIG. 1A). The high-affinity PD-1 mimic polypeptides did not demonstrate antagonism of the PD-1:PD-L2 interaction, while a native PD-1 mimic polypeptide did antagonize the PD-1:PD-L2 interaction. Thus, these particular high-affinity PD-1 mimic polypeptides had increased affinity for PD-L1 compared to the affinity for PD-L1 of the native PD-1 mimic polypeptide, but they had decreased affinity for PD-L2 compared to the affinity for PD-L2 of the native PD-1 mimic polypeptide (FIG. 1B). The produced high-affinity PD-1 mimic polypeptides were also able to compete for binding to mouse PD-L1 (FIG. 5C).

Figure 6A:
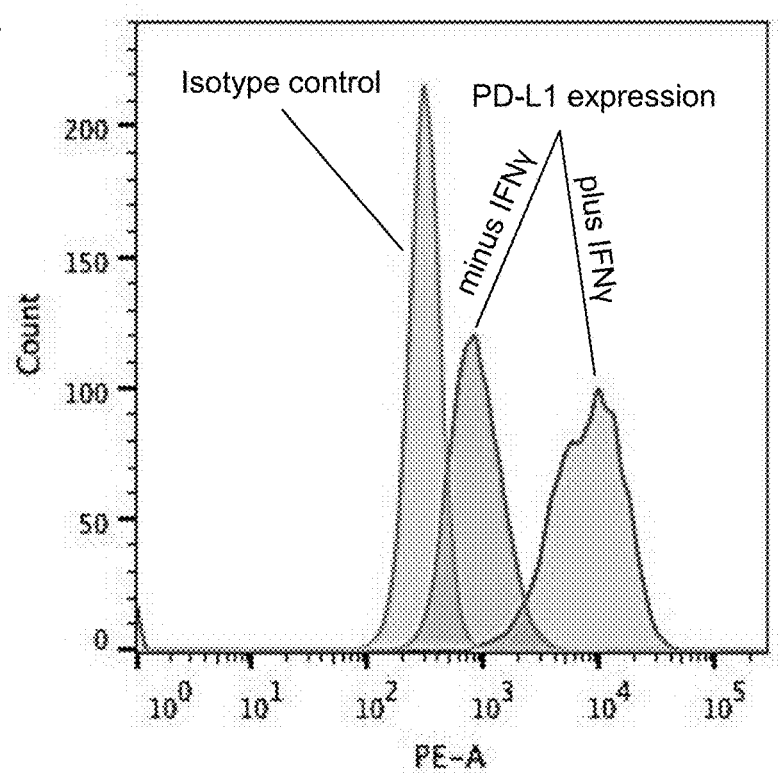
FIG. 6A-6B. High affinity PD-1 mimic polypeptides antagonize PD-L1 on human cancer cells.
Figure 6B:
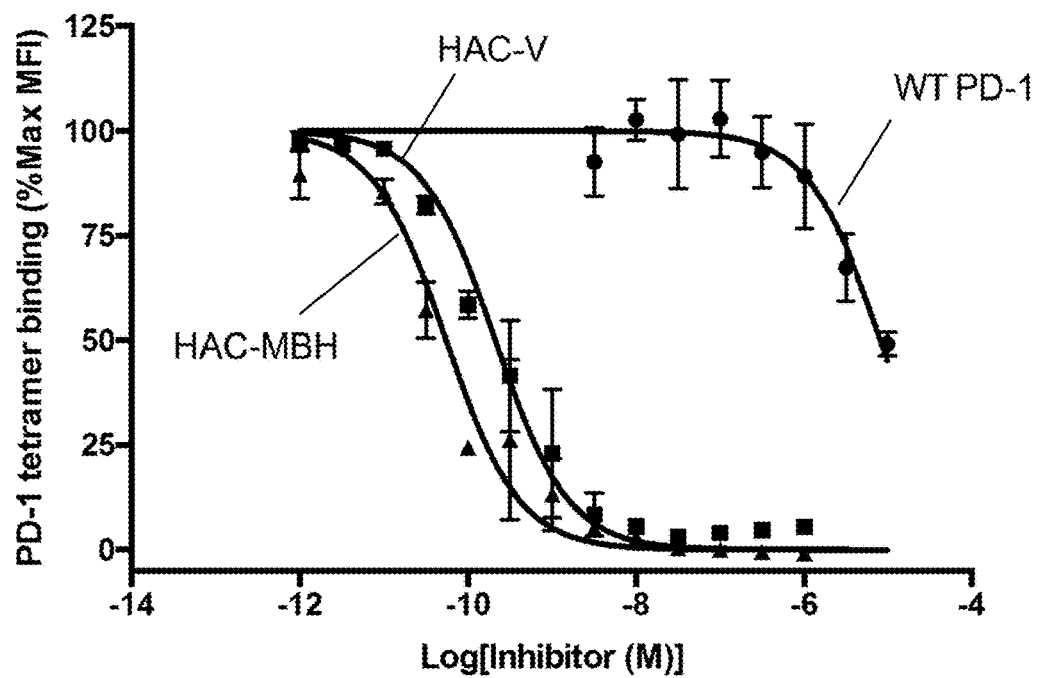

The ability of produced high affinity PD-1 mimic polypeptides to antagonize PD-L1 on human cancer cells was then tested. FIG. 6A demonstrates that PD-L1 was expressed on the human melanoma cell line SKMEL28 after induction by stimulation with 2000 U/mL human interferon-gamma (IFNγ) for 24 hours (PD-L1 staining was assessed by flow cytometry under induced (plus IFNγ) versus non-induced (minus IFNγ) conditions). IFNγ-stimulated SKMEL28 cells were stained with labeled native PD-1 mimic polypeptide streptavidin tetramers (a control PD-1 mimic polypeptide having wild-type human PD-1 sequences and conjugated to Alexa647) with variable concentrations of unlabeled high-affinity PD-1 mimic polypeptides (concentrations indicated on the x-axis) (FIG. 6B). An unlabeled native PD-1 mimic polypeptide (having wild-type human PD-1 sequences) was ineffective at preventing (required high concentrations in order to prevent) binding of the labeled native PD-1 mimic polypeptide to the SKMEL28 cells (IC50=8.2 µM). By contrast, HAC-V (a high-affinity PD-1 mimic polypeptide) potently inhibited binding of the labeled native PD-1 mimic polypeptide (IC50 of 210 pM). HAC-MBH (HAC-V, a high-affinity PD-1 mimic polypeptide, fused to the CH3 domain of human IgG1) inhibited binding of the labeled native PD-1 mimic polypeptide with additionally enhanced potency (IC50 of 55 pM).

Example 2: Engineering High-Affinity PD-1 Variants for Optimized Immunotherapy and immunoPET Imaging. (Some Data is Shared with Example 1)

Signaling through the immune checkpoint PD-1 enables tumor progression by dampening anti-tumor immune responses. Therapeutic blockade of the signaling axis between PD-1 and its ligand PD-L1 with monoclonal antibodies has shown remarkable clinical success in the treatment of cancer. However, antibodies have inherent limitations that can curtail their efficacy in this setting, including poor tissue/tumor penetrance and detrimental Fc-effector functions that deplete immune cells. To determine if PD-1/PD-L1 directed immunotherapy could be improved with smaller, non-antibody therapeutics, directed-evolution by yeast-surface display was used here to engineer the PD-1 ectodomain as a high-affinity (100 pM) competitive antagonist of PD-L1. In contrast to anti-PD-L1 monoclonal antibodies, high-affinity PD-1 demonstrated superior tumor penetration without inducing depletion of peripheral effector T cells. Consistent with these advantages, in syngeneic CT26 tumor models, high affinity PD-1 was effective in treating both small (~50 mm$^3$) and large tumors (>150 mm$^3$), whereas the activity of anti-PD-L1 antibodies was completely abrogated against large tumors. Furthermore, high-affinity PD-1 was radiolabeled and applied as a PET imaging tracer to efficiently distinguish between PD-L1-positive and PD-L1-negative tumors in living mice, providing an alternative to invasive biopsy and histological analysis. These results highlight the favorable pharmacology of small, non-antibody therapeutics for enhanced cancer immunotherapy and immune diagnostics.

Results

Directed Evolution of High-Affinity PD-1 Variants that Antagonize PD-L1.

Given its modest affinity for PD-L1 ($K_D$ of 8.2 μM)[18], the wild-type PD-1 ectodomain is a poor candidate to competitively antagonize the PD-1:PD-L1 interaction in a therapeutic context. The affinity of PD-1 for PD-L1 was therefore enhanced using directed evolution with yeast-surface display. The engineering strategy employed a two-library approach. A first library was used to identify mutational "hotspots" that impart large gains in affinity, and a second library served to determine the optimal combination of beneficial mutations derived from the first library.

Figure 7A:
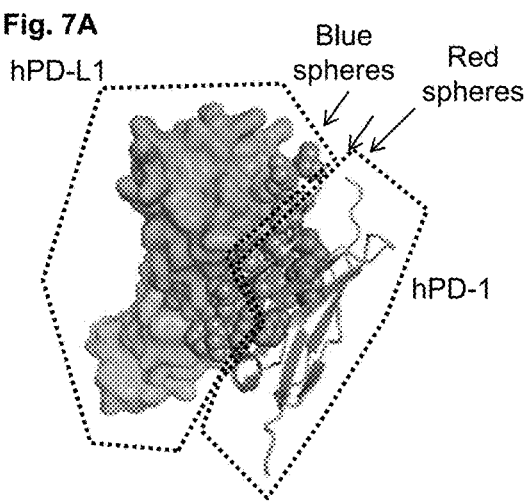
Figure 7B:
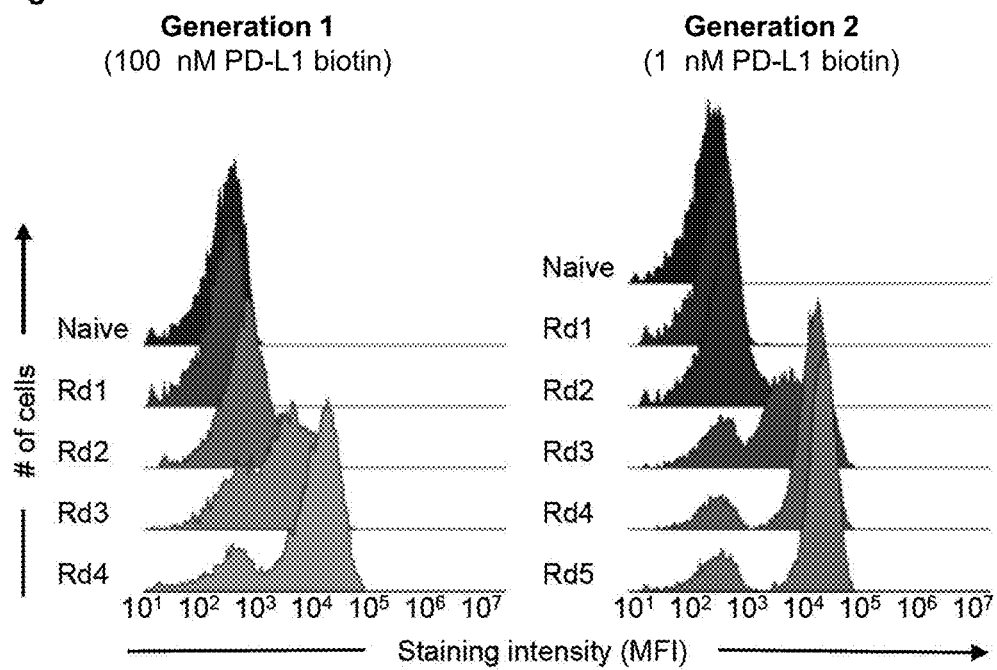

To design the initial, "first generation" library, the crystal structure of the complex between murine PD-1 (mPD-1) and human PD-L1 (hPD-L1)[19] was used to identify 22 corresponding residues in human PD-1 (hPD-1) at the contact interface with PD-L1 for randomization (FIG. 7A; FIG. 12A-12B). This library was displayed on the surface of the yeast and performed four rounds of selection using recombinant, biotinylated hPD-L1 ectodomain as the selection reagent (FIG. 7B, "Generation 1"). Biophysical characterization of the remaining clones showed a 400 to 500-fold increase in affinity for hPD-L1, as measured by surface plasmon resonance (FIG. 7C). However, the clones exhibited poor biochemical behavior, with decreased expression yield and a tendency towards aggregation. Inspection of the sequences of the variants (FIG. 7C) showed an average of 16 mutations per clone, with several of the randomized positions converging on a small set of mutations (e.g., V39, N41), while other positions appeared to completely diverge (e.g., S48, D52), or conversely, to have a strict preference for the original wild-type residue (e.g., P105, E111). The results suggested that the "first generation" variants likely contained a mixture of beneficial mutations, non-functional passenger mutations, and deleterious mutations, as would be expected given the very large theoretical diversity of the library (approximately 10$^{20}$) that was sampled with 10$^8$ yeast transformants.

Figures 13A, 13B:
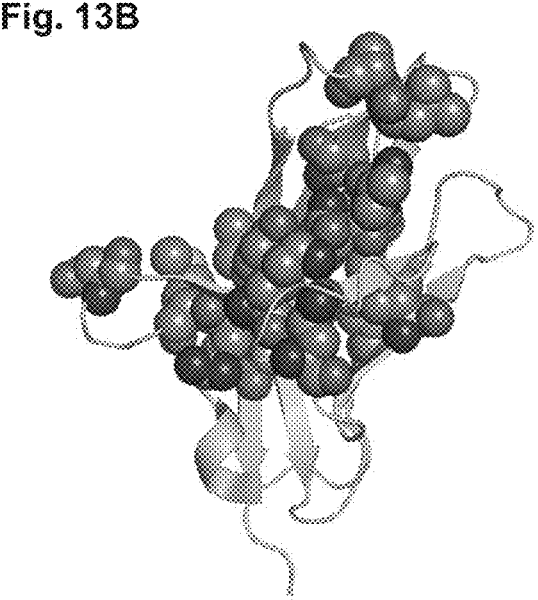
FIG. 13A-13B. Design of the "Second Generation" PD-1 library.

A "second generation" library was thus created to eliminate unnecessary and deleterious substitutions, while simultaneously optimizing combinations of mutations that impart enhanced affinity (FIG. 13A-13B). The library was focused onto those positions that appeared to be converging away from wild-type and also introduced variation at "core" positions within the PD-1 ectodomain (FIG. 7A). Through 5 rounds of selection, variants were obtained that strongly bound PD-L1 (FIG. 7B, "Generation 2"). Compared to wild-type hPD-1, the selected variants bound hPD-L1 with 15,000-40,000 fold enhanced affinity, and showed a strong trend toward convergence onto a consensus sequence of 10 amino acid substitutions comprising eight contact residues and two core residues (FIG. 7C). Two versions of this "high-affinity consensus" (HAC) PD-1 were produced, differing only by an isoleucine or valine at position 41 (termed HAC-I and HAC-V, respectively), and were found to be indistinguishable by affinity or biochemical behavior. Both HAC-PD-1 variants could be easily expressed, were monomeric, and bound hPD-L1 with $K_D$ values of approximately 100 pM (FIG. 7C). As with the other high-affinity variants, this increase in affinity was largely driven by a dramatic reduction in off-rate, yielding dissociation half-lives of approximately 40 minutes, compared to less than one second for the wild-type hPD-1:hPD-L1 interaction (FIG. 8A).

Figure 14:
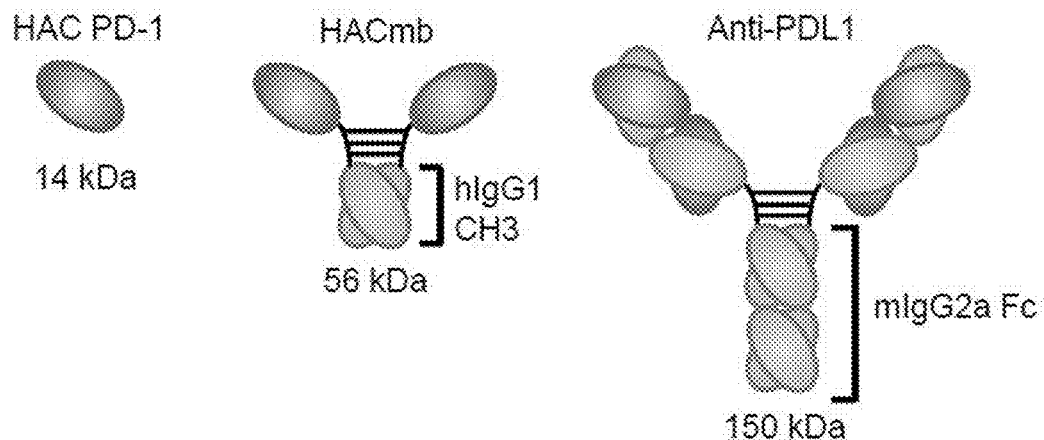
FIG. 14. Schematic diagram of HAC "microbody" (HACmb) design in comparison to individual HAC PD-1 monomer and anti-PD-L1 antibody. HACmb is HAC-V fused to the CH3 domain of human IgG1 linked by a disulfide-containing hinge sequence.

To assess the ability of the engineered PD-1 variants to antagonize PD-L1 on cancer cells, competition binding experiments were performed on human and murine melanoma cell lines. On human SK-MEL-28 cells, HAC-V blocked the binding of wild-type PD-1 tetramers with an $IC_{50}$ of 210 pM, a 40,000-fold enhancement in potency when compared to wild-type PD-1 ($IC_{50}$=8.2 μM) (FIG. 8B). Though selections were performed using human PD-L1, HAC-V also showed enhanced blockade of PD-L1 on murine B16-F10 cells ($IC_{50}$=69 nM) compared with wild-type hPD-1 ($IC_{50}$=2.6 μM), albeit with a decreased potency relative to its blocking on human cells (FIG. 8B). In order to generate a HAC-PD-1 variant that could more efficiently antagonize mPD-L1 for in vivo studies, the sequence of HAC-V was fused to the dimeric CH3 domain of human IgG1 to create a HAC "microbody" (HACmb; FIG. 14). By virtue of the increased avidity imparted by its dimeric structure, HACmb potently blocked both hPD-L1 ($IC_{50}$=55 pM) and mPD-L1 ($IC_{50}$=1.2 nM) on SKMEL28 and B16-F10 cells, respectively (FIG. 8B). The cross-reactivity of HAC-PD-1 for the second ligand of PD-1, PD-L2, was also characterized. In competition binding experiments on yeast displaying the ectodomain of hPD-L2, HAC-PD-1 did not measurably inhibit the PD-1:PD-L2 interaction, compared to wild-type PD-1 ($IC_{50}$=2.5 μM; FIG. 8B) Taken in aggregate, these results indicated that HAC-PD-1 can potently and specifically antagonize PD-L1 (and could therefore also serve as a modular scaffold for further engineering).

Tumor Penetration and T Cell Depletion Studies.

Figure 15A:
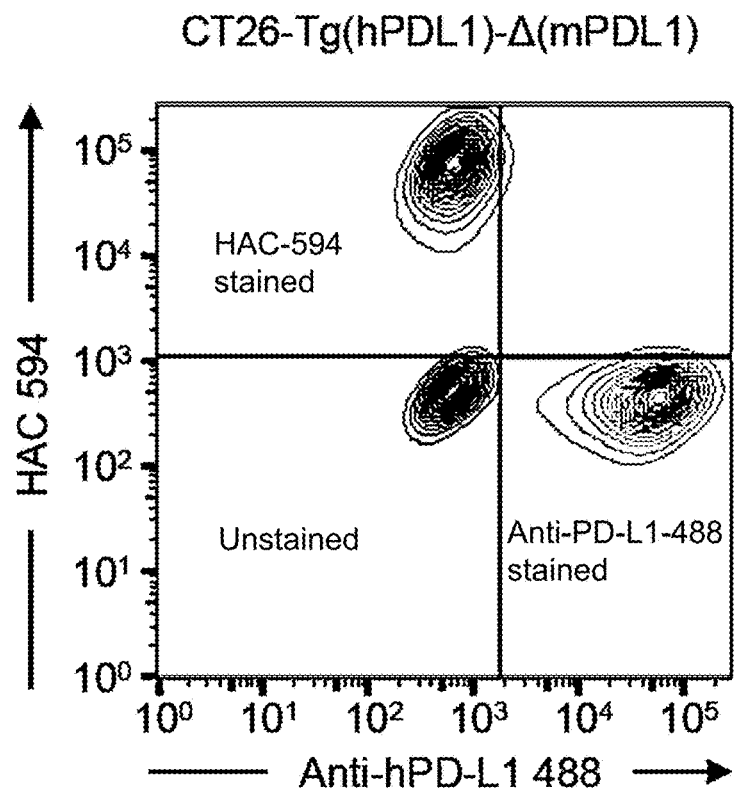
FIG. 15A-15B. In vitro and in vivo staining of hPD-L1 expressing cells.

In order to assess PD-L1 binding and tumor penetrance of HAC-PD-1 in vivo, genome editing techniques were used to generate sub-lines of the mouse colon cancer line CT26 that were either definitively negative for mPD-L1 expression, or negative for mPD-L1 but constitutively positive for hPD-L1 expression. These PD-L1 positive and negative cell lines could be readily distinguished by in vitro staining with either fluorescently-labeled anti-hPD-L1 antibody or fluorescently-labeled HAC-PD-1 protein (FIG. 15A). Using these engineered lines, mice were engrafted bilaterally with PD-L1 negative and hPD-L1 positive tumors. Once the tumors had grown to approximately 1 cm in diameter, a mixture of fluorophore-labeled anti-hPD-L1 antibody and fluorophore-labeled HAC-PD-1 was systemically delivered by intra-peritoneal injection. After 4 hours, the paired tumors were dissected and the degree of binding by each agent was assessed using both fluorescence microscopy and FACS analysis.

Figure 15B:
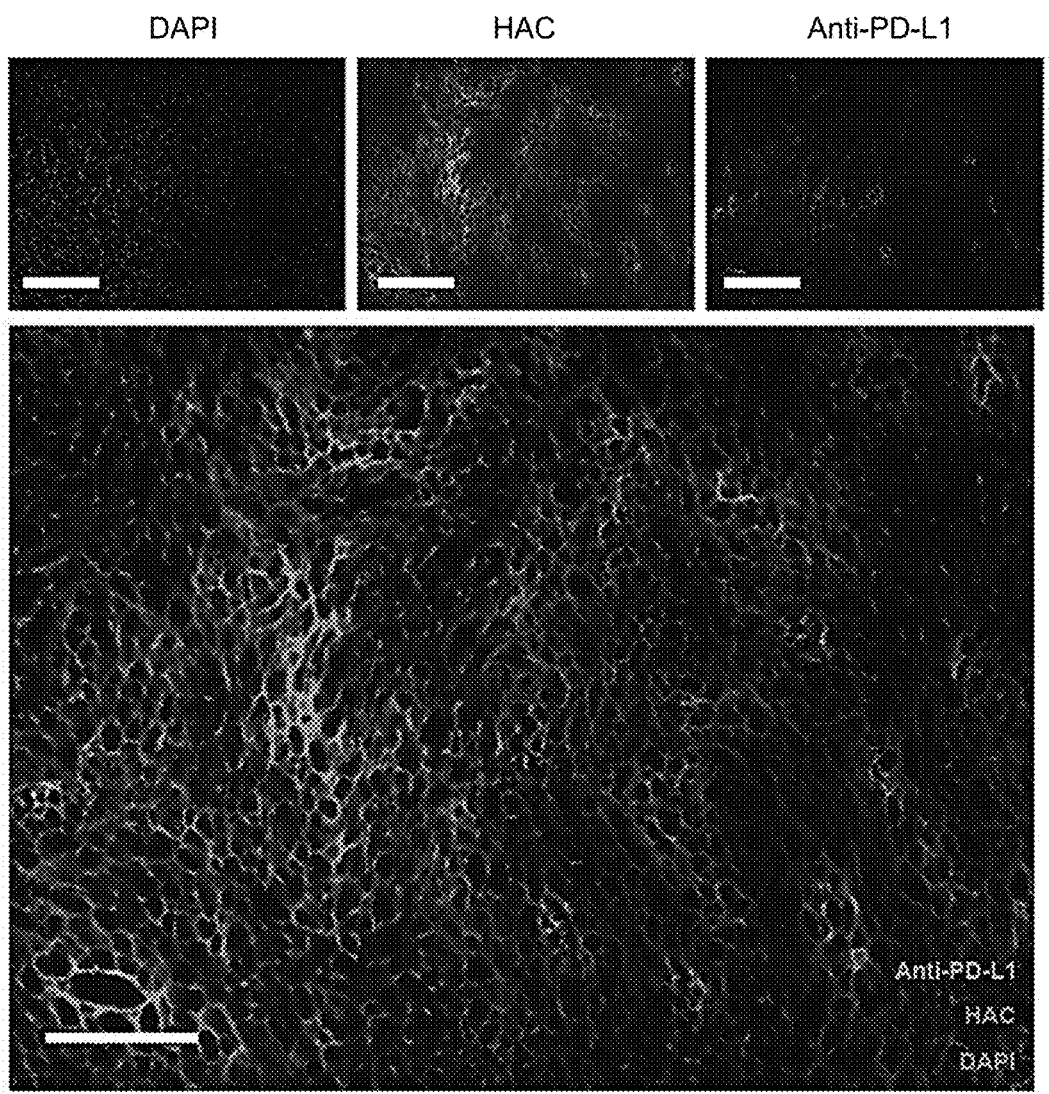

In all PD-L1 negative tumors, histological analysis revealed no detectable binding by either anti-PD-L1 antibody or HAC-PD-1, confirming the specificity of both agents (FIG. 9A). In contrast, binding of both the antibody and HAC-PD-1 in hPD-L1 positive tumors were clearly observed, but with strikingly different distributions. Whereas the antibody-associated fluorescence signal was limited to peripheral regions of the tumor and cells immediately adjacent to vessels, HAC-PD-1 staining was widespread, extending to regions deep within the tumor (FIG. 9A and FIG. 15B). These qualitative observations were supported by FACS analysis of paired PD-L1 positive and negative tumors following non-enzymatic dissociation. Neither the antibody nor HAC PD-1 interacted appreciably with the cells of PD-L1 negative tumors (FIG. 9B). However, in hPD-L1-expressing tumors, many cells were positive for HAC-PD-1 staining, and a substantial population was positive for both anti-PD-L1 antibody and HAC-PD-1 binding (FIG. 9B). In contrast, few if any cells were positive for anti-PD-L1 antibody staining only (FIG. 9B). Quantification of this signal over multiple experiments revealed a significant advantage for HAC-PD-1 binding ($p<1\times10^{-4}$), with more than twice as many cells on average bound by HAC-PD-1 than by anti-PD-L1 antibody (FIG. 9C). Taken together, these data illustrate that HAC-PD-1 was able to bind PD-L1 on tumor cells that were otherwise inaccessible to antibody binding.

Figure 16:
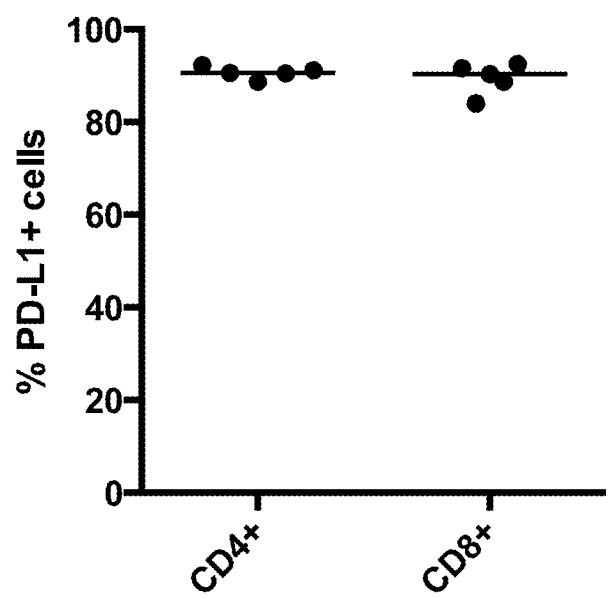
FIG. 16. Expression of PD-L1 on primary peripheral blood T cells in CT26-engrafted mice. Dot plot showing the percentage of PD-L1 positive CD4+ T cells and CD8+ T cells in the peripheral blood of Balb/c hosts 14 days post-engraftment with subcutaneous CT26 tumors.

In addition to its smaller size, HAC-PD-1 lacks an Fc domain, and therefore it was reasoned that, in contrast to antibodies, it would not contribute to an immune-mediated depletion of circulating T cell numbers. In order to test this hypothesis, wild-type Balb/c mice were engrafted with tumors derived from the syngeneic colon cancer line CT26, and beginning 14 days post-engraftment, administered daily treatments of PBS, anti-PD-L1 antibody, or HACmb (used in this case for its enhanced binding to mPD-L1). 72 hours after initiation of treatment, mice injected with anti-PD-L1 antibody exhibited a 15% decrease ($p=0.011$) in circulating peripheral blood CD8+ T cells (FIG. 9D). Though PD-L1 expression was detectable on the vast majority of CD4+ and CD8+ cells (FIG. 16), the depletive effect was specific to CD8+ T cells, sparing the CD4+ compartment (FIG. 9D). In contrast to the antibody, daily treatment with HACmb protein had no detectable effect on circulating T cell levels (FIG. 9D), although its effects on lymph node T cells were slightly more complex. As in the blood, treatment with anti-PD-L1 antibody led to a significant depletion of CD8+ T cells (FIG. 9E, ~20%, $p<1\times10^{-4}$). However, unlike in the blood, where it had no effect, treatment with HACmb did lead to a slight decrease in CD8+ T cell levels in the lymph nodes, although to a significantly lesser degree than anti-PD-L1 antibody (FIG. 9E, ~10%, $p=0.022$). This observation suggests that PD-1/PD-L1-directed agents may have pleiotropic effects on T cell dynamics that include Fc-mediated depletion as well as simulation of T cell trafficking into tumors.

Therapeutic Efficacy of HAC-PD-1 in Syngeneic Tumor Models.

Figure 10A:
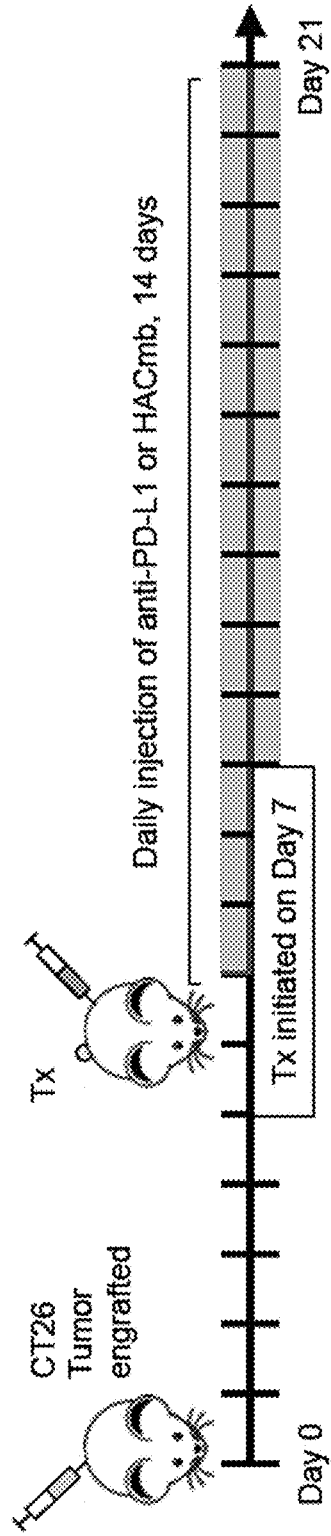
Figure 10B:
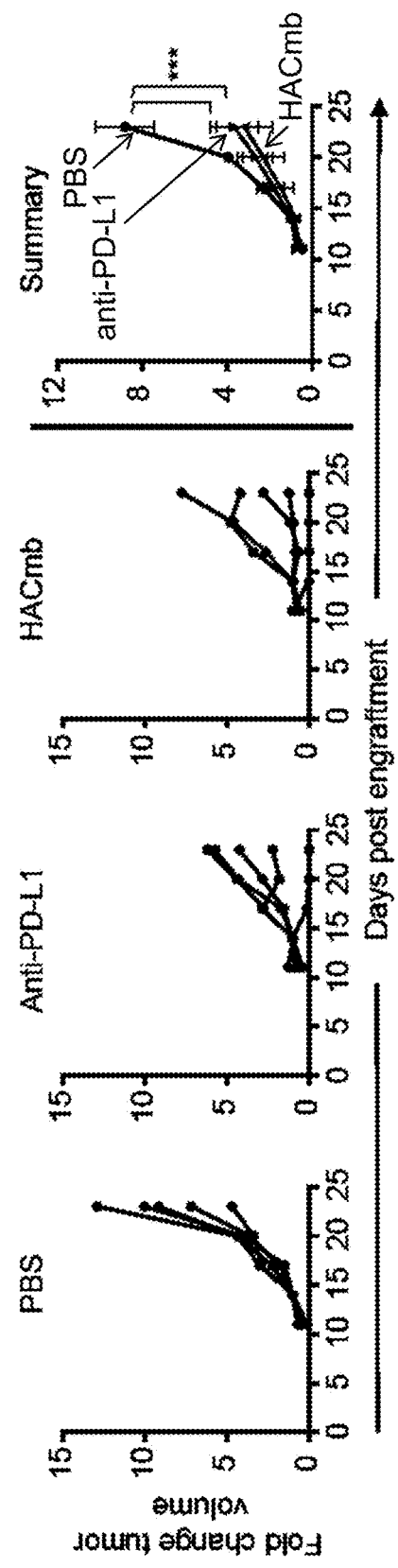

Given that HAC PD-1 agents effectively antagonized both human and mouse PD-L1, it was tested whether this blockade could by extension reproduce the anti-tumor effects of anti-PD-L1 antibodies. As an initial test of the in vivo efficacy of HAC-PD-1, wild type, immunocompetent Balb/c mice were engrafted with syngeneic CT26 tumors, which have previously been shown to be responsive to anti-PD-L1 antibodies. On day 7 post-engraftment, when tumors had reached approximately 50 mm³ in size on average, mice were randomized to treatment cohorts and began daily injections with PBS, anti-PD-L1 antibody, or HACmb (FIG. 10A). As expected, the tumors of PBS treated mice grew rapidly (FIG. 10B). However, by day 14 treatment with either anti-PD-L1 or HACmb significantly slowed tumor growth relative to controls (FIG. 10B, $p=2\times10^{-4}$ and $p<p<1\times10^{-4}$, respectively). These two agents displayed a near-identical efficacy in this small tumor study, with no statistical difference in tumor growth between the two treatment arms (FIG. 10B, $p=0.99$). From these in vivo therapeutic results it is concluded that, in the setting of relatively small tumors, HACmb is indistinguishably efficacious to well-validated anti-PD-L1 monoclonal antibody treatment.

Many reports of mouse cancer models depend on very early treatment of tumors in order to demonstrate robust therapeutic effects, as per the design of the initial experiment. However, given the superior tissue penetrance of HAC PD-1, and its ability to block PD-1:PD-L1 interactions without inducing counterproductive depletion of circulating T cells, it was hypothesized that its advantages in comparison to antibodies might be most apparent when attempting to treat larger, more challenging tumors. To this end, an experiment was initiated in which Balb/c mice were engrafted with CT26 cells, and their tumor volume was monitored daily; only when an individual tumor achieved a minimum volume of 150 mm³, or roughly three times the average starting size of the previous experiment, was the host mouse randomized into a cohort and treatment initiated. This simple change in experimental protocol had profound effects on the comparative efficacy of these agents. Whereas anti-PD-L1 antibody and HACmb were equivalent in treating very small CT26 tumors (FIG. 10B), in the case of larger tumors, even daily injection of anti-PD-L1 antibody failed to register any measurable efficacy over PBS treatment (FIG. 10D, left, $p=0.464$). In stark contrast, HACmb significantly reduced tumor growth in large tumors over the duration of the study, as compared to either PBS-treated (FIG. 10D, right, $p<1\times10^{-4}$) or antibody-treated mice (FIG. 10D, left, $p<1\times10^{-4}$).

It was next tested whether the superior efficacy of HACmb as a monotherapy would extend in the combination setting (e.g., with anti-CTLA4 antibodies). By itself, anti-CTLA4 antibody therapy was effective in this large tumor model, slowing the growth of tumors relative to PBS treatment (FIG. 10D, left and right, $p<1\times10^{-4}$); however, co-treatment with anti-PD-L1 antibody alongside anti-CTLA4 antibody failed to produce any additional benefit over anti-CTLA4 alone (FIG. 10D, left, $p=0.756$). In contrast, HACmb improved anti-CTLA4 therapy, as mice treated with a combination of anti-CTLA4 and HACmb had significantly smaller tumors as compared to either HACmb (FIG. 10D, $p=0.012$), or anti-CTLA4 alone (FIG. 10D, $p=0.006$).

In summary, these in vivo studies demonstrate that HAC PD-1 is effective in treating syngeneic mouse tumors. Importantly, the results illustrate that increases in tumor size disproportionately affect the efficacy of anti-PD-L1 antibodies (in fact rendering them ineffective once tumors have surpassed a certain size threshold), while HAC-PD-1 protein remains efficacious in a challenging and more clinically realistic tumor model. This observation thus suggests that anti-PD-1 or anti-PD-L1 antibodies may not fully capture the maximal therapeutic benefit of PD-1:PD-L1 blockade, and that further improvements are possible with optimized therapeutic agents.

In Vivo Detection of PD-L1 Expression by Positron Emission Tomography (PET) with $^{64}$Cu Radiolabeled HAC-PD-1.

Tumor PD-L1 expression has been suggested as a potential biomarker to predict response to PD-1- or PD-L1-directed immunotherapies. At present, PD-L1 expression on tumors is most commonly assessed through biopsy followed by immunohistochemical staining. However, in addition to the associated risk and contraindications of the biopsy procedure, the resulting tissue analysis is complicated by the heterogeneous spatial expression pattern of PD-L1 within a tumor. "ImmunoPET"—can provide a non-invasive means by which to measure the expression of PD-L1 throughout an entire tumor simultaneously, without the need to excise any tissue. It was reasoned that, owing to its high affinity and specificity for PD-L1, as well as its enhanced tissue penetration, a radiolabeled HAC-PD1 could thus serve as an effective PET probe to assess tumor PD-L1 expression.

Figure 17A:
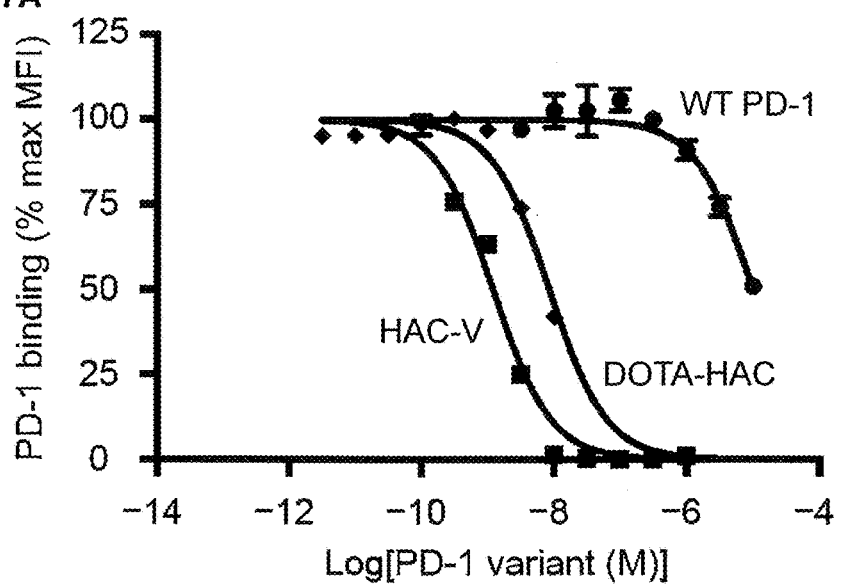
FIG. 17A-17B. Validation of DOTA-HAC PET tracer.
Figure 17B:
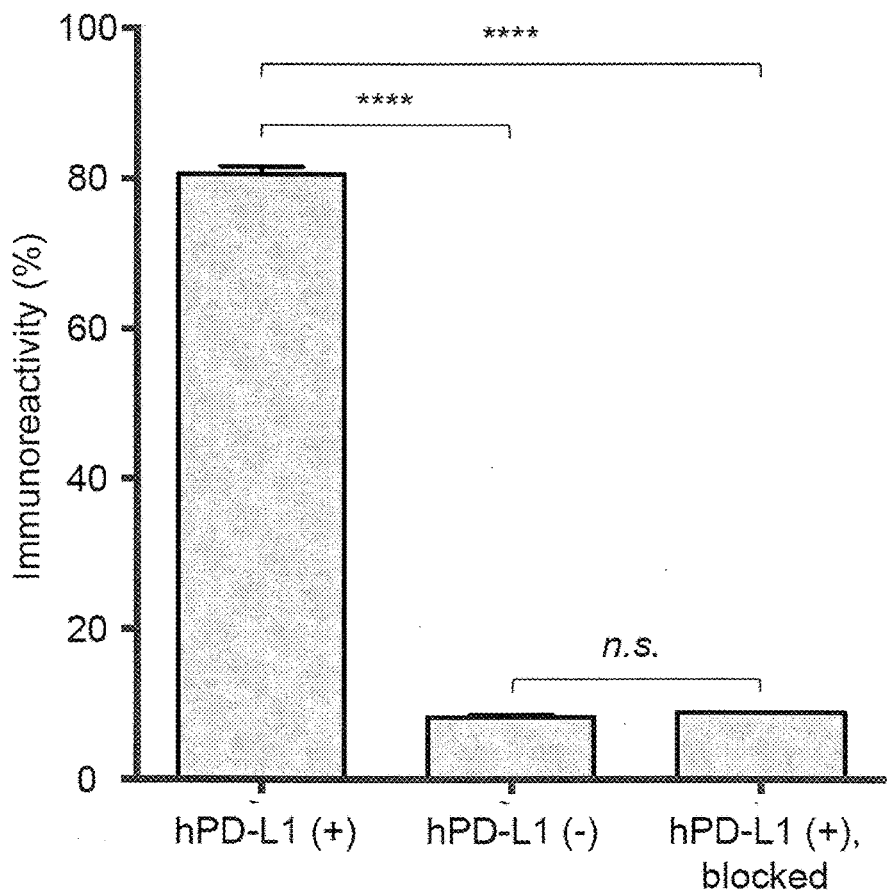

To develop a PET tracer based on the HAC-PD-1 scaffold, a mutated variant, HAC-N91C, was conjugated with the thiol-reactive bifunctional chelate DOTA-maleimide[20]. While the apparent hPD-L1 affinity of DOTA-HAC was weaker than its parent sequence HAC-V, DOTA-HAC nonetheless antagonized hPD-L1 1,200-fold more potently than WT PD-1 (FIG. 17A). Subsequent radiolabeling with $^{64}$Cu produced the hPD-L1-specific radio-protein $^{64}$Cu-DOTA-HAC, which possessed a specific activity of 8-10 µCi per µg and radiochemical purity greater than 98% (FIG. 17B). This PET tracer was used to visualize whole-body hPD-L1 expression in a living mouse.

Figure 11B:
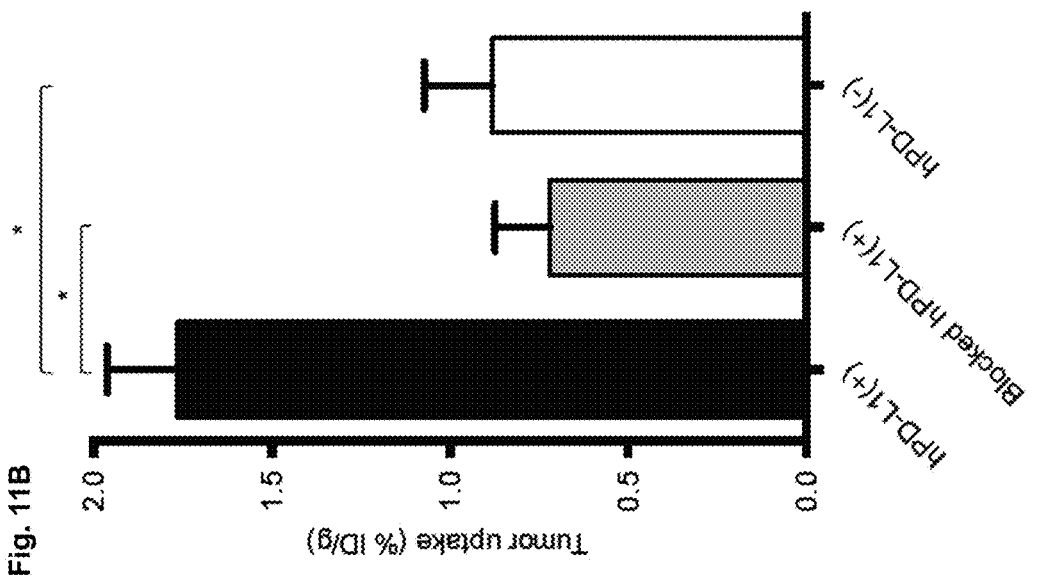
FIG. 11A-11B. MicroPET imaging of hPD-L1 with $^{64}$Cu-DOTA-HAC.
Figure 11A:
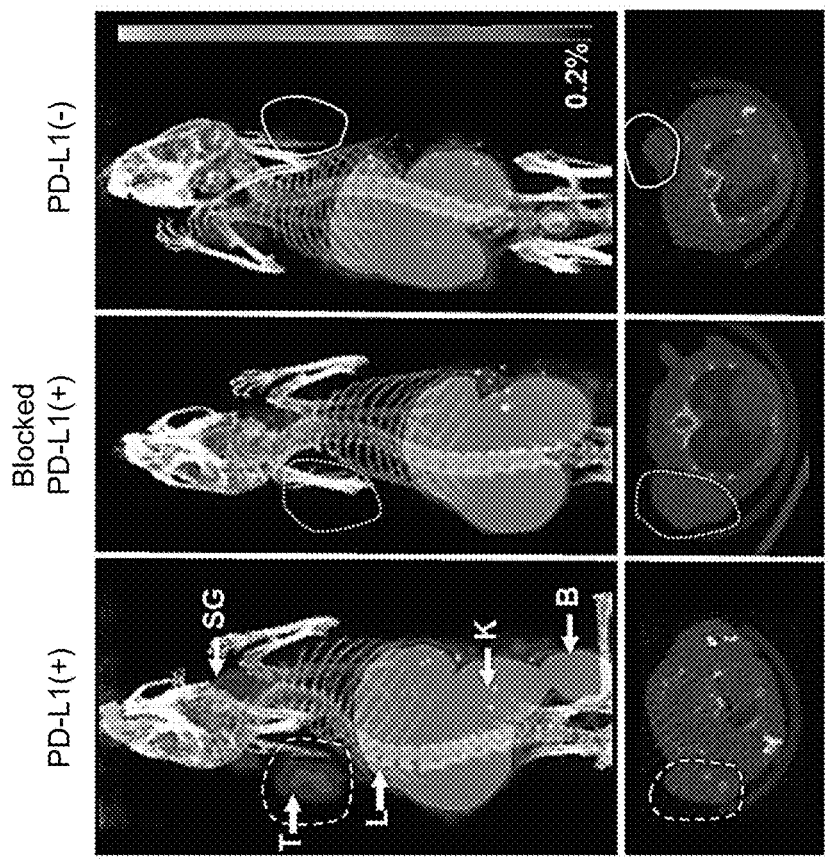
Figure 18A:
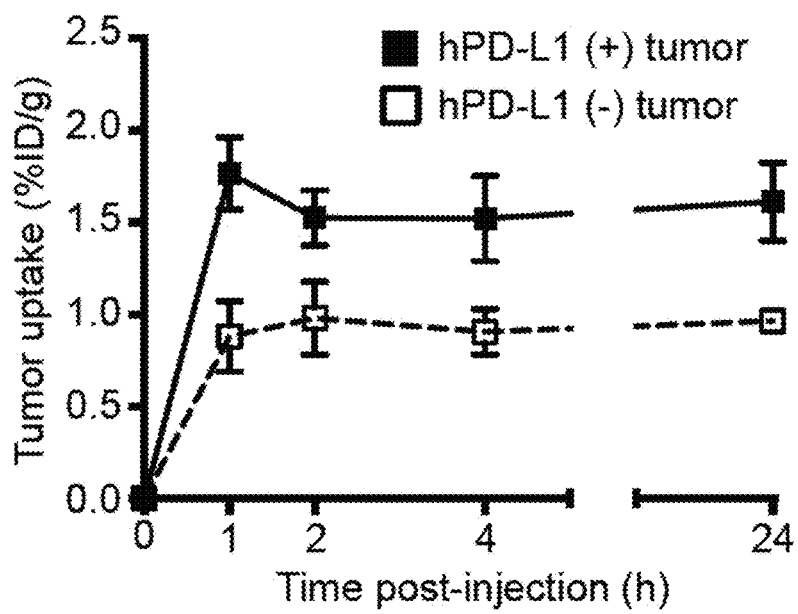
FIG. 18A-18E. $^{64}$Cu-DOTA-HAC MicroPET imaging dynamics.
Figure 18B:
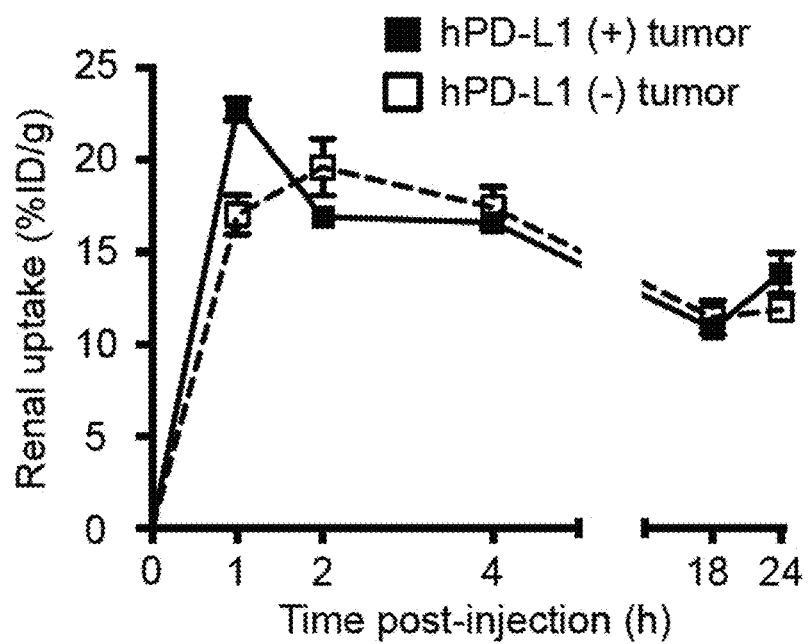
Figure 18C:
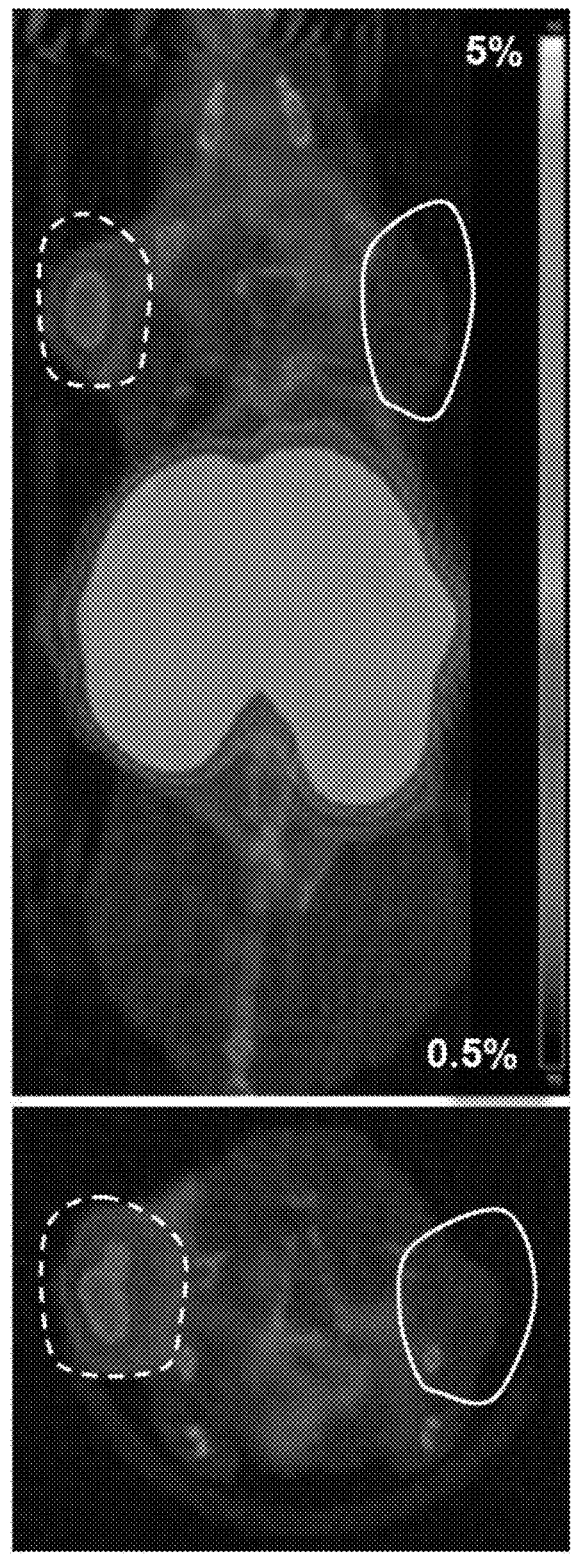
Figure 18D:
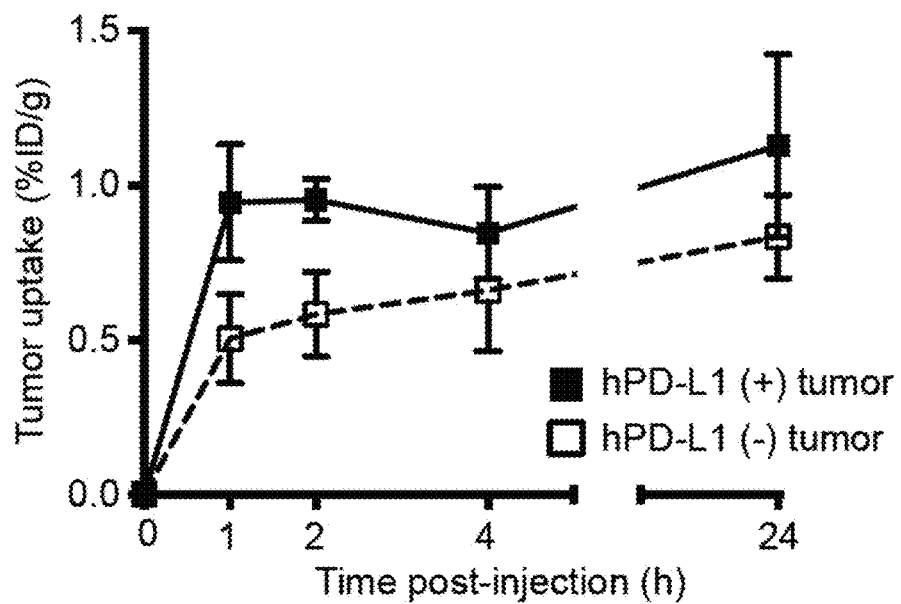
Figure 18E:
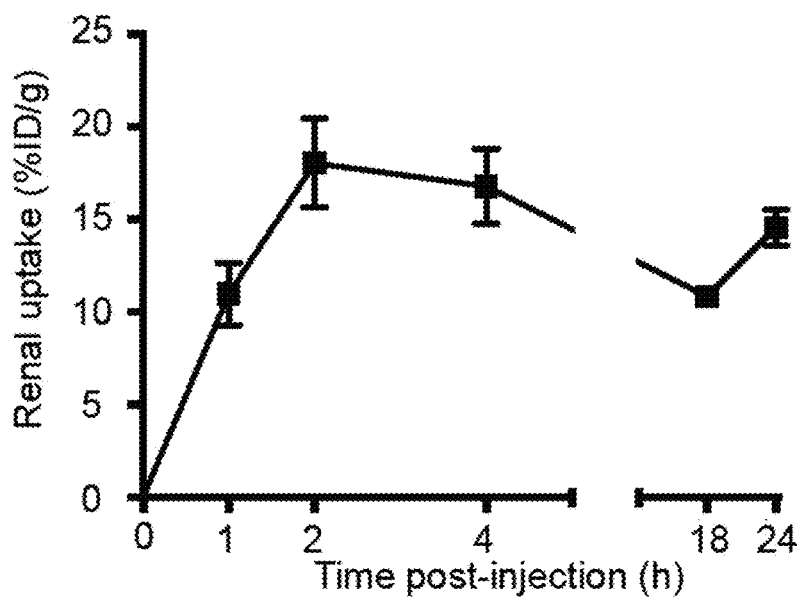
Figure 20A:
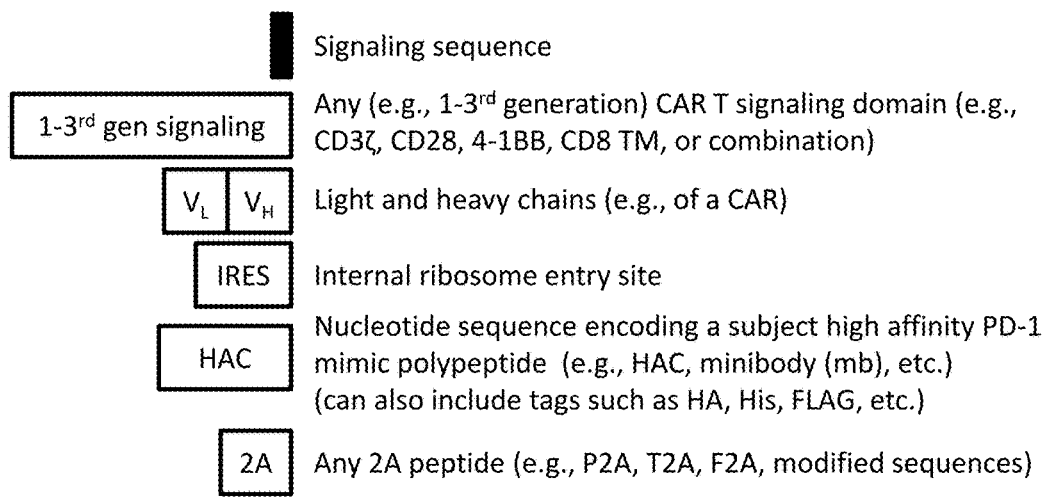
Figure 21A:
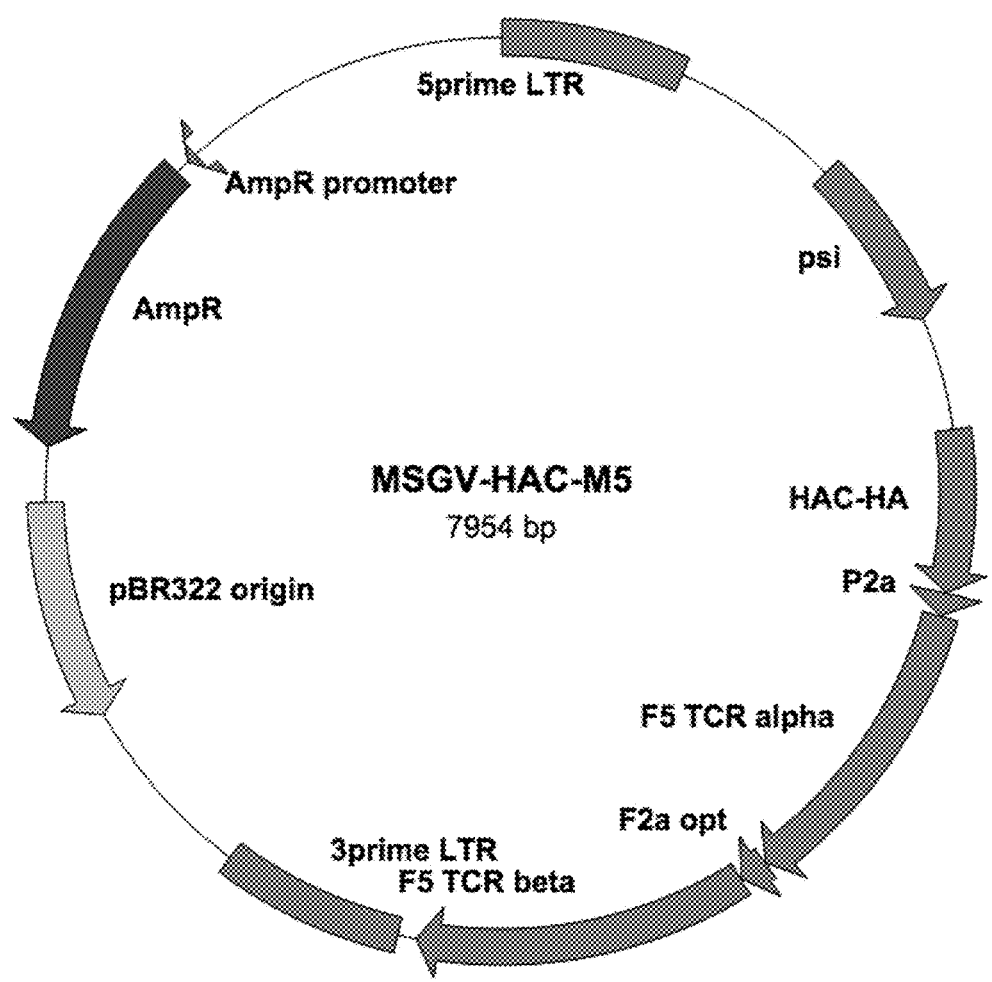
FIG. 21A-21D. Schematic depiction of example nucleic acids (DNA vectors) encoding a subject high affinity PD-1 mimic polypeptide.
Figure 21B:
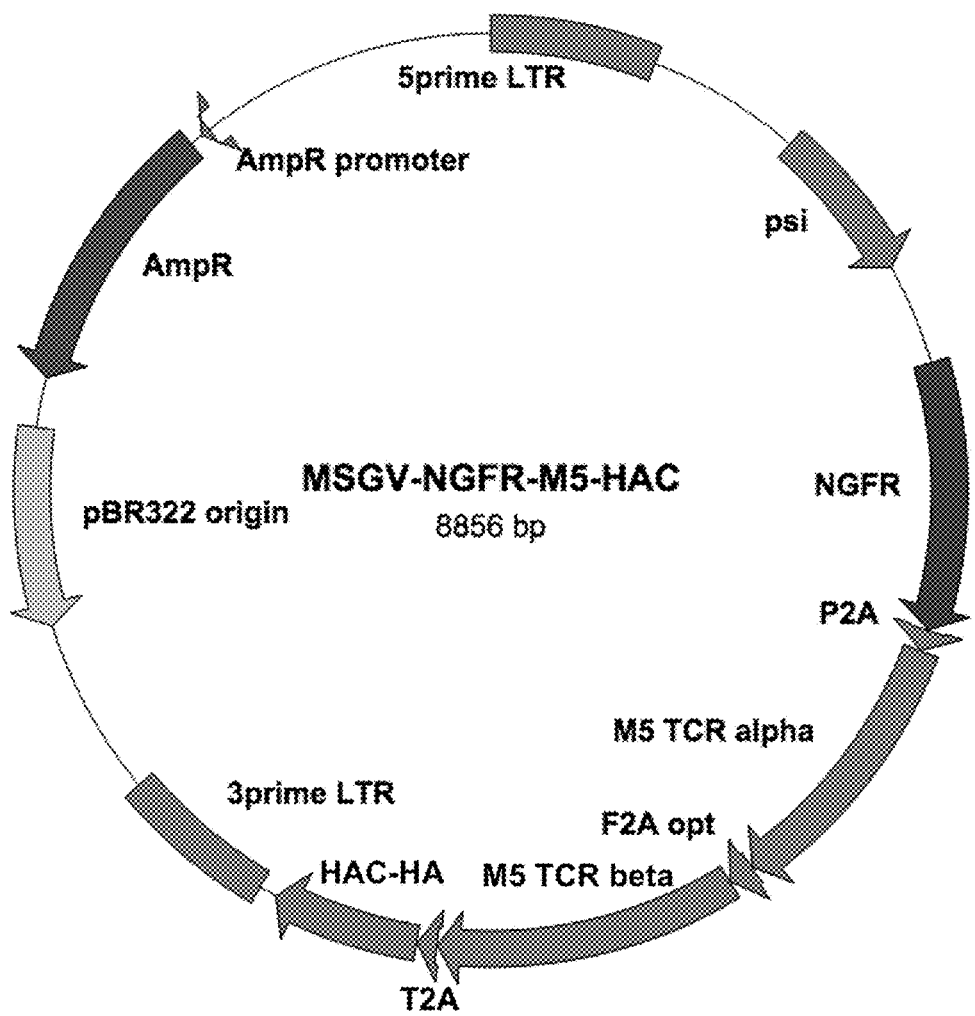
Figure 21C:
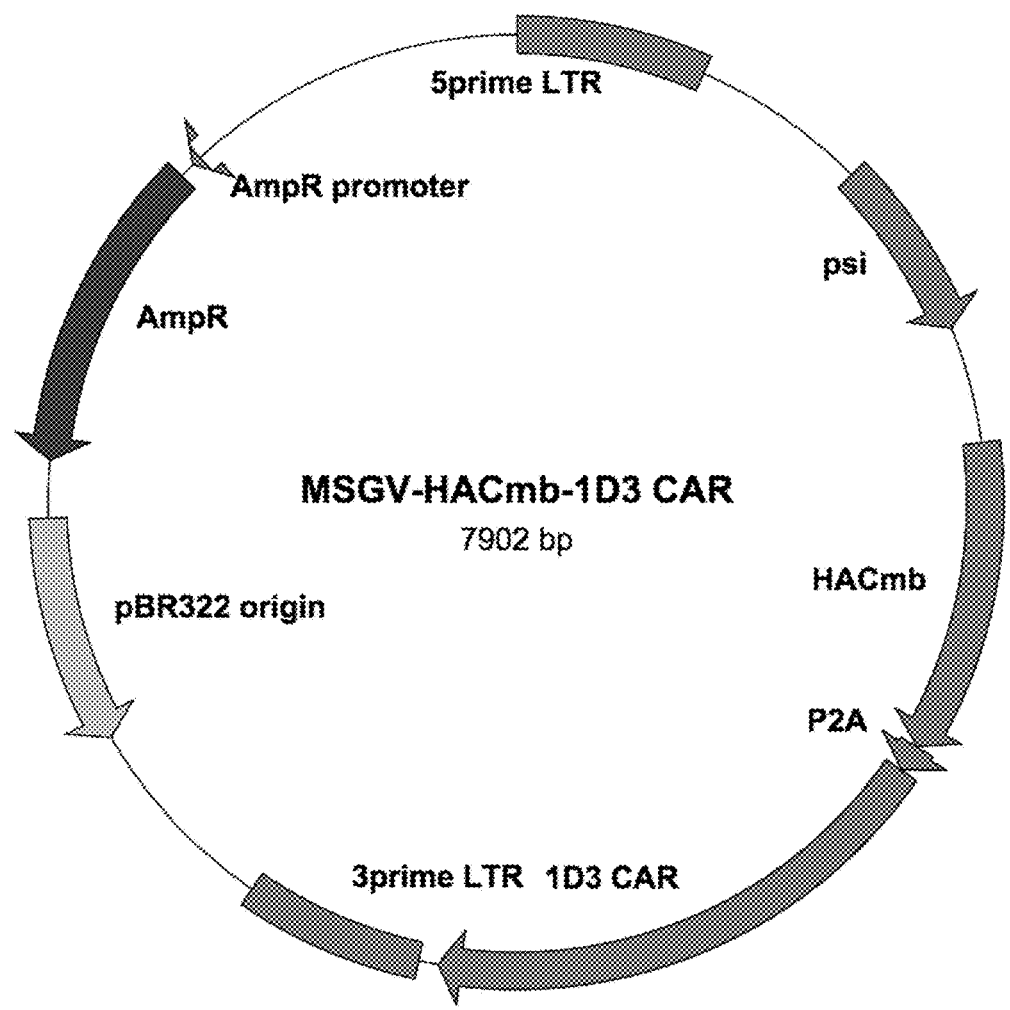
Figure 21D:
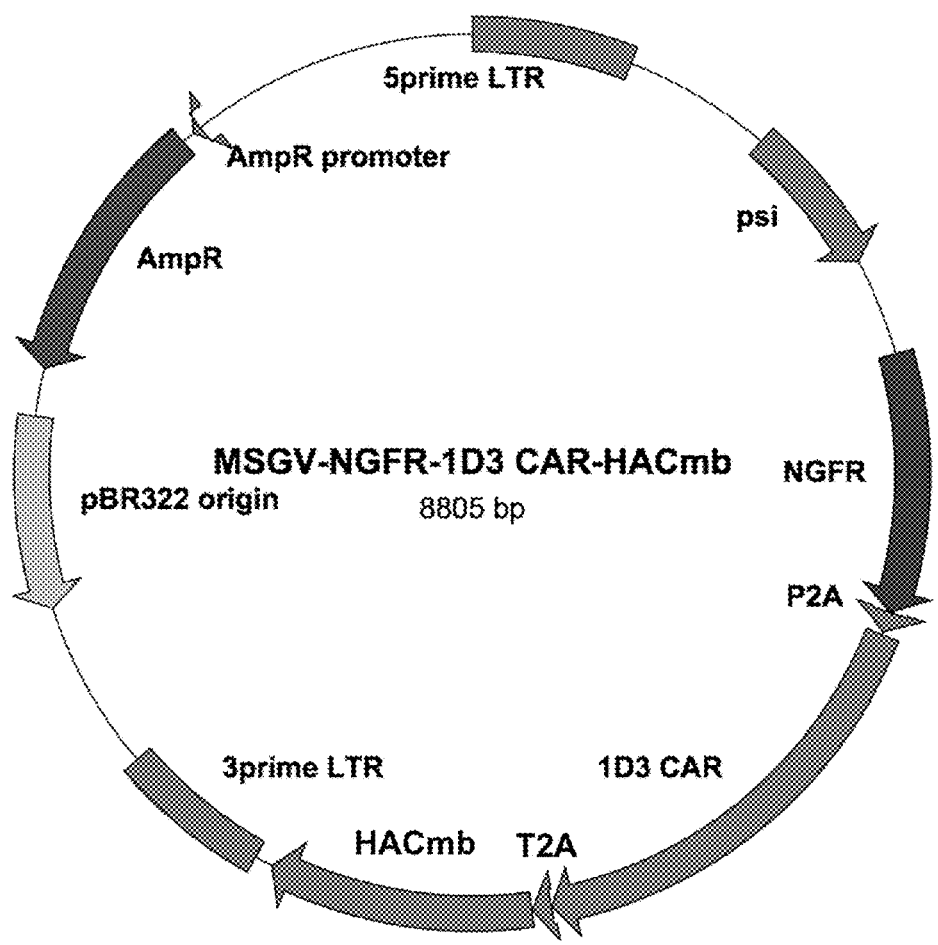

$^{64}$Cu-DOTA-HAC showed a strong tumor/muscle signal (6-fold enhancement, $p<0.05$) at 1 hour post injection (FIG. 11A, FIG. 18A), with high uptake in the kidney, indicating rapid renal clearance of free drug from blood, and high signal in the liver, consistent with copper-specific binding by liver-expressed proteins (FIG. 18B, FIG. 18E). The lack of signal within PD-L1 negative tumors (FIG. 11A, FIG. 18C), or in hPD-L1 positive tumors blocked by prior injection of 500 µg of cold HAC-PD1 (FIG. 11A-11B) indicated a high degree of specificity of $^{64}$Cu-DOTA-HAC-PD1 for PD-L1 binding. Additional scans were obtained at 2, 4, and 24 hours (FIG. 18A, FIG. 18D), and assessed biodistribution at 24 hours (FIG. 19A-19B). Maximal tumor uptake was observed at one hour after injection, though strong signal persisted within hPD-L1(+) tumors for at least 24 hours. In sum, the rapid and specific hPD-L1(+) tumor uptake of $^{64}$Cu-DOTA-HAC facilitates its use as a reagent for clinical imaging applications.

Discussion

Cancer immunotherapy is a treatment paradigm whose remarkable therapeutic potential is just beginning to be fully realized. Though success has been achieved in cancer patients with antibodies targeting the PD-1:PD-L1 axis, the data provided here show that additional efficacy can be achieved using an engineered PD-1 receptor decoy, HAC-PD-1. This protein does not share the antibody-inherent limitations of poor tumor penetration and unwanted depletion of effector T cells. Accordingly, it exerts enhanced anti-tumor activity compared to anti-PD-L1 antibodies towards larger and more established tumors. These results thus highlight the potential of small protein biologics as therapeutics for patients and their broad applicability in modulation of the immune system.

In addition to enhanced delivery to tumors, the modular nature of small proteins like HAC-PD-1 enables facile combination with other immunotherapeutics. This is a key consideration in light of the efficacy of combined checkpoint blockade with nivolumab (anti-PD-1) and ipilimumab (anti-CTLA4) in melanoma patients[21] and numerous preclinical studies that have demonstrated synergy between antibodies targeting PD-1/PD-L1 and additional immunomodulatory pathways, such as TIM-3[22], LAG-3[23], GITR[24], OX-40[25], and 4-1BB[26]. In the case of HAC-PD-1, multi-specific agents targeting synergistic immunomodulatory pathways can readily be elaborated by simply fusing multiple small protein modules, including other engineered receptor decoys or single-domain antibodies. This design leverages the co-expression of different immune checkpoint ligands and/or receptors on the same cells to provide enhanced avidity, and thus potency, to the combined agent. Furthermore, multi-specific therapeutics simplify treatment regimens by reducing the number of separately administered drugs, and by extension, reduce the costs associated with their separate manufacture and development.

Although generally well tolerated compared to some other cancer treatments, immunomodulatory drugs such as anti-PD-1 and anti-PD-L1 antibodies have toxicities that range from mild diarrhea to life-threating immune-related adverse events, including autoimmune hepatitis, pneumonitis, and colitis[8,9] Biomarkers and methods to identify which patients will respond to treatment are urgently needed to avoid unnecessary toxicity in patients who would not otherwise benefit from immunotherapy. Tumor PD-L1 expression by immunohistochemistry (IHC) has thus far proven a partial, but imperfect predictor of anti-PD-1/anti-PD-L1 response[27]. However, IHC may be an insensitive measure of tumor PD-L1 expression and it is conceivable that this method may mischaracterize PD-L1 positive tumors as negative. The work presented here demonstrates that HAC-PD-1 immunoPET imaging of tumor PD-L1 expression can be used as an alternative to immunohistochemistry. This non-invasive approach allows simultaneous imaging of the entire tumor and associated metastases, which may differ from the primary tumor in PD-L1 expression status. Furthermore, PET imaging can be used for repeat imaging of the same tumor at different time points (e.g., before and after treatment), thereby yielding a richer set of diagnostic information that would be difficult or impossible to achieve with traditional biopsy/IHC approaches.

Methods

Mice.

Animal studies were performed in compliance with approval from the Administrative Panel on Laboratory Animal Care at Stanford University. 6-8 week old Balb/c mice, used for syngeneic tumor engraftments and assessment of T cell levels in response to treatments, were obtained directly from The Jackson Laboratory. Nod.Cg-Prkdc.scid.IL2rg.tm1Wjl/SzJ (NSG) mice, used for in vivo assessment of tumor penetrance and PET studies, were obtained from in-house breeding stocks.

Cell Lines.

The human melanoma cell line SK-MEL-28, the murine melanoma cell line B16.F10, and murine colon carcinoma cell line CT26 were obtained from the ATCC. All cell lines were maintained in a humidified, 5% $CO_2$ incubator at 37° C. SK-MEL-28 cells were subcultured in EMEM medium (ATCC) supplemented with 10% fetal bovine serum (FBS; Thermo Fisher Scientific). B16.F10 cells were subcultured in DMEM medium (Life Technologies) supplemented with 10% FBS and 55 µM 2-mercaptoethanol (Sigma). CT26 cells were grown in RPMI supplemented with 10% FBS. Genetic variants of CT26 were created by simultaneous transduction of CT26 cells with Cas9-expressing lentivirus, and a lentiviral pool encoding a mixture of two mPD-L1-targeting sgRNAs [sequence GGCTCCAAAGGACTTG-TACG (SEQ ID NO: 56) and GGTCCAGCTCCCGTTC-TACA (SEQ ID NO: 57), respectively], designed using the tools at genome-engineering.org[28]. At 6 days post-infection, cells were induced to express high levels of PD-L1 through treatment with 100 ng/mL of mouse IFNγ, and at 7 days post-infection, cells were harvested and stained with APC-labeled 10F.9G2 antibody. The negative population was sorted, cultured, and the, several days later after recovery of cell numbers, these cells were subjected to two additional sequential rounds of sorting. This stable negative population was defined as CT26-Δ(mPD-L1). Lentivirus encoding for constitutive, EF1A-driven expression of hPD-L1 were generated and used to infect CT26-Δ(mPD-L1) cells in order to generate a human PD-L1 expressing mouse cancer line. These cells were harvested, stained with PE-anti-PD-L1 (clone MIH1, eBioscience), and sorted to purity. This sorting was repeated three times in total to generate the engineered sub-line CT26-Tg(hPD-L1)-Δ(mPD-L1).

Protein Expression and Purification.

The hPD-1 IgV domain (residues 26-147), hPD-L1 IgV and IgC domains (residues 19-239), high-affinity PD-1 variants, and HACmb were assembled as gBlocks by IDT and cloned in-frame into pAcGP67a with a carboxy-terminal 8× histidine tag for secretion from *Trichoplusia ni* (High Five) cells using baculovirus. The N91C mutation was introduced into HAC-V using PCR-mediated site-directed mutagenesis. Secreted protein was purified from conditioned medium by nickel-nitrilotriacetic acid (Ni-NTA) chromatography and desalted into phosphate buffered saline (PBS). Proteins used for functional or in vivo studies in mice were additionally subjected to column washes with Triton X-114 to remove endotoxin. Biotinylated proteins were obtained by addition of a carboxy-terminal biotin acceptor peptide sequence (GLNDIFEAQKIEWHE (SEQ ID NO: 58)) and enzymatic biotinylation with BirA ligase.

Protein Labeling with Amine- and Cysteine-Reactive Probes.

HAC-V N91C was expressed and purified as described above and reduced by application of tris(2-carboxyethyl) phosphine (TCEP) to a final concentration of 1 mM. The reduced protein was then combined with a 20-fold molar excess of AlexaFluor 594 C5 maleimide (Life Technologies), AlexaFluor 647 C2 maleimide (Life Technologies), or maleimido-mono-amide-DOTA (Macrocyclics) and incubated at room temperature for one hour and then 4° C. for an additional 12 hours. Excess free probe was removed by desalting the reaction mixture into PBS using a VivaSpin protein concentrator (Sartorius Stedim). For DOTA-HAC, reacted protein was exchanged into Hepes buffered saline (HBS; 10 mM Hepes pH 7.4, 150 mM NaCl) and concentrated to ~5 mg/mL. The number of chelators coupled per antibody (c/a) was estimated with matrix-assisted laser desorption/ionization time-of-flight mass spectrometry (MALDI-TOF-MS) by comparison of unreacted HAC-N91C and HAC-DOTA.

Low-endotoxin/azide-free Anti-hPD-L1 (clone 29E.2A3, BioLegend) was labeled with an 8-fold molar excess of AlexaFluor 488 NHS ester for two hours at room temperature (Life Technologies). Free dye was quenched by addition of TRIS pH 8.0 to a final concentration of 20 mM and the labeled antibody desalted with a VivaSpin protein concentrator.

Yeast Display and Directed Evolution.

The IgV domains of hPD-1 (residues 26-147), the IgV and IgC domains of hPD-L1 (residues 19-132), and hPD-L2 (residues 20-123) were displayed on the surface of *S. cerevisiae* strain EBY100 as N-terminal fusions to Aga2 using the pYAL vector as previously described.

Construction and Selection of the First-Generation hPD-1 Library:

As a crystal structure of hPD-1 complexed to hPD-L1 has yet to be reported, 22 likely contact residues were inferred through the structure of mPD-1 bound to hPD-L1 (PDB ID 3SBW). A library randomizing these residues was generated as described by FIG. 12s!-12B, using assembly PCR with primers listed in Table 2. The library had a theoretical diversity of approximately $9.5 \times 10^{19}$ unique protein sequences. The PCR products were further amplified with primers containing homology to the pYAL vector and co-electroporated together with linearized pYAL into EBY100 yeast. The resulting library contained $0.9 \times 10^8$ transformants.

Transformed yeast were recovered and expanded in liquid SDCAA medium at 30° C. and induced by dilution 1:10 into liquid SGCAA medium and cultured at 20° C. for 24 hours. Appropriate numbers of induced yeast were used in each round to ensure at least ten-fold coverage of the expected diversity of the library at each step, and not less than $10^8$ cells. All selection steps were carried out at 4° C. using MACS buffer (PBS with 0.5% bovine serum albumin and 2 mM EDTA). Prior to each round, pre-clearing against streptavidin-AlexaFluor 647 (produced in-house) was performed with anti-Cy5/Alexa Fluor 647 microbeads (Miltenyi) and an LD MACS column (Miltenyi). For rounds 1-3, positive selection was performed by labeling induced yeast with 1 μM biotinylated hPD-L1 for one hour at 4° C., followed secondary staining with streptavidin-AlexaFluor 647, and magnetic selection with anti-Cy5/AlexaFluor 647 microbeads and an LS MACS column (Miltenyi). For round four, positive selection was performed by staining with 10 nM biotinylated hPD-L1 and secondary labeling with streptavidin-AlexaFluor 647. Display levels were determined by staining with AlexaFluor 488-conjugated anti-cMyc (Cell Signaling Technologies) and the top 1% of display-normalized hPD-L1 binders were isolated using fluorescence activated cell sorting (FACS) with a FACS Aria cell sorter. After each round of selection, recovered yeast were expanded in SDCAA medium at 30° C. overnight and later induced at 20° C. by dilution 1:10 into SGCAA medium for 24 hours.

Construction and Selection of the Second-Generation hPD-1 Library:

The second generation library was designed to randomize ten contact positions from the first library that demonstrated convergence away from the wild-type residue, as well as seven additional core positions. The design, illustrated by FIG. 13, had a theoretical diversity of approximately $9.1 \times 10^9$ unique protein sequences. As for the first generation library, the second-generation library was constructed by assembly PCR with primers listed in Table 3 and co-electroporated with pYAL into EBY100 yeast. The resulting library yielded $1.2 \times 10^8$ transformants.

The second-generation library was selected similarly to the first-generation library with a few modifications. Round 1-3 were performed by staining with 1 μM biotinylated hPD-L1 and magnetic bead selection as described above. For rounds 4 and 5, kinetic selection was performed to select for variants with decreased off-rates. Briefly, yeast were stained with 10 nM biotinylated hPD-L1 for one hour at 4° C. After washing with MACS buffer, the yeast were then incubated with 1 μM non-biotinylated hPD-L1 for six hours at room temperature with agitation. Post-competed yeast were then stained with streptavidin-AlexaFluor 647 and AlexaFluor 488-conjugated anti-cMyc and the top 1% of display-normalized binders were isolated by FACS sorting.

Surface Plasmon Resonance.

Experiments were conducted using a Biacore T100 and carried out at 25° C. Biotinylated PD-L1 was immobilized onto a Biacore streptavidin (SA) sensor chip (GE Healthcare) to yield an Rmax of approximately 100 RU. An unrelated biotinylated protein (the IgSF domain of human CD47) was immobilized onto the reference surface with a matching RU value to control for nonspecific binding. Measurements were made with serial dilutions of the PD-1 variants in HBS-P+ buffer (10 mM HEPES pH 7.4, 150 mM NaCl, 0.005% surfactant P20) as indicated in FIG. 8A (GE Healthcare). The PD-L1 surface was regenerated by three 60 second injections of 50% v/v ethylene glycol, 100 mM glycine pH 9.5. All data were analyzed with the Biacore T100 evaluation software version 2.0 with a 1:1 Langmuir binding model.

PD-1 Cell Competition Binding Assays.

WT PD-1 tetramer was formed by incubating biotinylated WT PD-1 with AlexaFluor 647-conjugated streptavidin at a molar ration of 4:1. PD-L1 expression was induced on GFP-luciferase+SK-MEL-28 cells by overnight simulation with 2000 U/mL of human IFNγ. 100 nM WT PD-1 tetramer was then combined with titrating concentrations of WT PD-1 monomer, HAC-V, or HACmb and simultaneously added to 100,000 induced SK-MEL-28 cells. Cells were incubated with the reagent mixtures on ice for 60 minutes then washed to remove unbound tetramer. AlexaFluor 647 fluorescence intensity was quantified by flow cytometry using an Accuri C6 flow cytometer (BD Biosciences).

In Vivo Tumor Penetration Studies.

6-8 week old female Nod.Cg-Prkdc.scid.IL2rg.tm1Wjl/SzJ (NSG) mice were injected subcutaneously with $1 \times 10^6$ cells of the genetically modified colon cancer line CT26-Δ(mPD-L1) in their left shoulder, and $1 \times 10^6$ cells of CT26-Tg(hPD-L1)-Δ(mPD-L1) in their right shoulder, in a 50 μL suspension of 75% RPMI (Life Technologies) and 25% medium-density matrigel (Corning) for each injection. After 14 days, when tumors had grown to approximately 1 cm in diameter, mice were injected intraperitoneally with a mixture of 100 μg AlexaFluor 488-conjugated anti-PD-L1 antibody (clone 29E.2A3, BioLegend) and 100 μg AlexaFluor 594-conjugated HAC PD-1 monomer. After 4 hours, mice were euthanized and their tumors were dissected. After several rounds of washing with cold PBS to remove excess blood, each tumor was cut approximately in half. One half was incubated in a solution of 1% PFA in PBS overnight at 4° C. with rocking, washed in PBS, and embedded in Tissue Tek Optimal Cutting Temperature (O.C.T.) (Sakura). 7 micron frozen sections of these tissues were cut and thawed for 30 minutes, washed in acetone at 4° C. for 4 minutes, air-dried for 10 minutes, washed in PBS (three times, 5 minutes each), and labeled with Hoechst 33342 (Invitrogen) before mounting with Fluoromount G (Southern Biotech). Slides were visualized on an Eclipse e800 fluorescent microscope (Nikon) at 10× or 20× magnification. Basic photo processing, including fluorescence channel false-coloring, channel merge, and brightness and contrast adjustment, were performed using Adobe Photoshop (Adobe). For FACS analysis, the second half of each tumor was finely minced with a straight razor, and the minced tissue was pressed through a 100 μM mesh cell strainer, rinsed with PBS, and finally passed through a 40 μM cell strainer while in liquid suspension. Samples were kept as close to 4° C. as possible throughout all steps of processing. Finally, the resulting single-cell suspension was fixed in a 1% PFA solution, and analyzed for antibody- and HAC-derived fluorescence signal on an LSRFortessa FACS Analyzer (BD Biosciences).

T Cell Depletion Studies.

6-8 week old wild type female Balb/c mice were shaved on their lower dorsum and injected subcutaneously with $1 \times 10^6$ cells of the colon cancer line CT26 in a 50 μL suspension of 75% RPMI (Life Technologies) and 25% medium-density matrigel (Corning). Mice whose tumors failed to engraft within 7 days by visual inspection were excluded from further study. Those with visible, palpable tumors were randomized into treatment groups, 10 mice per group, using the tools at random.org. Mice were treated for 3 days by once-daily intraperitoneal injections of 100 μl PBS, 250 μg of anti-PD-L1 antibody (clone 10F.9G2, BioXcell), or 250 μg purified HACmb protein, each adjusted to a concentration of 2.5 mg/mL. After three days of treatment, peripheral blood and lymph nodes were collected from each mouse and stained with the following panel of antibodies (BioLegend): AlexaFluor488 CD45 (clone 30-F11), PerCP-Cy5-5 CD8 (clone 53-6.7), AlexaFluor700 Nk1.1 (clone PK136), APC-Cy7 B220 (clone RA3-6B2), PE-Dazzle CD11b (clone M1/70), PE-Cy5 F4/80 (clone BM8), PE-Cy7 CD4 (GK1.5), and APC PD-L1 (clone 10F.9G2). DAPI was used as a viability stain. Samples were analyzed on an LSRFortessa FACS Analyzer (BD Biosciences).

CT26 Tumor Models.

6-8 week old wild type female Balb/c mice were shaved on their lower dorsum and injected subcutaneously with $1 \times 10^6$ cells of the colon cancer line CT26 in a 50 μL suspension of 75% RPMI (Life Technologies) and 25% medium-density matrigel (Corning). Mice whose tumors failed to engraft within 7 days by visual inspection were excluded from further study. For small tumor treatment studies, mice were randomized into cohorts using the list randomization tools at random.org, and treatments were administered starting 7 days post-engraftment for all mice. In these small tumor studies, digital caliper measurements were taken every third day, and values were graphed as fold change, as normalized to the measured values on day 10. For large tumor studies, mice were engrafted as described above, and starting at day 8 tumors were measured on a daily basis. Mice were individually sorted into treatment cohorts and treatment was initiated only when tumors reached a threshold of 150 mm$^3$, approximately 10-14 days post-engraftment in all cases. Digital caliper measurements were taken every day for every mouse in the large tumor experiment for the duration of treatment. In order to reduce random day-to-day variability in measured values, the graphed tumor volumes in this experiment are averages as evaluated within a sliding window that includes the current day, the previous day, and the next day's measurements. Values from the large tumor study were graphed as absolute tumor volume (mm$^3$). In both experiments, mice were given daily treatment injections intraperitoneally for 14 days with 100 μl PBS, 250 μg of anti-PD-L1 antibody (clone 10F.9G2, BioXcell), or 250 μg purified HACmb protein, each adjusted to a concentration of 2.5 mg/mL. Tumors were approximated as ellipsoids with two radii x and y, where x is the largest measurable dimension of the tumor, and y is the dimension immediately perpendicular to x: Volume=$(4/3)*(\pi)*(x/2)*(y/2)^2$.

$^{64}$Cu-Labeling of DOTA-HAC.

DOTA-HAC was radiolabeled with $^{64}$CuCl$_2$ (University of Wisconsin, Madison): 500 μg of DOTA-HAC in 200 μl of 0.1 mM ammonium acetate buffer (pH 5.5) was reacted with ~370 MBq (~10 mCi) of neutralized $^{64}$CuCl$_2$ solution at 37° C. for 1 hour. After incubation, 5 mM ethylenediaminetetraacetic acid (EDTA) pH 7.0 was added at room temperature for 15 minutes to scavenge unchelated $^{64}$CuCl$_2$ in the reaction mixture. Purification of $^{64}$Cu-DOTA-HAC was performed using an SEC 3000 HPLC with a flow rate of 1.0 mL/min (0.1 M phosphate buffer, pH 7.0) Radiochemical purity was assessed by radio-HPLC. The final dose of radioconjugate was passed through a 0.2 μm filter into a sterile vial.

Radiotracer Cell Binding Assay

An in vitro cell binding assay was performed using hPDL1(+) cells, hPDL1(+) cells pre-blocked with HAC-V, and control hPDL1(−) cells to assess immunoreactivitiy. $2.5 \times 10^5$ cells in 0.1 mL were aliquotted in triplicate and washed with PBSA (PBS supplemented with 1% bovine serum albumin). Each tube was incubated with 0.1 mL, 5 nmol/L $^{64}$Cu-DOTA-HAC (5-6 MBq/nmol) for 45 minutes. After incubation cells were washed thrice with 1% PBSA. Activity in each cell pellet was quantified using a gamma counter (1470 WIZARD Automatic Gamma Counter; Perkin-Elmer).

Small Animal Micro-PET Imaging.

NSG mice bearing subcutaneous hPDL1 positive (n=4) or hPDL1 negative (n=4) CT26 tumors were injected intravenously with $^{64}$Cu-DOTA-HAC (~230 µCi/25 µg protein/200 µl PBS). One group also received a blocking dose (n=2) of 500 µg/200 µl cold HAC two hours pre injection of PET radiotracer. Mice were anesthetized and imaged on a Siemens Inveon small-animal multimodality PET/CT system (Preclinical Solutions; Siemens Healthcare) at time points of 1, 2, 4, and 24 hours post injection. CT raw images were acquired in the second bed position at 80 kVp/500 pA, half-scan 220° of rotation, 120 projections per bed position, with a cone beam micro-X-ray source (50-µm focal spot size) and a 2,048×3,072 pixel x-ray detector. CT datasets were reconstructed using a Shepp-Logan filter and cone-beam filtered back-projection. On the basis of attenuation correction from the CT scans, static PET images were acquired with the default coincidence timing window of 3.4 ns and energy window of 350 tO 650 keV. PET scan acquisition time lengths of 3 minutes (1, 2 hours), 5 minutes (4 hours), and 10 minutes (24 hours) were chosen based upon time post-injection. PET datasets were reconstructed using the two-dimensional ordered-subset expectation maximization (OSEM 2D) algorithm[29]. Image analysis was performed utilizing the Inveon Research Workspace (IRW). For each microPET scan, three dimensional regions of interest (ROI) were drawn over the liver, spleen, kidneys, and tumor on decay-corrected whole-body images. Percent injected dose per gram of tissue (% ID/g) in each organ was obtained from dividing the mean pixel value in the region of interest (ROI; nCi/cc) by the total injected dose. Partial volume correction was not performed. Statistical analysis was performed by two-way ANOVA (GraphPad).

Biodistribution Studies.

After completion of micro-PET/CT imaging at the 24 hour post-injection time point, mice were euthanized and dissected for biodistribution. Blood and organs (heart, lungs, liver, spleen, pancreas, stomach, small intestine, large intestine, kidney, muscle, bone, bone marrow, skin, brain, tumor, and tail) were collected and weighed. CPM values for each organ from gamma counter measurements were converted to percent-injected dose per gram of tissue. Data were decay corrected to injection time.

Tables

TABLE 2

Primers used to create "First Generation" PD-1 library

| Primer | Sequence (5' to 3') | SEQ ID NO: |
|---|---|---|
| D1aff_1F | CATTTTCAATTAAGATGCAGTTACTTCGCTG | 59 |
| D1aff_2R | AATAACAGAAAATATTGAAAAACAGCGAAGTAACTGCATCTTAATTG | 60 |
| D1aff_3F | TTACTTCGCTGTTTTTCAATATTTTCTGTTATTGCTAGCGTTTTAGCAG | 61 |
| D1aff_4R | GTCTATCTGGGGAATCTGCTAAAACGCTAGCAATAACAGAAAAT | 62 |
| D1aff_5F | TTTTAGCAGATTCCCCAGATAGACCATGGAACCCACCAAC | 63 |
| D1aff_6R | CAACAAAGCTGGGGAGAAAGTTGGTGGGTTCCATGGTC | 64 |
| D1aff_7F | AACTTTCTCCCCAGCTTTGTTGGTCGTCACTGAAGGTGA | 65 |
| D1aff_8R | GAACAAGTGAAAGTAGCGTTATCACCTTCAGTGACGACCA | 66 |
| D1aff_9F | GTGATAACGCTACTTTCACTTGTTCCTTCTCCAACACTTCC | 67 |
| D1aff_10R | GAAGGATTCGGAAGTGTTGGAGAAGGAACA | 68 |
| D1aff_11F | CAACACTTCCGAATCCTTCNDTTTGRWTTGGHWTAGAVW GTCCCCAVNTNDTVWWVYTNDTVNATTGGCTNHTTTCCCA GAAGATAGATCC | 69 |
| D1aff_12R | GAGTGACTCTGAATCTAGCATCTKGAHNTGGTNBGGATCT ATCTTCTGGGAAA | 70 |
| D1aff_13F | AGATGCTAGATTCAGAGTCACTCAATTGCCAAAC | 71 |
| D1aff_14R | GGACATGTGGAAATCTCTACCGTTTGGCAATTGAGTGACT CTGA | 72 |
| D1aff_15F | CGGTAGAGATTTCCACATGTCCGTCGTCAGAGCTAGAAGA AACG | 73 |
| D1aff_16R | GTAAGTACCGGAATCGTTTCTTCTAGCTCTGACGAC | 74 |

TABLE 2-continued

Primers used to create "First Generation" PD-1 library

| Primer | Sequence (5' to 3') | SEQ ID NO: |
| --- | --- | --- |
| D1aff_17F | GAAACGATTCCGGTACTTACNWTTGTGGTGCTATTNCTND TNHTSCTVNANYTCAAATTAAGVRWTCCTTGAGAGCTGAAT TGAG | 75 |
| D1aff_18R | GGATCCTCTTTCAGTGACTCTCAATTCAGCTCTCAAGGA | 76 |
| D1aff_19F | ATTGAGAGTCACTGAAAGAGGATCCGAACAAAAGCTTATC | 77 |
| D1aff_20R | CAAGTCTTCTTCGGAGATAAGCTTTTGTTCGGATCCTCTT | 78 |
| D1aff_21F | AAAGCTTATCTCCGAAGAAGACTTGGGTGGTGGTGG | 79 |
| D1aff_22R | CCACCAGATCCACCACCACCCAAGTC | 80 |

TABLE 3

Primers used to create "Second Generation" PD-1 library

| Primer | Sequence (5' to 3') | SEQ ID NO: |
| --- | --- | --- |
| 1F_AffMat_G2 | CATTTTCAATTAAGATGCAGTTACTTCGCTG | 81 |
| 2R_AffMat_G2 | AATAACAGAAAATATTGAAAAACAGCGAAGTAACTGC ATCTTAATTG | 82 |
| 3F_AffMat_G2 | TTACTTCGCTGTTTTTCAATATTTTCTGTTATTGCTAG CGTTTTAGCAG | 83 |
| 4R_AffMat_G2 | GTCTATCTGGGGAATCTGCTAAAACGCTAGCAATAA CAGAAAAT | 84 |
| 5F_AffMat_G2 | TTTTAGCAGATTCCCCAGATAGACCATGGAACCCAC CAAC | 85 |
| 6R_AffMat_G2 | CAACAAAGCTGGGGAGAAAGTTGGTGGGTTCCATGG TC | 86 |
| 7F_AffMat_G2 | AACTTTCTCCCCAGCTTTGTTGGTCGTCACTGAAGGT GA | 87 |
| 8R_AffMat_G2 | GAACAAGTGAAAGTAGCGTTATCACCTTCAGTGACG ACCAA | 88 |
| 9F_AffMat_G2 | GTGATAACGCTACTTTCACTTGTTCCTTCTCCAACAC TTCC | 89 |
| 10R_AffMat_G2 | GAAGGATTCGGAAGTGTTGGAGAAGGAACA | 90 |
| 11F_AffMat_G2 | CCAACACTTCCGAATCCTTCVRTNTTNWTTGGYWTY DTSAWTCCCCATCCDRTCAAACTGATAMATTGGCTG CTTTCCCAGAAG | 91 |
| 12R_AffMat_G2 | GACCTGGTTGGGATCTATCTTCTGGGAAAGCAGCCA AT | 92 |
| 13F_AffMat_G2 | GAAGATAGATCCCAACCAGGTCMAGATGCTAGATTC AGARYTACTCAATTGCCAAACGGTAGAG | 93 |
| 14R_AffMat_G2 | CTTCTAGCTCTGACGACGGASANGTGAAATCTCTA CCGTTTGGCAATTGAG | 94 |
| 15F_AffMat_G2 | TCCGTCGTCAGAGCTAGAAGAAACGATTCCGGTACT | 95 |
| 16R_AffMat_G2 | GCTCTCAAGGATTCCTTAATTTGAANCTTTGGAGCA WRGGAAATARYACCACAAANAWRAGTACCGGAATC GTTTCTTCTAGC | 96 |
| 17F_AffMat_G2 | TTCAAATTAAGGAATCCTTGAGAGCTGAATTGAGAGT CAC | 97 |
| 18R_AffMat_G2 | GTTCGGATCCTCTTTCAGTGACTCTCAATTCAGCTCT CAAG | 98 |

TABLE 3-continued

Primers used to create "Second Generation" PD-1 library

| Primer | Sequence (5' to 3') | SEQ ID NO: |
|---|---|---|
| 19F_AffMat_G2 | GTCACTGAAAGAGGATCCGAACAAAAGCTTATCTCCGAAGAAGAC | 99 |
| 20R_AffMat_G2 | CCACCAGATCCACCACCACCCAAGTCTTCTTCGGAGATAAGCTTTTG | 100 |

TABLE 4

Statistical analysis of large tumor study groups at treatment day 14

| Day 14 comparison | Mean Diff. | 95% CI of diff. | Significant? | Summary | Individual P value |
|---|---|---|---|---|---|
| PBS vs. HACmb | 507.6 | 320.1 to 695.2 | Yes | **** | <0.0001 |
| PBS vs. anti-PD-L1 | 69.97 | −117.6 to 257.5 | No | ns | 0.4636 |
| PBS vs. anti-CTLA4 | 480.7 | 293.2 to 668.3 | Yes | **** | <0.0001 |
| PBS vs. anti-CTLA4 + HACmb | 747.4 | 559.9 to 935.0 | Yes | **** | <0.0001 |
| PBS vs. anti-CTLA4 + anti-PD-L1 | 510.4 | 322.8 to 697.9 | Yes | **** | <0.0001 |
| HACmb vs. anti-PD-L1 | −437.7 | −625.2 to −250.1 | Yes | **** | <0.0001 |
| HACmb vs. anti-CTLA4 | −26.92 | −214.5 to 160.6 | No | ns | 0.7779 |
| HACmb vs. anti-CTLA4 + HACmb | 239.8 | 52.21 to 427.3 | Yes | * | 0.0124 |
| HACmb vs. anti-CTLA4 + anti-PD-L1 | 2.740 | −184.8 to 190.3 | No | ns | 0.9771 |
| anti-PD-L1 vs. anti-CTLA4 | 410.8 | 223.2 to 598.3 | Yes | **** | <0.0001 |
| anti-PD-L1 vs. anti-CTLA4 + HACmb | 677.4 | 489.9 to 865.0 | Yes | **** | <0.0001 |
| anti-PD-L1 vs. anti-CTLA4 + anti-PD-L1 | 440.4 | 252.9 to 628.0 | Yes | **** | <0.0001 |
| anti-CTLA4 vs. anti-CTLA4 + HACmb | 266.7 | 79.13 to 454.2 | Yes | ** | 0.0055 |
| anti-CTLA4 vs. anti-CTLA4 + anti-PD-L1 | 29.66 | −157.9 to 217.2 | No | ns | 0.7559 |
| anti-CTLA4 + HACmb vs. anti-CTLA4 + anti-PD-L1 | −237.0 | −424.6 to −49.47 | Yes | * | 0.0134 |

That which is claimed is:

1. A method of treating an individual having cancer, having a chronic infection, or having an immunological disorder associated with immunosuppression, the method comprising:
   administering to the individual a multispecific polypeptide comprising a first region corresponding to a high affinity programmed death-1 (PD-1) mimic polypeptide that:
   i) lacks a wild-type PD-1 transmembrane domain; and
   ii) comprises one or more amino acid changes selected from: (1) V39H or V39R; (2) L40V or L40I; (3) N41I or N41V; (4) Y43F or Y43H; (5) R44Y or R44L; (6) M45Q, M45E, M45L, or M45D; (7) S48D, S48L, S48N, S48G, or S48V; (8) N49C, N49G, N49Y, or N49S; (9) Q50K, Q50E, or Q50H; (10) T51V, T51L, or T51A; (11) D52F, D52R, D52Y, or D52V; (12) K53T or K53L; (13) A56S or A56L; (14) Q63T, Q63I, Q63E, Q63L, or Q63P; (15) G65N, G65R, G65I, G65L, G65F, or G65V; (16) Q66P; (17) V72I; (18) H82Q; (19) M83L or M83F; (20) R90K; (21) Y96F; (22) L97Y, L97V, or L97I; (23) A100I or A100V; (24) S102T or S102A; (25) L103I, L103Y, or L103F; (26) A104S, A104H, or A104D; (27) P105A; (28) K106G, K106E, K106I, K106V, K106R, or K106T; and (29) A107P, A107I, or A107V, wherein the amino acid position is relative to the PD-1 protein fragment set forth in SEQ ID NO: 2.

2. The method of claim 1, wherein the one or more amino acid changes increases the affinity of the high affinity PD-1 mimic polypeptide for programmed cell death 1 ligand 1 (PD-L1) as compared to the affinity for PD-L1 of the human wild type PD-1 polypeptide as set forth in SEQ ID NO: 1.

3. The method of claim 1, wherein the PD-1 mimic polypeptide has a $K_d$ of $1 \times 10^{-7}$ M or less for PD-L1.

4. The method of claim 1, wherein the one or more amino acid changes is located at an amino acid position of PD-1 that contacts PD-L1.

5. A method of treating an individual having cancer, having a chronic infection, or having an immunological disorder associated with immunosuppression, the method comprising:
   administering to the individual a multispecific polypeptide comprising a first region corresponding to a high affinity programmed death-1 (PD-1) mimic polypeptide that:
   i) lacks a wild-type PD-1 transmembrane domain; and
   ii) comprises amino acid changes located at amino acid positions selected from:

(a) V39, N41, Y43, M45, S48, N49, Q50, K53, A56, Q63, G65, Q66, L97, S102, L103, A104, K106, and A107;
(b) V39, N41, Y43, M45, S48, Q50, T51, D52F, K53, A56, Q63, G65, Q66, L97, S102, L103, A104, K106, and A107;
(c) V39, L40, N41, Y43, R44, M45, N49, K53, M83, L97, A100, and A107;
(d) V39, L40, N41, Y43, M45, N49, K53, Q66, M83, L97, and A107;
(e) V39, L40, N41, Y43, M45, N49, K53, Q66, H82, M83, L97, A100, and A107;
(f) V39, L40, N41, Y43, M45, N49, K53, M83, L97, A100, and A107;
(g) V39, L40, N41, Y43, R44, M45, N49, K53, L97, A100, and A107; and
(h) V39, L40, N41, Y43, M45, N49, K53, L97, A100, and A107;

wherein the amino acid positions are relative to the PD-1 protein fragment set forth in SEQ ID NO: 2.

6. The method of claim 5, wherein cancer cells of the cancer are positive for PD-L1 expression.

7. The method of claim 5, wherein the cancer comprises lung cancer, prostate cancer, breast cancer, bladder cancer, colon cancer, ovarian cancer, pancreatic cancer, kidney cancer, liver cancer, glioblastoma, medulloblastoma, leiomyosarcoma, head & neck squamous cell carcinomas, melanomas, neuroendocrine cancer, a leukemia, or a lymphoma.

8. A method of treating an individual having cancer, having a chronic infection, or having an immunological disorder associated with immunosuppression, the method comprising:
administering to the individual a multispecific polypeptide comprising a first region corresponding to a high affinity programmed death-1 (PD-1) mimic polypeptide that:
i) lacks a wild-type PD-1 transmembrane domain; and
ii) comprises amino acid changes selected from:
(a) {V39H or V39R}, {N41I or N41V}, {Y43F or Y43H}, {M45Q, M45E, M45L, or M45D}, {S48D, S48L, S48N, S48G, or S48V}, {N49C, N49G, N49Y, or N49S}, {Q50K, Q50E, or Q50H}, {K53T or K53L}, {A56S or A56L}, {Q63T, Q63I, Q63E, Q63L, or Q63P}, {G65N, G65R, G65I, G65L, G65F, or G65V}, {Q66P}, {L97Y, L97V, or L97I}, {S102T or S102A}, {L103I, L103Y, or L103F}, {A104S, A104H, or A104D}, {K106G, K106E, K106I, K106V, K106R, or K106T}, and {A107P, A107I, or A107V};
(b) {V39H or V39R}, {N41I or N41V}, {Y43F or Y43H}, {M45Q, M45E, M45L, or M45D}, {S48D, S48L, S48N, S48G, or S48V}, {Q50K, Q50E, or Q50H}, {T51V, T51L, or T51A}, {D52F, D52R, D52Y, or D52V}, {K53T or K53L}, {A56S or A56L}, {Q63T, Q63I, Q63E, Q63L, or Q63P}, {G65N, G65R, G65I, G65L, or G65F, or G65V}, {Q66P}, {L97Y, L97V, or L97I}, {S102T or S102A}, {L103I, L103Y, or L103F}, {A104S, A104H, or A104D}, {K106G, K106E, K106I, K106V, K106R, or K106T}, and {A107P, A107I, or A107V};
(c) {V39H or V39R}, {L40V or L40I}, {N41I or N41V}, {Y43F or Y43H}, {R44Y or R44L}, {M45Q, M45E, M45L, or M45D}, {N49C, N49G, N49Y, or N49S}, {K53T or K53L}, {M83L or M83F}, {L97Y, L97V, or L97I}, {A100I or A100V}, and {A107P, A107I, or A107V};
(d) {V39H or V39R}, {L40V or L40I}, {N41I or N41V}, {Y43F or Y43H}, {M45Q, M45E, M45L, or M45D}, {N49C, N49G, N49Y, or N49S}, {K53T or K53L}, {Q66P}, {M83L or M83F}, {L97Y, L97V, or L97I}, and {A107P, A107I, or A107V};
(e) {V39H or V39R}, {L40V or L40I}, {N41I or N41V}, {Y43F or Y43H}, {M45Q, M45E, M45L, or M45D}, {N49C, N49G, N49Y, or N49S}, {K53T or K53L}, {Q66P}, {H82Q}, {M83L or M83F}, {L97Y, L97V, or L97I}, {A100I or A100V}, and {A107P, A107I, or A107V};
(f) {V39H or V39R}, {L40V or L40I}, {N41I or N41V}, {Y43F or Y43H}, {M45Q, M45E, M45L, or M45D}, {N49C, N49G, N49Y, or N49S}, {K53T or K53L}, {M83L or M83F}, {L97Y, L97V, or L97I}, {A100I or A100V}, and {A107P, A107I, or A107V};
(g) {V39H or V39R}, {L40V or L40I}, {N41I or N41V}, {Y43F or Y43H}, {R44Y or R44L}, {M45Q, M45E, M45L, or M45D}, {N49C, N49G, N49Y, or N49S}, {K53T or K53L}, {L97Y, L97V, or L97I}, {A100I or A100V}, and {A107P, A107I, or A107V}; and
(h) {V39H or V39R}, {L40V or L40I}, {N41I or N41V}, {Y43F or Y43H}, {M45Q, M45E, M45L, or M45D}, {N49C, N49G, N49Y, or N49S}, {K53T or K53L}, {L97Y, L97V, or L97I}, {A100I or A100V}, and {A107P, A107I, or A107V};

wherein the amino acid changes are relative to the PD-1 protein fragment set forth in SEQ ID NO: 2.

9. The method of claim 8, wherein cancer cells of the cancer are positive for PD-L1 expression.

10. The method of claim 8, wherein the cancer comprises lung cancer, prostate cancer, breast cancer, bladder cancer, colon cancer, ovarian cancer, pancreatic cancer, kidney cancer, liver cancer, glioblastoma, medulloblastoma, leiomyosarcoma, head & neck squamous cell carcinomas, melanomas, neuroendocrine cancer, a leukemia, or a lymphoma.

11. A method of treating an individual having cancer, having a chronic infection, or having an immunological disorder associated with immunosuppression, the method comprising:
administering to the individual a multispecific polypeptide comprising a first region corresponding to a high affinity programmed death-1 (PD-1) mimic polypeptide that:
i) lacks a wild-type PD-1 transmembrane domain; and
ii) comprises amino acid changes selected from:
(a) V39R, N41V, Y43H, M45E, S48G, N49Y, Q50E, K53T, A56S, Q63T, G65L, Q66P, L97V, S102A, L103F, A104H, K106V, and A107I;
(b) V39R, N41V, Y43H, M45E, S48N, Q50H, T51A, D52Y, K53T, A56L, Q63L, G65F, Q66P, L97I, S102T, L103F, A104D, K106R, and A107I;
(c) V39H, L40V, N41V, Y43H, R44Y, M45E, N49G, K53T, M83L, L97V, A100I, and A107I;
(d) V39H, L40V, N41V, Y43H, M45E, N49G, K53T, Q66P, M83L, L97V, and A107I;
(e) V39H, L40V, N41V, Y43H, M45E, N49S, K53T, Q66P, H82Q, M83L, L97V, A100V, and A107I;
(f) V39H, L40I, N41I, Y43H, M45E, N49G, K53T, M83L, L97V, A100V, and A107I;
(g) V39H, L40V, N41I, Y43H, R44L, M45E, N49G, K53T, L97V, A100V, and A107I;
(h) V39H, L40V, N41I, Y43H, M45E, N49G, K53T, L97V, A100V, and A107I; and
(i) V39H, L40V, N41V, Y43H, M45E, N49G, K53T, L97V, A100V, and A107I;

wherein the amino acid changes are relative to the PD-1 protein fragment set forth in SEQ ID NO: 2.

12. The method of claim 1, wherein the high affinity PD-1 mimic polypeptide comprises the amino acid sequence set forth in any of SEQ ID NOs: 3-25, and 39-46.

13. The method of claim 1, wherein the high affinity PD-1 mimic polypeptide comprises the amino acid sequence set forth in SEQ ID NO: 4.

14. The method of claim 1, wherein cancer cells of the cancer are positive for PD-L1 expression.

15. The method of claim 1, wherein the cancer comprises lung cancer, prostate cancer, breast cancer, bladder cancer, colon cancer, ovarian cancer, pancreatic cancer, kidney cancer, liver cancer, glioblastoma, medulloblastoma, leiomyosarcoma, head & neck squamous cell carcinomas, melanomas, or neuroendocrine cancer.

16. The method of claim 1, wherein the cancer comprises a leukemia or a lymphoma.

17. The method of claim 1, wherein the multispecific polypeptide is administered to the individual by parenteral, intravenous, or subcutaneous administrative route.

* * * * *

SEQUENCE LISTING

<160> NUMBER OF SEQ ID NOS: 104

<210> SEQ ID NO 1
<211> LENGTH: 288
<212> TYPE: PRT
<213> ORGANISM: Homo sapiens

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Gly Gly
            165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
            245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 2
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 2

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Asp Arg Ser Gln Pro
        50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg
            115                 120

<210> SEQ ID NO 3
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 3

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe His Val Ile Trp His Arg Glu Ser Pro Ser
            35                  40                  45

```
Gly Gln Thr Asp Thr Leu Ala Ala Phe Pro Glu Asp Arg Ser Gln Pro
        50                  55                  60

Gly Gln Asp Ala Arg Phe Arg Val Thr Gln Leu Pro Asn Gly Arg Asp
 65                  70                  75                  80

Phe His Met Ser Val Val Arg Ala Arg Arg Asn Asp Ser Gly Thr Tyr
                    85                  90                  95

Val Cys Gly Val Ile Ser Leu Ala Pro Lys Ile Gln Ile Lys Glu Ser
                100                 105                 110

Leu Arg Ala Glu Leu Arg Val Thr Glu Arg
            115                 120

<210> SEQ ID NO 4
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 4

Asp Ser Pro Asp Arg Pro Trp Asn Pro Pro Thr Phe Ser Pro Ala Leu
 1               5                  10                  15

Leu Val Val Thr Glu Gly Asp Asn Ala Thr Phe Thr Cys Ser Phe Ser
                20                  25                  30

Asn Thr Ser Glu Ser Phe His Val Val Trp His Arg Glu Ser Pro Ser
            35                  40                  45

Gly Gln Thr Asp Thr Leu Ala Ala Phe Pro Glu Asp Arg Ser Gln Pro
        50                  55                  60

Gly Gln Asp Ala Arg Phe Arg Val Thr Gln Leu Pro Asn Gly Arg Asp
 65                  70                  75                  80

Phe His Met Ser Val Val Arg Ala Arg Arg Asn Asp Ser Gly Thr Tyr
                    85                  90                  95

Val Cys Gly Val Ile Ser Leu Ala Pro Lys Ile Gln Ile Lys Glu Ser
                100                 105                 110

Leu Arg Ala Glu Leu Arg Val Thr Glu Arg
            115                 120

<210> SEQ ID NO 5
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 5

Asp Ser Pro Asp Arg Pro Trp Asn Pro Pro Thr Phe Ser Pro Ala Leu
 1               5                  10                  15

Leu Val Val Thr Glu Gly Asp Asn Ala Thr Phe Thr Cys Ser Phe Ser
                20                  25                  30

Asn Thr Ser Glu Ser Phe His Val Val Trp His Arg Glu Ser Pro Ser
            35                  40                  45

Gly Gln Thr Asp Thr Leu Ala Ala Phe Pro Glu Asp Arg Ser Gln Pro
        50                  55                  60

Gly Pro Asp Ala Arg Phe Arg Val Thr Gln Leu Pro Asn Gly Arg Asp
 65                  70                  75                  80

Phe His Leu Ser Val Val Arg Ala Arg Arg Asn Asp Ser Gly Thr Tyr
                    85                  90                  95

Val Cys Gly Ala Ile Ser Leu Ala Pro Lys Ile Gln Ile Lys Glu Ser
```

```
                100                 105                 110
Leu Arg Ala Glu Leu Arg Val Thr Glu Arg
        115                 120

<210> SEQ ID NO 6
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 6

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe His Ile Ile Trp His Arg Glu Ser Pro Ser
        35                  40                  45

Gly Gln Thr Asp Thr Leu Ala Ala Phe Pro Glu Asp Arg Ser Gln Pro
    50                  55                  60

Gly Gln Asp Ala Arg Phe Arg Val Thr Gln Leu Pro Asn Gly Arg Asp
65                  70                  75                  80

Phe His Leu Ser Val Val Arg Ala Arg Arg Asn Asp Ser Gly Thr Tyr
                85                  90                  95

Val Cys Gly Val Ile Ser Leu Ala Pro Lys Ile Gln Ile Lys Glu Ser
            100                 105                 110

Leu Arg Ala Glu Leu Arg Val Thr Glu Arg
        115                 120

<210> SEQ ID NO 7
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 7

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe His Val Ile Trp His Leu Glu Ser Pro Ser
        35                  40                  45

Gly Gln Thr Asp Thr Leu Ala Ala Phe Pro Glu Asp Arg Ser Gln Pro
    50                  55                  60

Gly Gln Asp Ala Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Val Cys Gly Val Ile Ser Leu Ala Pro Lys Ile Gln Ile Lys Glu Ser
            100                 105                 110

Leu Arg Ala Glu Leu Arg Val Thr Glu Arg
        115                 120

<210> SEQ ID NO 8
<211> LENGTH: 122
<212> TYPE: PRT
<213> ORGANISM: Artificial sequence
<220> FEATURE:
```

<223> OTHER INFORMATION: Synthetic amino acid sequence

<400> SEQUENCE: 8

```
Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe His Val Val Trp His Arg Glu Ser Pro Ser
            35                  40                  45

Ser Gln Thr Asp Thr Leu Ala Ala Phe Pro Glu Asp Arg Ser Gln Pro
        50                  55                  60

Gly Pro Asp Ala Arg Phe Arg Val Thr Gln Leu Pro Asn Gly Arg Asp
65                  70                  75                  80

Phe Gln Leu Ser Val Val Arg Ala Arg Arg Asn Asp Ser Gly Thr Tyr
                85                  90                  95

Val Cys Gly Val Ile Ser Leu Ala Pro Lys Ile Gln Ile Lys Glu Ser
            100                 105                 110

Leu Arg Ala Glu Leu Arg Val Thr Glu Arg
        115                 120
```

<210> SEQ ID NO 9
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 9

```
Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe His Val Val Trp His Tyr Glu Ser Pro Ser
            35                  40                  45

Gly Gln Thr Asp Thr Leu Ala Ala Phe Pro Glu Asp Arg Ser Gln Pro
        50                  55                  60

Gly Gln Asp Ala Arg Phe Arg Val Thr Gln Leu Pro Asn Gly Arg Asp
65                  70                  75                  80

Phe His Leu Ser Val Val Arg Ala Arg Arg Asn Asp Ser Gly Thr Tyr
                85                  90                  95

Val Cys Gly Ile Ile Ser Leu Ala Pro Lys Ile Gln Ile Lys Glu Ser
            100                 105                 110

Leu Arg Ala Glu Leu Arg Val Thr Glu Arg
        115                 120
```

<210> SEQ ID NO 10
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 10

```
Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe His Leu Asn Trp Tyr Arg Gln Ser Pro Asp
```

```
            35                  40                  45

Cys Lys Val Phe Lys Leu Ala Ala Phe Pro Glu Asp Arg Ser Thr Pro
 50                  55                  60

Asn Pro Asp Cys Arg Phe Arg Val Thr Gln Leu Pro Asn Gly Arg Asp
 65                  70                  75                  80

Phe His Met Ser Val Val Arg Ala Arg Arg Asn Asp Ser Gly Thr Tyr
                 85                  90                  95

Tyr Cys Gly Ala Ile Thr Ile Ser Pro Gly Pro Gln Ile Lys Glu Ser
                100                 105                 110

Leu Arg Ala Glu Leu Arg Val Thr Glu Arg
                115                 120

<210> SEQ ID NO 11
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 11

Asp Ser Pro Asp Arg Pro Trp Asn Pro Thr Phe Ser Pro Ala Leu
 1               5                  10                  15

Leu Val Val Thr Glu Gly Asp Asn Ala Thr Phe Thr Cys Ser Phe Ser
                 20                  25                  30

Asn Thr Ser Glu Ser Phe His Leu Ile Trp Phe Arg Gln Ser Pro Leu
                 35                  40                  45

Gly Gln Leu Phe Lys Leu Ala Ala Phe Pro Glu Asp Arg Ser Ile Pro
 50                  55                  60

Arg Gln Asp Cys Arg Phe Arg Val Thr Gln Leu Pro Asn Gly Arg Asp
 65                  70                  75                  80

Phe His Met Ser Val Val Arg Ala Arg Arg Asn Asp Ser Gly Thr Tyr
                 85                  90                  95

Val Cys Gly Ala Ile Ser Tyr Ser Pro Glu Ile Gln Ile Lys Glu Ser
                100                 105                 110

Leu Arg Ala Glu Leu Arg Val Thr Glu Arg
                115                 120

<210> SEQ ID NO 12
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 12

Asp Ser Pro Asp Arg Pro Trp Asn Pro Thr Phe Ser Pro Ala Leu
 1               5                  10                  15

Leu Val Val Thr Glu Gly Asp Asn Ala Thr Phe Thr Cys Ser Phe Ser
                 20                  25                  30

Asn Thr Ser Glu Ser Phe His Leu Val Trp Phe Arg Gln Ser Pro Asn
                 35                  40                  45

Gly Gln Val Arg Lys Leu Ala Ala Phe Pro Glu Asp Arg Ser Glu Pro
 50                  55                  60

Ile Pro Asp Cys Arg Phe Arg Val Thr Gln Leu Pro Asn Gly Arg Asp
 65                  70                  75                  80

Phe His Met Ser Val Val Arg Ala Arg Arg Asn Asp Ser Gly Thr Tyr
                 85                  90                  95
```

Val Cys Gly Ala Ile Ser Tyr Ala Ala Ile Val Gln Ile Lys Glu Ser
            100                 105                 110

Leu Arg Ala Glu Leu Arg Val Thr Glu Arg
        115                 120

<210> SEQ ID NO 13
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 13

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Arg Leu Val Trp His Arg Glu Ser Pro Gly
        35                  40                  45

Tyr Glu Thr Asp Thr Leu Ala Ser Phe Pro Glu Asp Arg Ser Thr Pro
    50                  55                  60

Leu Pro Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Val Cys Gly Ala Ile Ala Phe His Pro Val Ile Gln Ile Lys Glu Ser
            100                 105                 110

Leu Arg Ala Glu Leu Arg Val Thr Glu Arg
        115                 120

<210> SEQ ID NO 14
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 14

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Arg Leu Val Trp His Arg Glu Ser Pro Asn
        35                  40                  45

Asn His Ala Tyr Thr Leu Ala Leu Phe Pro Glu Asp Arg Ser Leu Pro
    50                  55                  60

Phe Pro Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Ile Cys Gly Ala Ile Thr Phe Asp Pro Arg Ile Gln Ile Lys Glu Ser
            100                 105                 110

Leu Arg Ala Glu Leu Arg Val Thr Glu Arg
        115                 120

<210> SEQ ID NO 15
<211> LENGTH: 122
<212> TYPE: PRT
<213> ORGANISM: Artificial sequence

```
<220> FEATURE:
<223> OTHER INFORMATION: Synthetic amino acid sequence

<400> SEQUENCE: 15

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe His Leu Val Trp His Arg Leu Ser Pro Val
            35                  40                  45

Tyr Gln Thr Val Leu Leu Ala Ala Phe Pro Glu Asp Arg Ser Pro Pro
        50                  55                  60

Val Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Tyr Asp Pro Thr Ile Gln Ile Lys Glu Ser
                100                 105                 110

Leu Arg Ala Glu Leu Arg Val Thr Glu Arg
        115                 120

<210> SEQ ID NO 16
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 16

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe His Val Val Trp His Tyr Asp Ser Pro Ser
            35                  40                  45

Gly Gln Thr Asp Thr Leu Ala Ala Phe Pro Glu Asp Arg Ser Gln Pro
        50                  55                  60

Gly Pro Asp Cys Arg Phe Arg Ile Thr Gln Leu Pro Asn Gly Arg Asp
65                  70                  75                  80

Phe His Phe Ser Val Val Arg Ala Arg Arg Asn Asp Ser Gly Thr Tyr
                85                  90                  95

Ile Cys Gly Val Ile Ser Leu Ala Pro Lys Ile Gln Ile Lys Glu Ser
                100                 105                 110

Leu Arg Ala Glu Leu Arg Val Thr Glu Arg
        115                 120

<210> SEQ ID NO 17
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 17

Asp Ser Pro Asp Arg Pro Trp Asn Pro Pro Thr Phe Ser Pro Ala Leu
1               5                   10                  15

Leu Val Thr Glu Gly Asp Asn Ala Thr Phe Thr Cys Ser Phe Ser
                20                  25                  30
```

Asn Thr Ser Glu Ser Phe His Val Val Trp His Tyr Glu Ser Pro Ser
            35                  40                  45

Gly Gln Thr Asp Thr Leu Ala Ala Phe Pro Glu Asp Arg Ser Gln Pro
 50                  55                  60

Gly Pro Asp Cys Arg Phe Arg Val Thr Gln Leu Pro Asn Gly Arg Asp
65                  70                  75                  80

Phe His Phe Ser Val Val Arg Ala Arg Arg Asn Asp Ser Gly Thr Tyr
                85                  90                  95

Ile Cys Gly Val Ile Ser Leu Ala Pro Lys Ile Gln Ile Lys Glu Ser
            100                 105                 110

Leu Arg Ala Glu Leu Arg Val Thr Glu Arg
            115                 120

<210> SEQ ID NO 18
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 18

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe His Ile Ile Trp His Arg Glu Ser Pro Ser
            35                  40                  45

Cys Gln Thr Asp Thr Leu Ala Ala Phe Pro Glu Asp Arg Ser Gln Pro
 50                  55                  60

Gly Gln Asp Cys Arg Phe Arg Ile Thr Gln Leu Pro Asn Gly Arg Asp
65                  70                  75                  80

Phe His Phe Ser Val Val Arg Ala Arg Arg Asn Asp Ser Gly Thr Phe
                85                  90                  95

Val Cys Gly Val Ile Ser Leu Ala Pro Lys Ile Gln Ile Lys Glu Ser
            100                 105                 110

Leu Arg Ala Glu Leu Arg Val Thr Glu Arg
            115                 120

<210> SEQ ID NO 19
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 19

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe His Ile Ile Trp His Arg Glu Ser Pro Ser
            35                  40                  45

Gly Gln Thr Asp Thr Leu Ala Ala Phe Pro Glu Asp Arg Ser Gln Pro
 50                  55                  60

Gly Gln Asp Cys Arg Phe Arg Ile Thr Gln Leu Pro Asn Gly Arg Asp
65                  70                  75                  80

Phe His Phe Ser Val Val Arg Ala Arg Arg Asn Asp Ser Gly Thr Phe
                85                  90                  95

Val Cys Gly Val Ile Ser Leu Ala Pro Lys Ile Gln Ile Lys Glu Ser
            100                 105                 110

Leu Arg Ala Glu Leu Arg Val Thr Glu Arg
        115                 120

<210> SEQ ID NO 20
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 20

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Arg Leu Val Trp His Arg Glu Ser Pro Ser
        35                  40                  45

Gly Gln Thr Asp Thr Leu Ala Ala Phe Pro Glu Asp Arg Ser Gln Pro
    50                  55                  60

Gly Gln Asp Cys Arg Phe Arg Ile Thr Gln Leu Pro Asn Gly Arg Asp
65                  70                  75                  80

Phe His Phe Ser Val Val Arg Ala Arg Arg Asn Asp Ser Gly Thr Phe
                85                  90                  95

Val Cys Gly Ala Ile Ser Phe Ala Pro Lys Ile Gln Ile Lys Glu Ser
            100                 105                 110

Leu Arg Ala Glu Leu Arg Val Thr Glu Arg
        115                 120

<210> SEQ ID NO 21
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 21

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe His Val Val Trp His Arg Glu Ser Pro Ser
        35                  40                  45

Gly Gln Thr Asp Thr Leu Ala Ala Phe Pro Glu Asp Arg Ser Gln Pro
    50                  55                  60

Gly Gln Asp Cys Arg Phe Arg Ile Thr Gln Leu Pro Asn Gly Arg Asp
65                  70                  75                  80

Phe His Leu Ser Val Val Arg Ala Arg Arg Asn Asp Ser Gly Thr Phe
                85                  90                  95

Val Cys Gly Val Ile Ser Leu Ala Pro Lys Ile Gln Ile Lys Glu Ser
            100                 105                 110

Leu Arg Ala Glu Leu Arg Val Thr Glu Arg
        115                 120

<210> SEQ ID NO 22
<211> LENGTH: 122
<212> TYPE: PRT

<213> ORGANISM: Artificial sequence
<220> FEATURE:
<223> OTHER INFORMATION: Synthetic amino acid sequence

<400> SEQUENCE: 22

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe His Val Ile Trp His Arg Glu Ser Pro Ser
            35                  40                  45

Gly Gln Thr Asp Thr Leu Ala Ala Phe Pro Glu Asp Arg Ser Gln Pro
        50                  55                  60

Gly Pro Asp Cys Arg Phe Arg Ile Thr Gln Leu Pro Asn Gly Arg Asp
65                  70                  75                  80

Phe His Met Ser Val Val Arg Ala Arg Lys Asn Asp Ser Gly Thr Tyr
                85                  90                  95

Val Cys Gly Ile Ile Ser Leu Ala Pro Lys Ile Gln Ile Lys Glu Ser
                100                 105                 110

Leu Arg Ala Glu Leu Arg Val Thr Glu Arg
        115                 120

<210> SEQ ID NO 23
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 23

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe His Ile Ile Trp His Arg Glu Ser Pro Ser
            35                  40                  45

Gly Gln Thr Asp Thr Leu Ala Ala Phe Pro Glu Asp Arg Ser Gln Pro
        50                  55                  60

Gly Pro Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Val Cys Gly Val Ile Ser Leu Ala Pro Lys Ile Gln Ile Lys Glu Ser
                100                 105                 110

Leu Arg Ala Glu Leu Arg Val Thr Glu Arg
        115                 120

<210> SEQ ID NO 24
<211> LENGTH: 253
<212> TYPE: PRT
<213> ORGANISM: Artificial sequence
<220> FEATURE:
<223> OTHER INFORMATION: Synthetic amino acid sequence

<400> SEQUENCE: 24

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
                20                  25                  30

```
Asn Thr Ser Glu Ser Phe His Val Val Trp His Arg Glu Ser Pro Ser
         35                  40                  45

Gly Gln Thr Asp Thr Leu Ala Ala Phe Pro Glu Asp Arg Ser Gln Pro
 50                  55                  60

Gly Gln Asp Ala Arg Phe Arg Val Thr Gln Leu Pro Asn Gly Arg Asp
 65                  70                  75                  80

Phe His Met Ser Val Val Arg Ala Arg Arg Asn Asp Ser Gly Thr Tyr
                 85                  90                  95

Val Cys Gly Val Ile Ser Leu Ala Pro Lys Ile Gln Ile Lys Glu Ser
                100                 105                 110

Leu Arg Ala Glu Leu Arg Val Thr Glu Arg Pro Lys Ser Cys Asp
        115                 120                 125

Lys Thr His Thr Cys Pro Pro Cys Gly Gly Ser Ser Gly Gly Gly
        130                 135                 140

Ser Gly Gly Gln Pro Arg Glu Pro Gln Val Tyr Thr Leu Pro Pro Ser
145                 150                 155                 160

Arg Glu Glu Met Thr Lys Asn Gln Val Ser Leu Thr Cys Leu Val Lys
                165                 170                 175

Gly Phe Tyr Pro Ser Asp Ile Ala Val Glu Trp Glu Ser Asn Gly Gln
        180                 185                 190

Pro Glu Asn Asn Tyr Lys Thr Thr Pro Pro Val Leu Asp Ser Asp Gly
        195                 200                 205

Ser Phe Phe Leu Tyr Ser Lys Leu Thr Val Asp Lys Ser Arg Trp Gln
        210                 215                 220

Gln Gly Asn Val Phe Ser Cys Ser Val Met His Glu Ala Leu His Asn
225                 230                 235                 240

His Tyr Thr Gln Lys Ser Leu Ser Leu Ser Pro Gly Lys
                245                 250

<210> SEQ ID NO 25
<211> LENGTH: 349
<212> TYPE: PRT
<213> ORGANISM: Artificial sequence
<220> FEATURE:
<223> OTHER INFORMATION: Synthetic amino acid sequence

<400> SEQUENCE: 25

Asp Ser Pro Asp Arg Pro Trp Asn Pro Thr Phe Ser Pro Ala Leu
 1               5                  10                  15

Leu Val Val Thr Glu Gly Asp Asn Ala Thr Phe Thr Cys Ser Phe Ser
                 20                  25                  30

Asn Thr Ser Glu Ser Phe His Val Val Trp His Arg Glu Ser Pro Ser
         35                  40                  45

Gly Gln Thr Asp Thr Leu Ala Ala Phe Pro Glu Asp Arg Ser Gln Pro
 50                  55                  60

Gly Gln Asp Ala Arg Phe Arg Val Thr Gln Leu Pro Asn Gly Arg Asp
 65                  70                  75                  80

Phe His Met Ser Val Val Arg Ala Arg Arg Asn Asp Ser Gly Thr Tyr
                 85                  90                  95

Val Cys Gly Val Ile Ser Leu Ala Pro Lys Ile Gln Ile Lys Glu Ser
                100                 105                 110

Leu Arg Ala Glu Leu Arg Val Thr Glu Arg Ala Ala Ala Pro Pro Cys
        115                 120                 125

Pro Pro Cys Pro Ala Pro Glu Phe Leu Gly Gly Pro Ser Val Phe Leu
        130                 135                 140
```

```
Phe Pro Pro Lys Pro Lys Asp Thr Leu Met Ile Ser Arg Thr Pro Glu
145                 150                 155                 160

Val Thr Cys Val Val Val Asp Val Ser Gln Glu Asp Pro Glu Val Gln
            165                 170                 175

Phe Asn Trp Tyr Val Asp Gly Val Glu Val His Asn Ala Lys Thr Lys
        180                 185                 190

Pro Arg Glu Glu Gln Phe Asn Ser Thr Tyr Arg Val Val Ser Val Leu
    195                 200                 205

Thr Val Leu His Gln Asp Trp Leu Asn Gly Lys Glu Tyr Lys Cys Lys
210                 215                 220

Val Ser Asn Lys Gly Leu Pro Ser Ser Ile Glu Lys Thr Ile Ser Lys
225                 230                 235                 240

Ala Lys Gly Gln Pro Arg Glu Pro Gln Val Tyr Thr Leu Pro Pro Ser
            245                 250                 255

Gln Glu Glu Met Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Tyr Ser Arg Leu Thr Val Asp Lys Ser Arg Trp Gln
305                 310                 315                 320

Glu Gly Asn Val Phe Ser Cys Ser Val Met His Glu Ala Leu His Asn
                325                 330                 335

His Tyr Thr Gln Lys Ser Leu Ser Leu Ser Pro Gly Lys
            340                 345

<210> SEQ ID NO 26
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 26

Ala Ala Ala Ala Ala Ala Ala Ala Ala Ala
1               5                   10

<210> SEQ ID NO 27
<211> LENGTH: 111
<212> TYPE: PRT
<213> ORGANISM: Artificial sequence
<220> FEATURE:
<223> OTHER INFORMATION: Synthetic amino acid sequence

<400> SEQUENCE: 27

Pro Thr Phe Ser Pro Ala Leu Leu Val Val Thr Glu Gly Asp Asn Ala
1               5                   10                  15

Thr Phe Thr Cys Ser Phe Ser Asn Thr Ser Glu Ser Phe Val Leu Asn
            20                  25                  30

Trp Tyr Arg Met Ser Pro Ser Asn Gln Thr Asp Lys Leu Ala Ala Phe
        35                  40                  45

Pro Glu Asp Arg Ser Gln Pro Gly Gln Asp Cys Arg Phe Arg Val Thr
    50                  55                  60

Gln Leu Pro Asn Gly Arg Asp Phe His Met Ser Val Val Arg Ala Arg
65                  70                  75                  80

Arg Asn Asp Ser Gly Thr Tyr Leu Cys Gly Ala Ile Ser Leu Ala Pro
```

```
                85                  90                  95
Lys Ala Gln Ile Lys Glu Ser Leu Arg Ala Glu Leu Arg Val Thr
            100                 105                 110

<210> SEQ ID NO 28
<211> LENGTH: 91
<212> TYPE: PRT
<213> ORGANISM: Artificial sequence
<220> FEATURE:
<223> OTHER INFORMATION: Synthetic amino acid sequence

<400> SEQUENCE: 28

Ser Pro Ala Leu Leu Val Val Thr Glu Gly Asp Asn Ala Thr Phe Thr
1               5                   10                  15

Cys Ser Phe Ser Asn Thr Ser Glu Ser Phe Val Leu Asn Trp Tyr Arg
                20                  25                  30

Met Ser Pro Ser Asn Gln Thr Asp Lys Leu Ala Ala Phe Pro Glu Asp
            35                  40                  45

Arg Ser Gln Pro Gly Gln Asp Cys Arg Phe Arg Val Thr Gln Leu Pro
        50                  55                  60

Asn Gly Arg Asp Phe His Met Ser Val Val Arg Ala Arg Arg Asn Asp
65                  70                  75                  80

Ser Gly Thr Tyr Leu Cys Gly Ala Ile Ser Leu
                85                  90

<210> SEQ ID NO 29
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 29

Pro Ala Leu Leu Val Val Thr Glu Gly Asp Asn Ala Thr Phe Thr Cys
1               5                   10                  15

Ser Phe Ser Asn Thr Ser Glu Ser Phe Val Leu Asn Trp Tyr Arg Met
                20                  25                  30

Ser Pro Ser Asn Gln Thr Asp Lys Leu Ala Ala Phe Pro Glu Asp Arg
            35                  40                  45

Ser Gln Pro Gly Gln Asp Cys Arg Phe Arg Val Thr Gln Leu Pro Asn
        50                  55                  60

Gly Arg Asp Phe His Met Ser Val Val Arg Ala Arg Arg Asn Asp Ser
65                  70                  75                  80

Gly Thr Tyr Leu Cys Gly Ala Ile Ser Leu Ala Pro Lys Ala Gln Ile
                85                  90                  95

Lys Glu Ser Leu Arg Ala Glu Leu Arg Val Thr
            100                 105

<210> SEQ ID NO 30
<211> LENGTH: 108
<212> TYPE: PRT
<213> ORGANISM: Artificial sequence
<220> FEATURE:
<223> OTHER INFORMATION: Synthetic amino acid sequence

<400> SEQUENCE: 30

Pro Ala Leu Leu Val Val Thr Glu Gly Asp Asn Ala Thr Phe Thr Cys
1               5                   10                  15

Ser Phe Ser Asn Thr Ser Glu Ser Phe Val Leu Asn Trp Tyr Arg Met
                20                  25                  30
```

```
Ser Pro Ser Asn Gln Thr Asp Lys Leu Ala Ala Phe Pro Glu Asp Arg
        35                  40                  45

Ser Gln Pro Gly Gln Asp Cys Arg Phe Arg Val Thr Gln Leu Pro Asn
    50                  55                  60

Gly Arg Asp Phe His Met Ser Val Val Arg Ala Arg Asn Asp Ser
65                  70                  75                  80

Gly Thr Tyr Leu Cys Gly Ala Ile Ser Leu Ala Pro Lys Ala Gln Ile
                85                  90                  95

Lys Glu Ser Leu Arg Ala Glu Leu Arg Val Thr Glu
                100                 105

<210> SEQ ID NO 31
<211> LENGTH: 77
<212> TYPE: PRT
<213> ORGANISM: Artificial sequence
<220> FEATURE:
<223> OTHER INFORMATION: Synthetic amino acid sequence

<400> SEQUENCE: 31

Asn Ala Thr Phe Thr Cys Ser Phe Ser Asn Thr Ser Glu Ser Phe Val
1               5                   10                  15

Leu Asn Trp Tyr Arg Met Ser Pro Ser Asn Gln Thr Asp Lys Leu Ala
                20                  25                  30

Ala Phe Pro Glu Asp Arg Ser Gln Pro Gly Gln Asp Cys Arg Phe Arg
                35                  40                  45

Val Thr Gln Leu Pro Asn Gly Arg Asp Phe His Met Ser Val Val Arg
            50                  55                  60

Ala Arg Arg Asn Asp Ser Gly Thr Tyr Leu Cys Gly Ala
65                  70                  75

<210> SEQ ID NO 32
<211> LENGTH: 95
<212> TYPE: PRT
<213> ORGANISM: Artificial sequence
<220> FEATURE:
<223> OTHER INFORMATION: Synthetic amino acid sequence

<400> SEQUENCE: 32

Leu Val Val Thr Glu Gly Asp Asn Ala Thr Phe Thr Cys Ser Phe Ser
1               5                   10                  15

Asn Thr Ser Glu Ser Phe Val Leu Asn Trp Tyr Arg Met Ser Pro Ser
                20                  25                  30

Asn Gln Thr Asp Lys Leu Ala Ala Phe Pro Glu Asp Arg Ser Gln Pro
                35                  40                  45

Gly Gln Asp Cys Arg Phe Arg Val Thr Gln Leu Pro Asn Gly Arg Asp
            50                  55                  60

Phe His Met Ser Val Val Arg Ala Arg Arg Asn Asp Ser Gly Thr Tyr
65                  70                  75                  80

Leu Cys Gly Ala Ile Ser Leu Ala Pro Lys Ala Gln Ile Lys Glu
                85                  90                  95

<210> SEQ ID NO 33
<211> LENGTH: 87
<212> TYPE: PRT
<213> ORGANISM: Artificial sequence
<220> FEATURE:
<223> OTHER INFORMATION: Synthetic amino acid sequence

<400> SEQUENCE: 33
```

Pro Ala Leu Leu Val Thr Glu Gly Asp Asn Ala Thr Phe Thr Cys
1               5                   10                  15

Ser Phe Ser Asn Thr Ser Glu Ser Phe Val Leu Asn Trp Tyr Arg Met
            20                  25                  30

Ser Pro Ser Asn Gln Thr Asp Lys Leu Ala Ala Phe Pro Glu Asp Arg
            35                  40                  45

Ser Gln Pro Gly Gln Asp Cys Arg Phe Arg Val Thr Gln Leu Pro Asn
        50                  55                  60

Gly Arg Asp Phe His Met Ser Val Val Arg Ala Arg Asn Asp Ser
65                  70                  75                  80

Gly Thr Tyr Leu Cys Gly Ala
                85

<210> SEQ ID NO 34
<211> LENGTH: 112
<212> TYPE: PRT
<213> ORGANISM: Artificial sequence
<220> FEATURE:
<223> OTHER INFORMATION: Synthetic amino acid sequence

<400> SEQUENCE: 34

Pro Thr Phe Ser Pro Ala Leu Leu Val Val Thr Glu Gly Asp Asn Ala
1               5                   10                  15

Thr Phe Thr Cys Ser Phe Ser Asn Thr Ser Glu Ser Phe Val Leu Asn
            20                  25                  30

Trp Tyr Arg Met Ser Pro Ser Asn Gln Thr Asp Lys Leu Ala Ala Phe
            35                  40                  45

Pro Glu Asp Arg Ser Gln Pro Gly Gln Asp Cys Arg Phe Arg Val Thr
        50                  55                  60

Gln Leu Pro Asn Gly Arg Asp Phe His Met Ser Val Val Arg Ala Arg
65                  70                  75                  80

Arg Asn Asp Ser Gly Thr Tyr Leu Cys Gly Ala Ile Ser Leu Ala Pro
                85                  90                  95

Lys Ala Gln Ile Lys Glu Ser Leu Arg Ala Glu Leu Arg Val Thr Glu
            100                 105                 110

<210> SEQ ID NO 35
<211> LENGTH: 166
<212> TYPE: PRT
<213> ORGANISM: Artificial sequence
<220> FEATURE:
<223> OTHER INFORMATION: Synthetic amino acid sequence

<400> SEQUENCE: 35

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe
                165

<210> SEQ ID NO 36
<211> LENGTH: 290
<212> TYPE: PRT
<213> ORGANISM: Artificial sequence
<220> FEATURE:
<223> OTHER INFORMATION: Synthetic amino acid sequence

<400> SEQUENCE: 36

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
290

<210> SEQ ID NO 37
<211> LENGTH: 176
<212> TYPE: PRT
<213> ORGANISM: Artificial sequence
<220> FEATURE:
<223> OTHER INFORMATION: Synthetic amino acid sequence

<400> SEQUENCE: 37

Met Arg Ile Phe Ala Val Phe Ile Phe Met Thr Tyr Trp His Leu Leu
1               5                   10                  15

Asn Ala Pro Tyr Asn Lys Ile Asn Gln Arg Ile Leu Val Val Asp Pro
            20                  25                  30

Val Thr Ser Glu His Glu Leu Thr Cys Gln Ala Glu Gly Tyr Pro Lys
        35                  40                  45

Ala Glu Val Ile Trp Thr Ser Ser Asp His Gln Val Leu Ser Gly Lys
    50                  55                  60

Thr Thr Thr Thr Asn Ser Lys Arg Glu Glu Lys Leu Phe Asn Val Thr
65                  70                  75                  80

Ser Thr Leu Arg Ile Asn Thr Thr Asn Glu Ile Phe Tyr Cys Thr
                85                  90                  95

Phe Arg Arg Leu Asp Pro Glu Glu Asn His Thr Ala Glu Leu Val Ile
            100                 105                 110

Pro Glu Leu Pro Leu Ala His Pro Pro Asn Glu Arg Thr His Leu Val
        115                 120                 125

Ile Leu Gly Ala Ile Leu Leu Cys Leu Gly Val Ala Leu Thr Phe Ile
    130                 135                 140

Phe Arg Leu Arg Lys Gly Arg Met Met Asp Val Lys Lys Cys Gly Ile
145                 150                 155                 160

Gln Asp Thr Asn Ser Lys Lys Gln Ser Asp Thr His Leu Glu Glu Thr
                165                 170                 175

<210> SEQ ID NO 38
<211> LENGTH: 273
<212> TYPE: PRT
<213> ORGANISM: Artificial sequence
<220> FEATURE:
<223> OTHER INFORMATION: Synthetic amino acid sequence

<400> SEQUENCE: 38

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
            85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
            115                 120                 125

His Ile Leu Lys Val Pro Glu Thr Asp Glu Val Glu Leu Thr Cys Gln

```
              130                 135                 140
Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Gly Arg Asn Phe Ser Cys
            180                 185                 190

Val Phe Trp Asn Thr His Val Arg Glu Leu Thr Leu Ala Ser Ile Asp
                195                 200                 205

Leu Gln Ser Gln Met Glu Pro Arg Thr His Pro Thr Trp Leu Leu His
            210                 215                 220

Ile Phe Ile Pro Phe Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
                260                 265                 270

Ile

<210> SEQ ID NO 39
<211> LENGTH: 265
<212> TYPE: PRT
<213> ORGANISM: Artificial sequence
<220> FEATURE:
<223> OTHER INFORMATION: Synthetic amino acid sequence

<400> SEQUENCE: 39

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe His Val Val Trp His Arg Glu Ser Pro Ser
            35                  40                  45

Gly Gln Thr Asp Thr Leu Ala Ala Phe Pro Glu Asp Arg Ser Gln Pro
50                  55                  60

Gly Gln Asp Ala Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Val Cys Gly Val Ile Ser Leu Ala Pro Lys Ile Gln Ile Lys Glu Ser
            100                 105                 110

Leu Arg Ala Glu Leu Arg Val Thr Glu Arg Gly Gly Gly Ser Gly
            115                 120                 125

Gly Gly Gly Ser Ala Pro Thr Ser Ser Ser Thr Lys Lys Thr Gln Leu
130                 135                 140

Gln Leu Glu His Leu Leu Leu Asp Leu Gln Met Ile Leu Asn Gly Ile
145                 150                 155                 160

Asn Asn Tyr Lys Asn Pro Lys Leu Thr Arg Met Leu Thr Ala Lys Phe
                165                 170                 175

Tyr Met Pro Lys Lys Ala Thr Glu Leu Lys His Leu Gln Cys Leu Glu
            180                 185                 190

Glu Glu Leu Lys Pro Leu Glu Glu Val Leu Asn Leu Ala Gln Ser Lys
            195                 200                 205

Asn Phe His Leu Arg Pro Arg Asp Leu Ile Ser Asn Ile Asn Val Ile
210                 215                 220
```

```
Val Leu Glu Leu Lys Gly Ser Glu Thr Thr Phe Met Cys Glu Tyr Ala
225                 230                 235                 240

Asp Glu Thr Ala Thr Ile Val Glu Phe Leu Asn Arg Trp Ile Thr Phe
            245                 250                 255

Cys Gln Ser Ile Ile Ser Thr Leu Thr
            260                 265

<210> SEQ ID NO 40
<211> LENGTH: 299
<212> TYPE: PRT
<213> ORGANISM: Artificial sequence
<220> FEATURE:
<223> OTHER INFORMATION: Synthetic amino acid sequence

<400> SEQUENCE: 40

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe His Val Val Trp His Arg Glu Ser Pro Ser
            35                  40                  45

Gly Gln Thr Asp Thr Leu Ala Ala Phe Pro Glu Asp Arg Ser Gln Pro
        50                  55                  60

Gly Gln Asp Ala Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Val Cys Gly Val Ile Ser Leu Ala Pro Lys Ile Gln Ile Lys Glu Ser
                100                 105                 110

Leu Arg Ala Glu Leu Arg Val Thr Glu Arg Gly Gly Gly Ser Gly
            115                 120                 125

Gly Gly Gly Ser Asp Pro Ala Gly Leu Leu Asp Leu Arg Gln Gly Met
        130                 135                 140

Phe Ala Gln Leu Val Ala Gln Asn Val Leu Leu Ile Asp Gly Pro Leu
145                 150                 155                 160

Ser Trp Tyr Ser Asp Pro Gly Leu Ala Gly Val Ser Leu Thr Gly Gly
                165                 170                 175

Leu Ser Tyr Lys Glu Asp Thr Lys Glu Leu Val Val Ala Lys Ala Gly
            180                 185                 190

Val Tyr Tyr Val Phe Phe Gln Met Glu Leu Arg Arg Val Val Ala Gly
        195                 200                 205

Glu Gly Ser Gly Ser Val Ser Leu Ala Leu His Leu Met Pro Leu Arg
210                 215                 220

Ser Ala Ala Gly Ala Ala Leu Ala Leu Thr Val Asp Leu Pro Pro
225                 230                 235                 240

Ala Ser Ser Glu Ala Arg Asn Ser Ala Phe Gly Phe Gln Gly Arg Leu
                245                 250                 255

Leu His Leu Ser Ala Gly Gln Arg Leu Gly Val His Leu His Thr Glu
            260                 265                 270

Ala Arg Ala Arg His Ala Trp Gln Leu Thr Gln Gly Ala Thr Val Leu
        275                 280                 285

Gly Leu Phe Arg Val Thr Pro Glu Ile Pro Ala
    290                 295

<210> SEQ ID NO 41
```

```
<211> LENGTH: 278
<212> TYPE: PRT
<213> ORGANISM: Artificial sequence
<220> FEATURE:
<223> OTHER INFORMATION: Synthetic amino acid sequence

<400> SEQUENCE: 41

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe His Val Val Trp His Arg Glu Ser Pro Ser
            35                  40                  45

Gly Gln Thr Asp Thr Leu Ala Ala Phe Pro Glu Asp Arg Ser Gln Pro
        50                  55                  60

Gly Gln Asp Ala Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Val Cys Gly Val Ile Ser Leu Ala Pro Lys Ile Gln Ile Lys Glu Ser
            100                 105                 110

Leu Arg Ala Glu Leu Arg Val Thr Glu Arg Gly Gly Gly Ser Gly
        115                 120                 125

Gly Gly Gly Ser Gly Asp Gln Asn Pro Gln Ile Ala Ala His Val Ile
130                 135                 140

Ser Glu Ala Ser Ser Lys Thr Thr Ser Val Leu Gln Trp Ala Glu Lys
145                 150                 155                 160

Gly Tyr Tyr Thr Met Ser Asn Asn Leu Val Thr Leu Glu Asn Gly Lys
                165                 170                 175

Gln Leu Thr Val Lys Arg Gln Gly Leu Tyr Tyr Ile Tyr Ala Gln Val
            180                 185                 190

Thr Phe Cys Ser Asn Arg Glu Ala Ser Ser Gln Ala Pro Phe Ile Ala
        195                 200                 205

Ser Leu Cys Leu Lys Ser Pro Gly Arg Phe Glu Arg Ile Leu Leu Arg
210                 215                 220

Ala Ala Asn Thr His Ser Ser Ala Lys Pro Cys Gly Gln Gln Ser Ile
225                 230                 235                 240

His Leu Gly Gly Val Phe Glu Leu Gln Pro Gly Ala Ser Val Phe Val
                245                 250                 255

Asn Val Thr Asp Pro Ser Gln Val Ser His Gly Thr Gly Phe Thr Ser
            260                 265                 270

Phe Gly Leu Leu Lys Leu
        275

<210> SEQ ID NO 42
<211> LENGTH: 244
<212> TYPE: PRT
<213> ORGANISM: Artificial sequence
<220> FEATURE:
<223> OTHER INFORMATION: Synthetic amino acid sequence

<400> SEQUENCE: 42

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe His Val Val Trp His Arg Glu Ser Pro Ser
```

```
                35                  40                  45
Gly Gln Thr Asp Thr Leu Ala Ala Phe Pro Glu Asp Arg Ser Gln Pro
 50                  55                  60
Gly Gln Asp Ala Arg Phe Arg Val Thr Gln Leu Pro Asn Gly Arg Asp
 65                  70                  75                  80
Phe His Met Ser Val Val Arg Ala Arg Arg Asn Asp Ser Gly Thr Tyr
                 85                  90                  95
Val Cys Gly Val Ile Ser Leu Ala Pro Lys Ile Gln Ile Lys Glu Ser
                100                 105                 110
Leu Arg Ala Glu Leu Arg Val Thr Glu Arg Gly Gly Gly Ser Gly
            115                 120                 125
Gly Gly Gly Ser Trp Asn Ile His Gly Lys Glu Ser Cys Asp Val Gln
            130                 135                 140
Leu Tyr Ile Lys Arg Gln Ser Glu His Ser Ile Leu Ala Gly Asp Pro
145                 150                 155                 160
Phe Glu Leu Glu Cys Pro Val Lys Tyr Cys Ala Asn Arg Pro His Val
                165                 170                 175
Thr Trp Cys Lys Leu Asn Gly Thr Thr Cys Val Lys Leu Glu Asp Arg
                180                 185                 190
Gln Thr Ser Trp Lys Glu Lys Asn Ile Ser Phe Phe Ile Leu His
            195                 200                 205
Phe Glu Pro Val Leu Pro Asn Asp Asn Gly Ser Tyr Arg Cys Ser Ala
210                 215                 220
Asn Phe Gln Ser Asn Leu Ile Glu Ser His Ser Thr Thr Leu Tyr Val
225                 230                 235                 240
Thr Asp Val Lys

<210> SEQ ID NO 43
<211> LENGTH: 236
<212> TYPE: PRT
<213> ORGANISM: Artificial sequence
<220> FEATURE:
<223> OTHER INFORMATION: Synthetic amino acid sequence

<400> SEQUENCE: 43

Asp Ser Pro Asp Arg Pro Trp Asn Pro Pro Thr Phe Ser Pro Ala Leu
 1               5                  10                  15
Leu Val Val Thr Glu Gly Asp Asn Ala Thr Phe Thr Cys Ser Phe Ser
                 20                  25                  30
Asn Thr Ser Glu Ser Phe His Val Val Trp His Arg Glu Ser Pro Ser
             35                  40                  45
Gly Gln Thr Asp Thr Leu Ala Ala Phe Pro Glu Asp Arg Ser Gln Pro
 50                  55                  60
Gly Gln Asp Ala Arg Phe Arg Val Thr Gln Leu Pro Asn Gly Arg Asp
 65                  70                  75                  80
Phe His Met Ser Val Val Arg Ala Arg Arg Asn Asp Ser Gly Thr Tyr
                 85                  90                  95
Val Cys Gly Val Ile Ser Leu Ala Pro Lys Ile Gln Ile Lys Glu Ser
                100                 105                 110
Leu Arg Ala Glu Leu Arg Val Thr Glu Arg Gly Gly Gly Ser Gly
            115                 120                 125
Gly Gly Gly Ser Glu Val Glu Tyr Arg Ala Glu Val Gly Gln Asn Ala
            130                 135                 140
Tyr Leu Pro Cys Phe Tyr Thr Pro Ala Ala Pro Gly Asn Leu Val Pro
145                 150                 155                 160
```

```
Val Cys Trp Gly Lys Gly Ala Cys Pro Val Phe Glu Cys Gly Asn Val
            165                 170                 175

Val Leu Arg Thr Asp Glu Arg Asp Val Asn Tyr Trp Thr Ser Arg Tyr
            180                 185                 190

Trp Leu Asn Gly Asp Phe Arg Lys Gly Asp Val Ser Leu Thr Ile Glu
            195                 200                 205

Asn Val Thr Leu Ala Asp Ser Gly Ile Tyr Cys Cys Arg Ile Gln Ile
            210                 215                 220

Pro Gly Ile Met Asn Asp Glu Lys Phe Asn Leu Lys
225                 230                 235

<210> SEQ ID NO 44
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 44

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe His Val Val Trp His Arg Glu Ser Pro Ser
            35                  40                  45

Gly Gln Thr Asp Thr Leu Ala Ala Phe Pro Glu Asp Arg Ser Gln Pro
        50                  55                  60

Gly Gln Asp Ala Arg Phe Arg Val Thr Gln Leu Pro Asn Gly Arg Asp
65                  70                  75                  80

Phe His Met Ser Val Val Arg Ala Arg Arg Cys Asp Ser Gly Thr Tyr
                85                  90                  95

Val Cys Gly Val Ile Ser Leu Ala Pro Lys Ile Gln Ile Lys Glu Ser
            100                 105                 110

Leu Arg Ala Glu Leu Arg Val Thr Glu Arg
        115                 120

<210> SEQ ID NO 45
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 45

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe His Val Val Trp His Arg Glu Ser Pro Ser
            35                  40                  45

Gly Gln Thr Asp Thr Leu Ala Ala Phe Pro Glu Asp Arg Ser Gln Pro
        50                  55                  60

Gly Gln Asp Ala Arg Phe Arg Val Thr Gln Leu Pro Asn Gly Arg Asp
65                  70                  75                  80

Phe His Met Ser Val Val Cys Ala Arg Arg Asn Asp Ser Gly Thr Tyr
                85                  90                  95

Val Cys Gly Val Ile Ser Leu Ala Pro Lys Ile Gln Ile Lys Glu Ser
```

```
                    100                 105                 110

Leu Arg Ala Glu Leu Arg Val Thr Glu Arg
        115                 120

<210> SEQ ID NO 46
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 46

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe His Val Val Trp His Arg Glu Ser Pro Ser
        35                  40                  45

Gly Gln Thr Asp Thr Leu Ala Ala Phe Pro Glu Asp Arg Ser Gln Pro
    50                  55                  60

Gly Gln Asp Ala Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Val Cys Gly Val Ile Ser Leu Ala Pro Lys Ile Gln Ile Lys Glu Ser
            100                 105                 110

Leu Arg Ala Glu Leu Arg Val Thr Glu Cys
        115                 120

<210> SEQ ID NO 47
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 47

Gly Ser Gly Gly Ser
1               5

<210> SEQ ID NO 48
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 48

Gly Gly Ser Gly Gly Ser
1               5

<210> SEQ ID NO 49
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 49

Gly Gly Gly Ser
1
```

```
<210> SEQ ID NO 50
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 50

Gly Gly Ser Gly
1

<210> SEQ ID NO 51
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 51

Gly Gly Ser Gly Gly
1               5

<210> SEQ ID NO 52
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 52

Gly Ser Gly Ser Gly
1               5

<210> SEQ ID NO 53
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 53

Gly Ser Gly Gly Gly
1               5

<210> SEQ ID NO 54
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 54

Gly Gly Gly Ser Gly
1               5

<210> SEQ ID NO 55
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 55

Gly Ser Ser Ser Gly
1               5

<210> SEQ ID NO 56
```

<211> LENGTH: 20
<212> TYPE: DNA
<213> ORGANISM: Artificial Sequence
<220> FEATURE:
<223> OTHER INFORMATION: Synthetic sequence

<400> SEQUENCE: 56
ggctccaaag gacttgtacg                    20

<210> SEQ ID NO 57
<211> LENGTH: 20
<212> TYPE: DNA
<213> ORGANISM: Artificial Sequence
<220> FEATURE:
<223> OTHER INFORMATION: Synthetic sequence

<400> SEQUENCE: 57
ggtccagctc ccgttctaca                    20

<210> SEQ ID NO 58
<211> LENGTH: 15
<212> TYPE: PRT
<213> ORGANISM: Artificial Sequence
<220> FEATURE:
<223> OTHER INFORMATION: Synthetic sequence

<400> SEQUENCE: 58

Gly Leu Asn Asp Ile Phe Glu Ala Gln Lys Ile Glu Trp His Glu
1               5                   10                  15

<210> SEQ ID NO 59
<211> LENGTH: 31
<212> TYPE: DNA
<213> ORGANISM: Artificial sequence
<220> FEATURE:
<223> OTHER INFORMATION: Synthetic sequence

<400> SEQUENCE: 59
cattttcaat taagatgcag ttacttcgct g                    31

<210> SEQ ID NO 60
<211> LENGTH: 47
<212> TYPE: DNA
<213> ORGANISM: Artificial sequence
<220> FEATURE:
<223> OTHER INFORMATION: Synthetic sequence

<400> SEQUENCE: 60
aataacagaa aatattgaaa aacagcgaag taactgcatc ttaattg                    47

<210> SEQ ID NO 61
<211> LENGTH: 49
<212> TYPE: DNA
<213> ORGANISM: Artificial sequence
<220> FEATURE:
<223> OTHER INFORMATION: Synthetic sequence

<400> SEQUENCE: 61
ttacttcgct gttttcaat attttctgtt attgctagcg ttttagcag                    49

<210> SEQ ID NO 62
<211> LENGTH: 44
<212> TYPE: DNA
<213> ORGANISM: Artificial sequence
<220> FEATURE:
<223> OTHER INFORMATION: Synthetic sequence

```
<400> SEQUENCE: 62
gtctatctgg ggaatctgct aaaacgctag caataacaga aaat                44

<210> SEQ ID NO 63
<211> LENGTH: 40
<212> TYPE: DNA
<213> ORGANISM: Artificial sequence
<220> FEATURE:
<223> OTHER INFORMATION: Synthetic sequence

<400> SEQUENCE: 63
ttttagcaga ttccccagat agaccatgga acccaccaac                     40

<210> SEQ ID NO 64
<211> LENGTH: 38
<212> TYPE: DNA
<213> ORGANISM: Artificial sequence
<220> FEATURE:
<223> OTHER INFORMATION: Synthetic sequence

<400> SEQUENCE: 64
caacaaagct ggggagaaag ttggtgggtt ccatggtc                       38

<210> SEQ ID NO 65
<211> LENGTH: 39
<212> TYPE: DNA
<213> ORGANISM: Artificial sequence
<220> FEATURE:
<223> OTHER INFORMATION: Synthetic sequence

<400> SEQUENCE: 65
aactttctcc ccagctttgt tggtcgtcac tgaaggtga                      39

<210> SEQ ID NO 66
<211> LENGTH: 41
<212> TYPE: DNA
<213> ORGANISM: Artificial sequence
<220> FEATURE:
<223> OTHER INFORMATION: Synthetic sequence

<400> SEQUENCE: 66
gaacaagtga aagtagcgtt atcaccttca gtgacgacca a                   41

<210> SEQ ID NO 67
<211> LENGTH: 41
<212> TYPE: DNA
<213> ORGANISM: Artificial sequence
<220> FEATURE:
<223> OTHER INFORMATION: Synthetic sequence

<400> SEQUENCE: 67
gtgataacgc tactttcact tgttccttct ccaacacttc c                   41

<210> SEQ ID NO 68
<211> LENGTH: 30
<212> TYPE: DNA
<213> ORGANISM: Artificial sequence
<220> FEATURE:
<223> OTHER INFORMATION: Synthetic sequence

<400> SEQUENCE: 68
gaaggattcg gaagtgttgg agaaggaaca                                30

<210> SEQ ID NO 69
<211> LENGTH: 91
```

```
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t

<400> SEQUENCE: 69
caacacttcc gaatccttcn dtttgrwttg ghwtagavwg tccccavntn dtvwwvytnd      60
tvnattggct nhtttcccag aagatagatc c                                    91

<210> SEQ ID NO 70
<211> LENGTH: 53
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

<400> SEQUENCE: 70
gagtgactct gaatctagca tctkgahntg gtnbggatct atcttctggg aaa            53

<210> SEQ ID NO 71
<211> LENGTH: 34
<212> TYPE: DNA
<213> ORGANISM: Artificial sequence
<220> FEATURE:
<223> OTHER INFORMATION: Synthetic sequence

<400> SEQUENCE: 71
agatgctaga ttcagagtca ctcaattgcc aaac                                 34

<210> SEQ ID NO 72
<211> LENGTH: 44
<212> TYPE: DNA
<213> ORGANISM: Artificial sequence
<220> FEATURE:
<223> OTHER INFORMATION: Synthetic sequence

<400> SEQUENCE: 72
ggacatgtgg aaatctctac cgtttggcaa ttgagtgact ctga                      44
```

<210> SEQ ID NO 73
<211> LENGTH: 44
<212> TYPE: DNA
<213> ORGANISM: Artificial sequence
<220> FEATURE:
<223> OTHER INFORMATION: Synthetic sequence

<400> SEQUENCE: 73
cggtagagat tccacatgt ccgtcgtcag agctagaaga aacg          44

<210> SEQ ID NO 74
<211> LENGTH: 36
<212> TYPE: DNA
<213> ORGANISM: Artificial sequence
<220> FEATURE:
<223> OTHER INFORMATION: Synthetic sequence

<400> SEQUENCE: 74
gtaagtaccg gaatcgtttc ttctagctct gacgac          36

<210> SEQ ID NO 75
<211> LENGTH: 85
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 75
gaaacgattc cggtacttac nwttgtggtg ctattnctnd tnhtsctvna nytcaaatta          60
agvrwtcctt gagagctgaa ttgag          85

<210> SEQ ID NO 76
<211> LENGTH: 39
<212> TYPE: DNA
<213> ORGANISM: Artificial sequence
<220> FEATURE:
<223> OTHER INFORMATION: Synthetic sequence

<400> SEQUENCE: 76
ggatcctctt tcagtgactc tcaattcagc tctcaagga          39

<210> SEQ ID NO 77
<211> LENGTH: 40
<212> TYPE: DNA
<213> ORGANISM: Artificial sequence
<220> FEATURE:
<223> OTHER INFORMATION: Synthetic sequence

<400> SEQUENCE: 77
attgagagtc actgaaagag gatccgaaca aaagcttatc         40

<210> SEQ ID NO 78
<211> LENGTH: 40
<212> TYPE: DNA
<213> ORGANISM: Artificial sequence
<220> FEATURE:
<223> OTHER INFORMATION: Synthetic sequence

<400> SEQUENCE: 78
caagtcttct tcggagataa gcttttgttc ggatcctctt         40

<210> SEQ ID NO 79
<211> LENGTH: 36
<212> TYPE: DNA
<213> ORGANISM: Artificial sequence
<220> FEATURE:
<223> OTHER INFORMATION: Synthetic sequence

<400> SEQUENCE: 79
aaagcttatc tccgaagaag acttgggtgg tggtgg         36

<210> SEQ ID NO 80
<211> LENGTH: 26
<212> TYPE: DNA
<213> ORGANISM: Artificial sequence
<220> FEATURE:
<223> OTHER INFORMATION: Synthetic sequence

<400> SEQUENCE: 80
ccaccagatc caccaccacc caagtc         26

<210> SEQ ID NO 81
<211> LENGTH: 31
<212> TYPE: DNA
<213> ORGANISM: Artificial sequence
<220> FEATURE:
<223> OTHER INFORMATION: Synthetic sequence

<400> SEQUENCE: 81
cattttcaat taagatgcag ttacttcgct g         31

<210> SEQ ID NO 82
<211> LENGTH: 47
<212> TYPE: DNA
<213> ORGANISM: Artificial sequence
<220> FEATURE:
<223> OTHER INFORMATION: Synthetic sequence

<400> SEQUENCE: 82
aataacagaa atattgaaa aacagcgaag taactgcatc ttaattg         47

<210> SEQ ID NO 83
<211> LENGTH: 49
<212> TYPE: DNA
<213> ORGANISM: Artificial sequence
<220> FEATURE:
<223> OTHER INFORMATION: Synthetic sequence

<400> SEQUENCE: 83
ttacttcgct gttttttcaat attttctgtt attgctagcg ttttagcag         49

<210> SEQ ID NO 84
<211> LENGTH: 44
<212> TYPE: DNA
<213> ORGANISM: Artificial sequence
<220> FEATURE:
<223> OTHER INFORMATION: Synthetic sequence

<400> SEQUENCE: 84
gtctatctgg ggaatctgct aaaacgctag caataacaga aaat                    44

<210> SEQ ID NO 85
<211> LENGTH: 40
<212> TYPE: DNA
<213> ORGANISM: Artificial sequence
<220> FEATURE:
<223> OTHER INFORMATION: Synthetic sequence

<400> SEQUENCE: 85
ttttagcaga ttccccagat agaccatgga acccaccaac                         40

<210> SEQ ID NO 86
<211> LENGTH: 38
<212> TYPE: DNA
<213> ORGANISM: Artificial sequence
<220> FEATURE:
<223> OTHER INFORMATION: Synthetic sequence

<400> SEQUENCE: 86
caacaaagct ggggagaaag ttggtgggtt ccatggtc                           38

<210> SEQ ID NO 87
<211> LENGTH: 39
<212> TYPE: DNA
<213> ORGANISM: Artificial sequence
<220> FEATURE:
<223> OTHER INFORMATION: Synthetic sequence

<400> SEQUENCE: 87
aactttctcc ccagctttgt tggtcgtcac tgaaggtga                          39

<210> SEQ ID NO 88
<211> LENGTH: 41
<212> TYPE: DNA
<213> ORGANISM: Artificial sequence
<220> FEATURE:
<223> OTHER INFORMATION: Synthetic sequence

<400> SEQUENCE: 88
gaacaagtga aagtagcgtt atcaccttca gtgacgacca a                       41

<210> SEQ ID NO 89
<211> LENGTH: 41
<212> TYPE: DNA
<213> ORGANISM: Artificial sequence
<220> FEATURE:
<223> OTHER INFORMATION: Synthetic sequence

<400> SEQUENCE: 89
gtgataacgc tactttcact tgttccttct ccaacacttc c                       41

<210> SEQ ID NO 90
<211> LENGTH: 30
<212> TYPE: DNA
<213> ORGANISM: Artificial sequence
<220> FEATURE:
<223> OTHER INFORMATION: Synthetic sequence

<400> SEQUENCE: 90
gaaggattcg gaagtgttgg agaaggaaca                                              30

<210> SEQ ID NO 91
<211> LENGTH: 84
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 91
ccaacacttc cgaatccttc vrtnttnwtt ggywtydtsa wtccccatcc drtcaaactg              60
atamattggc tgctttccca gaag                                                    84

<210> SEQ ID NO 92
<211> LENGTH: 38
<212> TYPE: DNA
<213> ORGANISM: Artificial sequence
<220> FEATURE:
<223> OTHER INFORMATION: Synthetic sequence

<400> SEQUENCE: 92
gacctggttg ggatctatct tctgggaaag cagccaat                                     38

<210> SEQ ID NO 93
<211> LENGTH: 64
<212> TYPE: DNA
<213> ORGANISM: Artificial sequence
<220> FEATURE:
<223> OTHER INFORMATION: Synthetic sequence

<400> SEQUENCE: 93
gaagatagat cccaaccagg tcmagatgct agattcagar ytactcaatt gccaaacggt              60
agag                                                                          64

<210> SEQ ID NO 94
<211> LENGTH: 52
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (23)..(23)
<223> OTHER INFORMATION: n is a, c, g, or t

<400> SEQUENCE: 94
cttctagctc tgacgacgga sangtggaaa tctctaccgt ttggcaattg ag                     52

<210> SEQ ID NO 95
<211> LENGTH: 36
<212> TYPE: DNA
<213> ORGANISM: Artificial sequence
<220> FEATURE:
<223> OTHER INFORMATION: Synthetic sequence

<400> SEQUENCE: 95
tccgtcgtca gagctagaag aaacgattcc ggtact                                    36

<210> SEQ ID NO 96
<211> LENGTH: 83
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t

<400> SEQUENCE: 96
gctctcaagg attccttaat ttgaancttt ggagcawrgg aaataryacc acaaanawra        60
gtaccggaat cgtttcttct agc                                                83

<210> SEQ ID NO 97
<211> LENGTH: 40
<212> TYPE: DNA
<213> ORGANISM: Artificial sequence
<220> FEATURE:
<223> OTHER INFORMATION: Synthetic sequence

<400> SEQUENCE: 97
ttcaaattaa ggaatccttg agagctgaat tgagagtcac                               40

<210> SEQ ID NO 98
<211> LENGTH: 41
<212> TYPE: DNA
<213> ORGANISM: Artificial sequence
<220> FEATURE:
<223> OTHER INFORMATION: Synthetic sequence

<400> SEQUENCE: 98
gttcggatcc tctttcagtg actctcaatt cagctctcaa g                             41

<210> SEQ ID NO 99
<211> LENGTH: 45
<212> TYPE: DNA
<213> ORGANISM: Artificial sequence
<220> FEATURE:
<223> OTHER INFORMATION: Synthetic sequence

<400> SEQUENCE: 99
gtcactgaaa gaggatccga acaaaagctt atctccgaag aagac                         45

<210> SEQ ID NO 100
<211> LENGTH: 47
<212> TYPE: DNA
<213> ORGANISM: Artificial sequence
<220> FEATURE:
<223> OTHER INFORMATION: Synthetic sequence

<400> SEQUENCE: 100
ccaccagatc caccaccacc caagtcttct tcggagataa gcttttg                       47

<210> SEQ ID NO 101
<211> LENGTH: 7954
<212> TYPE: DNA
<213> ORGANISM: Artificial Sequence
<220> FEATURE:
<223> OTHER INFORMATION: synthetic sequence

<400> SEQUENCE: 101

```
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga     180
acagatggtc cccagatgcg gtcccgccct cagcagtttc tagagaacca tcagatgttt     240
ccagggtgcc ccaaggacct gaaaatgacc ctgtgcctta tttgaactaa ccaatcagtt     300
cgcttctcgc ttctgttcgc gcgcttctgc tccccgagct caataaaaga gcccacaacc     360
cctcactcgg cgcgccagtc ctccgataga ctgcgtcgcc cgggtacccg tattcccaat     420
aaagcctctt gctgtttgca tccgaatcgt ggactcgctg atccttggga gggtctcctc     480
agattgattg actgcccacc tcgggggtct ttcatttgga ggttccaccg agatttggag     540
accctgcct agggaccacc gaccccccg ccgggaggta agctggccag cggtcgtttc     600
gtgtctgtct ctgtctttgt gcgtgtttgt gccggcatct aatgtttgcg cctgcgtctg     660
tactagttag ctaactagct ctgtatctgg cggacccgtg gtggaactga cgagttcgga     720
acacccggcc gcaaccctgg gagacgtccc agggacttcg ggggccgttt ttgtggcccg     780
acctgagtcc taaaatcccg atcgtttagg actctttggt gcaccccct tagaggaggg     840
atatgtggtt ctggtaggag acgagaacct aaaacagttc ccgcctccgt ctgaattttt     900
gctttcggtt tgggaccgaa gccgcgccgc gcgtcttgtc tgctgcagca tcgttctgtg     960
ttgtctctgt ctgactgtgt ttctgtattt gtctgaaaat atgggcccgg gctagcctgt    1020
taccactccc ttaagtttga ccttaggtca ctggaaagat gtcgagcgga tcgctcacaa    1080
ccagtcggta gatgtcaaga agagacgttg ggttaccttc tgctctgcag aatggccaac    1140
ctttaacgtc ggatggccgc gagacggcac ctttaaccga gacctcatca cccaggttaa    1200
gatcaaggtc ttttcacctg gcccgcatgg acacccagac caggtcccct acatcgtgac    1260
ctgggaagcc ttggcttttg accccctcc ctgggtcaag ccctttgtac accctaagcc    1320
tccgcctcct cttcctccat ccgccccgtc tctccccctt gaacctcctc gttcgacccc    1380
gcctcgatcc tcccttttatc cagccctcac tccttctcta ggcgccccca tatggccata    1440
tgagatctta tatggggcac ccccgcccct tgtaaacttc cctgaccctg acatgacaag    1500
agttactaac agccctctc tccaagctca cttacaggct ctctacttag tccagcacga    1560
agtctggaga cctctggcgg cagcctacca agaacaactg gaccgaccgg tggtacctca    1620
cccttaccga gtcggcgaca cagtgtgggt ccgccgacac cagactaaga acctagaacc    1680
tcgctggaaa ggaccttaca cagtcctgct gaccaccccc accgccctca agtagacgg    1740
catcgcagct tggatacacg ccgccacgt gaaggctgcc gaccccgggg gtggaccatc    1800
ctctagaccg ccatgtaccg catgcaactt ttgtcctgta ttgctctgtc cctggccctc    1860
gttaccaatt ctgactcccc agacaggcct tggaacccac ccaccttctc accagccctg    1920
ttggtggtga ctgaggggga taatgctacc tttacttgca gcttcagcaa caccagtgaa    1980
tcctttcatg tcgtctggca tagggagtcc ccctctgggc aaactgatac actggcagcc    2040
ttccccgaag acagatctca gccaggccag gatgcccggt tccgagtgac tcagttgcca    2100
aacggtcggg actttcacat gtctgttgtg cgggctcgga gaaatgacag cggcacttat    2160
gtatgcggtg tgatctccct cgcaccaaag atccagataa aggaatctct gagggcagaa    2220
ctgagggtta ctgaaagagg atcatacca tacgatgttc cagattacgc tggctccgga    2280
```

```
gccaccaact tcagcctgct gaagcaggcc ggcgacgtgg aggagaaccc cggccccgcg    2340
gccgccatgg cgacgggttc aagaacttcc ctacttcttg catttggcct gctttgtttg    2400
ccgtggttac aggaagcctc agcacaacag aaggaggtgg agcagaattc tggacccctc    2460
agtgttccag agggagccat tgcctctctc aactgcactt acagtgaccg aggttcccag    2520
tccttcttct ggtacagaca atattctggg aaaagccctg agttgataat gttcatatac    2580
tccaatggtg acaagaaga tggaaggttt acagcacagc tcaataaagc cagccagtat    2640
gtttctctgc tcatcagaga ctcccagccc agtgattcag ccacctacct ctgtgccgtg    2700
aacttcggag gaggaaagct tatcttcgga cagggaacgg agttatctgt gaaacccaat    2760
atccagaacc ctgaccctgc cgtgtaccag ctgagagact ctaaatccag tgacaagtct    2820
gtctgcctat tcaccgattt tgattctcaa acaaatgtgt cacaaagtaa ggattctgat    2880
gtgtatatca cagacaaatg cgtgctagac atgaggtcta tggacttcaa gagcaacagt    2940
gctgtggcct ggagcaacaa atctgacttt gcatgtgcaa acgccttcaa caacagcatt    3000
attccagaag acaccttctt ccccagccca gaaagttcct gtgatgtcaa gctggtcgag    3060
aaaagctttg aaacagatac gaacctaaac tttcaaaacc tgtcagtgat tgggttccga    3120
atcctcctcc tgaaagtggc cgggtttaat ctgctcatga cgctgcggct gtggtccagc    3180
agggcaaaac gttcgggttc gggtgcgcca gtaaagcaga cattaaactt tgatttgctg    3240
aaacttgcag gtgatgtaga gtcaaatcca ggtccaatgg caacagggag ccgaacctct    3300
ctgctccttg ctttcgggct cctttgccta ccgtgcctgc aggagggctc ggcagggatc    3360
acccaggcac aacatctcca gatcctggca gcaggacggc gcatgacact gagatgtacc    3420
caggatatga gacataatgc catgtactgg tatagacaag atctaggact ggggctaagg    3480
ctcatccatt attcaaatac tgcaggtacc actggcaaag gagaagtccc tgatggttat    3540
agtgtctcca gagcaaacac agatgatttc cccctcacgt tggcgtctgc tgtaccctct    3600
cagacatctg tgtacttctg tgccagcagc ctaagtttcg gcactgaagc tttctttgga    3660
caaggcacca gactcacagt tgtagaggac ctgaacaagg tgttcccacc cgaggtcgct    3720
gtgtttgagc catcagaagc agagatctcc cacacccaaa aggccacact ggtgtgcctg    3780
gccacaggct tcttccctga ccacgtggag ctgagctggt gggtgaatgg gaaggaggtg    3840
cacagtgggg tctgcacgga cccgcagccc ctcaaggagc agcccgccct caatgactcc    3900
agatactgcc tgagcagccg cctgagggtc tcggccacct tctggcagaa cccccgcaac    3960
cacttccgct gtcaagtcca gttctacggg ctctcggaga tgacgagtg gacccaggat    4020 agggccaaac ccgtcaccca gatcgtcagc gccgaagcct ggggtagagc agactgtggc    4080
tttacctcgg tgtcctacca gcaagggtc ctgtctgcca ccatcctcta tgagatcctg    4140
ctagggaagg ccaccctgta tgctgtgctg gtcagcgccc ttgtgttgat ggccatggtc    4200
aagagaaagg atttctaaag gatccgataa aataaaagat tttatttagt ctccagaaaa    4260 agggggaat gaaagacccc acctgtaggt ttggcaagct agcttaagta acgccatttt    4320
gcaaggcatg gaaaatacat aactgagaat agagaagttc agatcaaggt taggaacaga    4380
gagacagcag aatatgggcc aaacaggata tctgtggtaa gcagttcctg ccccggctca    4440
gggccaagaa cagatggtcc ccagatgcgg tcccgccctc agcagtttct agagaaccat    4500
cagatgtttc cagggtgccc caaggacctg aaatgaccct gtgccttatt tgaactaacc    4560
aatcagttcc ttctcgcttc tgttcgcgcg cttctgctcc cccagcctca ataaaagagc    4620
ccacaacccc tcactcggcg cgccagtcct ccgatagact gcgtcgcccg ggtacccgtg    4680
```

```
tatccaataa accctcttgc agttgcatcc gacttgtggt ctcgctgttc cttgggaggg    4740
tctcctctga gtgattgact acccgtcagc gggggtcttt catgggtaac agtttcttga    4800
agttggagaa caacattctg agggtaggag tcgaatatta agtaatcctg actcaattag    4860
ccactgtttt gaatccacat actccaatac tcctgaaatc catcgatgga gttcattatg    4920
gacagcgcag aaagagctgg ggagaattgt gaaattgtta ccgctcaca attccacaca     4980 acatacgagc cggaagcata aagtgtaaag cctggggtgc ctaatgagtg agctaactca    5040
cattaattgc gttgcgctca ctgcccgctt tccagtcggg aaacctgtcg tgccagctgc    5100
attaatgaat cggccaacgc gcggggagag gcggtttgcg tattgggcgc tcttccgctt    5160
cctcgctcac tgactcgctg cgctcggtcg ttcggctgcg gcgagcggta tcagctcact    5220
caaaggcggt aatacggtta tccacagaat caggggataa cgcaggaaag aacatgtgag    5280
caaaaggcca gcaaaaggcc aggaaccgta aaaaggccgc gttgctggcg ttttccata    5340 ggctccgccc ccctgacgag catcacaaaa atcgacgctc aagtcagagg tggcgaaacc    5400
cgacaggact ataaagatac caggcgtttc ccctggaag ctccctcgtg cgctctcctg     5460
ttccgaccct gccgcttacc ggatacctgt ccgcctttct cccttcggga agcgtggcgc    5520
tttctcatag ctcacgctgt aggtatctca gttcggtgta ggtcgttcgc tccaagctgg    5580
gctgtgtgca cgaaccccc gttcagcccg accgctgcgc cttatccggt aactatcgtc     5640
ttgagtccaa cccggtaaga cacgacttat cgccactggc agcagccact ggtaacagga    5700
ttagcagagc gaggtatgta ggcggtgcta cagagttctt gaagtggtgg cctaactacg    5760
gctacactag aaggacagta tttggtatct gcgctctgct gaagccagtt accttcggaa    5820
aaagagttgg tagctcttga tccggcaaac aaaccaccgc tggtagcggt ggtttttttg    5880
tttgcaagca gcagattacg cgcagaaaaa aaggatctca agaagatcct ttgatctttt    5940
ctacggggtc tgacgctcag tggaacgaaa actcacgtta agggattttg gtcatgagat    6000
tatcaaaaag gatcttcacc tagatccttt taaattaaaa atgaagtttt aaatcaatct    6060
aaagtatata tgagtaaact tggtctgaca gttaccaatg cttaatcagt gaggcaccta    6120
tctcagcgat ctgtctattt cgttcatcca tagttgcctg actccccgtc gtgtagataa    6180
ctacgatacg ggagggctta ccatctggcc ccagtgctgc aatgataccg cgagacccac    6240
gctcaccggc tccagattta tcagcaataa accagccagc cggaagggcc gagcgcagaa    6300
gtggtcctgc aactttatcc gcctccatcc agtctattaa ttgttgccgg gaagctagag    6360
taagtagttc gccagttaat agtttgcgca acgttgttgc cattgctaca ggcatcgtgg    6420
tgtcacgctc gtcgtttggt atggcttcat tcagctccgg ttcccaacga tcaaggcgag    6480
ttacatgatc ccccatgttg tgcaaaaaag cggttagctc cttcggtcct ccgatcgttg    6540
tcagaagtaa gttggccgca gtgttatcac tcatggttat ggcagcactg cataattctc    6600
ttactgtcat gccatccgta agatgctttt ctgtgactgg tgagtactca accaagtcat    6660
tctgagaata gtgtatgcgg cgaccgagtt gctcttgccc ggcgtcaata cgggataata    6720
ccgcgccaca tagcagaact ttaaaagtgc tcatcattgg aaaacgttct cggggcgaa    6780 aactctcaag gatcttaccg ctgttgagat ccagttcgat gtaacccact cgtgcaccca    6840
actgatcttc agcatctttt actttcacca gcgtttctgg gtgagcaaaa acaggaaggc    6900
aaaatgccga aaaaaggga ataagggcga cacggaaatg ttgaatactc atactcttcc    6960
tttttcaata ttattgaagc atttatcagg gttattgtct catgagcgga tacatatttg    7020
```

```
aatgtattta gaaaaataaa caaatagggg ttccgcgcac atttccccga aaagtgccac      7080
ctgacgtcta agaaaccatt attatcatga cattaaccta taaaaatagg cgtatcacga      7140 ggcccttteg tctcgcgcgt ttcggtgatg acggtgaaaa cctctgacac atgcagctcc      7200
cggagacggt cacagcttgt ctgtaagcgg atgccgggag cagacaagcc cgtcagggcg      7260
cgtcagcggg tgttggcggg tgtcggggct ggcttaacta tgcggcatca gagcagattg      7320
tactgagagt gcaccatatg cggtgtgaaa taccgcacag atgcgtaagg agaaaatacc      7380
gcatcaggcg ccattcgcca ttcaggctgc gcaactgttg ggaagggcga tcggtgcggg      7440
cctcttcgct attacgccag ctggcgaaag gggatgtgc tgcaaggcga ttaagttggg      7500
taacgccagg gttttcccag tcacgacgtt gtaaaacgac ggccagtgcc acgctctccc      7560
ttatgcgact cctgcattag gaagcagccc agtagtaggt tgaggccgtt gagcaccgcc      7620
gccgcaagga atggtgcatg caaggagatg cgcccaaca gtcccccggc cacggggcct      7680
gccaccatac ccacgccgaa acaagcgctc atgagcccga agtggcgagc ccgatcttcc      7740
ccatcggtga tgtcggcgat ataggcgcca gcaaccgcac ctgtggcgcc ggtgatgccg      7800
gccacgatgc gtccggcgta gaggcgattt aaagacagga tatcagtggt ccaggctcta      7860
gttttgactc aacaatatca ccagctgaag cctatagagt acgagccata gataaaataa      7920
aagattttat ttagtctcca gaaaaagggg ggaa                                 7954

<210> SEQ ID NO 102
<211> LENGTH: 8856
<212> TYPE: DNA
<213> ORGANISM: Artificial Sequence
<220> FEATURE:
<223> OTHER INFORMATION: synthetic sequence

<400> SEQUENCE: 102
tgaaagaccc cacctgtagg tttggcaagc tagcttaagt aacgccattt tgcaaggcat        60
ggaaaataca taactgagaa tagagaagtt cagatcaagg ttaggaacag agagacagca       120
gaatatgggc caaacaggat atctgtggta agcagttcct gccccggctc agggccaaga       180
acagatggtc cccagatgcg gtcccgccct cagcagtttc tagagaacca tcagatgttt       240
ccagggtgcc ccaaggacct gaaaatgacc ctgtgcctta tttgaactaa ccaatcagtt       300
cgcttctcgc ttctgttcgc gcgcttctgc tccccgagct caataaaaga gcccacaacc       360
cctcactcgg cgcgccagtc tccgataga ctgcgtcgcc cgggtacccg tattcccaat       420
aaagcctctt gctgtttgca tccgaatcgt ggactcgctg atccttggga gggtctcctc       480
agattgattg actgcccacc tcgggggtct ttcatttgga ggttccaccg agatttggag       540 accccctgcct agggaccacc gacccccccg ccggggaggta agctggccag cggtcgtttc       600
gtgtctgtct ctgtctttgt gcgtgtttgt gccggcatct aatgtttgcg cctgcgtctg       660
tactagttag ctaactagct ctgtatctgg cggacccgtg gtggaactga cgagttcgga       720
acacccggcc gcaaccctgg gagacgtccc agggacttcg ggggccgttt ttgtggcccg       780
acctgagtcc taaaatcccg atcgtttagg actctttggt gcacccccct tagaggaggg       840
atatgtggtt ctggtaggag acgagaacct aaaacagttc ccgcctccgt ctgaattttt       900
gctttcggtt tgggaccgaa gccgcgccgc gcgtcttgtc tgctgcagca tcgttctgtg       960
ttgtctctgt ctgactgtgt ttctgtattt gtctgaaaat atgggccggg ctagcctgt       1020 taccactccc ttaagtttga ccttaggtca ctggaaagat gtcgagcgga tcgctcacaa      1080
ccagtcggta gatgtcaaga agagacgttg ggttaccttc tgctctgcag aatggccaac      1140
```

```
ctttaacgtc ggatggccgc gagacggcac ctttaaccga gacctcatca cccaggttaa    1200
gatcaaggtc ttttcacctg gcccgcatgg acacccagac caggtcccct acatcgtgac    1260
ctgggaagcc ttggcttttg accccctcc ctgggtcaag ccctttgtac accctaagcc     1320
tccgcctcct cttcctccat ccgccccgtc tctccccctt gaacctcctc gttcgacccc    1380
gcctcgatcc tcccttatc cagccctcac tccttctcta ggcgccccca tatggccata    1440
tgagatctta tatggggcac ccccgcccct tgtaaacttc cctgaccctg acatgacaag    1500
agttactaac agcccctctc tccaagctca cttacaggct ctctacttag tccagcacga    1560
agtctggaga cctctggcgg cagcctacca agaacaactg gaccgaccgg tggtacctca    1620
cccttaccga gtcggcgaca cagtgtgggt ccgccgacac cagactaaga acctagaacc    1680
tcgctggaaa ggaccttaca cagtcctgct gaccaccccc accgcccctca agtagacgg     1740
catcgcagct tggatacacg ccgcccacgt gaaggctgcc gaccccgggg gtggaccatc     1800
ctctagaccg ccatgtcggg ggcaggtgcc accggccgcg ccatggacgg gccgcgcctg     1860
ctgctgttgc tgcttctggg ggtgtcccctt ggaggtgcca aggaggcatg ccccacaggc    1920
ctgtacacac acagcggtga gtgctgcaaa gcctgcaacc tgggcgaggg tgtggcccag    1980
ccttgtggag ccaaccagac cgtgtgtgag ccctgcctgg acagcgtgac gttctccgac    2040
gtggtgagcg cgaccgagcc gtgcaagccg tgcaccgagt gcgtggggct ccagagcatg    2100
tcggcgccat gcgtggaggc cgacgacgcc gtgtgccgct gcgcctacgg ctactaccag    2160
gatgagacga ctgggcgctg cgaggcgtgc cgcgtgtgcg aggcgggctc gggcctcgtg    2220
ttctcctgcc aggacaagca gaacaccgtg tgcgaggagt gccccgacgg cacgtattcc    2280
gacgaggcca accacgtgga cccgtgcctg ccctgcaccg tgtgcgagga caccgagcgc    2340
cagctccgcg agtgcacacg ctgggccgac gccgagtgcg aggagatccc tggccgttgg    2400
attacacggt ccacaccccc agagggctcg gacagcacag cccccagcac ccaggagcct    2460
gaggcacctc cagaacaaga cctcatagcc agcacggtgg caggtgtggt gaccacagtg    2520
atgggcagct cccagcccgt ggtgacccga ggcaccaccg acaacctcat ccctgtctat    2580
tgctccatcc tggctgctgt ggttgtgggt cttgtggcct acatagcctt caagaggtgg    2640
aacagctccg gctccggagc caccaacttc agcctgctga gcaggccgg cgacgtggag     2700
gagaaccccg gccccgcggc cgccatggcg acgggttcaa gaacttccct acttcttgca    2760
tttggcctgc tttgtttgcc gtggttacag gaagcctcag cacaacagaa ggaggtggag    2820
cagaattctg gaccctcag tgttccagag ggagccattg cctctctcaa ctgcacttac     2880
agtgaccgag gttcccagtc cttcttctgg tacagacaat attctgggaa agccctgag    2940
ttgataatgt tcatatactc caatggtgac aaagaagatg gaaggtttac agcacagctc    3000
aataaagcca gccagtatgt ttctctgctc atcagagact cccagcccag tgattcagcc    3060
acctacctct gtgccgtgaa cttcggagga ggaaagctta tcttcggaca gggaacggag    3120
ttatctgtga acccaatat ccagaaccct gaccctgccg tgtaccagct gagagactct    3180
aaatccagtg acaagtctgt ctgcctattc accgattttg attctcaaac aaatgtgtca    3240
caaagtaagg attctgatgt gtatatcaca gacaaatgcg tgctagacat gaggtctatg    3300
gacttcaaga gcaacagtgc tgtggcctgg agcaacaaat ctgactttgc atgtgcaaac    3360
gccttcaaca acagcattat tccagaagac accttcttcc ccagcccaga aagttcctgt    3420
gatgtcaagc tggtcgagaa aagctttgaa acagatacga acctaaactt tcaaaacctg    3480
```

```
tcagtgattg ggttccgaat cctcctcctg aaagtggccg ggtttaatct gctcatgacg    3540
ctgcggctgt ggtccagcag ggcaaaacgt tcgggttcgg gtgcgccagt aaagcagaca    3600
ttaaactttg atttgctgaa acttgcaggt gatgtagagt caaatccagg tccaatggca    3660
acagggagcc gaacctctct gctccttgct ttcgggctcc tttgcctacc gtgcctgcag    3720
gagggctcgg cagggatcac ccaggcacca acatctcaga tcctggcagc aggacggcgc    3780
atgacactga gatgtaccca ggatatgaga cataatgcca tgtactggta tagacaagat    3840
ctaggactgg ggctaaggct catccattat tcaaatactg caggtaccac tggcaaagga    3900
gaagtccctg atggttatag tgtctccaga gcaaacacag atgatttccc cctcacgttg    3960
gcgtctgctg taccctctca gacatctgtg tacttctgtg ccagcagcct aagtttcggc    4020
actgaagctt tctttggaca aggcaccaga ctcacagttg tagaggacct gaacaaggtg    4080
ttcccacccg aggtcgctgt gtttgagcca tcagaagcag atctcccca cacccaaaag    4140
gccacactgg tgtgcctggc cacaggcttc ttccctgacc acgtggagct gagctggtgg    4200
gtgaatggga aggaggtgca cagtggggtc tgcacgaccc gcagcccct caaggagcag    4260
cccgccctca atgactccag atactgcctg agcagccgcc tgagggtctc ggccaccttc    4320
tggcagaacc ccgcaacca cttccgctgt caagtccagt tctacgggct ctcggagaat    4380
gacgagtgga cccaggatag ggccaaaccc gtcacccaga tcgtcagcgc cgaagcctgg    4440
ggtagagcag actgtggctt tacctcggtg tcctaccagc aaggggtcct gtctgccacc    4500
atcctctatg agatcctgct agggaaggcc accctgtatg ctgtgctggt cagcgccctt    4560
gtgttgatgg ccatggtcaa gagaaaggat ttcggttctg gcgagggtcg gggggtctctg    4620
ctgacctgcg gtgatgtcga ggaaaatcca ggtcccatgt accgcatgca actttgtcc    4680
tgtattgctc tgtccctggc cctcgttacc aattctgact ccccagacag gccttggaac    4740
ccacccacct tctcaccagc cctgttggtg gtgactgagg gggataatgc tactttact    4800
tgcagcttca gcaacaccag tgaatccttt catgtcgtct ggcatagga gtccccctct    4860
gggcaaactg atacactggc agccttcccc gaagacagat ctcagccagg ccaggatgcc    4920
cggttccgag tgactcagtt gccaaacggt cgggactttc acatgtctgt tgtgcgggct    4980
cggagaaatg acagcggcac ttatgtatgc ggtgtgatct ccctcgcacc aaagatccag    5040
ataaaggaat ctctgagggc agaactgagg gttactgaaa gaggatcata cccatacgat    5100
gttccagatt acgcttaatg aggatccgat aaaataaaag attttattta gtctccagaa    5160
aaaggggga atgaaagacc ccacctgtag gtttggcaag ctagcttaag taacgccatt    5220
ttgcaaggca tggaaaatac ataactgaga atagagaagt tcagatcaag gttaggaaca    5280
gagagacagc agaatatggg ccaaacagga tatctgtggt aagcagttcc tgccccggct    5340
cagggccaag aacagatggt ccccagatgc ggtcccgccc tcagcagttt ctagagaacc    5400
atcagatgtt tccagggtgc cccaaggacc tgaaatgacc ctgtgcctta tttgaactaa    5460
ccaatcagtt cgcttctcgc ttctgttcgc gcgcttctgc tccccgagct caataaaaga    5520
gcccacaacc cctcactcgg cgcgccagtc ctccgataga ctgcgtcgcc cgggtacccg    5580
tgtatccaat aaaccctctt gcagttgcat ccgacttgtg gtctcgctgt tccttgggag    5640
ggtctcctct gagtgattga ctacccgtca gcgggggtct ttcatgggta acagtttctt    5700
gaagttggag aacaacattc tgagggtagg agtcgaatat taagtaatcc tgactcaatt    5760
agccactgtt ttgaatccac atactccaat actcctgaaa tccatcgatg gagttcatta    5820
tggacagcgc agaaagagct ggggagaatt gtgaaattgt tatccgctca caattccaca    5880
```

```
caacatacga gccggaagca taaagtgtaa agcctggggt gcctaatgag tgagctaact    5940
cacattaatt gcgttgcgct cactgcccgc tttccagtcg ggaaacctgt cgtgccagct    6000
gcattaatga atcggccaac gcgcggggag aggcggtttg cgtattgggc gctcttccgc    6060
ttcctcgctc actgactcgc tgcgctcggt cgttcggctg cggcgagcgg tatcagctca    6120
ctcaaaggcg gtaatacggt tatccacaga atcaggggat aacgcaggaa agaacatgtg    6180
agcaaaaggc cagcaaaagg ccaggaaccg taaaaaggcc gcgttgctgg cgtttttcca    6240
taggctccgc cccccctgacg agcatcacaa aaatcgacgc tcaagtcaga ggtggcgaaa    6300
cccgacagga ctataaagat accaggcgtt tccccctgga agctccctcg tgcgctctcc    6360
tgttccgacc ctgccgctta ccggatacct gtccgccttt ctcccttcgg aagcgtggc    6420
gctttctcat agctcacgct gtaggtatct cagttcggtg taggtcgttc gctccaagct    6480
gggctgtgtg cacgaacccc ccgttcagcc cgaccgctgc gccttatccg gtaactatcg    6540
tcttgagtcc aacccggtaa gacacgactt atcgccactg gcagcagcca ctggtaacag    6600
gattagcaga gcgaggtatg taggcggtgc tacagagttc ttgaagtggt ggcctaacta    6660
cggctacact agaaggacag tatttggtat ctgcgctctg ctgaagccag ttaccttcgg    6720
aaaaagagtt ggtagctctt gatccggcaa acaaaccacc gctggtagcg gtggtttttt    6780
tgtttgcaag cagcagatta cgcgcagaaa aaaggatct caagaagatc ctttgatctt    6840
ttctacgggg tctgacgctc agtggaacga aaactcacgt taagggattt tggtcatgag    6900
attatcaaaa aggatcttca cctagatcct tttaaattaa aaatgaagtt ttaaatcaat    6960
ctaaagtata tatgagtaaa cttggtctga cagttaccaa tgcttaatca gtgaggcacc    7020
tatctcagcg atctgtctat ttcgttcatc catagttgcc tgactccccg tcgtgtagat    7080
aactacgata cgggagggct taccatctgg ccccagtgct gcaatgatac cgcgagaccc    7140
acgctcaccg gctccagatt tatcagcaat aaaccagcca gccggaaggg ccgagcgcag    7200
aagtggtcct gcaactttat ccgcctccat ccagtctatt aattgttgcc gggaagctag    7260
agtaagtagt tcgccagtta atagtttgcg caacgttgtt gccattgcta caggcatcgt    7320
ggtgtcacgc tcgtcgtttg gtatggcttc attcagctcc ggttcccaac gatcaaggcg    7380
agttacatga tcccccatgt tgtgcaaaaa agcggttagc tccttcggtc ctccgatcgt    7440
tgtcagaagt aagttggccg cagtgttatc actcatggtt atggcagcac tgcataattc    7500
tcttactgtc atgccatccg taagatgctt ttctgtgact ggtgagtact caaccaagtc    7560
attctgagaa tagtgtatgc ggcgaccgag ttgctcttgc ccggcgtcaa tacgggataa    7620
taccgcgcca catagcagaa ctttaaaagt gctcatcatt ggaaaacgtt cttcggggcg    7680
aaaactctca aggatcttac cgctgttgag atccagttcg atgtaaccca ctcgtgcacc    7740
caactgatct tcagcatctt ttactttcac cagcgtttct gggtgagcaa aaacaggaag    7800
gcaaaatgcc gcaaaaaagg gaataagggc gacacgaaa tgttgaatac tcatactctt    7860
ccttttttcaa tattattgaa gcatttatca gggttattgt ctcatgagcg gatacatatt    7920
tgaatgtatt tagaaaaata acaaataggg gttccgcgc acatttcccc gaaaagtgcc    7980
acctgacgtc taagaaacca ttattatcat gacattaacc tataaaaata ggcgtatcac    8040
gaggcccttt cgtctcgcgc gtttcggtga tgacggtgaa aacctctgac acatgcagct    8100
cccggagacg gtcacagctt gtctgtaagc ggatgccggg agcagacaag cccgtcaggg    8160
cgcgtcagcg ggtgttggcg ggtgtcgggg ctggcttaac tatgcggcat cagagcagat    8220
```

| | |
|---|---:|
| tgtactgaga gtgcaccata tgcggtgtga ataccgcac agatgcgtaa ggagaaaata | 8280 |
| ccgcatcagg cgccattcgc cattcaggct gcgcaactgt tgggaagggc gatcggtgcg | 8340 |
| ggcctcttcg ctattacgcc agctggcgaa aggggatgt gctgcaaggc gattaagttg | 8400 |
| ggtaacgcca gggttttccc agtcacgacg ttgtaaaacg acggccagtg ccacgctctc | 8460 |
| ccttatgcga ctcctgcatt aggaagcagc ccagtagtag gttgaggccg ttgagcaccg | 8520 |
| ccgccgcaag gaatggtgca tgcaaggaga tggcgcccaa cagtcccccg gcacggggc | 8580 |
| ctgccaccat acccacgccg aaacaagcgc tcatgagccc gaagtggcga gcccgatctt | 8640 |
| ccccatcggt gatgtcggcg atataggcgc cagcaaccgc acctgtggcg ccggtgatgc | 8700 |
| cggccacgat gcgtccggcg tagaggcgat ttaaagacag gatatcagtg gtccaggctc | 8760 |
| tagttttgac tcaacaatat caccagctga agcctataga gtacgagcca tagataaaat | 8820 |
| aaaagatttt atttagtctc cagaaaaagg ggggaa | 8856 |

<210> SEQ ID NO 103
<211> LENGTH: 7902
<212> TYPE: DNA
<213> ORGANISM: Artificial Sequence
<220> FEATURE:
<223> OTHER INFORMATION: synthetic sequence

<400> SEQUENCE: 103

| | |
|---|---:|
| tgaaagaccc cacctgtagg tttggcaagc tagcttaagt aacgccattt tgcaaggcat | 60 |
| ggaaaataca taactgagaa tagagaagtt cagatcaagg ttaggaacag agagacagca | 120 |
| gaatatgggc caaacaggat atctgtggta agcagttcct gccccggctc agggccaaga | 180 |
| acagatggtc cccagatgcg gtcccgccct cagcagtttc tagagaacca tcagatgttt | 240 |
| ccagggtgcc ccaaggacct gaaaatgacc ctgtgcctta tttgaactaa ccaatcagtt | 300 |
| cgcttctcgc ttctgttcgc gcgcttctgc tccccgagct caataaaaga gcccacaacc | 360 |
| cctcactcgg cgcgccagtc ctccgataga ctgcgtcgcc cgggtacccg tattcccaat | 420 |
| aaagcctctt gctgtttgca tccgaatcgt ggactcgctg atccttggga gggtctcctc | 480 |
| agattgattg actgcccacc tcgggggtct ttcatttgga ggttccaccg agatttggag | 540 |
| accccctgcct agggaccacc gacccccccg ccgggaggta agctggccag cggtcgtttc | 600 |
| gtgtctgtct ctgtctttgt gcgtgtttgt gccggcatct aatgtttgcg cctgcgtctg | 660 |
| tactagttag ctaactagct ctgtatctgg cggacccgtg gtggaactga cgagttcgga | 720 |
| acacccggcc gcaaccctgg gagacgtccc agggacttcg ggggccgttt tgtggcccg | 780 |
| acctgagtcc taaaatcccg atcgtttagg actctttggt gcaccccct tagaggaggg | 840 |
| atatgtggtt ctggtaggag acgagaacct aaaacagttc ccgcctccgt ctgaatttt | 900 |
| gctttcggtt tgggaccgaa gccgcgccgc gcgtcttgtc tgctgcagca tcgttctgtg | 960 |
| ttgtctctgt ctgactgtgt ttctgtattt gtctgaaaat atgggcccgg ctagcctgt | 1020 |
| taccactccc ttaagtttga ccttaggtca ctggaaagat gtcgagcgga tcgctcacaa | 1080 |
| ccagtcggta gatgtcaaga agagacgttg ggttaccttc tgctctgcag aatggccaac | 1140 |
| ctttaacgtc ggatggccgc gagacggcac ctttaaccga gacctcatca cccaggttaa | 1200 |
| gatcaaggtc ttttcacctg gcccgcatgg acacccagac caggtcccct acatcgtgac | 1260 |
| ctgggaagcc ttggcttttg acccccctc ctgggtcaag ccctttgtac accctaagcc | 1320 |
| tccgcctcct cttcctccat ccgccccgtc tctccccctt gaacctcctc gttcgacccc | 1380 |
| gcctcgatcc tccctttatc cagccctcac tccttctcta ggcgccccca tatggccata | 1440 |

```
tgagatctta tatggggcac ccccgcccct tgtaaacttc cctgaccctg acatgacaag    1500
agttactaac agcccctctc tccaagctca cttacaggct ctctacttag tccagcacga    1560
agtctggaga cctctggcgg cagcctacca agaacaactg gaccgaccgg tggtacctca    1620
cccttaccga gtcggcgaca cagtgtgggt ccgccgacac cagactaaga acctagaacc    1680
tcgctggaaa ggaccttaca cagtcctgct gaccaccccc accgccctca agtagacgg     1740 catcgcagct tggatacacg ccgcccacgt gaaggctgcc gaccccgggg gtggaccatc    1800
ctctagaccg ccatgtaccg catgcaactt ttgtcctgta ttgctctgtc cctggccctc    1860
gttaccaatt ctgattcccc agatagacca tggaacccac caactttctc cccagctttg    1920
ttggtcgtca ctgaaggtga taacgctact ttcacttgtt ccttctccaa cacttccgaa    1980
tccttccatg ttgtttggca tcgtgaatcc ccatccggtc aaactgatac attggctgct    2040
ttcccagaag atagatccca accaggtcaa gatgctagat tcagagttac tcaattgcca    2100
aacggtagag atttccacat gtccgtcgtc agagctagaa gaaacgattc cggtacttat    2160
gtttgtggtg ttatttccct tgctccaaag attcaaatta aggaatcctt gagagctgaa    2220
ttgagagtca ctgaaagaga gcccaaatct tgtgacaaaa ctcacacatg cccaccgtgc    2280
ggcggaggtt ctagtggagg cggtagtgga ggacagcccc gagaaccaca ggtgtacacc    2340
ctgcccccat cccgggagga gatgaccaag aaccaggtca gcctgacctg cctggtcaaa    2400
ggcttctatc ccagcgacat cgccgtggag tgggagagca atgggcagcc ggagaacaac    2460
tacaagacca cgcctcccgt gctggactcc gacggctcct tcttcctcta cagcaagctc    2520
accgtggaca agagcaggtg gcagcagggg aacgtcttct catgctccgt gatgcatgag    2580
gctctgcaca accactacac gcagaagagc ctctccctgt ctccgggtaa aggatcatac    2640
ccatacgatg ttccagatta cgctggctcc ggagccacca cttcagcct gctgaagcag     2700 gccggcgacg tggaggagaa ccccggcccc gcggccgcca tgggtgtccc tacccagctc    2760
ctgggactgc tcctgctgtg gatcaccgac gccatctgcg acatccagat gacccagagc    2820
cctgccagcc tgtctaccag cctgggcgag acagtgacca tccagtgtca ggccagcgag    2880
gacatctact ctggcctggc ttggtatcag cagaagcccg gcaagagccc tcagctgctg    2940
atctacggcg ccagcgacct gcaggacggc gtgcctagca gattcagcgg cagcggctcc    3000
ggaacccagt acagcctgaa gatcaccagc atgcagaccg aggacgaggg cgtgtacttc    3060
tgccagcaag gcctgaccta ccctagaacc ttcggaggag gcaccaagct ggaactgaag    3120
ggcggaggcg gaagtggagg cggaggatct ggcggcggag gctctgaagt gcagctgcag    3180
cagtctggcg ctgaactggt ccggcctggc actagcgtga agctgtcctg caaggtgtcc    3240
ggcgacacca tcaccttcta ctacatgcac ttcgtgaagc agaggccagg acagggcctg    3300
gaatggatcg gcagaatcga ccctgaggac gagagcacca agtacagcga agttcaag     3360 aacaaggcca ccctgaccgc cgacaccagc agcaacaccg cctacctgaa gctgtctagc    3420
ctgacctccg aggacaccgc cacctacttt tgcatctacg gcggctacta cttcgactac    3480
tggggccagg gcgtgatggt caccgtgtcc agcatcgagt tcatgtaccc ccctcctac     3540 ctggacaacg agagaagcaa cggcaccatc atccacatca agaaaagca cctgtgccac    3600 acccagagca gccccaagct gttctgggcc ctggtggtgg tggccggcgt gctgttctgt    3660
tacgccctgc tggtcacagt ggccctgtgc gtgatctgga ccaacagcag aagaaacaga    3720
ggcggccaga gcgactacat gaacatgacc cccagaaggc caggcctgac cagaaagccc    3780
```

| | |
|---|---|
| taccagccct acgccctgc cagagacttc gccgcctaca gacccagagc caagttcagc | 3840 |
| agatccgccg agacagccgc caacctgcag gaccctaacc agctgttcaa cgagctgaac | 3900 |
| ctgggcagac gggaggaatt tgacgtgctg aaaagaaga gagccaggga ccccgagatg | 3960 |
| ggcggcaagc agcagagaag aagaaaccct caggaaggcg tctacaacgc cctgcagaaa | 4020 |
| gacaagatgg ccgaggccta cagcgagatc ggcaccaagg gcgagagaag aaggggcaag | 4080 |
| ggccacgatg gcctgttcca gggcctgtcc accgccacca aggacacctt cgacgccctg | 4140 |
| cacatgcaga ccctggcccc cagatgagga tccgataaaa taaaagattt tatttagtct | 4200 |
| ccagaaaaag gggggaatga agacccccac ctgtaggttt ggcaagctag cttaagtaac | 4260 |
| gccattttgc aaggcatgga aaatacataa ctgagaatag agaagttcag atcaaggtta | 4320 |
| ggaacagaga gacagcagaa tatgggccaa acaggatatc tgtggtaagc agttcctgcc | 4380 |
| ccggctcagg gccaagaaca gatggtcccc agatgcggtc ccgccctcag cagtttctag | 4440 |
| agaaccatca gatgtttcca gggtgcccca aggacctgaa atgaccctgt gccttatttg | 4500 |
| aactaaccaa tcagttcgct tctcgcttct gttcgcgcgc ttctgctccc cgagctcaat | 4560 |
| aaaagagccc acaacccctc actcggcgcg ccagtcctcc gatagactgc gtcgcccggg | 4620 |
| tacccgtgta tccaataaac cctcttgcag ttgcatccga cttgtggtct cgctgttcct | 4680 |
| tgggagggtc tcctctgagt gattgactac ccgtcagcgg gggtctttca tgggtaacag | 4740 |
| tttcttgaag ttggagaaca acattctgag ggtaggagtc gaatattaag taatcctgac | 4800 |
| tcaattagcc actgttttga atccacatac tccaatactc ctgaaatcca tcgatggagt | 4860 |
| tcattatgga cagcgcagaa agagctgggg agaattgtga aattgttatc cgctcacaat | 4920 |
| tccacacaac atacgagccg gaagcataaa gtgtaaagcc tggggtgcct aatgagtgag | 4980 |
| ctaactcaca ttaattgcgt tgcgctcact gcccgctttc cagtcgggaa acctgtcgtg | 5040 |
| ccagctgcat taatgaatcg gccaacgcgc ggggagaggc ggtttgcgta ttgggcgctc | 5100 |
| ttccgcttcc tcgctcactg actcgctgcg ctcggtcgtt cggctgcggc gagcggtatc | 5160 |
| agctcactca aaggcggtaa tacggttatc cacagaatca ggggataacg caggaaagaa | 5220 |
| catgtgagca aaaggccagc aaaaggccag gaaccgtaaa aaggccgcgt tgctggcgtt | 5280 |
| tttccatagg ctccgccccc ctgacgagca tcacaaaaat cgacgctcaa gtcagaggtg | 5340 |
| gcgaaacccg acaggactat aaagatacca ggcgtttccc cctggaagct ccctcgtgcg | 5400 |
| ctctcctgtt ccgaccctgc cgcttaccgg atacctgtcc gcctttctcc cttcgggaag | 5460 |
| cgtggcgctt tctcatagct cacgctgtag gtatctcagt tcggtgtagg tcgttcgctc | 5520 |
| caagctgggc tgtgtgcacg aaccccccgt tcagcccgac cgctgcgcct tatccggtaa | 5580 |
| ctatcgtctt gagtccaacc cggtaagaca cgacttatcg ccactggcag cagccactgg | 5640 |
| taacaggatt agcagagcga ggtatgtagg cggtgctaca gagttcttga agtggtggcc | 5700 |
| taactacggc tacactagaa ggacagtatt tggtatctgc gctctgctga gccagttac | 5760 |
| cttcggaaaa agagttggta gctcttgatc cggcaaacaa accaccgctg gtagcggtgg | 5820 |
| tttttttgtt tgcaagcagc agattacgcg cagaaaaaaa ggatctcaag aagatccttt | 5880 |
| gatcttttct acgggtctg acgctcagtg aacgaaaac tcacgttaag gattttggt | 5940 |
| catgagatta tcaaaaagga tcttcaccta gatccttta aattaaaaat gaagttttaa | 6000 |
| atcaatctaa agtatatatg agtaaacttg gtctgacagt taccaatgct taatcagtga | 6060 |
| ggcacctatc tcagcgatct gtctatttcg ttcatccata gttgcctgac tccccgtcgt | 6120 |
| gtagataact acgatacggg agggcttacc atctggcccc agtgctgcaa tgataccgcg | 6180 |

```
agacccacgc tcaccggctc cagatttatc agcaataaac cagccagccg aagggccga      6240 gcgcagaagt ggtcctgcaa ctttatccgc ctccatccag tctattaatt gttgccggga     6300
agctagagta agtagttcgc cagttaatag tttgcgcaac gttgttgcca ttgctacagg     6360
catcgtggtg tcacgctcgt cgtttggtat ggcttcattc agctccggtt cccaacgatc     6420
aaggcgagtt acatgatccc ccatgttgtg caaaaaagcg gttagctcct tcggtcctcc     6480
gatcgttgtc agaagtaagt tggccgcagt gttatcactc atggttatgg cagcactgca     6540
taattctctt actgtcatgc catccgtaag atgcttttct gtgactggtg agtactcaac     6600
caagtcattc tgagaatagt gtatgcgcg accgagttgc tcttgcccgg cgtcaatacg      6660
ggataatacc gcgccacata gcagaacttt aaaagtgctc atcattggaa aacgttcttc     6720
ggggcgaaaa ctctcaagga tcttaccgct gttgagatcc agttcgatgt aacccactcg     6780
tgcacccaac tgatcttcag catctttac tttcaccagc gtttctgggt gagcaaaaac      6840
aggaaggcaa aatgccgcaa aaaagggaat aaggcgaca cggaaatgtt gaatactcat      6900
actcttcctt tttcaatatt attgaagcat ttatcagggt tattgtctca tgagcggata     6960
catatttgaa tgtatttaga aaataaaca aatagggggtt ccgcgcacat ttccccgaaa     7020
agtgccacct gacgtctaag aaaccattat tatcatgaca ttaacctata aaaataggcg     7080
tatcacgagg ccctttcgtc tcgcgcgttt cggtgatgac ggtgaaaacc tctgacacat     7140
gcagctcccg gagacggtca cagcttgtct gtaagcggat gccgggagca gacaagcccg     7200
tcagggcgcg tcagcgggtg ttggcgggtg tcggggctgg cttaactatg cggcatcaga     7260
gcagattgta ctgagagtgc accatatgcg gtgtgaaata ccgcacagat gcgtaaggag     7320
aaaataccgc atcaggcgcc attcgccatt caggctgcgc aactgttggg aagggcgatc     7380
ggtgcgggcc tcttcgctat tacgccagct ggcgaaaggg ggatgtgctg caaggcgatt     7440
aagttgggta acgccagggt ttcccagtc acgacgttgt aaaacgacgg ccagtgccac      7500
gctctccctt atgcgactcc tgcattagga agcagcccag tagtaggttg aggccgttga     7560
gcaccgccgc cgcaaggaat ggtgcatgca aggagatggc gcccaacagt cccccggcca     7620
cggggcctgc caccataccc acgccgaaac aagcgctcat gagcccgaag tggcgagccc     7680
gatcttcccc atcggtgatg tcggcgatat aggcgccagc aaccgcacct gtggcgccgg     7740
tgatgccggc cacgatgcgt ccggcgtaga ggcgatttaa agacaggata tcagtggtcc     7800
aggctctagt tttgactcaa caatatcacc agctgaagcc tatagagtac gagccataga     7860
taaaataaaa gatttatttt agtctccaga aaaaggggg aa                        7902

<210> SEQ ID NO 104
<211> LENGTH: 8805
<212> TYPE: DNA
<213> ORGANISM: Artificial Sequence
<220> FEATURE:
<223> OTHER INFORMATION: synthetic sequence

<400> SEQUENCE: 104
tgaaagaccc cacctgtagg tttggcaagc tagcttaagt aacgccattt tgcaaggcat        60
ggaaaataca taactgagaa tagagaagtt cagatcaagg ttaggaacag agagacagca       120
gaatatgggc caaacaggat atctgtggta agcagttcct gccccggctc agggccaaga       180
acagatggtc cccagatgcg gtcccgccct cagcagtttc tagagaacca tcagatgttt       240
ccagggtgcc ccaaggacct gaaaatgacc ctgtgcctta tttgaactaa ccaatcagtt       300
```

```
cgcttctcgc ttctgttcgc gcgcttctgc tccccgagct caataaaaga gcccacaacc    360
cctcactcgg cgcgccagtc ctccgataga ctgcgtcgcc cgggtacccg tattcccaat    420
aaagcctctt gctgtttgca tccgaatcgt ggactcgctg atccttggga gggtctcctc    480
agattgattg actgcccacc tcgggggtct ttcatttgga ggttccaccg agatttggag    540
accccctgcct agggaccacc gaccccccg ccgggaggta agctggccag cggtcgtttc    600
gtgtctgtct ctgtctttgt gcgtgtttgt gccggcatct aatgtttgcg cctgcgtctg    660
tactagttag ctaactagct ctgtatctgg cggacccgtg gtggaactga cgagttcgga    720
acacccggcc gcaaccctgg gagacgtccc agggacttcg ggggccgttt ttgtggcccg    780
acctgagtcc taaaatcccg atcgtttagg actctttggt gcaccccct tagaggaggg    840
atatgtggtt ctggtaggag acgagaacct aaaacagttc ccgcctccgt ctgaattttt    900
gctttcggtt tgggaccgaa gccgcgccgc gcgtcttgtc tgctgcagca tcgttctgtg    960
ttgtctctgt ctgactgtgt ttctgtattt gtctgaaaat atgggcccgg gctagcctgt    1020
taccactccc ttaagtttga ccttaggtca ctggaaagat gtcgagcgga tcgctcacaa    1080
ccagtcggta gatgtcaaga agagacgttg ggttaccttc tgctctgcag aatggccaac    1140
ctttaacgtc ggatggccgc gagacggcac ctttaaccga gacctcatca cccaggttaa    1200
gatcaaggtc ttttcacctg gcccgcatgg acacccagac caggtcccct acatcgtgac    1260
ctgggaagcc ttggcttttg acccccctcc ctgggtcaag ccctttgtac accctaagcc    1320
tccgcctcct cttcctccat ccgcccgtc tctccccctt gaacctcctc gttcgacccc    1380
gcctcgatcc tccctttatc cagccctcac tccttctcta ggcgcccca tatggccata    1440
tgagatctta tatggggcac ccccgcccct tgtaaacttc cctgaccctg acatgacaag    1500
agttactaac agcccctctc tccaagctca cttacaggct ctctacttag tccagcacga    1560
agtctggaga cctctggcgg cagcctacca agaacaactg gaccgaccgg tggtacctca    1620
cccttaccga gtcggcgaca cagtgtgggt ccgccgacac cagactaaga acctagaacc    1680
tcgctggaaa ggaccttaca cagtcctgct gaccaccccc accgccctca agtagacgg    1740
catcgcagct tggatacacg ccgcccacgt gaaggctgcc gaccccgggg gtggaccatc    1800
ctctagaccg ccatgtcggg ggcaggtgcc accggccgcg ccatggacgg gccgcgcctg    1860
ctgctgttgc tgcttctggg ggtgtccctt ggaggtgcca aggaggcatg ccccacaggc    1920
ctgtacacac acagcggtga gtgctgcaaa gcctgcaacc tgggcgaggg tgtggcccag    1980
ccttgtggag ccaaccagac cgtgtgtgag ccctgcctgg acagcgtgac gttctccgac    2040
gtggtgagcg cgaccgagcc gtgcaagccg tgcaccgagt gcgtggggct ccagagcatg    2100
tcggcgccat gcgtggaggc cgacgacgcc gtgtgccgct cgcctacgg ctactaccag    2160
gatgagacga ctgggcgctg cgaggcgtgc cgcgtgtgcg aggcgggctc gggcctcgtg    2220
ttctcctgcc aggacaagca gaacaccgtg tgcgaggagt gccccgacgg cacgtattcc    2280
gacgaggcca accacgtgga cccgtgcctg ccctgcaccg tgtgcgagga caccgagcgc    2340
cagctccgcg agtgcacacg ctgggccgac gccgagtgcg aggagatccc tggccgttgg    2400
attacacggt ccacaccccc agagggctcg gacagcacag cccccagcac ccaggagcct    2460
gaggcacctc cagaacaaga cctcatagcc agcacggtgg caggtgtggt gaccacagtg    2520
atgggcagct cccagcccgt ggtgaccga ggcaccaccg acaacctcat ccctgtctat    2580
tgctccatcc tggctgctgt ggttgtgggt cttgtggcct acatagcctt caagaggtgg    2640
aacagctccg gctccggagc caccaacttc agcctgctga gcaggccgg cgacgtggag    2700
```

```
gagaacccg gccccgcggc cgctatgggt gtccctaccc agctcctggg actgctcctg    2760
ctgtggatca ccgacgccat ctgcgacatc cagatgaccc agagccctgc cagcctgtct    2820
accagcctgg gcgagacagt gaccatccag tgtcaggcca gcgaggacat ctactctggc    2880
ctggcttggt atcagcagaa gcccggcaag agccctcagc tgctgatcta cggcgccagc    2940
gacctgcagg acggcgtgcc tagcagattc agcggcagcg gctccggaac ccagtacagc    3000
ctgaagatca ccagcatgca gaccgaggac gagggcgtgt acttctgcca gcaaggcctg    3060
acctacccta gaaccttcgg aggaggcacc aagctggaac tgaagggcgg aggcggaagt    3120
ggaggcggag gatctggcgg cggaggctct gaagtgcagc tgcagcagtc tggcgctgaa    3180
ctggtccggc ctggcactag cgtgaagctg tcctgcaagg tgtccggcga caccatcacc    3240
ttctactaca tgcacttcgt gaagcagagg ccaggacagg gcctgaaatg gatcggcaga    3300
atcgaccctg aggacgagag caccaagtac agcgagaagt tcaagaacaa ggccaccctg    3360
accgccgaca ccagcagcaa caccgcctac ctgaagctgt ctagcctgac ctccgaggac    3420
accgccacct acttttgcat ctacggcggc tactacttcg actactgggg ccagggcgtg    3480
atggtcaccg tgtccagcat cgagttcatg taccccctc cctacctgga caacgagaga    3540
agcaacggca ccatcatcca catcaaagaa aagcacctgt gccacaccca gagcagcccc    3600
aagctgttct gggccctggt ggtggtggcc ggcgtgctgt tctgttacgg cctgctggtc    3660
acagtggccc tgtgcgtgat ctggaccaac agcagaagaa acagaggcgg ccagagcgac    3720
tacatgaaca tgaccccag aaggccaggc ctgaccagaa agccctacca gccctacgcc    3780
cctgccagag acttcgccgc ctacagaccc agagccaagt tcagcagatc cgccgagaca    3840
gccgccaacc tgcaggaccc taaccagctg ttcaacgagc tgaacctggg cagacgggag    3900
gaatttgacg tgctggaaaa gaagagagcc agggaccccg atgggcgg caagcagcag    3960 agaagaagaa accctcagga aggcgtctac aacgccctgc agaaagacaa gatggccgag    4020
gcctacagcg agatcggcac caagggcgag agaagaaggg gcaagggcca cgatggcctg    4080
ttccagggcc tgtccaccgc caccaaggac accttcgacg ccctgcacat gcagaccctg    4140 gccccagag gttctggcga gggtcggggg tctctgctga cctgcggtga tgtcgaggaa    4200
aatccaggtc ccatgtaccg catgcaactt ttgtcctgta ttgctctgtc cctggccctc    4260
gttaccaatt ctgattcccc agatagacca tggaacccac caactttctc cccagctttg    4320
ttggtcgtca ctgaaggtga taacgctact ttcacttgtt ccttctccaa cacttccgaa    4380
tccttccatg ttgtttggca tcgtgaatcc ccatccggtc aaactgatac attggctgct    4440
ttcccagaag atagatccca accaggtcaa gatgctagat tcagagttac tcaattgcca    4500
aacggtagag atttccacat gtccgtcgtc agagctagaa gaaacgattc cggtacttat    4560
gtttgtggtg ttatttccct tgctccaaag attcaaatta aggaatcctt gagagctgaa    4620
ttgagagtca ctgaaagaga gcccaaatct tgtgacaaaa ctcacacatg cccaccgtgc    4680
ggcggaggtt ctagtggagg cggtagtgga ggacagcccc gagaaccaca ggtgtacacc    4740
ctgcccccat cccgggagga gatgaccaag aaccaggtca gcctgacctg cctggtcaaa    4800
ggcttctatc ccagcgacat cgccgtggag tgggagagca atgggcagcc ggagaacaac    4860
tacaagacca cgcctcccgt gctggactcc gacggctcct tcttcctcta cagcaagctc    4920
accgtggaca gagcaggtg gcagcagggg aacgtcttct catgctccgt gatgcatgag    4980
gctctgcaca accactacac gcagaagagc ctctcccctgt ctccgggtaa aggatcatac    5040
```

```
ccatacgatg ttccagatta cgcttaatga ggatccgata aaataaaaga tttatttag     5100
tctccagaaa aaggggggaa tgaaagaccc cacctgtagg tttggcaagc tagcttaagt     5160
aacgccattt tgcaaggcat ggaaaataca taactgagaa tagagaagtt cagatcaagg     5220
ttaggaacag agagacagca gaatatgggc caaacaggat atctgtggta agcagttcct     5280
gccccggctc agggccaaga acagatggtc cccagatgcg gtcccgccct cagcagtttc     5340
tagagaacca tcagatgttt ccagggtgcc caaggacct gaaatgaccc tgtgccttat      5400
ttgaactaac caatcagttc gcttctcgct tctgttcgcg cgcttctgct ccccgagctc     5460
aataaaagag cccacaaccc ctcactcggc gcgccagtcc tccgatagac tgcgtcgccc     5520
gggtacccgt gtatccaata aaccctcttg cagttgcatc cgacttgtgg tctcgctgtt     5580
ccttgggagg gtctcctctg agtgattgac tacccgtcag cggggtcttc tcatgggtaa     5640
cagtttcttg aagttggaga acaacattct gagggtagga gtcgaatatt aagtaatcct    5700
gactcaatta gccactgttt tgaatccaca tactccaata ctcctgaaat ccatcgatgg     5760
agttcattat ggacagcgca gaaagagctg gggagaattg tgaaattgtt atccgctcac    5820
aattccacac aacatacgag ccggaagcat aaagtgtaaa gcctggggtg cctaatgagt     5880
gagctaactc acattaattg cgttgcgctc actgcccgct ttccagtcgg gaaacctgtc     5940
gtgccagctg cattaatgaa tcggccaacg cgcgggaga ggcggtttgc gtattgggcg      6000
ctcttccgct tcctcgctca ctgactcgct gcgctcggtc gttcggctgc ggcgagcggt     6060
atcagctcac tcaaaggcgg taatacggtt atccacagaa tcagggata acgcaggaaa     6120
gaacatgtga gcaaaaggcc agcaaaaggc caggaaccgt aaaaaggccg cgttgctggc     6180
gttttccat aggctccgcc cccctgacga gcatcacaaa aatcgacgct caagtcagag      6240
gtggcgaaac ccgacaggac tataaagata ccaggcgttt ccccctggaa gctccctcgt    6300
gcgctctcct gttccgaccc tgccgcttac cggatacctg tccgcctttc tcccttcggg    6360
aagcgtggcg ctttctcata gctcacgctg taggtatctc agttcggtgt aggtcgttcg    6420
ctccaagctg ggctgtgtgc acgaaccccc cgttcagccc gaccgctgcg ccttatccgg    6480
taactatcgt cttgagtcca acccggtaag acacgactta tcgccactgg cagcagccac    6540
tggtaacagg attagcagag cgaggtatgt aggcggtgct acagagttct tgaagtggtg    6600
gcctaactac ggctacacta aaggacagt atttggtatc tgcgctctgc tgaagccagt     6660
taccttcgga aaaagagttg gtagctcttg atccggcaaa caaaccaccg ctggtagcgg    6720
tggtttttt gtttgcaagc agcagattac gcgcagaaaa aaggatctc aagaagatcc      6780
tttgatcttt tctacggggt ctgacgctca gtggaacgaa aactcacgtt aagggatttt    6840
ggtcatgaga ttatcaaaaa ggatcttcac ctagatcctt taaattaaa aatgaagttt     6900
taaatcaatc taaagtatat atgagtaaac ttggtctgac agttaccaat gcttaatcag    6960
tgaggcacct atctcagcga tctgtctatt tcgttcatcc atagttgcct gactccccgt    7020
cgtgtagata actacgatac gggagggctt accatctggc cccagtgctg caatgatacc    7080
gcgagaccca cgctcaccgg ctccagattt atcagcaata aaccagccag ccggaagggc    7140
cgagcgcaga agtggtcctg caactttatc cgcctccatc cagtctatta attgttgccg    7200
ggaagctaga gtaagtagtt cgccagttaa tagtttgcgc aacgttgttg ccattgctac    7260
aggcatcgtg gtgtcacgct cgtcgtttgg tatggcttca ttcagctccg gttcccaacg    7320
atcaaggcga gttacatgat cccccatgtt gtgcaaaaaa gcggttagct ccttcggtcc    7380
tccgatcgtt gtcagaagta agttggccgc agtgttatca ctcatggtta tggcagcact    7440
```

```
gcataattct cttactgtca tgccatccgt aagatgcttt tctgtgactg gtgagtactc    7500
aaccaagtca ttctgagaat agtgtatgcg gcgaccgagt tgctcttgcc cggcgtcaat    7560
acgggataat accgcgccac atagcagaac tttaaaagtg ctcatcattg gaaaacgttc    7620 ttcgggggcga aaactctcaa ggatcttacc gctgttgaga tccagttcga tgtaacccac    7680
tcgtgcaccc aactgatctt cagcatcttt tactttcacc agcgtttctg ggtgagcaaa    7740
aacaggaagg caaaatgccg caaaaaaggg aataagggcg acacggaaat gttgaatact    7800
catactcttc cttttcaat attattgaag catttatcag ggttattgtc tcatgagcgg    7860
atacatattt gaatgtattt agaaaaataa acaaatagg gttccgcgca catttccccg     7920
aaaagtgcca cctgacgtct aagaaaccat tattatcatg acattaacct ataaaaatag    7980
gcgtatcacg aggccctttc gtctcgcgcg tttcggtgat gacggtgaaa acctctgaca    8040
catgcagctc ccggagacgg tcacagcttg tctgtaagcg gatgccggga gcagacaagc    8100
ccgtcagggc gcgtcagcgg gtgttggcgg gtgtcgggc tggcttaact atgcggcatc    8160
agagcagatt gtactgagag tgcaccatat gcggtgtgaa ataccgcaca gatgcgtaag    8220
gagaaaatac cgcatcaggc gccattcgcc attcaggctg cgcaactgtt gggaagggcg    8280
atcggtgcgg gcctcttcgc tattacgcca gctggcgaaa gggggatgtg ctgcaaggcg    8340
attaagttgg gtaacgccag ggttttccca gtcacgacgt tgtaaaacga cggccagtgc    8400
cacgctctcc cttatgcgac tcctgcatta ggaagcagcc cagtagtagg ttgaggccgt    8460
tgagcaccgc cgccgcaagg aatggtgcat gcaaggagat ggcgcccaac agtcccccgg    8520
ccacggggcc tgccaccata cccacgccga aacaagcgct catgagcccg aagtggcgag    8580
cccgatcttc cccatcggtg atgtcggcga tataggcgcc agcaaccgca cctgtggcgc    8640
cggtgatgcc ggccacgatg cgtccggcgt agaggcgatt taaagacagg atatcagtgg    8700
tccaggctct agttttgact caacaatatc accagctgaa gcctatagag tacgagccat    8760
agataaaata aaagatttta tttagtctcc agaaaaaggg gggaa                    8805
```